(12) United States Patent
La Porte et al.

(10) Patent No.: US 12,139,816 B2
(45) Date of Patent: *Nov. 12, 2024

(54) PROTEASE-RESISTANT SYSTEMS FOR POLYPEPTIDE DISPLAY AND METHODS OF MAKING AND USING THEREOF

(71) Applicant: CytomX Therapeutics, Inc., South San Francisco, CA (US)

(72) Inventors: Sherry Lynn La Porte, San Francisco, CA (US); Stephen James Moore, Danville, CA (US); James William West, Bend, OR (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/521,042

(22) Filed: Nov. 8, 2021

(65) Prior Publication Data
US 2022/0235351 A1 Jul. 28, 2022

Related U.S. Application Data

(60) Continuation of application No. 16/806,567, filed on Mar. 2, 2020, now Pat. No. 11,198,864, which is a
(Continued)

(51) Int. Cl.
*C40B 30/06* (2006.01)
*C07K 14/00* (2006.01)
(Continued)

(52) U.S. Cl.
CPC ............ *C40B 30/06* (2013.01); *C07K 14/001* (2013.01); *C07K 14/705* (2013.01); *C07K 16/18* (2013.01);
(Continued)

(58) Field of Classification Search
None
See application file for complete search history.

(56) References Cited

U.S. PATENT DOCUMENTS

RE30,985 E 6/1982 Cartaya
4,399,216 A 8/1983 Axel et al.
(Continued)

FOREIGN PATENT DOCUMENTS

EP 0 036776 9/1981
WO WO 1987/001195 2/1987
(Continued)

OTHER PUBLICATIONS

*Escherichia coli OmpX*, Accession No. P0A917.
(Continued)

*Primary Examiner* — Christian C Boesen
(74) *Attorney, Agent, or Firm* — Rothwell, Figg, Ernst & Manbeck, P.C.

(57) ABSTRACT

The present invention generally relates to bacterial polypeptide display systems, libraries using these bacterial display systems, and methods of making and using these systems, including methods for improved display of polypeptides on the extracellular surface of bacteria using circularly permuted transmembrane bacterial polypeptides that have been modified to increase resistance to protease degradation and to enhance polypeptide display characteristics.

9 Claims, 34 Drawing Sheets

Specification includes a Sequence Listing.

Related U.S. Application Data division of application No. 15/082,864, filed on Mar. 28, 2016, now Pat. No. 10,947,531, which is a division of application No. 13/963,769, filed on Aug. 9, 2013, now Pat. No. 9,309,510.

(60) Provisional application No. 61/682,164, filed on Aug. 10, 2012.

(51) Int. Cl.
| | |
|---|---|
| C07K 14/705 | (2006.01) |
| C07K 16/18 | (2006.01) |
| C07K 16/28 | (2006.01) |
| C12N 15/10 | (2006.01) |
| C12Q 1/37 | (2006.01) |
| G01N 33/68 | (2006.01) |
| C40B 40/02 | (2006.01) |

(52) U.S. Cl.
CPC ...... *C07K 16/2809* (2013.01); *C07K 16/2866* (2013.01); *C12N 15/1037* (2013.01); *C12N 15/1044* (2013.01); *C12Q 1/37* (2013.01); *G01N 33/6845* (2013.01); *C07K 2317/622* (2013.01); *C07K 2319/02* (2013.01); *C07K 2319/03* (2013.01); *C07K 2319/21* (2013.01); *C40B 40/02* (2013.01)

(56) References Cited

U.S. PATENT DOCUMENTS

| | | | |
|---|---|---|---|
| 4,551,433 | A | 5/1985 | DeBoer |
| 4,560,655 | A | 12/1985 | Baker |
| 4,657,866 | A | 4/1987 | Kumar |
| 4,767,704 | A | 8/1988 | Cleveland |
| 4,927,762 | A | 5/1990 | Darfler |
| 5,831,005 | A | 11/1998 | Zuckerman |
| 5,877,278 | A | 3/1999 | Zuckermann |
| 5,977,301 | A | 11/1999 | Zuckerman |
| 7,256,038 | B2 | 8/2007 | Daugherty et al. |
| 7,612,019 | B2 | 11/2009 | Daugherty et al. |
| 7,666,817 | B2 | 2/2010 | Daugherty et al. |
| 8,293,685 | B2 | 10/2012 | Daugherty et al. |
| 8,361,933 | B2 | 1/2013 | Daugherty et al. |
| 9,309,510 | B2 | 4/2016 | La Porte |
| 2005/0196406 | A1 | 9/2005 | Daugherty et al. |
| 2007/0065878 | A1 | 5/2007 | Daugherty et al. |
| 2007/0099267 | A1 | 5/2007 | Harvey et al. |
| 2010/0113303 | A1 | 5/2010 | Daugherty et al. |
| 2010/0173349 | A1 | 7/2010 | Daugherty et al. |
| 2013/0123141 | A1 | 5/2013 | Daugherty et al. |
| 2016/0264961 | A1 | 9/2016 | La Porte et al. |

FOREIGN PATENT DOCUMENTS

| | | |
|---|---|---|
| WO | WO 1990/03430 | 4/1990 |
| WO | WO 2005/047461 | 5/2005 |
| WO | WO 2007/027935 | 3/2007 |
| WO | WO 2009/014726 | 1/2009 |
| WO | WO 2009/025846 | 2/2009 |
| WO | WO 2010/081173 | 7/2010 |
| WO | WO 2010/096838 | 8/2010 |

OTHER PUBLICATIONS

*Serratia marcescens OmpX*, Accession No. AAS78634.
*Salmonella enterica* subsp. *enterica serovar Choleraesuis* str. SC-B67 ail and ompX homolog, Accession No. YP_219185.
*Salmonella enterica* subsp. *enterica serovar Typhi OmpX precursor*, Accession No. CAD05280.
*Enterobacter cloacae OmpX*, Accession No. P25253.
*Yersinia pseudotuberculosis IP 32953 OmpX*, Accession No. YP_071052.
*Shigella flexneri OmpX precursor*, Accession No. P0A920.
*Escherichia coli OmpX precursor*, Accession No. P0A918.
*Escherichia coli OmpX precursor*, Accession No. P0A919.
*Salmonella enterica* subsp. *enterica serovar Typhi Ty2 OmpX*, Accession No. NP_805818.
*Shigella flexneri 2a str. 301 OmpX*, Accession No. NP_706692.
*Yersinia pestis KIM OmpX*, Accession No. NP_ 669000.
*Salmonella enterica* subsp. *enterica serovar Typhi str. CT18 OmpX*, Accession No. NP_ 455368.
*Salmonella typhimurium LT2 OmpX*, Accession No. NP_459810.
*Escherichia coli 0157:H7 str. Sakai OmpX*, Accession No. NP_308919.
*Escherichia coli 0157:H7 EDL933 OmpX*, Accession No. NP_286578.
*Shigella flexneri 2a str. 2457T OmpX*, Accession No. NP_836469.
*Salmonella enterica* subsp. *enterica serovar Choleraesuis str. SC-B67 OmpX*, Accession No. YP 215816.
*Yersinia pestis C092 OmpX*, Accession No. NP_406040.
*Yersinia pestis biovar Microtus str. 91001 OmpX*, Accession No. NP_993650.
*Escherichia coli CFT073 OmpX*, Accession No. NP_752830.
*Salmonella enterica* subsp. *enterica serovar Paratyphi A str. ATCC 9150 OmpX*, Accession No. YP_151143.
*Erwinia carotovora* subsp. *atroseptica SCRI1043 OmpX*, Accession No. YP_050855.
*Escherichia coli APEC 01 OmpX precursor*, Accession No. ABJ00194.
*Shigella boydii Sb227 OmpX*, Accession No. YP 407207.
*Escherichia coli UTI89 OmpX*, Accession No. ABE06304.
*Yersinia pestis KIM OmpX*, Accession No. NP_669349.
*Yersinia pestis KIM OmpX*, Accession No. NP_668646.
*Escherichia coli 0157:H7 EDL933 OmpX*, Accession No. AAG55186.
*Shigella flexneri 2a str. 2457T OmpX*, Accession No. 15 AAP16275.
*Escherichia coli APEC 01 OmpX precursor*, Accession No. YP_851908.
*Escherichia coli UTI89 OmpX*, Accession No. YP_539835.
*Shigella sonnei Ss046 OmpX*, Accession No. YP_309776.
Barnes and Sato, (1980) Methods for growth of cultured cells in serum-free medium. *Anal. Biochem* 102:255.
Benoist et al., (1981) In vivo sequence requirements of the SV40 early promoter region. *Nature* 290:304-310.
Bessette and Daugherty (2004) Flow cytometric screening of cDNA expression libraries for fluorescent proteins. *Biotechnology Progress* 20:963-967.
Boder et al., (1998) Optimal Screening of Surface-Displayed Polypeptide Libraries *Biotechnol. Prog.* 14, 55-62.
Boder et al., (2000) Directed evolution of antibody fragments with monovalent femtomolar antigen-binding affinity *Proc. Natl. Acad. Sci. U.S.A.* 97(20), 10701-10705.
Boshart et al., (1985) A very strong enhancer is located upstream of an immediate early gene of human cytomegalovirus. *Cell* 41:521-530.
Boulware and Daugherty, (2006) Protease specificity determination by using cellular libraries of peptide substrates (CLiPS). *PNAS* 103(20), 7583-7588.
Casadaban and Cohen, (1980) Analysis of gene control signals by DNA fusion and cloning in *Escherichia coli. JMB* 138, 179-207.
Chadwick et al., (1997) Safety of a single aerosol administration of escalating doses of the cationic lipid GL-67/DOPE/DMPE-PEG5000 formulation to the lungs of normal volunteers. *Gene Therapy* 4:937-942.
Chang et al., (1978) Nature Phenotypic expression in *E. coli* of a DNA sequence coding for mouse dihydrofolate reductase. *Nature* 275(5681):617-624.
Dalbie-McFarland et al., (1982) Oligonucleotide-directed mutagenesis as a general and powerful method for studies of protein function. *Proc. Natl. Acad. Sci USA* 79:6409-6413.
Daugherty et al., (2000) Quantitative analysis of the effect of the mutation frequency on the affinity maturation of single chain Fv antibodies. *Proc. Natl. Acad. Sci. U.S.A.* 97(5):2029-2034.
Daugherty et al., (2000) Flow cytometric screening of cell-based libraries. *J. Immunol. Methods* 243(1-2): 211-227.
Deboer et al., (1983) The tac promoter: a functional hybrid derived from the trp and lac promoters. *Proc. Natl. Acad. Sci. USA* 80:21-25.
Deshayes et al., (2002) Rapid identification of small binding motifs with high-throughput phage display: discovery of peptidic antagonists of IGF-1 function. *Chem Biol.*9(4):495-505.

(56) References Cited

OTHER PUBLICATIONS

Dijkema et al., (1985) Cloning and expression of the chromosomal immune interferon gene of the rat. *The EMBO Journal* vol. 4 No. 3 pp. 761-767.

Edge, (1981) Total synthesis of a human leukocyte interferon gene. *Nature* 292:756-762.

Eldridge et al. "An in vitro selection strategy for conferring protease resistance to ligand binding peptides", Protein Engineering, Design & Selection (2009) 22(11):691-698.

Feldhaus et al., (2003) Flow-cytometric isolation of human antibodies from a nonimmune *Saccharomyces cerevisiae* surface display library. *Nat. Biotechnol.* 21(2):163-170.

Fields and Sternglanz (1994) The two-hybrid system: an assay for protein-protein interactions. *Trends in Genetics* 10(8):286-292.

Ford et al., (1991) Fusion tails for the recovery and purification of recombinant proteins. *Protein Expression and Purification* 2:95-107.

Gao and Huang (1995), Cationic liposome-mediated gene transfer. Gene Therapy 2:710-722.

Georgiou et al., (1997) Display of heterologous proteins on the surface of microorganisms: from the screening of combinatorial libraries to live recombinant vaccines. *Nat. Biotechnol.* 15(1):29-34.

Georgiou, (2000) Analysis of large libraries of protein mutants using flow cytometry Adv. Protein Chem. 55:293-315.

Giebel et al., (1995) Screening of cyclic peptide phage libraries identifies ligands that bind streptavidin with high affinities. *Biochemistry* 34:15430-15435.

Goddard et al., (1997) A second dose of a CFTR cDNA-liposome complex is as effective as the first dose in restoring cAMP-dependent chloride secretion to null CF mice trachea. *Gene Therapy*, 4:1231-1236.

Goeddel et al., (1979) Direct expression in *Escherichia coli* of a DNA sequence coding for human growth hormone. *Nature* 281:544-548.

Goeddel et al., (1980) Synthesis of human fibroblast interferon by *E. coli*. Nucleic Acids Res. 8:4057-4074.

Gokhale et al., (1997) Antisense raf oligodeoxyribonucleotide is protected by liposomal encapsulation and inhibits Raf-1 protein expression in vitro and in vivo: implication for gene therapy of radioresistant cancer. *Gene Therapy* 4:1289-1299.

Gorman et al., (1982) The Rous sarcoma virus long terminal repeat is a strong promoter when introduced into a variety of eukaryotic cells by DNA-mediated transfection. *Proc. Natl. Acad. Sci. USA* 79:6777-6781.

Gorman et al., (1997) Efficient in vivo delivery of DNA to pulmonary cells using the novel lipid EDMPC. *Gene Therapy* 4:983-992.

Griffiths and Tawfik, (2000) Man-made enzymes—from design to in vitro compartmentalization. *Curr. Opin. Biotechnol.* 11(4):338-353.

Grussenmeyer et al., (1985) Complexes of polyoma virus medium T antigen and cellular proteins. *Proc. Natl. Acad. Sci. USA* 82:7952-7954.

Guzman et al., (1995) Tight Regulation, Modulation, and High-Level Expression by Vectors Containing the Arabinose $P_{BAD}$ Promoter. *J Bacteriol.* Jul. 1995; 177(14):4121-4130.

Ham et al., "Media and growth requirements", Methods Enzymol. (1979) 58:44-93.

Hamer et al., (1982) Regulation in vivo of a cloned mammalian gene: cadmium induces the transcription of a mouse metallothionein gene in SV40 vectors. *J. Mol. Appl. Gen* 1:273-288.

Hopp et al., (1988) A Short Polypeptide Marker Sequence Useful for Recombinant Protein Identification and Purification. *Nature Biotechnology* 6:1204-1210.

Hopp and Woods, (1981) Prediction of protein antigenic determinants from amino acid sequences. *Proc. Natl. Acad. Sci. USA* 78:3824-3828.

Jabaiah and Daugherty, (2011) Directed Evolution of Protease Beacons that Enable Sensitive Detection of Endogenous MT1-MMP Activity in Tumor Cell Lines. *Chemistry & Biology* 18(3):392-401.

Jabaiah, A.M. et al. (Sep. 2012) "Identification of protease exosite-interacting peptides that enhance substrate cleavage kinetics" *Biol Chem*, 393(9):933-941. NIH Public Access Author Manuscript, available Dec. 11, 2013, 16 pages.

James et al., (2003) Antibody multispecificity mediated by conformational diversity. *Science* 299(5611):1362-1367.

Janowicz et al. (1982) "Synthesis of *Escherichia coli* outer membrane OmpA protein in yeasts" *Gene*, 20:347-358.

Jay et al., (1984) Chemical synthesis of a biologically active gene for human immune interferon-gamma. Prospect for site-specific mutagenesis and structure-function studies. *J. Biol. Chem.* 259(10):6311-6317.

Johnston et al., (1982) Isolation of the yeast regulatory gene GAL4 and analysis of its dosage effects on the galactose/melibiose regulon. *Proc. Natl. Acad. Sci. USA* 79:6971-6975.

Jung et al., "Surface Display of Zymomonas Mobilis Levansucrase by Using the Icenucleation Protein of Pseudomonas Syringae", Nat. Biotechnol. (1998) 16(6):576-580.

Kenrick, Rice and Daugherty, (2007) Flow Cytometric Sorting of Bacterial Surface-Displayed Libraries. *Current Protocols in Cytometry* 4.6.1-4.6.27. Published online Oct. 2007 in Wiley Interscience.

Kiick et al., (2001) Identification of an expanded set of translationally active methionine analogues in *Escherichia coli*. *FEBS Letters* 502:25-30.

Kiick et al., (2002) Incorporation of azides into recombinant proteins for chemoselective modification by the Staudinger ligation. *Proc. Natl. Acad. Sci. USA* 99(1): 19-24.

Kim et al., (2000) Isolation of peptide ligands that inhibit glutamate racemase activity from a random phage display library. *J. Biomol. Screen* 5(6):435-440.

Kirshenbaum et al., (2002) Biosynthesis of proteins incorporating a versatile set of phenylalanine analogues. *ChemBioChem* 3(2-3):235-237.

Kjaergaard et al., (2001) Novel Zn(2+)-chelating peptides selected from a fimbria-displayed random peptide library. *Appl. Environ. Microbiol.* 67(12):5467-5473.

Kodadek, (2001) Protein microarrays: prospects and problems. *Chem. Biol.* 8(2):105-115.

Kyte and Doolittle, (1982) A simple method for displaying the hydropathic character of a protein. *J. Mol. Biol.* 157:105-132.

Lowman, (1997) Bacteriophage display and discovery of peptide leads for drug development. *Ann. Rev. Biophys. Biomol. Struct.* 26:401-424.

McKnight, (1982) Functional relationships between transcriptional control signals of the thymidine kinase gene of herpes simplex virus. *Cell* 31:355-365.

Mecsas, J. et al. (Feb. 1995) "Identification and Characterization of an Outer Membrane Protein, OmpX, in *Escherichia coli* That Is Homologous to a Family of Outer Membrane Proteins Including Ail of *Yersinia enterocolitica*" *J Bacteriol*, 177(3):799-804.

Monahan et al., (1998) Direct intramuscular injection with recombinant AAV vectors results in sustained expression in a dog model of hemophilia. *Gene Therapy* 4:40-49.

Nakamura et al., (2002) Stable "zeta" peptides that act as potent antagonists of the high-affinity IgE receptor. *Proc. Natl. Acad. Sci. USA* 99(3):1303-1308.

Nambair et al., (1984) Total synthesis and cloning of a gene coding for the ribonuclease S protein. *Science* 223:1299-1301.

Nguyen et al., (2000) Improving SH3 domain ligand selectivity using a non-natural scaffold. *Chem. Biol.* 7(7):463-473.

Nilsson et al., (1991) Expression and purification of recombinant insulin-like growth factors from *Escherichia coli*. *Methods Enzymol.* 198:3-16.

Nilsson et al., (1985) Immobilization and purification of enzymes with staphylococcal protein A gene fusion vectors. *EMBO J.* 4:1075-1080.

Olsen et al., (2003) High-throughput FACS method for directed evolution of substrate specificity. *Methods Mol. Biol.* 230:329-342.

Onodera et al., (1998), Successful peripheral T-lymphocyte-directed gene transfer for a patient with severe combined immune deficiency caused by adenosine deaminase deficiency. *Blood* 91:30-36.

Pasqualini and Ruoslahti (1996) Organ targeting in vivo using phage display peptide libraries. Nature 380 (6572):364-366.

(56) References Cited

OTHER PUBLICATIONS

Poul et al., (2000) Selection of tumor-specific internalizing human antibodies from phage libraries. *J. Mol. Biol.* 301(5):1149-1161.

Rice et al., (2006) Bacterial display using circularly permuted outer membrane protein OmpX yields high affinity peptide ligands. *Protein Sci.* 15:825-836.

Scheraga, (1992) Predicting Three-Dimensional Structures of Oligopeptides *Rev. Computational Chem.* 11173-142.

Schwartz and Dayhoff, (1978) Matrices for Detecting Distant Relationships. In *Atlas of Protein Sequence and Structure* M.O. Dayhoff ed., vol. 5, Suppl. 3:353-358, National Biomedical Research Foundation, Washington, DC.

Sharma et al., (2000) Efficient introduction of aryl bromide functionality into proteins in vivo. *FEBS Letters* 467(1):37-40.

Shusta et al., (1999) Biosynthetic polypeptide libraries. *Curr. Opin. Biotechnol.* 10(2):117-122.

Siebenlist et al., *E. coli* RNA polymerase interacts homologously with two different promoters. *Cell* (1980) 20:269-281.

Silver et al., (1984) Amino terminus of the yeast GAL4 gene product is sufficient for nuclear localization. *Proc. Natl. Sci. USA* 81:5951-5955.

Simon et al., (1992) Peptoids: a modular approach to drug discovery. *Proc. Natl.Acad. Sci. USA* 89(20):9367-9371.

Smith and Johnson, (1988) Single-step purification of polypeptides expressed in *Escherichia coli* as fusions with glutathione S-transferase. *Gene* 67:31-40.

Smith and Waterman, (1981) Comparison of Biosequences. *Advances in Appl. Math.* 2:482-489.

Smith and Fernadez (2004) Effect of DNA copy number on genetic stability of phage-displayed peptides. *Biotechniques* 36(4):610-618.

StÅhl & Uhlén (1997) "Bacterial surface display: trends and progress" *Trends in Biotechnol*, 15(5):185-192.

Stemmer et al., (1995) Single-step assembly of a gene and entire plasmid from large numbers of oligodeoxyribonucleotides. *Gene* 164:49-53.

Takeuchi et al., (2000). Cellular localization of membrane-type serine protease 1 and identification of protease-activated receptor-2 and single-chain urokinase-type plasminogen activator as substrates. *J Biol Chem.* Aug. 25, 2000;275(34):26333-26342.

Van Bloois, E. (Feb. 2011) "Decorating microbes: surface display of proteins on *Escherichia coli*" *Trends in Biotechnology*, 29(2):79-86.

Whaley et al., (2000) Selection of peptides with semiconductor binding specificity for directed nanocrystal assembly. *Nature* 405(6787):665-668.

Yang et al., (1995) CDR walking mutagenesis for the affinity maturation of a potent human anti-HIV-1 antibody into the picomolar range. *J. Mol. Biol.* 254(3): 392-403.

Zoller and Smith, (1983) Oligonucleotide-directed mutagenesis of DNA fragments cloned into M13 vectors. *Methods Enzymol.* 100:468-500.

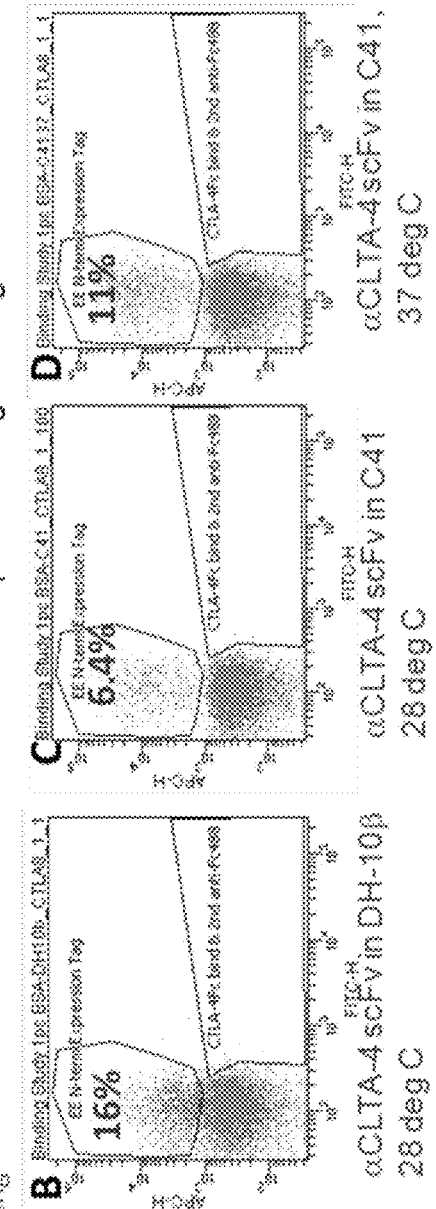
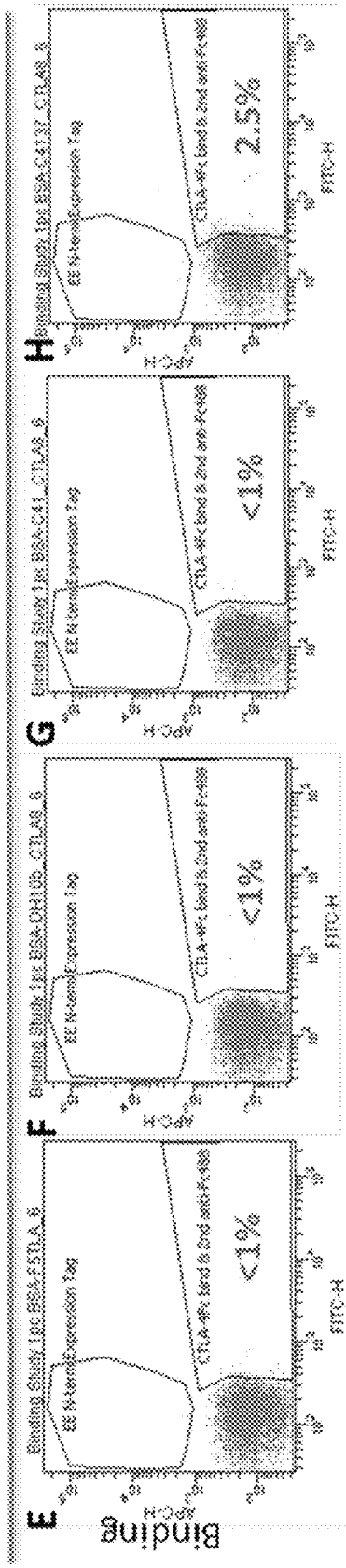
FIGURE 18A FIGURE 18B FIGURE 18C FIGURE 18D
FIGURE 18E FIGURE 18F FIGURE 18G FIGURE 18H Anti-gp130 scFv expression Anti-gp130 scFv binding gp130

FIGURE 19A FIGURE19B
Bacterial Strain
A CLiPS  B CYTX-DP-F5
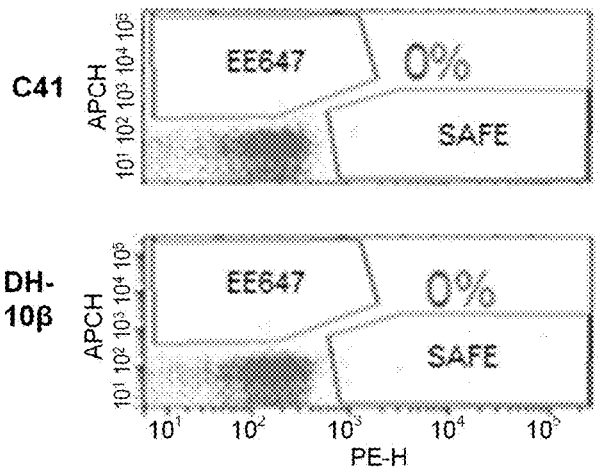
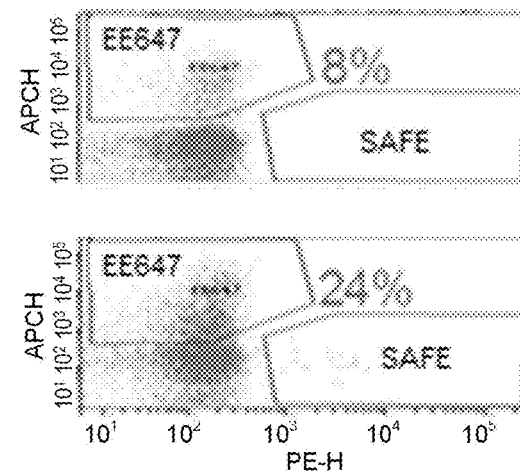
anti-CTLA-4 clone 2
C CLiPS  D CYTX-DP-CTLA4
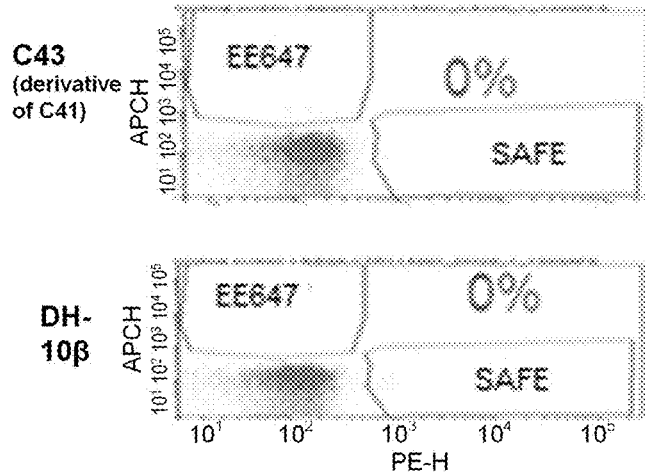
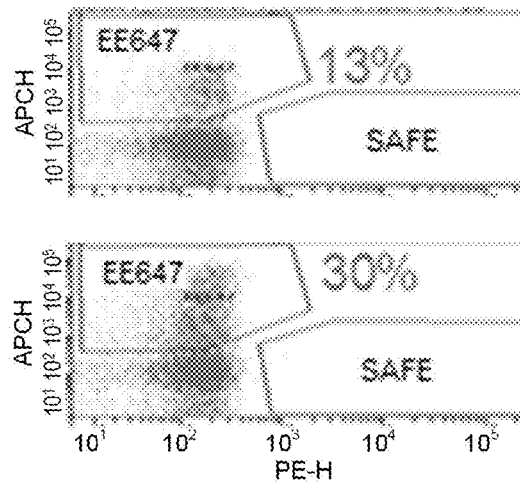
FIGURE 19C  FIGURE19D

P1'

CYTX-DP

Phage Display*

P2

P3

P4

*Takeuchi, T. et al., *J Biol Chem* 275, 26333-26342 (2000).

PROTEASE-RESISTANT SYSTEMS FOR POLYPEPTIDE DISPLAY AND METHODS OF MAKING AND USING THEREOF

RELATED APPLICATIONS

This application is a continuation of U.S. patent application Ser. No. 16/806,567 filed Mar. 2, 2020, which is a divisional application of U.S. patent application Ser. No. 15/082,864, filed Mar. 28, 2016, now U.S. Pat. No. 10,947,531 issued Mar. 16, 2021, which is a divisional application of U.S. patent application Ser. No. 13/963,769, filed Aug. 9, 2013, now U.S. Pat. No. 9,309,510, issued Apr. 12, 2016, which claims the benefit of U.S. Provisional Application No. 61/682,164, filed Aug. 10, 2012, the contents of each of which are incorporated herein by reference in their entireties.

INCORPORATION OF SEQUENCE LISTING

The contents of the text file named "CYTM020D02US_SeqList.txt", which was created on Feb. 28, 2020 and is 136,000 bytes in size, are hereby incorporated by reference in their entirety.

FIELD OF THE INVENTION

The present invention generally relates to bacterial polypeptide display systems, to libraries using these bacterial display systems, and to methods of making and using these systems, including methods for improved display of polypeptides on the extracellular surface of bacteria using circularly permuted transmembrane bacterial polypeptides that have been modified to increase resistance to protease degradation and to enhance polypeptide display characteristics.

BACKGROUND OF THE INVENTION

Polypeptide display technologies have substantially impacted basic and applied research applications ranging from drug discovery to materials synthesis. Previous expression vectors for polypeptide display libraries using host cells suffer from a variety of problems. The problems of the prior art methods include (1) only small peptides may be expressed, (2) large libraries cannot be selected, (3) the polypeptides are not expressed on the outer membrane surface, but are instead expressed in the periplasmic space between the inner and the outer membranes, (4) polypeptides that are displayed on the outer membrane surface do not properly bind or interact with large molecules and certain targets, and (5) analyzing expression on fimbriae or flagella results in loss of some desired polypeptides due to mechanical shearing.

Protein display on the surface of bacterial cells holds the potential to simplify and accelerate the process of ligand isolation since experimental procedures with bacteria are efficient, and screening can be performed using FACS. Although several different bacterial display systems have been reported, their usefulness has been restricted by technical limitations including accessibility on the cell surface, inability to display highly diverse sequences, adverse effects on cell growth and viability, and difficulty in expressing long polypeptides. In addition, utility has been hampered by protease sensitivity of systems when exposed to complex mixtures that include proteases.

Thus, a need exists for a more robust display methodology that requires minimal technical expertise, is less labor intensive, and speeds the process of ligand isolation from weeks to days as compared to prior methods.

SUMMARY OF THE INVENTION

The present invention relates to carrier polypeptides (CPs) and uses thereof. As used herein, the term carrier polypeptide refers to a transmembrane polypeptide that is designed to display a molecule, referred to herein as display moiety or displayed moiety (DM), on either or both of the N- and C-termini of the CP. In some embodiments, the CP is barrel-shaped beta sheet transmembrane polypeptide having protease resistant sequences in at least one extracellular region of the polypeptide, such as in an extracellular loop of the polypeptide or at the N- and/or C-termini of the CP. In some embodiments, the CP is a circularly permuted beta barrel-shaped beta transmembrane polypeptide having glycine-serine rich sequences, or other flexible peptide sequences, at the N- and/or C-termini of the CP or in other extracellular regions of the CP. CPs provided herein include carrier polypeptides referred to herein as "CYTX-CPs."

The CYTX-CP includes at least the amino acid sequence: YYGITAGPAYRIN DWASIYGVVGVGYGSGPGGSYGFSYGAGLQFNP-MENVALDFSYEQSRIRSVDVGTW ILSVGYRFGSKSR-RATSTVTGGYAQSDAQGQMNKMGGFNLKYRY-EEDNSPLGVIGSF TYT (SEQ ID NO: 1) or an amino acid sequence that is at least 90%, 91%, 92%, 93%, 94%, 95%, 96%, 97%, 98% or 99% identical to the amino acid sequence of SEQ ID NO: 1.

In some embodiments, the CYTX-CP includes at least the amino acid sequence: YYGITAGPAYRIND-WASIYGVVGVGYGSGPGGSYGFSYGAGLQFNP-MENV ALDFSYEQSRIRSVDVGTWILSVGYRFGSKSR-RATSTVTGGYAQSDAQGQMNKMGG FNLKYRYEEDNSPLGVIGSFTYTGGSGGSSGQTAAG (SEQ ID NO: 56) or an amino acid sequence that is at least 90%, 91%, 92%, 93%, 94%, 95%, 96%, 97%, 98% or 99% identical to the amino acid sequence of SEQ ID NO: 56.

In some embodiments, the CYTX-CP includes at least the amino acid sequence: YYGITAGPAYRIND-WASIYGVVGVGYGSGPGGSYGFSYGAGLQFNP-MENV ALDFSYEQSRIRSVDVGTWILSVGYRFGSKSR-RATSTVTGGYAQSDAQGQMNKMGG FNLKYRYEEDNSPLGVIGSFTYTGGSGGSSGQAAAG (SEQ ID NO: 57) or an amino acid sequence that is at least 90%, 91%, 92%, 93%, 94%, 95%, 96%, 97%, 98% or 99% identical to the amino acid sequence of SEQ ID NO: 57.

The invention also provides polypeptide display platforms (DPs) that include (i) one or more carrier polypeptides (CPs) having at least a transmembrane portion and N- and C-termini that are exposed when the CP is displayed on the outer membrane of a replicable biological entity, and (ii) one or more displayed moieties (DMs), such as for example, at least one polypeptide or other biological molecule. Suitable DMs include, by way of non-limiting example, a substrate sequence (S), e.g., a peptide sequence that is cleaved by one or more proteases; a masking moiety (MM), e.g., a peptide sequence that reduces the ability of an antibody or antibody fragment (AB) to bind a target; an exosite (EX); an allosteric binding site (AS); an antibody or antibody fragment (AB); a receptor (R); a ligand (L); an inhibitor (I); and any combination thereof. In some embodiments, CPs having only one DM have the general structural arrangement from N-terminus to C-terminus as follows: DM-CP or CP-DM.

In some embodiments, CPs having only one DM include, for example, DPs having a structural arrangement from N-terminus to C-terminus such as MM-CP, CP-MM; S-CP, CP-S; EX-CP, CP-EX; AB-CP, CP-AB, AS-CP, CP-AS, R-CP, CP-R, L-CP, CP-L, I-CP, or CP-I. In some embodiments, the CP includes at least the amino acid sequence of SEQ ID NO: 1. In some embodiments, the CP includes at least the amino acid sequence of SEQ ID NO: 56. In some embodiments, the CP includes at least the amino acid sequence of SEQ ID NO: 57.

In some embodiments, the DM is a masking moiety (MM), e.g., a peptide sequence that reduces the ability of an antibody or antibody fragment (AB) to bind a target. In some embodiments, the target is a target selected from those shown in Table 1.

In some embodiments, the DM is a substrate sequence (S), e.g., a peptide sequence that is cleaved by one or more proteases. In some embodiments, the protease is a protease selected from those shown in Table 2.

The DP can also include additional elements, including, by way of non-limiting example, a tag (T), such as a protease resistant N-terminal tag, a protease-resistant C-terminal tag or both N-terminal and C-terminal protease resistant tags (e.g., T1 and T2). In some embodiments, the DP includes an N-terminal tag that includes the amino acid sequence EYMPME (SEQ ID NO: 8). In some embodiments, the DP includes a C-terminal tag that includes a histidine tag, such as, for example, an 8-His tag (HHHHHHHH, SEQ ID NO: 13). In some embodiments, the DP includes an N-terminal tag that includes the amino acid sequence EYMPME (SEQ ID NO: 8) and a C-terminal tag that includes an 8-HIS tag (HHHHHHHH, SEQ ID NO: 13).

These DP embodiments have the general structural arrangement from N-terminus to C-terminus as follows: T1-DM-CP-T2 or T1-CP-DM-T2, where DM can be any suitable displayed molecule, such as, for example, a substrate, an antibody or fragment thereof, or a masking moiety. Additional non-limiting examples of DPs include T1-DM-CP, DM-CP-T2, T1-CP-DM, and CP-DM-T2.

In some embodiments, the DP includes more than one DM. In some embodiments, DM is a combination of displayed moieties, such as, for example, MM-AB or AB-MM; MM-S-AB or AB-S-MM, S-AB or AB-S such that the DP has the structural arrangement such as, e.g., T1-DM1-DM2-CP-T2 or T1-CP-DM1-DM2-T2; T1-DM1-DM2-DM3-CP-T2 or T1-CP-DM1-DM2-DM3-T2 and so on. In some embodiments, the DP includes at least two DM and each DM need not be adjacent to each other. For example, the DP can include the structural arrangement DM1-T1-DM2-CP-T2 or T1-CP-DM1-T2-DM2; or the DP can include the structural arrangement T1-DM1-CP-DM2-T2, such as, for example, EX-T1-S-CP-T2 or T1-CP-S-T2-EX; or T1-S-CP-EX-T2 or T1-EX-CP-S-T2.

In some embodiments, the DP can also include one or more linkers between two adjacent elements within the DP. For example, in some embodiments, the DP includes one or more of the following: a linker between the N-terminal tag and the DM, a linker between the DM and transmembrane portion of the CP, a linker between the transmembrane portion of the CP and the C-terminal tag. Examples of DPs with linkers in a variety of locations are shown in FIGS. 23-25 and 29-31.

The invention also provides replicable biological entities (RBEs) that express one or more polypeptide DPs on the outer surface, e.g., outer membrane or extracellular surface, of the RBE. These RBE are used to create libraries of candidate DMs for evaluation, screening and other analytical assessment. In some embodiments, the replicable biological entity is a bacterial cell, a yeast cell or a mammalian cell. In some embodiments, the replicable biological entity is a bacterial cell. In some embodiments, the bacterial cell is *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis,* or *Klebsiella pneumoniae*. RBEs of the embodiments typically display mature DPs in their outer surface. RBEs of the embodiments also include DPs with signal sequences as well as nucleic acid sequences encoding such mature DPs and signal sequence-containing DPs intracellularly.

The invention also provides nucleic acids and/or expression vectors encoding one or more CPs and/or one or more DPs, where the CP and/or DP is/are designed to be more protease-resistant, to allow for the display of larger polypeptides, and/or to exhibit improved display characteristics.

Previous carrier proteins using different circularly permuted polypeptides are described, for example, in PCT Publication No. WO 2005/047461; PCT Publication No. WO 2009/014726; U.S. Pat. Nos. 8,361,933; 8,293,685; 7,256,038; 7,612,019; U.S. Patent Application Publication No. 2010/0113303; PCT Publication No. WO 2007/027935; U.S. Pat. No. 7,666,817; U.S. Patent Application Publication No. 20100173349, and US Patent Application Publication No. 20130123141, each of which is hereby incorporated by reference in its entirety.

Previous methods of identifying and using protease cleavage sites within a displayed polypeptide to allow for selective cleavage of a detectable moiety, e.g., peptide substrate, in a specific disease microenvironment are described, for example, in PCT Publication No. WO 2005/047461; PCT Publication No. WO 2009/014726; U.S. Pat. Nos. 8,361,933; 8,293,685; 7,256,038; 7,612,019; U.S. Patent Application Publication No. 2010/0113303; PCT Publication No. WO 2007/027935; U.S. Pat. No. 7,666,817; U.S. Patent Application Publication No. 20100173349, and US Patent Application Publication No. 20130123141, each of which is hereby incorporated by reference in its entirety.

The CPs and DPs described herein provide unexpected advantages over these and other previous systems. For example, the systems provided herein allow for the display of larger polypeptides, including polypeptides that are at least about 200 amino acids in length. The display proteins and systems provided herein exhibit increased flexibility of the N- and C-termini linkers, have truncated extracellular loops, particularly loop 3 of the transmembrane protein, and are able to display large, intact and functional molecules such as scFv and other antibody fragments at either the C- or N-termini. In some embodiments antibody fragments are displayed at both the N- and C-termini of a CP; for example, a light chain comprising a variable light (VL) domain and a constant light (CL) domain could be displayed on one terminus and a heavy chain comprising a variable heavy (VH) domain and a constant heavy (CH) domain (e.g., $CH_1$) could be expressed on the other terminus in such a conformation as to allow the heavy chain and the light chain to bind to each other. In some embodiments a receptor and its ligand can be displayed at the N- and C-termini, or C- and N-termini, respectively; such a display system could be used to screen for inhibitors of receptor-ligand interactions. Display on the systems provided herein can be enhanced through *E. coli* strain selection and culture conditions.

The display peptides and systems described herein provide a novel scaffold for protein engineering for use in antibody affinity maturation and other protein engineering goals with the potential for rapid screening in a native-like format of activatable antibodies and proteins, such as by way of non-limiting example, those described in PCT Publication Nos. WO 2009/025846, WO 2010/081173; and WO 2010/096838, each of which is herein incorporated by reference in their entirety. The display peptides and systems described herein can also be used to screen for substrates and/or masks to be used in activatable antibodies in the presence of the antibody.

In some embodiments, the systems provided herein include a circularly permuted transmembrane bacterial CP, such as for example, an *E. coli* transmembrane protein, in which the N- and C-termini of the expressed, circularly permuted CP are located outside the outer membrane of a replicable biological entity. Previous systems have used a circularly permuted variant OmpX transmembrane protein, which is shown in FIG. 6A. With N- and C-termini outside the outer membrane by design, peptide display has been possible, enabling sorting of peptide libraries with FACS. (See e.g., Rice et al, Protein Sci. 2006).

The CPs and/or DPs and methods of using these CPs and/or DPs provided herein utilize a different circularly permuted, modified transmembrane bacterial protein for polypeptide display, one that is designed to provide improved display characteristics and increased resistance to protease degradation. These modified transmembrane proteins are collectively referred to herein as CYTX carrier proteins (CYTX-CPs). In some embodiments, the CYTX-CP includes at least the amino acid sequence of SEQ ID NO: 1. In some embodiments, the CYTX-CP includes at least the amino acid sequence of SEQ ID NO: 56. In some embodiments, the CYTX-CP includes at least the amino acid sequence of SEQ ID NO: 57.

Display platforms that use these CYTX-CPs to present display moieties on the outer surface of the CYTX-CP are called "CYTX-DP" (CYTX Display Platforms). CYTX-DPs that are used to identify peptide substrate sequences for a given protease or other enzyme are called "CYTX-DP-S" or "CYTX-DP-Substrate" platforms. No structural arrangement is intended by the order of abbreviations used herein. CYTX-DPs that are used to display masking moieties, are referred to herein as "CYTX-DP-MM" or "CYTX-DP-Mask" or "CYTX-DP-Masking Moiety" platforms. CYTX-DPs that are used to display antibodies, antibody fragments and other immunological polypeptides are referred to herein as "CYTX-DP-AB" or "CYTX-DP-Antibody" platforms. CYTX-DPs that are used to display activatable antibodies that include a masking moiety and a substrate are referred to herein as "CYTX-DP-Activatable Antibody" platforms and can display the activatable antibody either as MM-S-AB or AB-S-MM (i.e., they are "CYTX-DP-MM-S-AB" or "CYTX-DP-AB-S-MM" platforms. These platforms are particularly useful as they allow the selection of masks or substrates in the context of the antibody or antibody binding fragment thereof. In some embodiments, a library of CYTX-DP-Activatable Antibodies varies the MM sequences to allow for the selection of a MM while keeping the S and AB constant. In some embodiments, a library of CYTX-DP Activatable Antibodies varies the S sequences to allow for the selection of a S while keeping the MM and AB constant.

In some embodiments, the displayed moiety (DM) is a polypeptide of greater than 25 amino acids, greater than 50 amino acids, greater than 75 amino acids, greater than 100 amino acids, greater than 125 amino acids, greater than 150 amino acids, greater than 175 amino acids, greater than 200 amino acids, greater than 225 amino acids, greater than 250 amino acids, greater than 275 amino acids, greater than 300 amino acids long, greater than 350 amino acids long, greater than 400 amino acids long, or greater than 450 amino acids long. In some embodiments, the DM is a polypeptide of no more than 8 amino acids, of no more than 10 amino acids, of no more than 15 amino acids, of no more than 20 amino acids, of no more than 25 amino acids, of no more than 30 amino acids, of no more than 35 amino acids, or of no more than 40 amino acids. For example, in some embodiments, the displayed polypeptide includes an active scFv or other antibody fragment, such as a light chain variable domain, a heavy chain variable domain, one or more variable domains with or without one or more constant domains, or combinations of antibody domains wherein one domain may be displayed on one part of the DP and another domain may be displayed on another part of the DP.

The CPs and/or DPs provided herein are useful for screening or otherwise analyzing samples from a variety of environments, including complex mixtures with high protease activity and other protease-rich environments such as tumor sites, synovial fluid, tissue extracts, conditioned media from protease-expressing cells (such as conditioned media from tumor cells), sera, or venoms.

In some embodiments, the present invention provides a carrier polypeptide and a displayed moiety or an expression vector capable of expressing and displaying the CP and DM on an outer surface of a replicable biological entity within an extracellular loop of the CP such that the DM is capable of interacting with a given ligand. In some embodiments, the carrier protein is a CYTX-CP.

In some embodiments, an extracellular loop of the carrier protein is opened, resulting in an N-terminus exposed on the outer surface, a C-terminus exposed on the outer surface, or both. In some embodiments, the native C-terminus and the native N-terminus are fused together via a peptide linker. In some embodiments, the N-terminus and the C-terminus exposed to the outer surface are accessible by a ligand. In some embodiments, the C-terminus of the DM is fused to the N-terminus of the CP. In some embodiments, the N-terminus of the DM is fused to the C-terminus of the CP. In some embodiments, the carrier CP is a CYTX-CP.

In some embodiments, the replicable biological entity is a bacterial cell, a yeast cell or a mammalian cell. In some embodiments, the replicable biological entity is a bacterial cell. In some embodiments, the bacterial cell is *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis,* or *Klebsiella pneumoniae.*

In some embodiments, the expression vector further comprises a low copy origin of replication, such as a p15A origin of replication.

In some embodiments, the expression vector further comprises a bacteriocidal antibiotic resistance protein encoding gene. In some embodiments, the bacteriocidal antibiotic resistance protein encoding gene encodes chloramphenicol acetyltransferase, beta-lactamase, or a protein that renders a bacterium resistant to ampicillin, penicillin, tetracycline, or any other antibiotic known to those skilled in the art.

In some embodiments, the expression vector further comprises at least one Sfi1 endonuclease restriction enzyme site.

In some embodiments, the expression vector further comprises an arabinose araBAD *E. coli* operon promoter. In some embodiments, expression is induced with the addition of L-arabinose and stopped by the removal of arabinose and the addition of glucose.

In some embodiments, the present invention provides a host cell that comprises an expression vector as provided herein.

In some embodiments, the present invention provides a method of making a polypeptide display library that comprises creating a plurality of DPs and/or expression vectors capable of expressing a plurality of DPs described herein and inducing expression.

In some embodiments, the present invention provides a polypeptide DM expressed on the outer surface of a replicable biological entity by inducing expression of an expression vector described herein. In some embodiments, the polypeptide DM is expressed in the second extracellular loop of a CYTX-CP.

In some embodiments, the present invention provides an assay method for detecting, monitoring, or measuring a given ligand in a sample that comprises inducing an expression vector described herein to express the polypeptide DM and then contacting the polypeptide DM with the sample and observing whether the polypeptide DM interacts with the ligand.

In some embodiments, the carrier polypeptide comprises the amino acid sequence of SEQ ID NO: 1 or an amino acid sequence that is at least 90%, 91%, 92%, 93%, 94%, 95%, 96%, 97%, 98% or 99% identical to the amino acid sequence of SEQ ID NO: 1.

In some embodiments, the carrier polypeptide comprises the amino acid sequence of SEQ ID NO: 56 or an amino acid sequence that is at least 90%, 91%, 92%, 93%, 94%, 95%, 96%, 97%, 98% or 99% identical to the amino acid sequence of SEQ ID NO: 56.

In some embodiments, the carrier polypeptide comprises the amino acid sequence of SEQ ID NO: 57 or an amino acid sequence that is at least 90%, 91%, 92%, 93%, 94%, 95%, 96%, 97%, 98% or 99% identical to the amino acid sequence of SEQ ID NO: 57.

In some embodiments, the carrier polypeptide comprises the amino acid sequence of SEQ ID NO: 4, which contains an EagI restriction site on the C-terminus prior to the histidine tag, or an amino acid sequence that is at least 90%, 91%, 92%, 93%, 94%, 95%, 96%, 97%, 98% or 99% identical to the amino acid sequence of SEQ ID NO: 4.

In some embodiments, the carrier polypeptide comprises the amino acid sequence shown below in SEQ ID NO: 58, which contains a NotI restriction site on the C-terminus prior to the histidine tag, or an amino acid sequence that is at least 90%, 91%, 92%, 93%, 94%, 95%, 96%, 97%, 98% or 99% identical to the amino acid sequence of SEQ ID NO: 58:
GQSGQEYMPMEGGSGQSGQGSG-
SNSGSSGGQGGSGGSGGSGGSGGSAYYGITAGP
AYRIND-
WASIYGVVGVGYGSGPGGSYGFSYGAGLQFNPMEN-
VALDFSYEQSRIRS VDVGTWILSVGYRFGSKSRRAT-
STVTGGYAQSDAQGQMNKMGGFNLKYRYEEDN
SPLGVIGSFTYTGGSGGSSGQAAAGHHHHHHHH*
(SEQ ID NO: 58)

In some embodiments, the display platform comprises the amino acid sequence of SEQ ID NO: 81 or an amino acid sequence that is at least 90%, 91%, 92%, 93%, 94%, 95%, 96%, 97%, 98% or 99% identical to the amino acid sequence of SEQ ID NO: 81.

In some embodiments, the display platform comprises the amino acid sequence of SEQ ID NO: 82 or an amino acid sequence that is at least 90%, 91%, 92%, 93%, 94%, 95%, 96%, 97%, 98% or 99% identical to the amino acid sequence of SEQ ID NO: 82.

The invention also provides nucleic acid molecules encoding the carrier polypeptides disclosed herein, as well as nucleic acid molecules encoding polypeptides that incorporate the CPs disclosed herein, such as, for example, the CYTX-DPs disclosed herein, including the CYTX-DPs for Substrate Selection (S-CPs). The invention also provides vectors that include these nucleic acids. The CPs described herein and polypeptides that incorporate the CPs disclosed herein are produced by culturing a cell under conditions that lead to expression of the CP or polypeptide that incorporates the CP, wherein the cell includes these nucleic acid molecules and/or vectors.

In some embodiments, the nucleic acid molecule encodes a polypeptide that comprises the amino acid sequence of SEQ ID NO: 1 or a nucleotide sequence that is at least 90%, 91%, 92%, 93%, 94%, 95%, 96%, 97%, 98% or 99% identical to a nucleotide sequence that encodes a polypeptide that comprises the amino acid sequence of SEQ ID NO: 1.

In some embodiments, the nucleic acid molecule encodes a polypeptide that comprises the amino acid sequence of SEQ ID NO: 56 or a nucleotide sequence that is at least 90%, 91%, 92%, 93%, 94%, 95%, 96%, 97%, 98% or 99% identical to a nucleotide sequence that encodes a polypeptide that comprises the amino acid sequence of SEQ ID NO: 56.

In some embodiments, the nucleic acid molecule encodes a polypeptide that comprises the amino acid sequence of SEQ ID NO: 57 or a nucleotide sequence that is at least 90%, 91%, 92%, 93%, 94%, 95%, 96%, 97%, 98% or 99% identical to a nucleotide sequence that encodes a polypeptide that comprises the amino acid sequence of SEQ ID NO: 57.

In some embodiments, the nucleic acid molecule encodes a polypeptide that comprises the amino acid sequence of SEQ ID NO: 4 or a nucleotide sequence that is at least 90%, 91%, 92%, 93%, 94%, 95%, 96%, 97%, 98% or 99% identical to a nucleotide sequence that encodes a polypeptide that comprises the amino acid sequence of SEQ ID NO: 4.

In some embodiments, the carrier polypeptide is encoded by a nucleic acid molecule that comprises the nucleotide sequence of SEQ ID NO: 5 or a nucleotide sequence that is at least 90%, 91%, 92%, 93%, 94%, 95%, 96%, 97%, 98% or 99% identical to the nucleotide sequence of SEQ ID NO: 5.

The invention also provides methods of CPs described herein and polypeptides that incorporate the CPs disclosed herein. In one embodiment, the method includes the steps of (a) culturing a cell that includes a nucleic acid construct that encodes the CP or a polypeptide that incorporates the CP under conditions that lead to expression of the CP or the polypeptide that incorporates the CP; and (b) recovering the CP or the polypeptide that incorporates the CP.

The present invention provides a method for screening a library of cells or other RBE presenting DPs, e.g., CYTX-DPs, to identify a peptide substrate for an enzyme, by contacting an enzyme with a cell library enriched for expression of peptide display scaffolds, wherein each peptide display scaffold includes a CP, e.g., a CYTX-CP, a candidate peptide (DM) (in this embodiment, a substrate (S)) and a detectable moiety (T), wherein the cells of the cell library exhibit a T signal prior to contacting with the enzyme; and detecting the presence or absence of a T signal, wherein a decrease in the T signal in the presence of the enzyme as compared to the absence of the enzyme indicates that at least one cell of the cell library expresses a candidate peptide that is a substrate for the enzyme. In some embodiments, the substrate (S) is in an activatable antibody context; i.e., the DM comprises MM-S-AB or AB-S-MM.

The present invention provides a method for screening a library of cells or other RBE presenting DPs, e.g., CYTX-DPs, to identify an antibody or antigen-binding fragment thereof (AB), by contacting a target with a cell library enriched for expression of peptide display scaffolds, wherein each peptide display scaffold includes a CP, e.g., a CYTX-CP and a candidate polypeptide (DM) (in this embodiment, an AB), and detecting the level of binding between the target and the candidate polypeptides. The level of binding can be detecting using suitable means.

The present invention provides a method for screening a library of cells or other RBE presenting DPs, e.g., CYTX-DPs, to identify a masking moiety (MM), e.g., a peptide that reduces the ability of an antibody or antibody fragment (AB) to bind a target in an activatable antibody context, by contacting a target with a cell library enriched for expression of peptide display scaffolds, wherein each peptide display scaffold includes a CP, e.g., a CYTX-CP, a candidate peptide (DM) (in this embodiment, a peptide MM), and an antibody or antigen-binding fragment thereof (AB) that is specific for the target, and detecting the level of binding between the target and the AB. The level of binding can be detecting using suitable means. At least one of cell of the cell library expresses a candidate peptide that is a MM, when the candidate peptide reduces or otherwise inhibits the ability of the AB to bind to the target.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

BRIEF DESCRIPTION OF THE DRAWINGS

This invention is further understood by reference to the drawings wherein:

FIG. 1A and FIG. 1B show a schematic method of screening using protease-resistant CYTX-DP. Panel A shows an initial enrichment step where cells are screened for those that properly display the candidate substrate peptides (examples of DMs) in the display scaffolds. A detectable moiety is added to a culture of cells and only those cells that display the reporter substrates on the surface of the cell as fusions to the N-terminus of CYTX-DP. Panel B shows a detection step where the enriched cells are contacted with an enzyme and substrate cleavage is detected by flow cytometry. Substrate libraries are screened by depleting the library pool of clones that do not display a peptide and then enriching clones with hydrolyzed substrates.

FIG. 2 shows a schematic diagram of a dual color (e.g., fluorescent signals at two different wavelengths) peptide display screening method. In the absence of a cleavage, typically both a first fluorescent signal at a first wavelength (e.g., Alexa 488, depicted herein as light grey) at the C-terminus of the diagramed scaffold and a second fluorescent signal at a second wavelength (e.g., PE, depicted herein as dark grey) at the N-terminus are detected. When cleavage occurs, only the C-terminal fluorescent signal (e.g., Alexa 488) is detected, since the N-terminal fluorescent signal (e.g., PE) is removed when the enzyme cleaves the substrate.

Figures 3A, 3B, 3C, 3D:
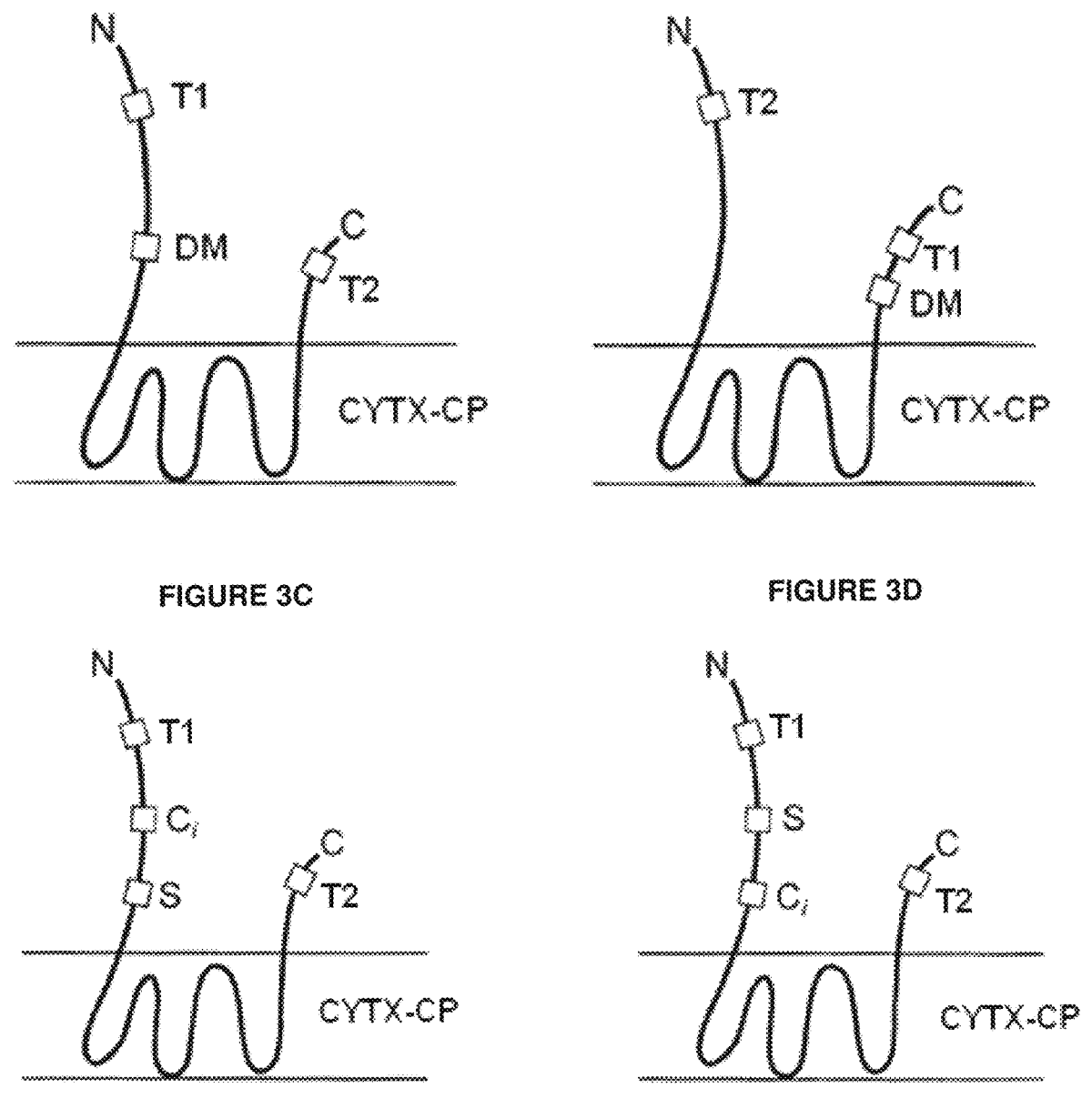

FIGS. 3A, 3B, 3C, 3D, 3E, and 3F show schematics of exemplary peptide display scaffolds. Panel A shows an exemplary peptide display scaffold including a transmembrane protein (CYTX-CP), an N-terminal domain including the DM, a candidate peptide (DM), and a first detectable moiety (T1), and a C-terminal domain including a second detectable moiety (T2). Panel B shows an exemplary peptide display scaffold including a transmembrane protein (CYTX-CP), a C-terminal domain including the DM, a candidate peptide (DM), and a first detectable moiety (T1), and an N-terminal domain including a second detectable moiety (T2). Panels C and D show exemplary peptide display scaffolds including a transmembrane protein (CYTX-CP), an N-terminal domain including the first DM, a candidate inhibitor peptide (C1), the second DM, a substrate for the enzyme (S) and a first detectable moiety (T1), and a C-terminal domain including a second detectable moiety (T2). Panels E and F show exemplary peptide display scaffolds including a transmembrane protein (CYTX-CP), a C-terminal domain including the first DM, a candidate inhibitor peptide (Ci), the second DM, a substrate for the enzyme (S) and a first detectable moiety (T1), and an N-terminal domain including a second detectable moiety (T2).

FIGS. 4A, 4B, 4C, and 4D show schematics of exemplary peptide display scaffolds. Panels A and B show exemplary peptide display scaffolds including a transmembrane protein (CYTX-CP), an N-terminal domain including the first DM, a candidate substrate peptide (Cs), the second DM, an allosteric regulator for the enzyme (A) and a first detectable moiety (T1), and a C-terminal domain including a second detectable moiety (T2). Panels C and D show exemplary peptide display scaffolds including a transmembrane protein (CYTX-CP), a C-terminal domain including the first DM, a candidate substrate peptide (Cs), the second DM, an allosteric regulator for the enzyme (A), and a first detectable moiety (T1), and an N-terminal domain including a second detectable moiety (T2).

FIGS. 5A, 5B, 5C, 5D, 5E, and 5F show schematics of exemplary peptide display scaffolds. Panel A shows an exemplary peptide display scaffold including a transmembrane protein (CYTX-CP), an N-terminal domain including the first DM, a first candidate peptide (C1), and a first detectable moiety (T1), and a C-terminal domain including the second DM, a second candidate peptide (C2), and a second detectable moiety (T2). Panel B shows an exemplary peptide display scaffold including a transmembrane protein (CYTX-CP), a C-terminal domain including the first DM, a first candidate peptide (C1), and a first detectable moiety (T1), and an N-terminal domain including the second DM, a second candidate peptide (C2), and a second detectable moiety (T2). Panel C shows an exemplary peptide display scaffold including a transmembrane protein (CYTX-CP), an N-terminal domain including the first DM, an allosteric regulator (A) and a first detectable moiety (T1), and a C-terminal domain including the second DM, a candidate substrate (Cs) and a second detectable moiety (T2). Panel D shows an exemplary peptide display scaffold including a transmembrane protein (CYTX-CP), a C-terminal domain including the first DM, an allosteric regulator (A), and a first detectable moiety (T1), and an N-terminal domain including the second DM, a candidate substrate (Cs), and a second detectable moiety (T2). Panel E shows an exemplary peptide display scaffold including a transmembrane protein (CYTX-CP), an N-terminal domain including the first DM, a known substrate (S), and a first detectable moiety (T1), and a C-terminal domain including the second DM, a candidate inhibitor (C3) and a second detectable moiety (T2). Panel F shows an exemplary peptide display scaffold including a transmembrane protein (CYTX-CP), a C-terminal domain including the first DM, a known substrate (S), and a first detectable moiety (T1), and an N-terminal domain including the second DM, a candidate inhibitor (C3) and a second detectable moiety (T2).

FIG. 6A is an illustration depicting the native *E. coli* OmpX transmembrane protein in both three-dimensional representation (left structure) and two dimensional representation (middle structure), and a circularly permuted version of the OmpX transmembrane protein (right structure).

FIG. 6B is an illustration depicting one embodiment of a protease-resistant, circularly permuted variant of the OmpX polypeptide, referred to herein as "CYTX-CP," in which loop 3 is shorter and potential protease cleavage sites in loops 2 and 3 have been replaced with a flexible glycine-serine based peptide sequence.

FIG. 6C is an illustration depicting one embodiment of a protease-resistant display scaffold, referred to herein as "CYTX-DP", in which the N-terminus of the CYTX-CP is operably linked to the C-terminus of the DM, i.e., a random candidate peptide library that, in turn, is operably linked to the sequence EYMPMEGGSG (SEQ ID NO: 31) and, and the C-terminus of the CYTX-CP is operably linked to a histidine tag to produce a display scaffold that is more compact, more flexible and more resistant to proteases that previous display scaffolds.

Figure 9:
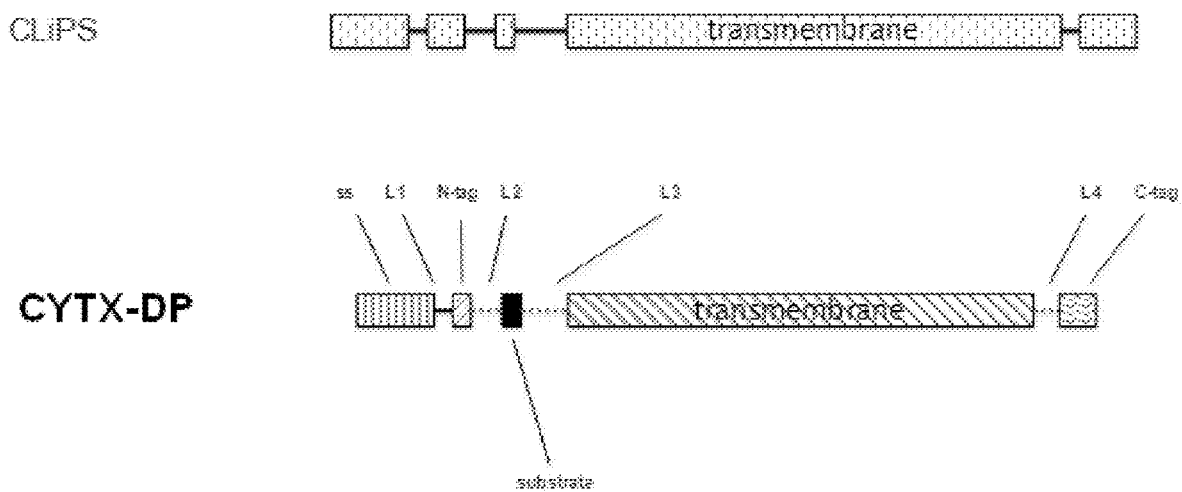

FIG. 9 is an illustration comparing previous display systems with one embodiment of the CYTX-DP display systems provided herein in which the structures in the tags, linkers, and transmembrane region have been modified: The CYTX-CP transmembrane region is compact, the linkers have shifted, and the N- and C-terminal tags are different. The signal peptides (ss) are the same, and the substrate site (example of a DM) remains flexible with new flexible restriction sites (unlabeled).

Figure 10:

FIG. 10 is a DNA sequence alignment between the CYTX-DP display system (line 1 (SEQ ID NO: 84)) and the CLiPS display system (line 2 (SEQ ID NO: 85)) starting with N-terminal Tag through Stop codon. Between them, there is 25.3% difference and 74.7% identity.

Figure 11:
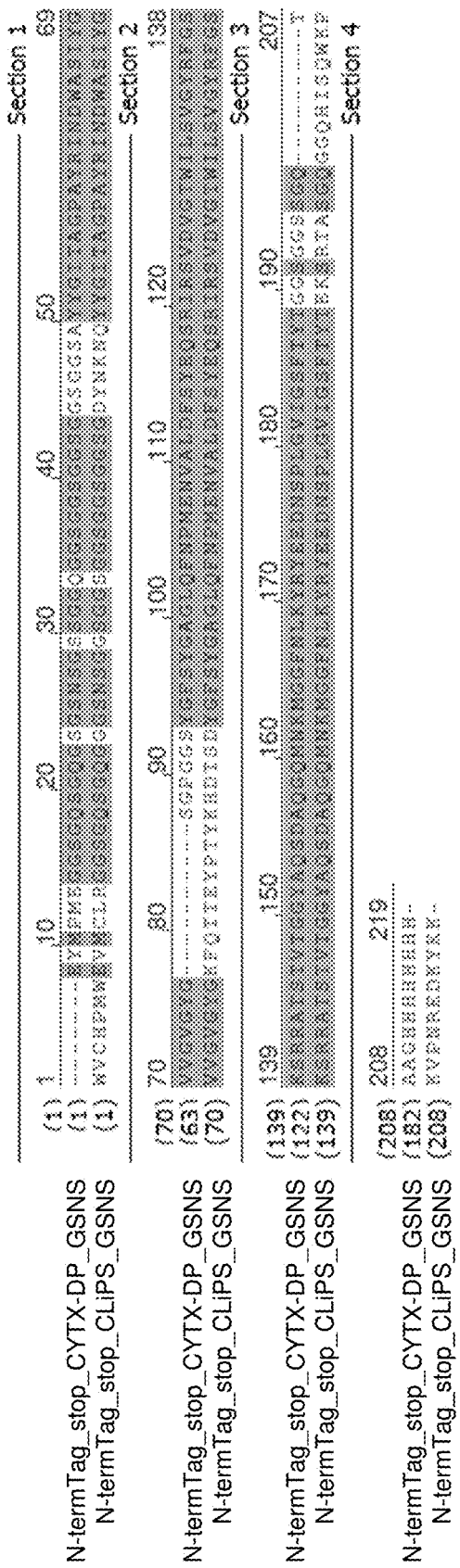

FIG. 11 is an amino acid sequence alignment between the CYTX-DP display system (line 1 (SEQ ID NO: 86)) and CLiPS (line 2 (SEQ ID NO: 87)) starting with N-terminal Tag through Stop codon. Between them, there is 28.8% difference and 71.2% identity.

Figure 12:
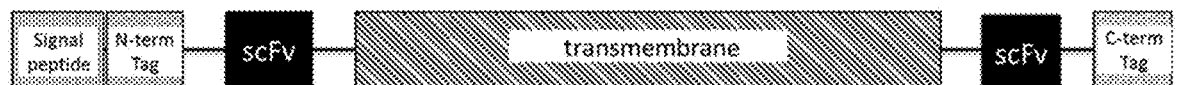
Figure 12:
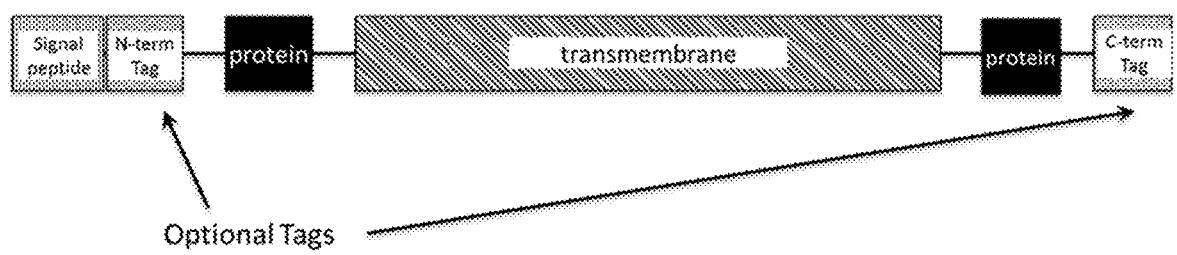

FIG. 12 is a schematic diagram of one embodiment of the CYTX-DP display system for display of antibody fragments (scFv) and proteins. A scFv or protein can be expressed at either the N-terminal or C-terminal end of the display platform with or without epitope tags. It is to be appreciated that the mature form of these display platforms lacks the signal peptide.

Figure 13:
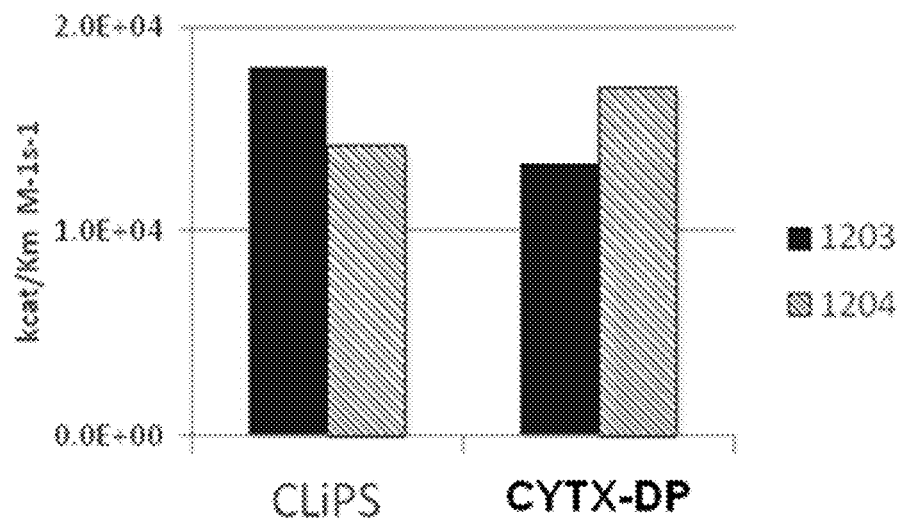

FIG. 13 is a graph demonstrating that the observed second order rate constant ($k_{cat}/K_M$, depicted here as kcat/Km) for each substrate was comparable across both the CLiPS and CYTX-DP platforms.

Figure 14A:
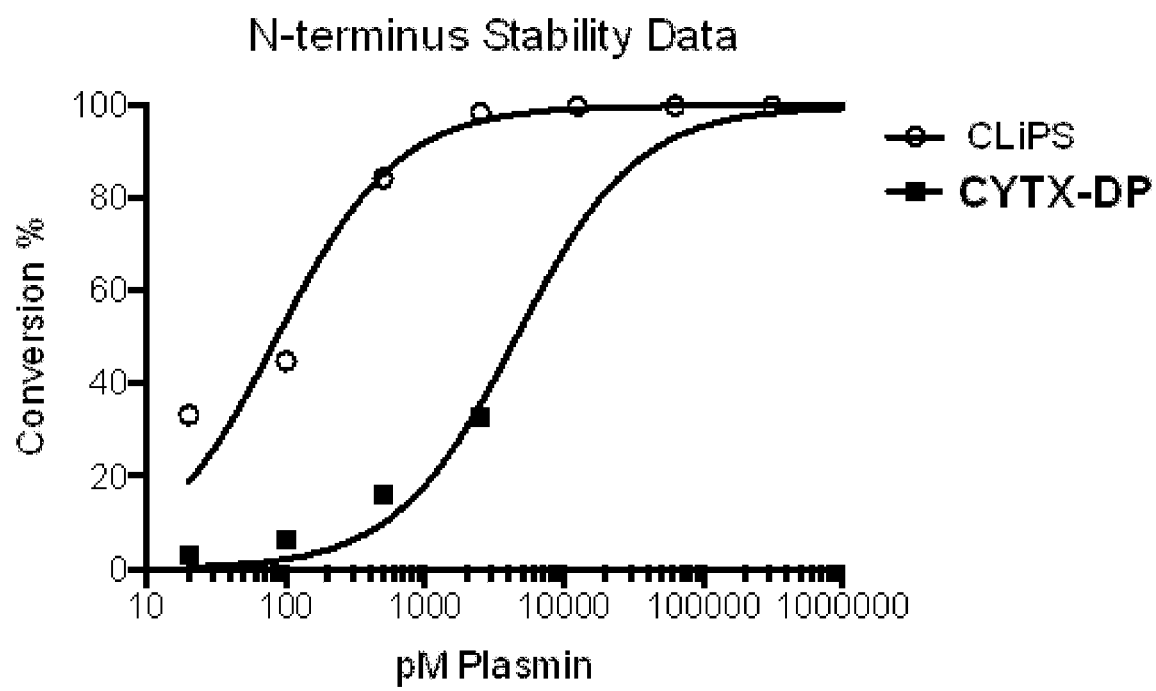
Figure 14B:
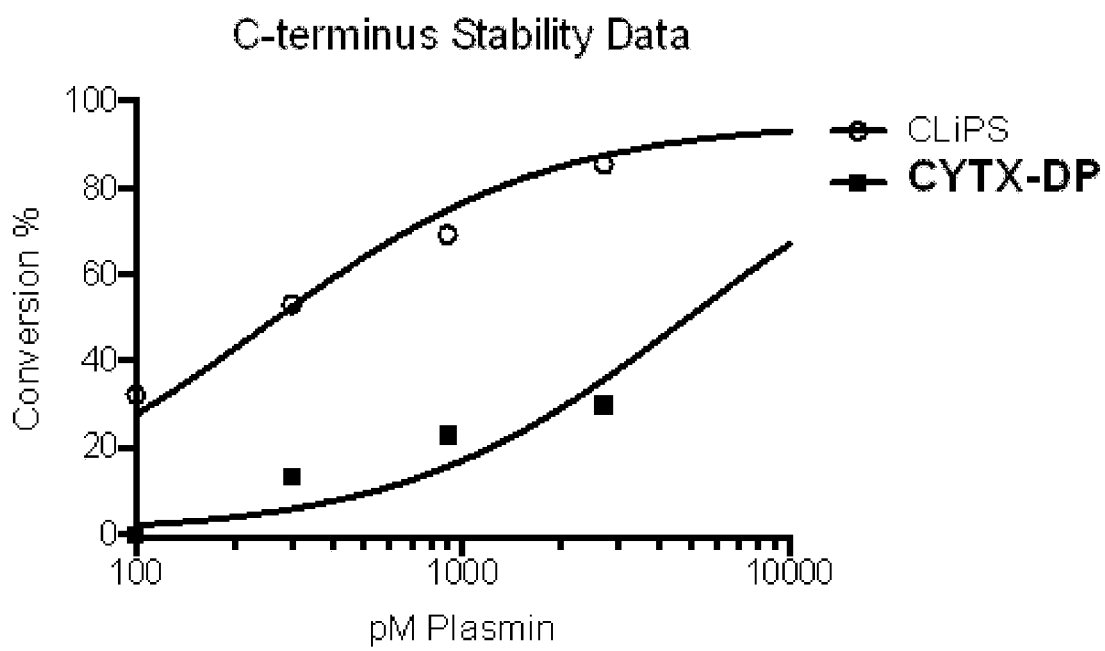

FIGS. 14A and 14B are a series of graphs depicting the N-terminus stability (14A) and C-terminus stability for the CLiPS and CYTX-DP platforms. FIG. 14A demonstrates that the CYTX-DP platform is 52-fold more stable than the CLiPS platform, using a non-linear regression fit to determine an $EC_{50}$. FIG. 14B demonstrates that the CYTX-DP platform is 21-fold more stable than the CLiPS platform, using a non-linear regression fit to determine an $EC_{50}$. $EC_{50}$=the concentration of protease required to reduce signal by 50%.

Figure 15:
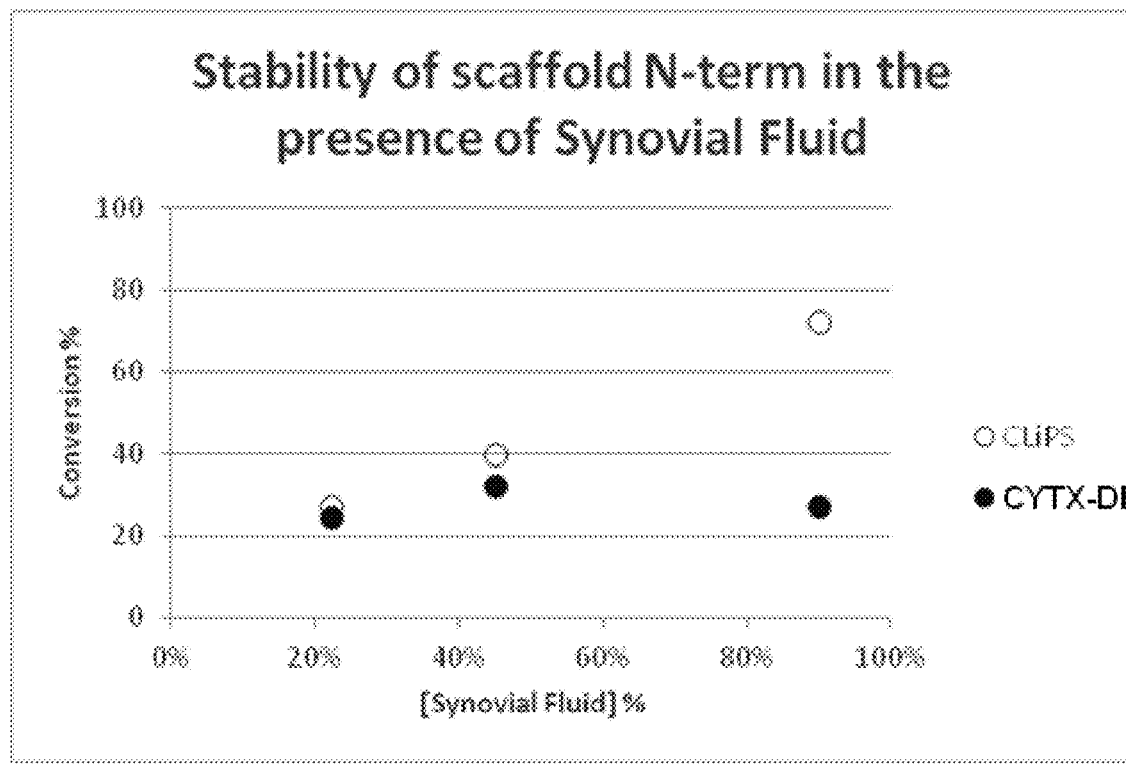

FIG. 15 is a graph depicting that the N-terminal affinity tag of the CYTX-DP platform shows increased resistance over CLiPS in the presence of synovial fluid during a 1 hr incubation at 37° C. Conversion % refers to percent cleavage of the platform by synovial fluid.

Figure 16:
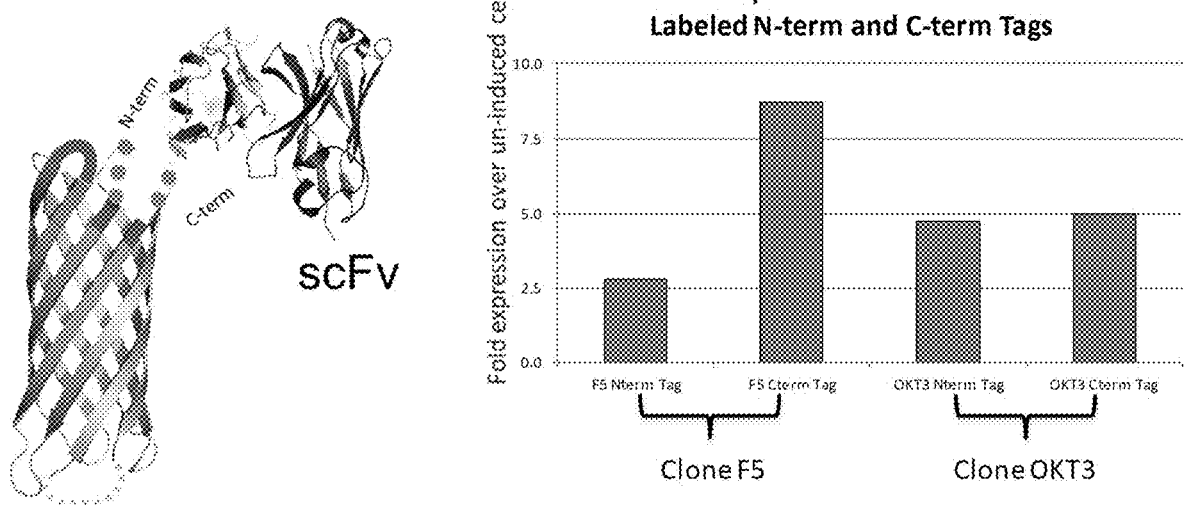

FIG. 16 is a graph and an illustration depicting the expression of scFv at the C-terminus of a CYTX-CP in the CYTX-DP platform. Either an F5 scFv (shown below as SEQ ID NO: 44) or an OKT3 scFv (shown below as SEQ ID NO: 45) was expressed fused to the C-terminus of CYTX-CP based upon fluorescence labeling of all cells. Measurement of both N-terminal and C-terminal tags indicated that arabinose-induced cells expressed from 2.8- to 9-fold more CYTX-DP-scFvF5-Cterm or CYTX-DP-scFvOKT3-Cterm than un-induced cells when labeled with the tags at either the N- or C-terminus.

Figure 17:
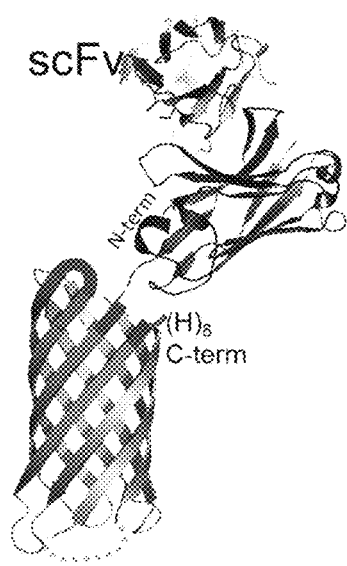
Figure 17:
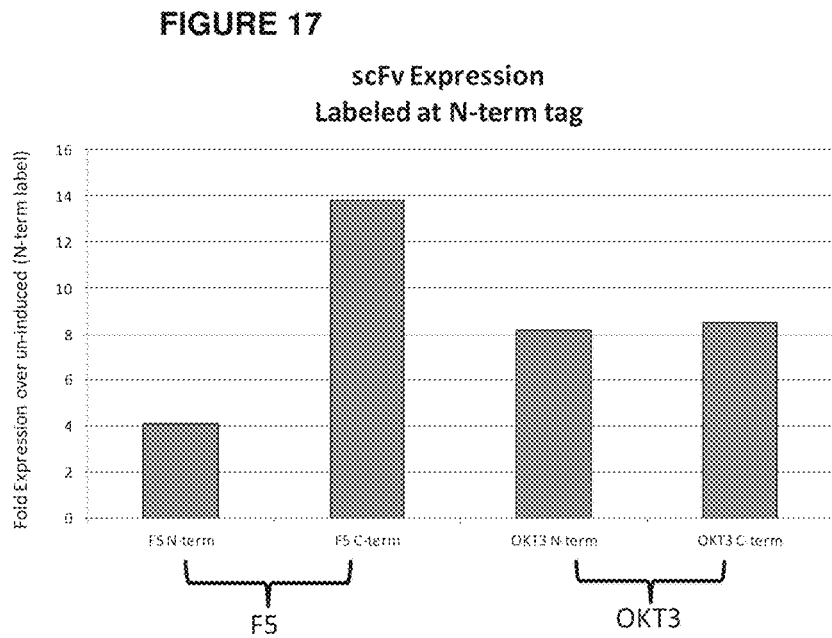
Figure 18I:
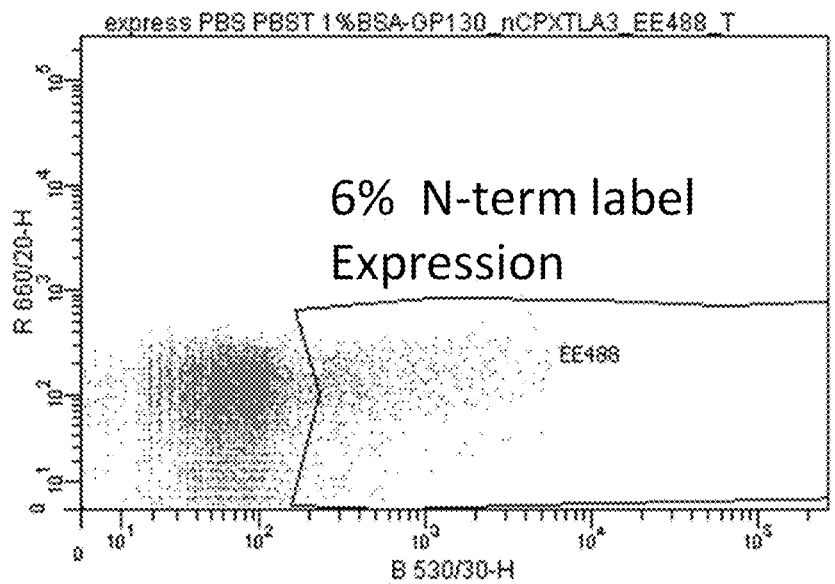
Figure 18J:
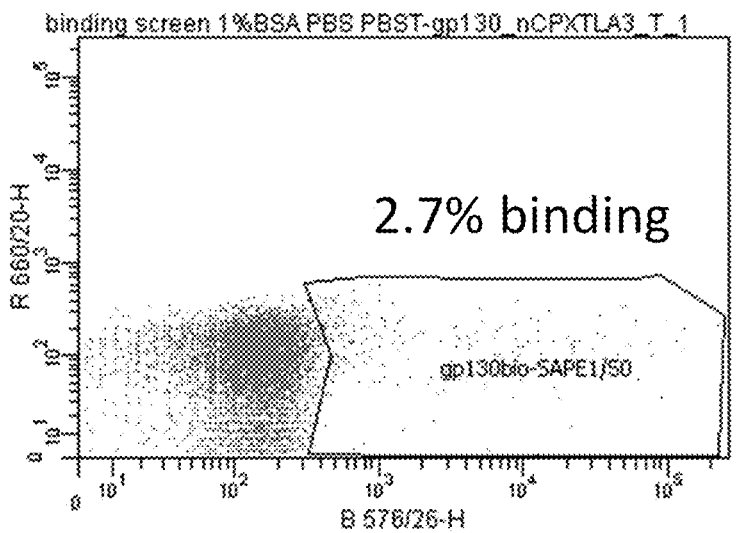

FIG. 17 is a graph and an illustration depicting the expression of scFv at either the N-terminus or the C-terminus of a CYTX-CP in the CYTX-DP platform. Two different scFvs, F5 and OKT3, were each displayed at either the N- or C-termini, as determined by measurement of N-terminal tags in arabinose-induced and un-induced cells transformed with vectors encoding a CYTX-DP-scFvF5-Nterm, CYTX-DP-scFvF5-Cterm, CYTX-DP-scFvOKT3-Nterm, or CYTX-DP-scFvOKT3-Cterm display platform.

FIGS. 18A, 18B, 18C, 18D, 18E, 18F, 18G, 18H, 18I, and 18J are a series of plots demonstrating that improved expression on the CYTX-DP platform corresponds to improved antigen binding. Display platforms comprising either scFv F5 (CYTX-DP-scFvF5-Nterm) or anti-CTLA-4 clone 2 antibody (CYTX-DP-antiCTLA4-Nterm) were expressed in either E. coli DH-10β or E. coli C41(DE3), at either 28° C. or 37° C., as indicated in FIG. 18. Panels A-D depict expression by the various systems. Panels E-H depict the ability of the systems to bind CTLA-4 antigen. When antiCTLA-4 is expressed at >10% (panel D), the antibody was able to bind to CTLA-4 antigen at 2.5% (panel H). Expression of the anti-gp130 antibody scFv in C43(DE3) E. coli. Panel I shows N-terminal labeling with anti-EE epitope tag antibody conjugated with Alex488. Six percent of the population is expressing the anti-EE epitope tag. Panel J shows that the anti-gp130 scFv expressing bacteria bind biotinylated soluble, human gp130 and are labeled with secondary streptavidin-PE (SAPE) at 1/50 dilution. 2.7% of the population binds soluble gp130.

FIGS. 19A, 19B, 19C, and 19D are a series of plots comparing scFv expression in the CYTX-DP platform and the CLiPS platform. Expression of F5 scFv and anti-CTLA-4 antibody was significantly more robust in E. coli strains transformed with CYTX-DP platforms (CYTX-DP-scFvF5-Nterm or CYTX-DP-antiCTLA4-Nterm, respectively) than in E. coli strains C41(DE3) or C43 (DE3) transformed with CLiPS platforms encoding F5 scFv or anti-CTLA-4.

Figure 20:
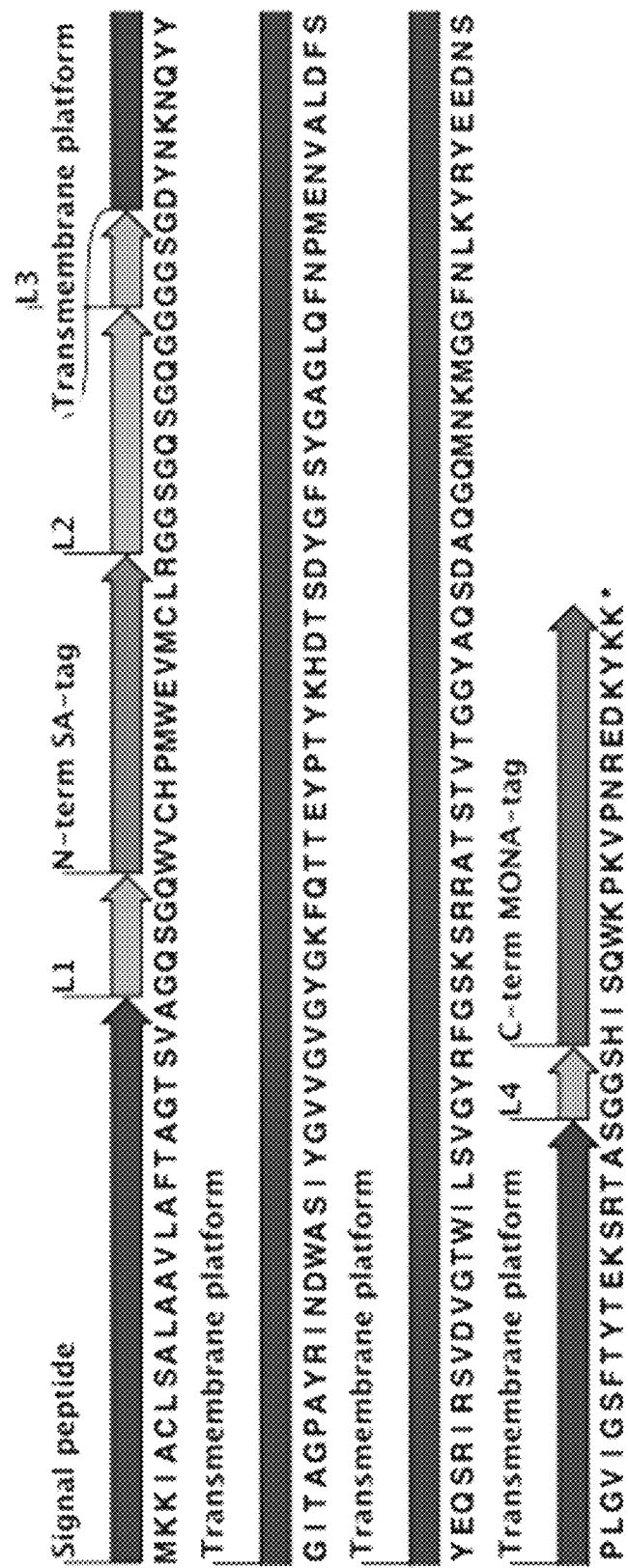

FIG. 20 is an illustration depicting the amino acid sequence (SEQ ID NO: 25) of a CLiPS platform referred to herein as eCLiPS3.0-NSUB_SP. eCLiPS3.0-NSUB_SP includes the following elements: Signal Peptide (SEQ ID NO: 6)—Linker L1 (SEQ ID NO: 7)—N-terminal SA-tag (SEQ ID NO: 14)—Linker L2 (SEQ ID NO: 9)—Linker L3 (SEQ ID NO: 15)—CLiPS3.0 transmembrane platform (SEQ ID NO: 16)—Linker L4 (SEQ ID NO: 17)—C-terminal MONA tag (SEQ ID NO: 18).

Figure 21:
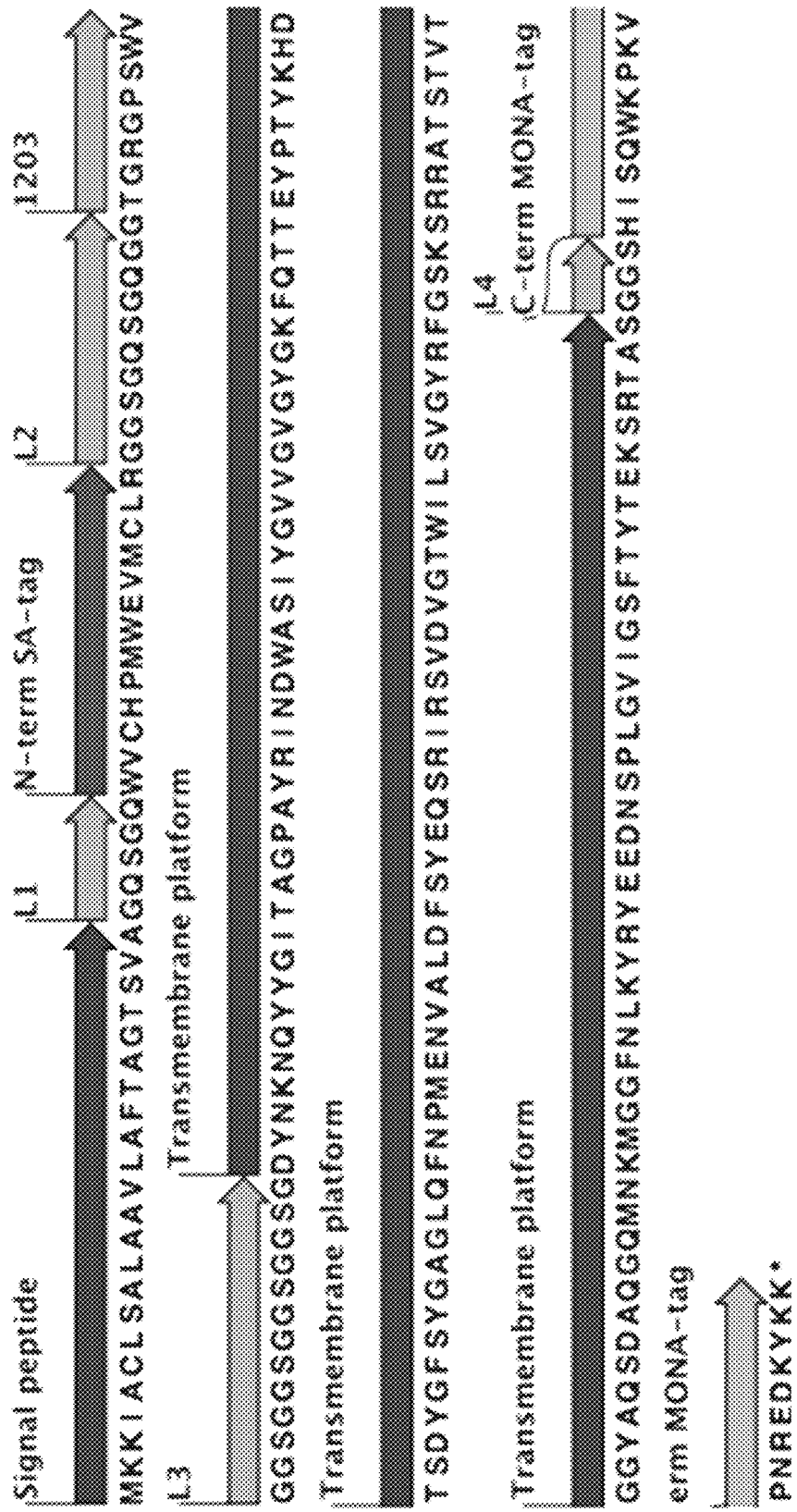

FIG. 21 is an illustration depicting the amino acid sequence (SEQ ID NO: 26) of a CLiPS platform referred to herein as eCLiPS3.0-1203_SP. eCLiPS3.0-1203_SP includes the following elements: Signal Peptide (SEQ ID NO: 6)—Linker L1 (SEQ ID NO: 7)—N-terminal SA-tag (SEQ ID NO: 14)—Linker L2 (SEQ ID NO: 9)-1203 Substrate (SEQ ID NO: 19)—Linker L3 (SEQ ID NO: 20)—CLiPS3.0 transmembrane platform (SEQ ID NO: 16)—Linker L4 (SEQ ID NO: 17)—C-terminal MONA tag (SEQ ID NO: 18).

Figure 22:
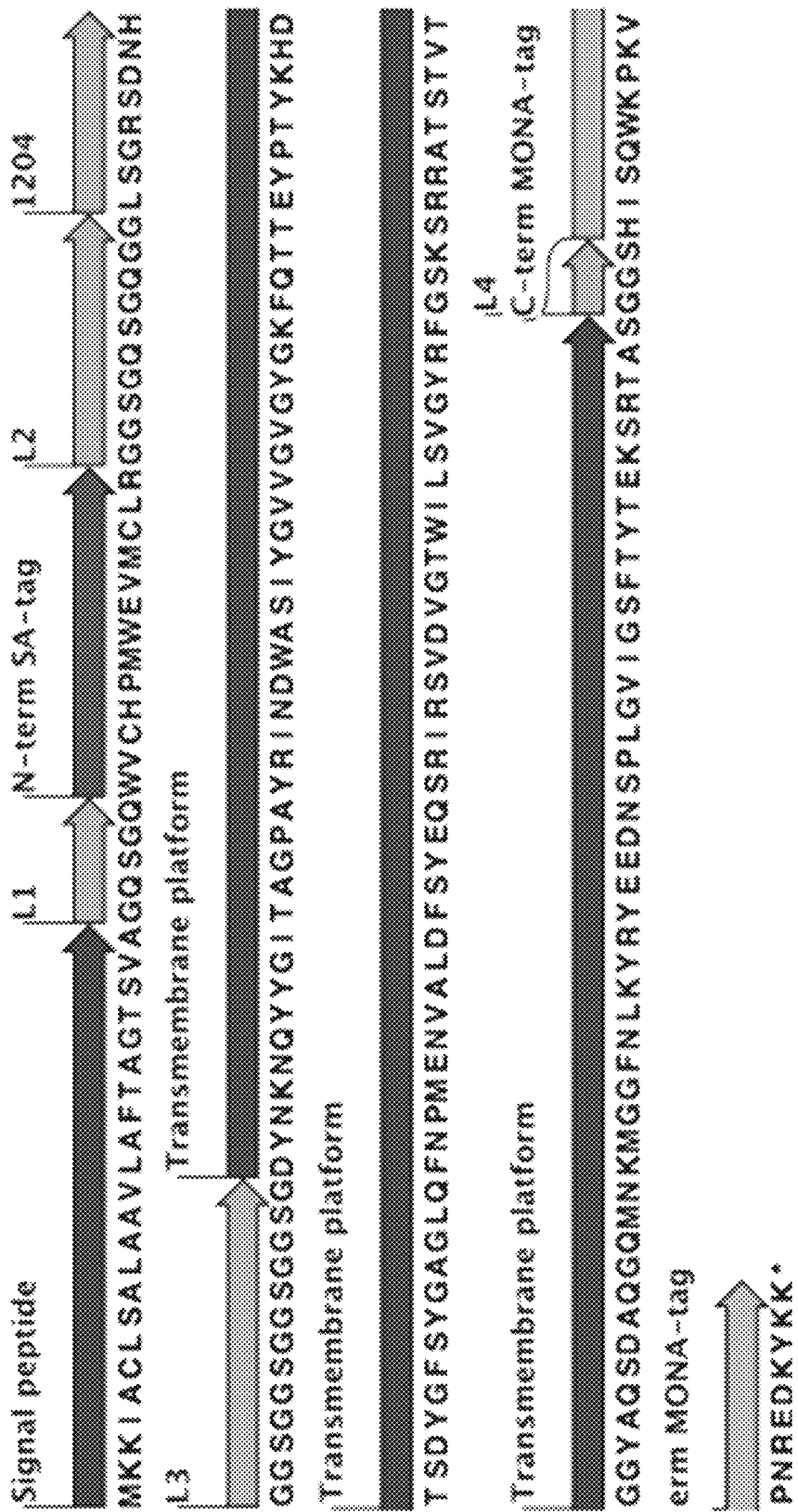

FIG. 22 is an illustration depicting the amino acid sequence (SEQ ID NO: 27) of a CLiPS platform referred to herein as eCLiPS3.0-1204_SP. eCLiPS3.0-1204_SP includes the following elements: Signal Peptide (SEQ ID NO: 6)—Linker L1 (SEQ ID NO: 7)—N-terminal SA-tag (SEQ ID NO: 14)—Linker L2 (SEQ ID NO: 9)-1204 Substrate (SEQ ID NO: 21)—Linker L3 (SEQ ID NO: 20)—CLiPS3.0 transmembrane platform (SEQ ID NO: 16)—Linker L4 (SEQ ID NO: 17)—C-terminal MONA tag (SEQ ID NO: 18).

Figure 23:
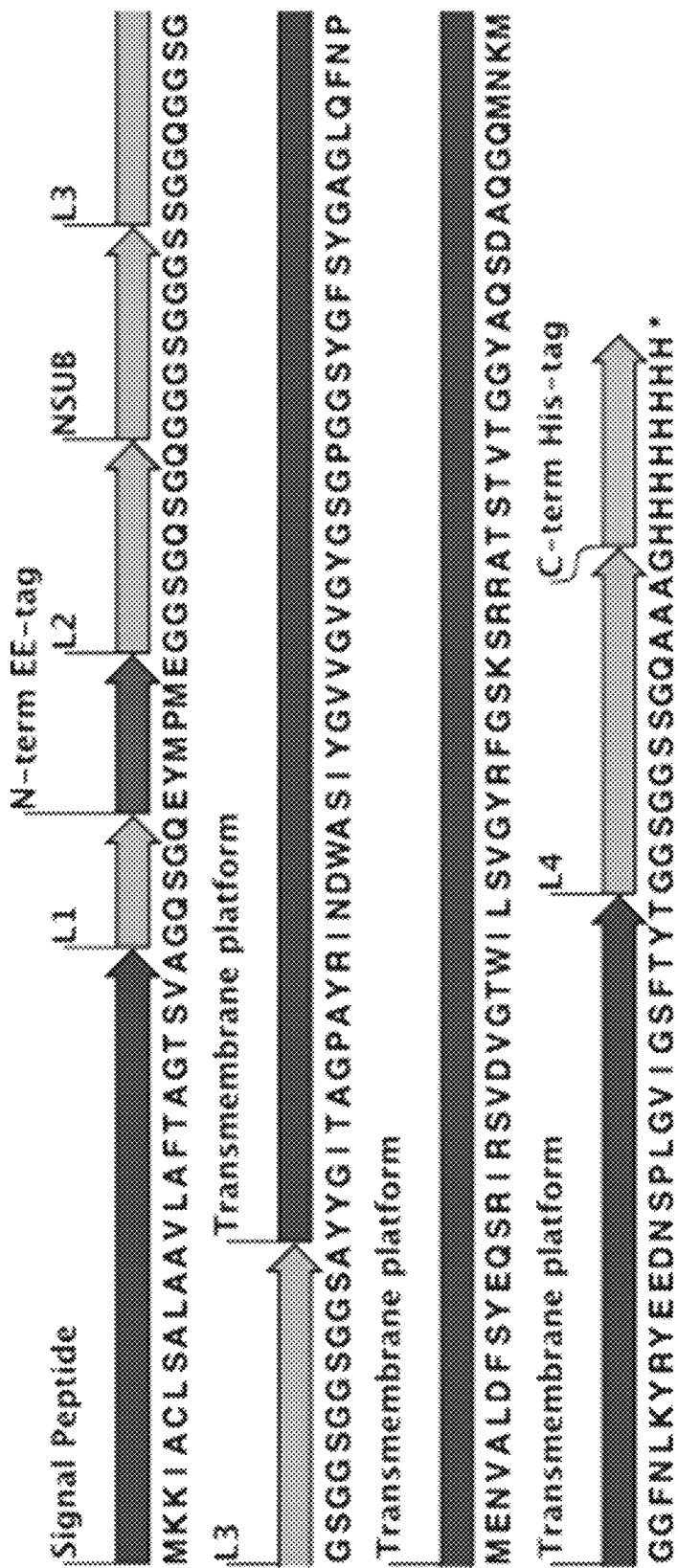

FIG. 23 is an illustration depicting the amino acid sequence (SEQ ID NO: 28) of one embodiment of a display platform referred to herein as CYTX-DP-NSUB_SP. The CYTX-DP-NSUB_SP display platform includes the following elements: Signal Peptide (SEQ ID NO: 6)—Linker L1 (SEQ ID NO: 7)—N-terminal EE-tag (SEQ ID NO: 8)—Linker L2 (SEQ ID NO: 22)—NSUB sequence (SEQ ID NO: 23)—Linker L3 (SEQ ID NO: 24)—CYTX CP transmembrane portion (SEQ ID NO: 1)—Linker L4 (SEQ ID NO: 12)—C-terminal His tag (SEQ ID NO: 13).

Figure 24:
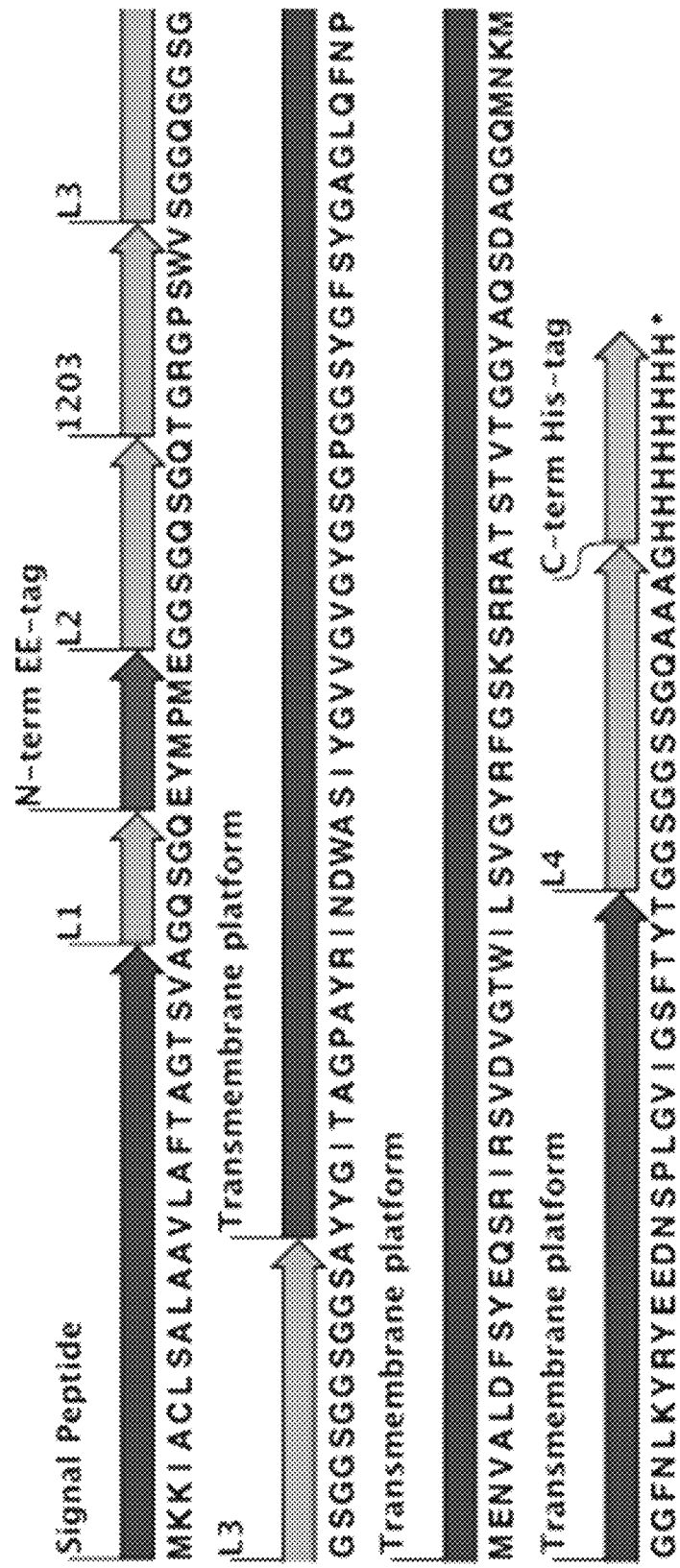

FIG. 24 is an illustration depicting the amino acid sequence (SEQ ID NO: 29) of one embodiment of a display platform referred to herein as CYTX-DP-1203_SP. The CYTX-DP-1203_SP display platform includes the following elements: Signal Peptide (SEQ ID NO: 6)—Linker L1 (SEQ ID NO: 7)—N-terminal EE-tag (SEQ ID NO: 8)—Linker L2 (SEQ ID NO: 22)-1203 Substrate (SEQ ID NO: 19)—Linker L3 (SEQ ID NO: 24)—CYTX CP transmembrane portion (SEQ ID NO: 1)—Linker L4 (SEQ ID NO: 12)—C-terminal His tag (SEQ ID NO: 13).

Figure 25:
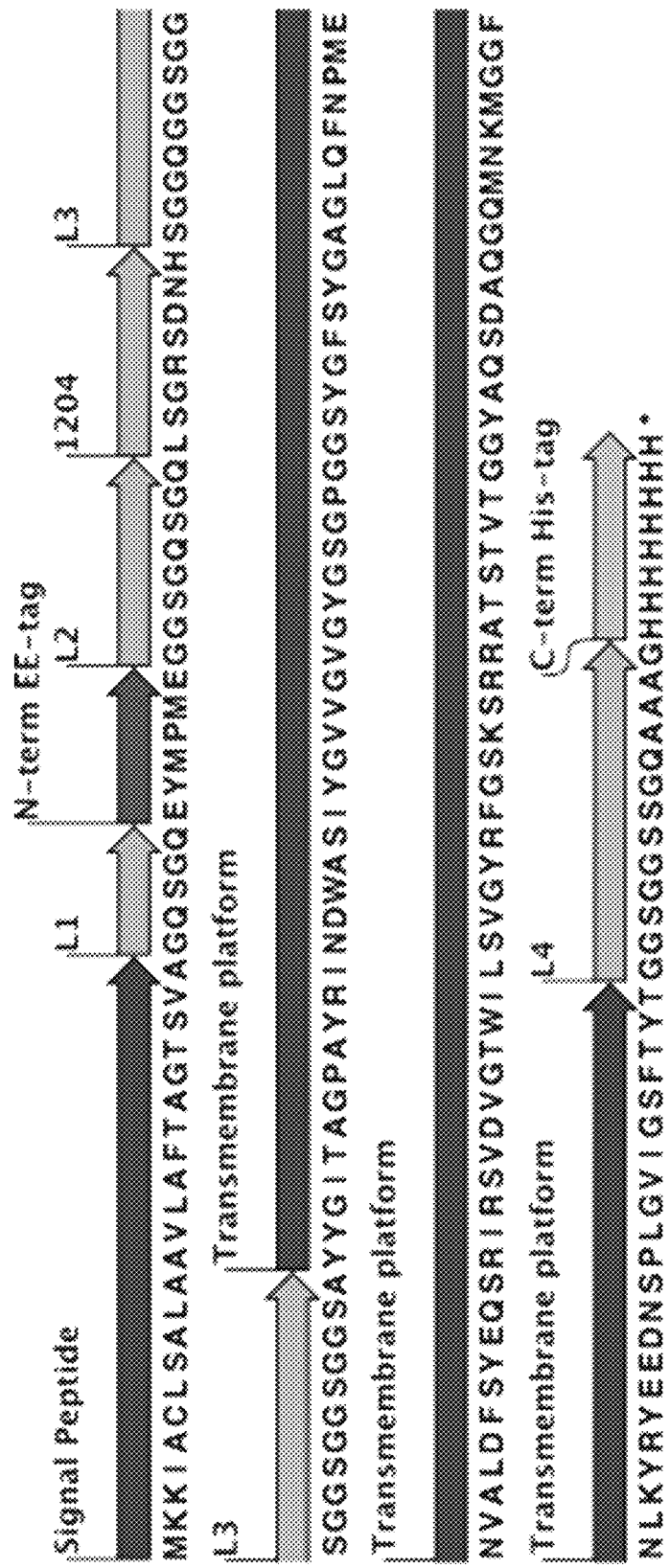

FIG. 25 is an illustration depicting the amino acid sequence (SEQ ID NO: 30) of one embodiment of a display platform referred to herein as CYTX-DP-1204_SP. The CYTX-DP-1204_SP platform includes the following elements: Signal Peptide (SEQ ID NO: 6)—Linker L1 (SEQ ID NO: 7)—N-terminal EE-tag (SEQ ID NO: 8)—Linker L2 (SEQ ID NO: 22)-1204 Substrate (SEQ ID NO: 21)—Linker L3 (SEQ ID NO: 24)—CYTX CP transmembrane portion (SEQ ID NO: 1)—Linker L4 (SEQ ID NO: 12)—C-terminal His tag (SEQ ID NO: 13).

Figure 26:
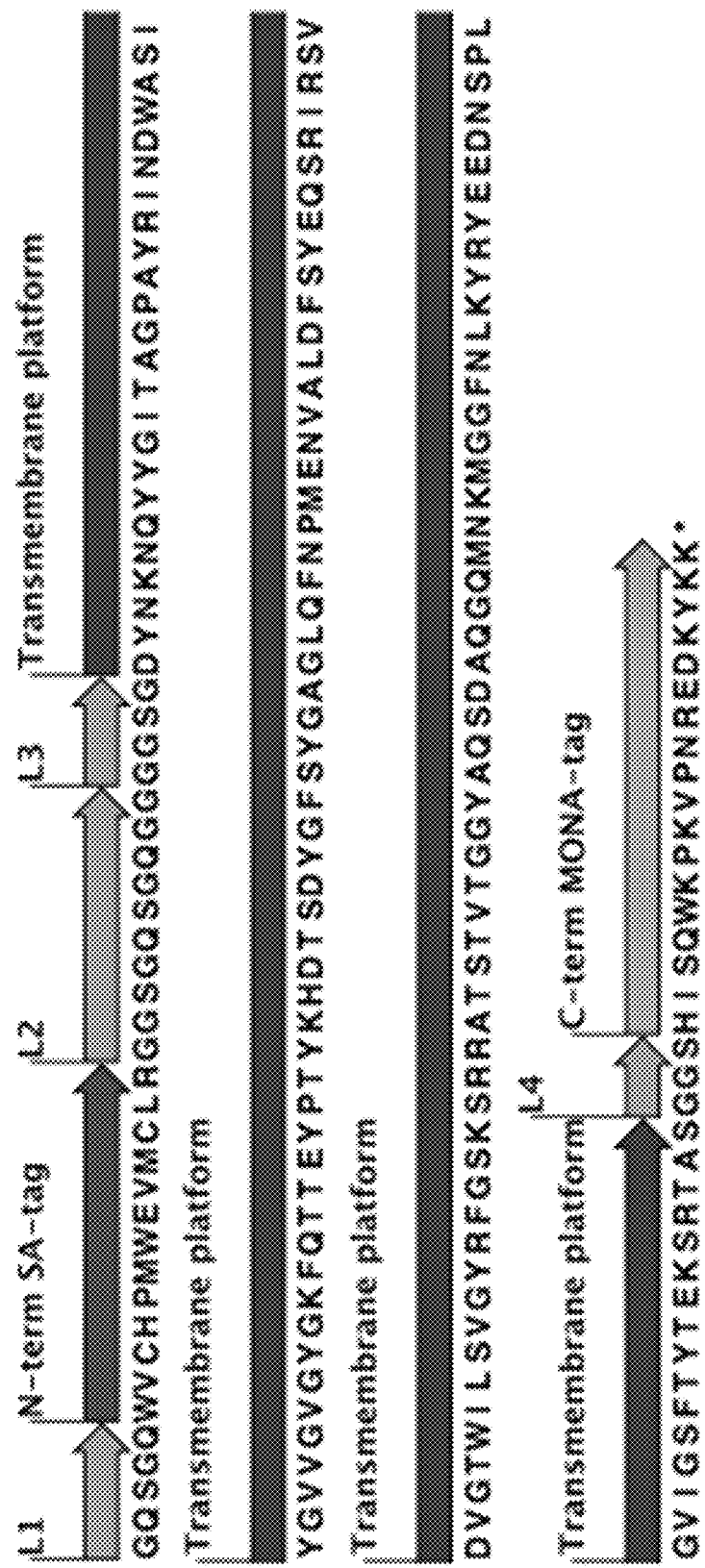

FIG. 26 is an illustration depicting the amino acid sequence (SEQ ID NO: 47) of a CLiPS platform referred to herein as eCLiPS3.0-NSUB. eCLiPS3.0-NSUB is the same as eCLiPS3.0-NSUB_SP except that eCLiPS3.0-NSUB lacks a signal peptide.

Figure 27:
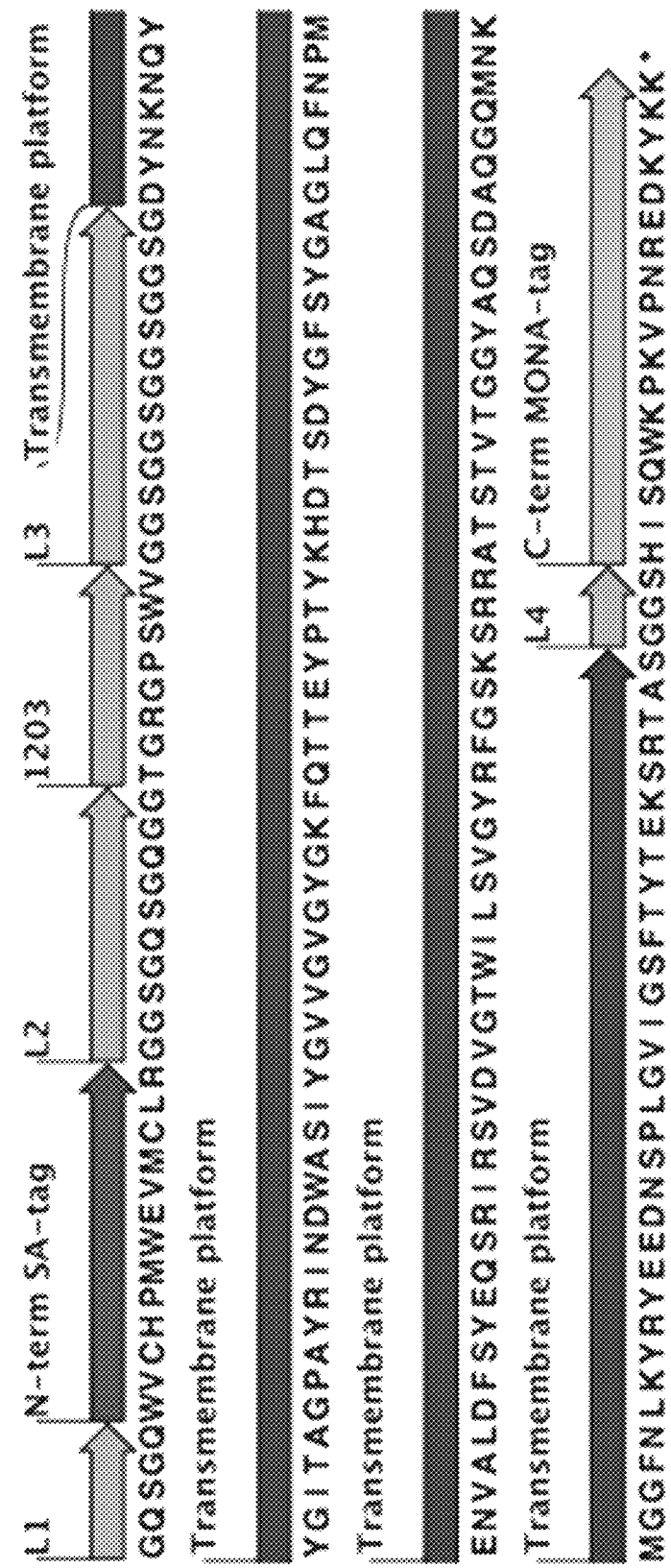

FIG. 27 is an illustration depicting the amino acid sequence (SEQ ID NO: 48) of a CLiPS platform referred to herein as eCLiPS3.0-1203. eCLiPS3.0-1203 is the same as eCLiPS3.0-1203_SP except that eCLiPS3.0-1203 lacks a signal peptide.

Figure 28:
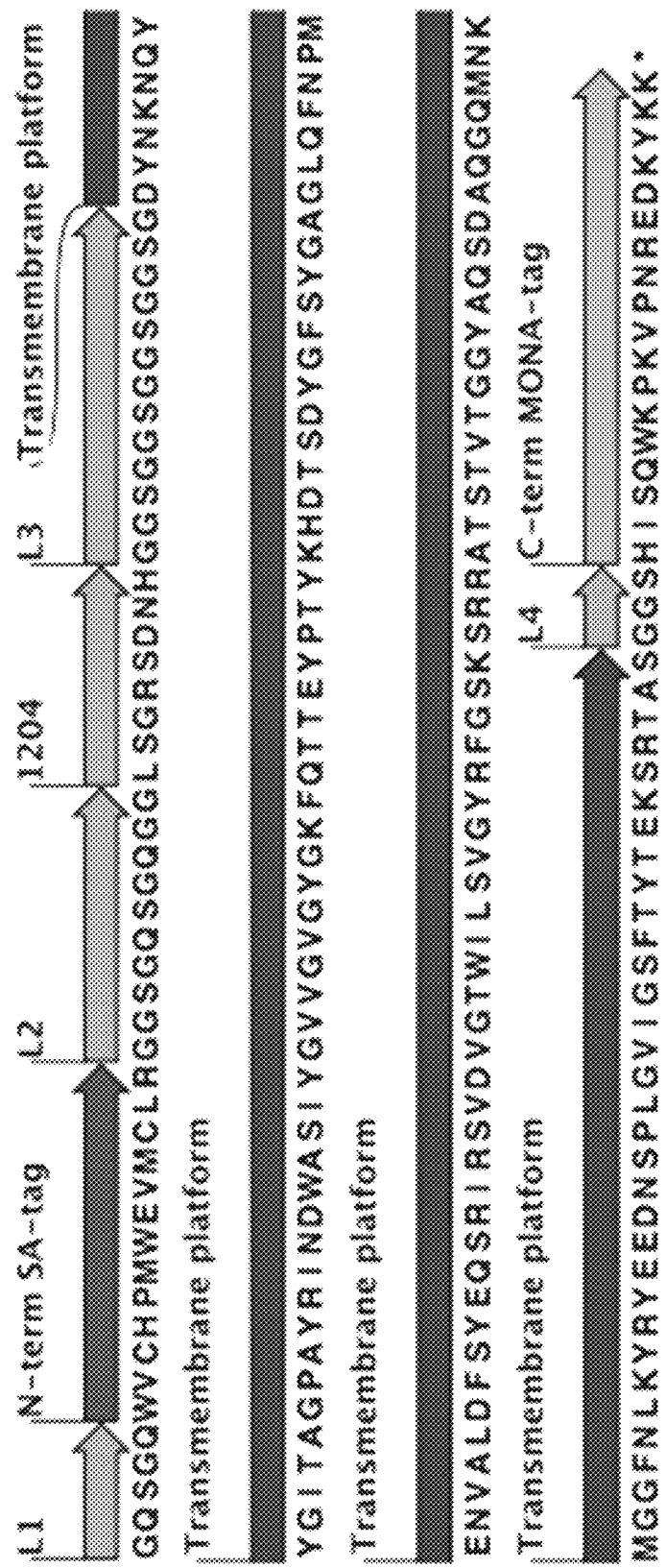

FIG. 28 is an illustration depicting the amino acid sequence (SEQ ID NO: 49) of a CLiPS platform referred to herein as eCLiPS3.0-1204. eCLiPS3.0-1204 is the same as eCLiPS3.0-1204_SP except that eCLiPS3.0-1204 lacks a signal peptide.

Figure 29:
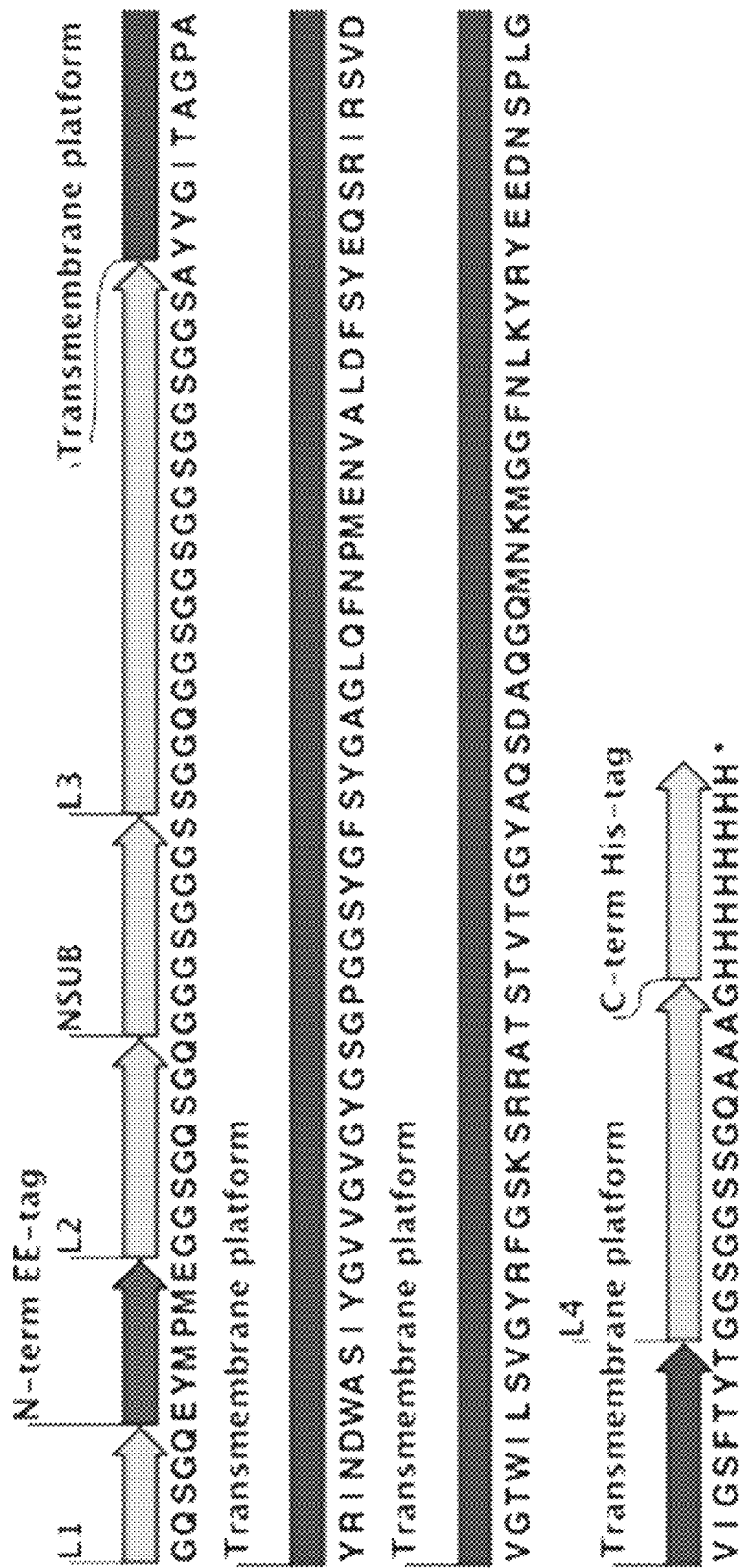

FIG. 29 is an illustration depicting the amino acid sequence (SEQ ID NO: 50) of one embodiment of a display platform referred to herein as CYTX-DP-NSUB. The CYTX-DP-NSUB display platform is the same as the CYTX-DP-NSUB_SP display platform except that CYTX-DP-NSUB lacks a signal peptide.

Figure 30:
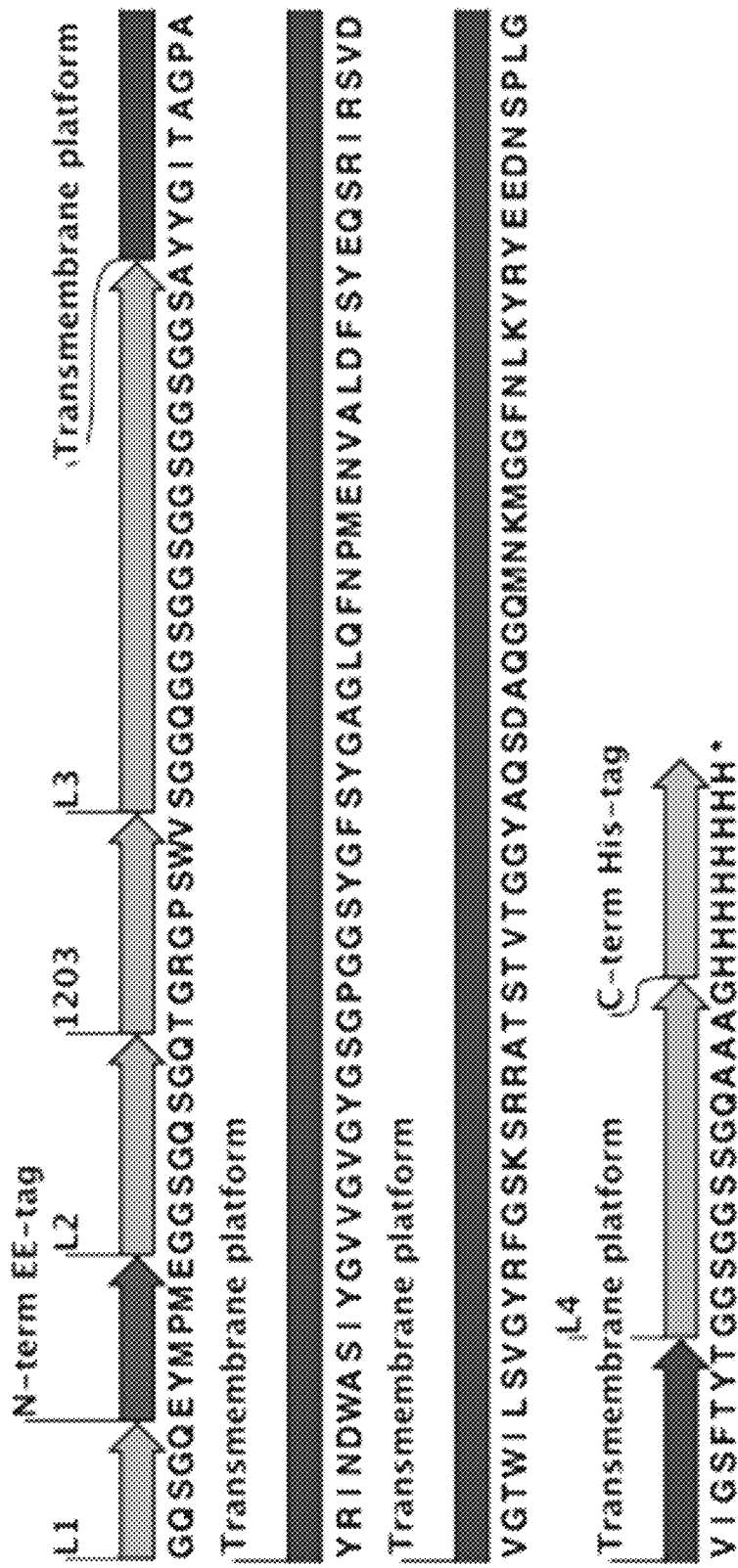

FIG. 30 is an illustration depicting the amino acid sequence (SEQ ID NO: 51) of one embodiment of a display platform referred to herein as CYTX-DP-1203. The CYTX-DP-1203 display platform is the same as the CYTX-DP-1203_SP display platform except that CYTX-DP-1203 lacks a signal peptide.

Figure 31:
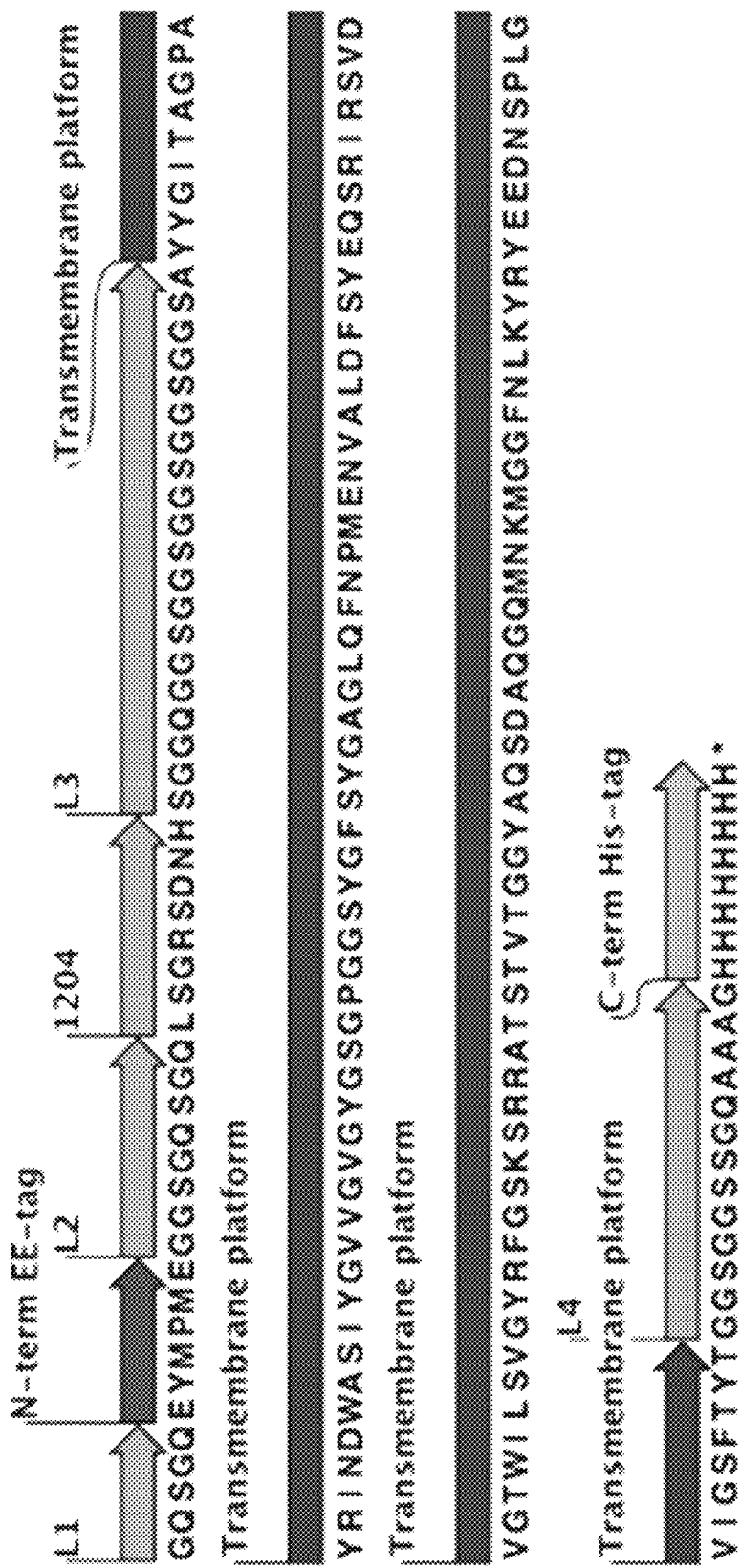

FIG. 31 is an illustration depicting the amino acid sequence (SEQ ID NO: 52) of one embodiment of a display platform referred to herein as CYTX-DP-1204. The CYTX-DP-1204 display platform is the same as the CYTX-DP-1204_SP display platform except that CYTX-DP-1204 lacks a signal peptide.

Figure 32A:
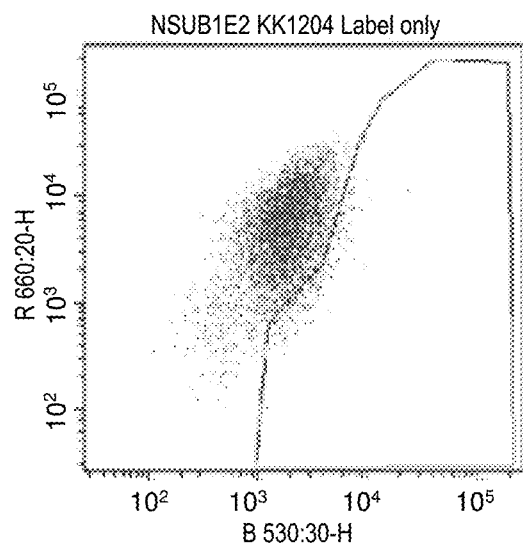
Figure 32B:
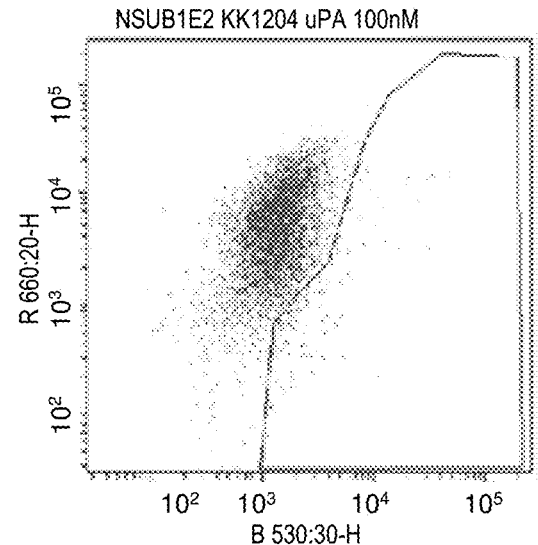
Figure 32C:
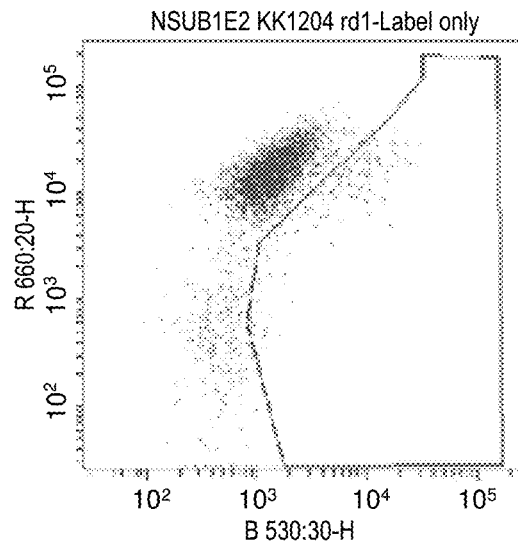
Figure 32D:
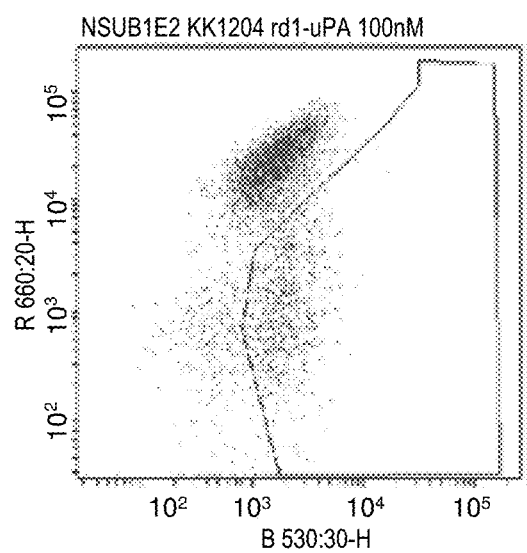

FIGS. 32A, 32B, 32C, and 32D are a series of graphs depicting various populations analyzed by flow cytometry. FIG. 32A depicts an initial spiked sample at 1:100 (ss1204:ssNSUB) with label only. FIG. 32B depicts an initial spiked sample at 1:100 (ss1204:ssNSUB) cleaved with 100 nM uPA then labeled. FIG. 32C depicts a post-sort sample with label only. FIG. 32D depicts a post-sort sample (ss1204:ssNSUB) cleaved with 100 nM uPA, then labeled.

Figure 33:
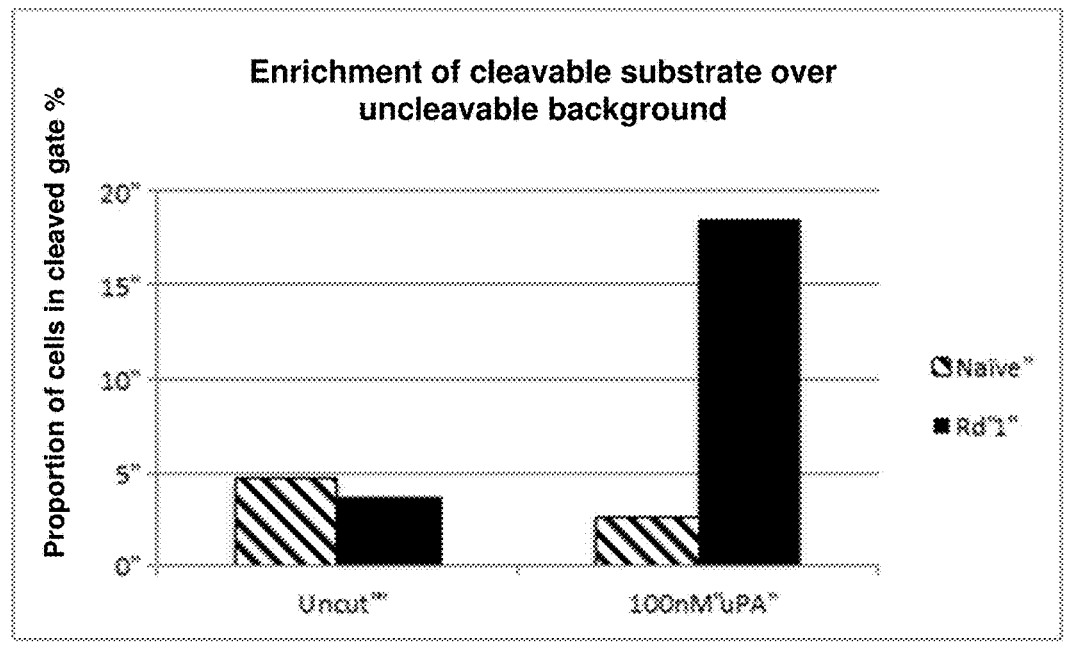

FIG. 33 is a graph depicting the percentage of cells in the P3 gate.

Figure 34:
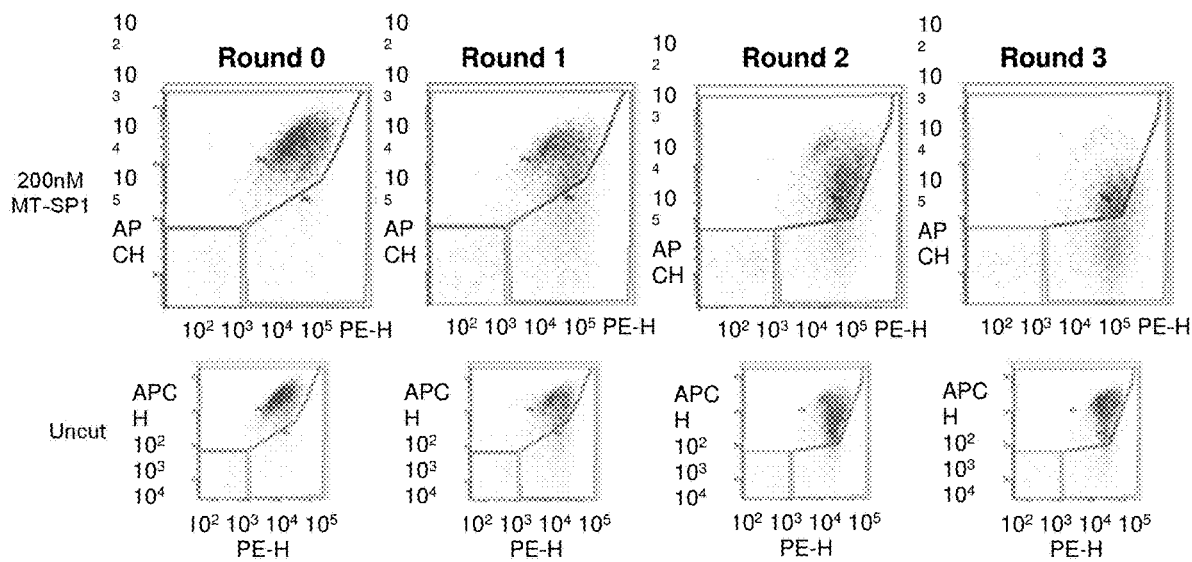

FIG. 34 is a series of graphs depicting the enrichment of MT-SP1 substrates.

Figure 35:
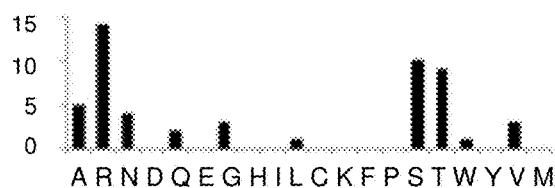
Figure 35:
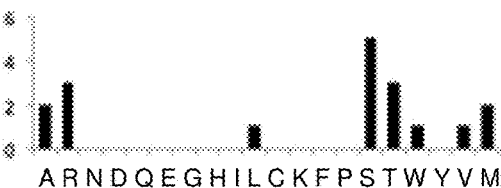
Figure 35:
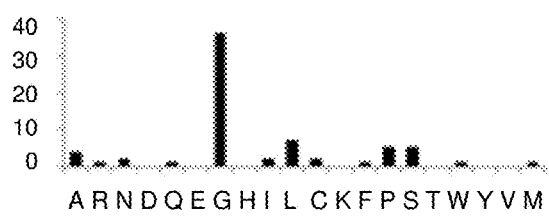
Figure 35:
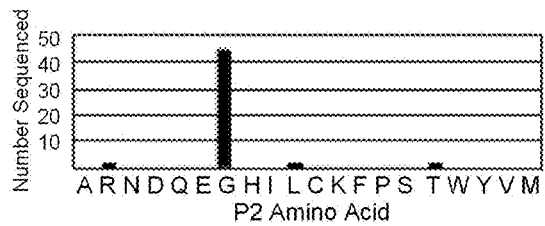
Figure 35:
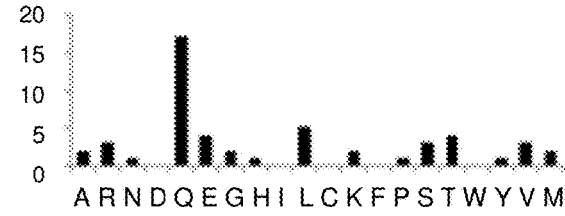
Figure 35:
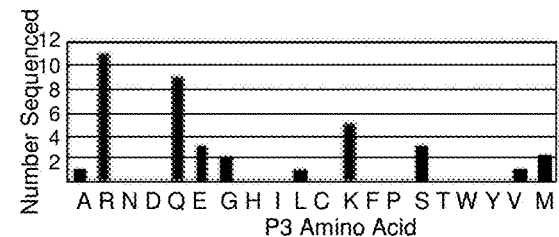
Figure 35:
Figure 35:
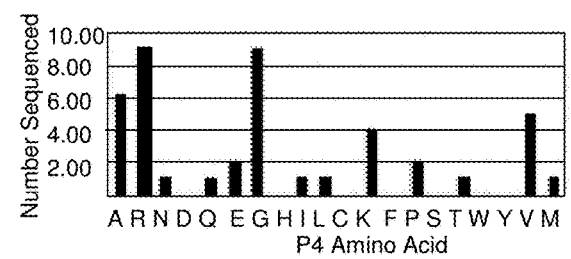

FIG. 35 is a series of graphs depicting positional analysis of MT-SP1 substrates using the display platforms (DPs) of the disclosure versus phage display.

DETAILED DESCRIPTION OF THE INVENTION

The present invention relates to display platforms in which a surface localized polypeptide, referred to herein to as a carrier protein (CP), is efficiently expressed on the outer surface of a replicable biological entity, where the carrier protein, also referred to herein as carrier polypeptide, displays one or more given polypeptide(s) or other molecule(s), a "displayed moiety" (DM) polypeptide to produce a display platform (DP).

The purpose of "cell surface display" systems is to present polypeptides on living cells to extracellular targets of any size and molecular composition. The application of bacterial display technology to a broad range of protein engineering applications, however, has been hindered by the absence of robust, validated display scaffolds. The present invention is based on the discovery of circularly permuted transmembrane bacterial polypeptides with enhanced properties such as increased resistance to protease degradation and improved display of larger polypeptides, for use in bacterial display. Larger polypeptides include not just longer amino acid sequences, but also polypeptides having a larger molecular weight.

As described in the Examples provided herein, semi-rational design and directed evolution were used to create circularly permuted outer membrane protein variants also presenting both the N- and C-termini, but showing significantly enhanced display of a diverse group of peptides, microproteins, and repeat proteins compared to previous display systems using circularly permuted OmpX display polypeptides including those described in PCT Publication No. WO 2005/047461; U.S. Pat. Nos. 7,256,038; 7,612,019;

U.S. Patent Application Publication No. 2010/0113303; PCT Publication No. WO 2007/027935; U.S. Pat. No. 7,666,817; U.S. Patent Application Publication No. 20100173349, each of which is hereby incorporated by reference in its entirety.

In particular, the new circularly permuted transmembrane bacterial protein, referred to herein as "CYTX-CP," has been designed to remove potential protease cleavage sites within the exposed extracellular loops of the native OmpX sequence, within linker sequences separating the epitope tags from the scaffold and within the N- and C-epitope terminal tags. In some embodiments, these potential protease cleavage sites were substituted with a flexible peptide sequence comprised predominantly of glycine and serine residues (i.e., "Gly-Ser linkers"). This approach provides a potential route to enhance the performance of a variety of cell surface display scaffolds in presenting displayed moieties (DM). Thus, the methods described herein can be used to make library screens more efficient and less biased towards peptides that are difficult to display. The CYTX-CPs of the invention include at least the amino acid sequence of SEQ ID NO: 1. In some embodiments, the CYTX-CPs of the invention include at least the amino acid sequence of SEQ ID NO: 56. In some embodiments, the CYTX-CPs of the invention include at least the amino acid sequence of SEQ ID NO: 57.

The disclosure provides a CYTX-CP comprising any circularly permuted bacterial outer membrane protein (Omp) that comprises one or more extracellular loops. In some embodiments, the Omp is OmpX. In some embodiments, the Omp is OmpA. In some embodiments, the Omp is OmpG.

In some embodiments, the polypeptide display platforms (DPs) include (i) one or more carrier polypeptides (CPs) having at least a transmembrane portion and N- and C-termini that are exposed when the CP is displayed on the outer membrane of a replicable biological entity, and (ii) a displayed moiety (DM), such as for example, a polypeptide or other biological molecule. Suitable DMs include, by way of non-limiting example, a substrate sequence (S), e.g., a peptide sequence that is cleaved by one or more proteases; a masking moiety (MM), e.g., a peptide sequence that reduces the ability of an antibody or antibody fragment (AB) to bind a target; an exosite (EX); an allosteric binding site (AS); an antibody or antibody fragment (AB); a receptor (R); a ligand (L); an inhibitor (I); and any combination thereof. In some embodiments, CPs having only one DM have the general structural arrangement from N-terminus to C-terminus as follows: DM-CP or CP-DM.

In some embodiments, the DM is a masking moiety (MM), e.g., a peptide sequence that reduces the ability of an antibody or antibody fragment (AB) to bind a target. In some embodiments, the target is a target selected from those shown below in Table 1.

TABLE 1

| Exemplary Targets | | | | | |
|---|---|---|---|---|---|
| 1-92-LFA-3 | CD117 | ERBB3 | IGF1R | MUC1 | TLR4 |
| Anti-Lewis-Y | CD132 (IL-2RG) | F protein of RSV | IL1B | Mucin-16 | TLR6 |
| Apelin J receptor | CD133 | FAP | IL1R | Na/K ATPase | TLR7 |
| APRIL | CD137 | FGF-2 | IL2 | Neutrophil elastase | TLR8 |
| BAFF | CD138 | FGF8 | IL11 | NGF | TLR9 |
| C5 complement | CD172A | FGFR1 | IL12 | Nicastrin | TNFalpha |
| C-242 | CEACAM5 (CEA) | FGFR2 | IL12p40 | Notch Receptors | TNFR |
| CD2 | CEACAM6 (NCA-90) | FGFR3 | IL-12R, IL-12Rbeta1 | Notch 1 | TRAIL-R1 |
| CD3 | CLAUDIN-3 | FGFR4 | IL13 | Notch 2 | TRAIL-R2 |
| CD9 | CLAUDIN-4 | Folate receptor | IL13R | Notch 3 | Transferrin |
| CD11a | cMet | G-CSF | IL15 | Notch 4 | Transferrin receptor |
| CD19 | Collagen | G-CSFR | IL17 | NOV | TRK-A |
| CD20 | Cripto | GLUT1 | IL18 | OSM-R | TRK-B |
| CD22 | CSFR | GLUT4 | IL21 | PAR2 | uPAR |
| CD25 | CSFR-1 | GM-CSF | IL23 | PDGF-AA | VCAM-1 |
| CD28 | CTLA-4 | GM-CSFR | IL23R | PDGF-BB | VEGF |
| CD30 | CTGF | GP IIb/IIIa receptors | IL27/IL27R (wsx1) | PDGFRalpha | VEGF-A |
| CD33 | CXCL10 | Gp130 | IL29 | PDGFRbeta | VEGF-B |
| CD40 | CXCL13 | GPIIB/IIIA | IL-31R | PD-1 | VEGF-C |
| CD40L | CXCR1 | GPNMB | IL31/IL31R | PD-L1, PD-L2 | VEGF-D |
| CD41 | CXCR2 | HER2/neu | IL2R | Phosphatidyl-serine | VEGFR1 |
| CD44 | CXCR4 | HGF | IL4 | P1GF | VEGFR2 |
| CD47 | CYR61 | hGH | IL4R | PSCA | VEGFR3 |
| CD52 | DL44 | Hyaluronidase | IL6, IL6R | PSMA | WISP-1 |
| CD56 | DLL4 | IFNalpha | Insulin Receptor | RAAG12 | WISP-2 |
| CD64 | DPP-4 | IFNbeta | Jagged Ligands | RAGE | WISP-3 |
| CD70 | EGFR | IFNgamma | Jagged 1 | SLC44A4 | Alpha-4 integrin |
| CD80 | Endothelin B receptor (ETBR) | IgE | Jagged 2 | Sphingosine 1 Phosphate | Alpha-V integrin |

TABLE 1-continued

Exemplary Targets

| | | | | | |
|---|---|---|---|---|---|
| CD86 | EpCAM | IgE Receptor (FceRI) | LIF-R | TGFbeta | alpha4beta 1 integrin |
| CD95 | EPHA2 | IGF | MRP4 | TLR2 | alpha4beta 7 integrin |

In some embodiments, the DM is a substrate sequence (S), e.g., a peptide sequence that is cleaved by one or more proteases. In some embodiments, the protease is a protease selected from those shown in Table 2.

TABLE 2

Exemplary Proteases

| | | |
|---|---|---|
| ADAMS, ADAMTS, e.g. | Cathepsin S | MMP-15 |
| ADAM8 | Cathepsin V/L2 | MMP-19 |
| ADAM9 | Cathepsin X/Z/P | MMP-23 |
| ADAM10 | | MMP-24 |
| ADAM12 | | MMP-26 |
| ADAM15 | Cysteine proteinases, e.g., | MMP-27 |
| ADAM17/TACE | Cruzipain | |
| ADAMTS1 | Legumain | |
| ADAMTS4 | | Serine proteases, e.g., |
| ADAMTS5 | | activated protein C |
| | | Cathepsin A |
| | KLKs, e.g., | Cathepsin G |
| | KLK4 | Chymase |
| Aspartate proteases, e.g., | KLK5 | coagulation factor proteases (e.g., FVIIa, FIXa, FXa, FXIa, FXIIa) |
| | | Elastase |
| BACE | KLK6 | Granzyme B |
| | KLK7 | Guanidinobenzoatase |
| | KLK8 | Human Neutrophil Elastase |
| Aspartic cathepsins, e.g., | KLK10 | NS3/4A |
| Cathepsin D | KLK11 | Plasmin |
| Cathepsin E | KLK13 | PSA |
| | KLK14 | tPA |
| | | Thrombin |
| | | Tryptase |
| Caspases, e.g., | | uPA |
| Caspase 1 | Metallo proteinases, e.g., | |
| Caspase 2 | Meprin | |
| Caspase 3 | Neprilysin | Type II Transmembrane |
| Caspase 4 | PSMA | Serine Proteases (TTSPs), e.g., |
| Caspase 5 | BMP-1 | DESC1 |
| Caspase 6 | | DPP-4 |
| Caspase 7 | MMPs, e.g., | FAP |
| Caspase 8 | MMP-1 | Hepsin |
| Caspase 9 | MMP-2 | Matriptase-2 |
| Caspase 10 | MMP-3 | MT-SP1/Matriptase |
| Caspase 14 | MMP-7 | TMPRSS2 |
| | MMP-8 | TMPRSS3 |
| | MMP-9 | TMPRSS4 |
| Cysteine cathepsins, e.g., | MMP-10 | |
| Cathepsin B | MMP-11 | |
| Cathepsin C | MMP-12 | |
| Cathepsin K | MMP-13 | |
| Cathepsin L | MMP-14 | |

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a peptide" includes a mixture of two or more such peptides, and the like.

As used herein, a "replicable biological entity" refers to self-replicating biological cells, including bacterial, yeast, protozoal, and mammalian cells, and various viruses capable of infecting these cells known in the art, and the like.

The term "CPX" as used herein refers to a circularly permuted variant of a bacterial outer membrane protein OmpX (see U.S. Pat. No. 7,256,038, which is herein incorporated by reference in its entirety). The CPX protein consists of the native OmpX signal sequence, which is cleaved after translocation; a sequence with an embedded SfiI restriction site (GQSGQ) (SEQ ID NO: 7) after which peptides may be inserted; a flexible linking sequence (GGQSGQ) (SEQ ID NO 32); amino acids S54-5 F148 of the mature OmpX; a GGSG linker joining the native C- and N-termini of OmpX; and amino acids A1-S53 of the mature OmpX. CPX can be used as a protein scaffold for bacterial display of peptides and proteins at the surface of a bacterial cell. Furthermore, for purposes of the present invention, the term "eCPX" refers to a protein that includes modifications, such as deletions, additions and substitutions, for example, replacement of the linker joining the native N- and C-termini of OmpX, substitutions at positions 165 and 166 (numbered with reference to the sequence of native OmpX from *Escherichia coli*, SEQ ID NO: 1 in PCT Publication No. WO 2009/014726), incorporation of alternate restriction sites after which polypeptides or peptides may be inserted, or the addition of linkers between the N-terminus or C-terminus of eCPX and a DM, so long as the protein maintains biological activity (i.e., ability to efficiently display polypeptides) (see e.g., PCT Publication No. WO 2009/014726). These modifications may be deliberate, as through site-directed mutagenesis, or may be accidental, such as through mutations of hosts that produce the proteins or errors due to PCR amplification.

As used herein, the term "CYTX-CP" refers to a circularly permuted variant of an OmpX protein having one or more of the following mutations: (i) potential protease cleavage sites on the exposed portion of the OmpX protein (i.e., outside the outer membrane) have been replaced, for example, with a glycine-serine based flexible peptide sequence; (ii) one or more epitope tags has been modified to minimize tag proteolysis; (iii) modifications in loop 2 of the OmpX protein; and/or (iv) modifications in loop 3 of the OmpX protein. For example, modification of loop 2 and/or loop 3 can include replacing a portion of the loop with a shorter, non-cleavable amino acid sequence. Modification of loop 2 and/or loop 3 can include replacing existing potential cleavage sites within the loop with flexible, glycine-serine based amino acid sequences that are generally non-cleavable by proteases. In some embodiments, a CYTX-CP is derived from an Omp other than OmpX that has at least one extracellular loop. Examples include, but are not limited to, circularly permuted OmpA and OmpG proteins.

An advantage of using CP, e.g., CYTX-CP, in bacterial display is that both its N- and C-termini are exterior to the cell, which allows polypeptides to be displayed from either terminus or from both termini simultaneously. The term CP includes circularly permuted variants of OmpX from any strain of bacteria, such as *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis*, or *Klebsiella pneumoniae*. The GenBank database contains complete sequences for OmpX proteins from a variety of bacterial isolates, which could be used to produce CP proteins of the invention. The GenBank database also contains complete sequences for other Omp proteins from a variety of bacterial isolates, which could be used to produce CP proteins of the invention.

As used herein, the terms "protein", "polypeptide" and "peptide" are used interchangeably to refer to two or more amino acids linked together.

The terms "polypeptide", "peptide", "protein", and "amino acid sequence" as used herein generally refer to any compound comprising naturally occurring or synthetic amino acid polymers or amino acid-like molecules including but not limited to compounds comprising amino and/or imino molecules. No particular size is implied by use of the term "peptide", "oligopeptide", "polypeptide", or "protein" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, multiple antigenic peptide (MAP) forms, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and 5,977,301; Nguyen et al. (2000) *Chem Biol.* 7(7):463-473; and Simon et al. (1992) *Proc. Natl. Acad. Sci. USA* 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length.

Typically, polypeptides useful in this invention can have a maximum length suitable for the intended application. In some embodiments, the polypeptide is between about 3 and 300 amino acid residues in length. In some embodiments, the polypeptide is more than 300 amino acid residues in length. In some embodiments, the polypeptide is more than 350 amino acid residues in length. In some embodiments, the polypeptide is more than 400 amino acid residues in length. In some embodiments, the polypeptide is more than 450 amino acid residues in length. In some embodiments, the DM is a polypeptide of no more than 8 amino acids, of no more than 10 amino acids, of no more than 15 amino acids, or of no more than 40 amino acids. Generally, one skilled in art can easily select the maximum length in view of the teachings herein. Further, peptides as described herein, for example synthetic peptides, may include additional molecules such as labels or other chemical moieties (e.g., streptavidin conjugated to phycoerythrin, Alexa dye conjugated to anti-T7 tag, Alexa dye conjugated to an anti-EE antibody, Alexa dye conjugated to an anti-His antibody). Such moieties may further enhance interaction of the peptides with a ligand and/or further detection of polypeptide display.

Thus, reference to peptides also includes derivatives of the amino acid sequences of the invention including one or more non-naturally occurring amino acid. A first polypeptide is "derived from" a second polypeptide if it is (i) encoded by a first polynucleotide derived from a second polynucleotide encoding the second polypeptide, or (ii) displays sequence identity to the second polypeptide as described herein. Sequence (or percent) identity can be determined as described below. In some embodiments, derivatives exhibit at least about 50% percent identity, in some embodiments, at least about 80%, and in some embodiments, between about 85% and 99% (or any value therebetween) to the sequence from which they were derived. Such derivatives can include post-expression modifications of the polypeptide, for example, glycosylation, acetylation, phosphorylation, and the like.

Amino acid derivatives can also include modifications to the native sequence, such as deletions, additions and substitutions (generally conservative in nature), so long as the polypeptide maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: increasing efficiency of bacterial display, level of expression, or stability of the polypeptide. Polypeptides described herein can be made recombinantly, synthetically, or in tissue culture.

Polypeptides presented according to the present invention (1) alleviate disruption of the energetic structural stability of the carrier polypeptide thus allowing presentation of suitable number of copies of the DM exhibiting acceptable viability, (2) are capable of interacting physically with arbitrary compositions of matter (biological or non-biological), and (3) exhibit a biological activity (e.g., affinity, specificity, catalysis, assembly etc.) substantially similar to the corresponding free polypeptide in solution. In other words, the displayed polypeptide interacts with or binds a given target molecule in a manner that is substantially similar to that when the polypeptide is in its native environment and not attached to the biological entity.

As used herein, a "fusion protein" refers to the expression product of two or more nucleic acid molecules that are not natively expressed together as one expression product. For example, a native protein X comprising subunit A and subunit B, which are not natively expressed together as one expression product, is not a fusion protein. However, recombinant DNA methods known in the art may be used to express subunits A and B together as one expression product to yield a fusion protein comprising subunit A fused to subunit B. A fusion protein may comprise amino acid sequences that are heterologous, e.g., not of the same origin, not of the same protein family, not functionally similar, and the like.

The polypeptides expressed and displayed according to the present invention may be large polypeptides yet still retain the ability to bind or interact with given ligands in a manner similar to the native polypeptide or the polypeptide in solution. As provided herein, the expression vectors of the present invention use utilize a low copy origin of replication and a regulatable promoter in order to minimize the metabolic burden of the biological entity and the clonal representation of the polypeptide library is not affected by growth competition during library propagation. The expression vectors of the present invention utilize an antibacterial resistance gene to a bacteriocidal antibiotic that prevents plasmid loss and outgrowth of cells resistant to the antibiotic. Additionally, the expression vectors of the present invention lack a dual system, such as 13-lactamase, which results in a smaller expression vector that imposes a smaller burden on cell growth and improves library screening. The expression vectors of the present invention also utilize a restriction site that allows digestion by a particular enzyme to generate overhangs that cannot react with incorrect DNA substrates, e.g., such sites enable directional cloning. Examples of such restriction sites include by are not limited to EagI, NotI and SfiI.

As used herein, a "ligand" refers to a molecule(s) that binds to another molecule(s), e.g., an antigen binding to an antibody, a hormone or neurotransmitter binding to a receptor, or a substrate or allosteric effector binding to an enzyme and include natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

As used herein, a "receptor" refers to a molecular structure within a cell or on the surface characterized by (1) selective binding of a specific substance and (2) a specific physiologic effect that accompanies the binding, e.g., membrane receptors for peptide hormones, neurotransmitters, antigens, complement fragments, and immunoglobulins and nuclear receptors for steroid hormones and include natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

As used herein, "specifically binds" refers to the character of a receptor that recognizes and interacts with a ligand but does not substantially recognize and interact with other molecules in a sample under given conditions.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., a-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carboxylic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

An "isolated" nucleic acid molecule or polypeptide refers to a nucleic acid molecule or polypeptide that is in an environment that is different from its native environment in which the nucleic acid molecule or polypeptide naturally occurs. Isolated nucleic acid molecules or polypeptides includes those having nucleotides or amino acids flanking at least one end that is not native to the given nucleic acid molecule or polypeptide. For example, a promoter P for a protein X is inserted at the 5' end of a protein Y that does not natively have P at its 5' end. Protein Y is thus considered to be "isolated".

The term "polynucleotide", as known in the art, generally refers to a nucleic acid molecule. A "polynucleotide" can include both double- and single-stranded sequences and refers to, but is not limited to, prokaryotic sequences, eukaryotic mRNA, cDNA from viral, prokaryotic or eukaryotic mRNA, genomic RNA and DNA sequences from viral (e.g., RNA and DNA viruses and retroviruses), prokaryotic DNA or eukaryotic (e.g., mammalian) DNA, and especially synthetic DNA sequences. The term also captures sequences that include any of the known base analogs of DNA and RNA, and includes modifications such as deletions, additions and substitutions (generally conservative in nature), to the native sequence. These modifications may be deliberate, as through site-directed mutagenesis, or may be accidental, such as through mutations of hosts including polynucleotides encoding CP or a variant thereof. Modifications of polynucleotides may have any number of effects including, for example, facilitating expression/bacterial display of the polypeptide product at the surface of a host cell.

A polynucleotide can encode a biologically active (e.g., CP or a variant thereof) protein or polypeptide. Depending on the nature of the polypeptide encoded by the polynucleotide, a polynucleotide can include as little as 10 nucleotides, e.g., where the polynucleotide encodes a linker, tag or label, or an antigen or epitope for bacterial display. Typically, the polynucleotide encodes peptides of at least 6, 7, 8, 9, 10, 11, 12, 13, 14, 15, 16, 17, 18, 19, 20, 21, 22, 23, 24, 25, 30 or even more amino acids. The disclosure provides polynucleotides that encode polypeptides of at least 40, 50, 75, 100, 125, 150, 175, 200, 225, 250, 275, 300, 325, 350, 375, 400, 425, 450, or even more amino acids. In some embodiments, the DM is a polypeptide of no more than 8 amino acids, of no more than 10 amino acids, of no more than 15 amino acids, or of no more than 40 amino acids.

"Recombinant" as used herein to describe a nucleic acid molecule means a polynucleotide of genomic, cDNA, viral, semisynthetic, or synthetic origin that, by virtue of its origin or manipulation is not associated with all or a portion of the polynucleotide with which it is associated in nature. The term "recombinant" as used with respect to a protein, polypeptide, or peptide means a polypeptide produced by expression of a recombinant polynucleotide. In general, the gene of interest is cloned and then expressed in transformed organisms, as described further below. The host organism expresses the foreign gene to produce the protein under expression conditions.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A transcription termination sequence may be located 3' to the coding sequence. Typical "control elements," include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

The term "derived from" is used herein to identify the original source of a molecule but is not meant to limit the method by which the molecule is made, which can be, for example, by chemical synthesis or recombinant means.

The terms "variant," "analog" and "mutein" refer to biologically active derivatives of the reference molecule that retain desired activity (e.g., efficient polypeptide display) as described herein. In general, the terms "variant" and "analog" refer to compounds having a native polypeptide sequence and structure with one or more amino acid additions, substitutions and/or deletions (e.g., in the linker joining native N- and C-termini or at positions 165 and 166), relative to the native molecule, so long as the modifications do not destroy biological activity and that are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). In some embodiments, the analog or mutein has at least the same polypeptide display efficiency as the native OmpX molecule. Methods for making polypeptide analogs and muteins are known in the art and are described further below.

Analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods (see e.g., Proc. Natl. Acad. Sci. U.S.A. 78:3824-3828(1981)) and Kyte-Doolittle plots (see e.g., J. Mol. Biol. 157:105-132(1982)), well known in the art.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, so long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the peptide. Active fragments of a particular protein or peptide will generally include at least about 5-10 contiguous amino acid residues of the full-length molecule, in some embodiments, at least about 15-25 contiguous amino acid residues of the full-length molecule, and in some embodiments, at least about 20-50 or more contiguous amino acid residues of the full-length molecule, or any integer between 5 amino acids and the full-length sequence, provided that the fragment in question retains biological activity, such as ligand-binding activity, as defined herein.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, in some embodiments, 80%-85%, and in some embodiments, 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50%, in some embodiments, at least about 75%, in some embodiments, at least about 80%-85%, in some embodiments, at least about 90%, and in some embodiments, at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, DC, which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Expression Systems Using Protease-Resistant Circularly Permuted OmpX Variants

As provided herein, the carrier polypeptides (CPs), display platforms (DPs), nucleic acids, expression vectors and libraries of the present invention incorporate (1) the use of a regulatable expression vector that allows on-off control of carrier polypeptide production, (2) efficient restriction sites immediately adjacent to the randomized site to facilitate high-efficiency cloning, (3) random polypeptides inserted into non-conserved sites of carrier polypeptide extracellular loops that efficiently presents a DM to a given ligand, (4) time and temperature-controlled induction periods to obtain optimal display levels that result in higher quality results, (5) the use of a bacterial strain having a high plasmid transformation efficiency for transformation, (6) the use of optimized library construction protocols to construct the largest libraries, (7) the use of multiple-plasmid transformation to yield a larger number of unique DMs for a given number of host cells, (8) the use of cell concentration to enable complete processing of larger numbers of sequences (e.g., $10^{11}$-$10^{13}$), or (9) a combination thereof.

The systems provided herein provide a number of advantages over previous expression systems. For example, the systems provided herein are more resistant to protease degradation as compared to prior expression systems, including, for example, those described in PCT Publication No. WO 2005/047461, WO 2007/027935 and WO 2009/014726, each of which is hereby incorporated by reference in their entirety. In addition, the systems provided herein allow for the stable display of a larger number of polypeptides and other amino acid sequences.

In the systems provided herein, a circularly permuted outer membrane protein X (OmpX) variant was used as the template for the new display scaffold. The modifications made in the display and selection scaffold results in a protein that is at least 5% smaller, for example, at least 10% smaller, at least 15%, at least 20% or at least 25% smaller, and shares less than 100% identity with the OmpX proteins described, for example, in PCT Publication No. WO 2005/047461, WO 2007/027935 and WO 2009/014726, e.g., less than 95%, less than 90%, less than 85%, less than 80% identity with the OmpX proteins described, for example, in PCT Publication No. WO 2005/047461, WO 2007/027935 and WO 2009/014726. The systems provided herein demonstrate improved cell surface display allowing for more extensive libraries and improved quality of screening. Previous systems were susceptible to degradation by a variety of proteases and comprised smaller DMs.

The systems provided herein overcome these problems with previous systems. The systems provided herein allow for unbiased substrate screening of tissue extracts/biological fluids (positive and negative selections), the screening process of a wide panel of purified proteases (negative selections) and the screening of larger polypeptide domain libraries.

The systems provided herein were generated by identifying potential protease cleavage sites within the exposed extracellular loops of the published OmpX sequence (see e.g., Rice et al., "Bacterial display using circularly permuted outer membrane protein OmpX yields high affinity peptide ligands." Protein Sci. 2006 15(4):825-36; see also PCT Publication No. WO 2005/047461; PCT Publication No. WO 2009/014726; U.S. Pat. Nos. 7,256,038; 7,612,019; U.S. Patent Application Publication No. 2010/0113303; PCT Publication No. WO 2007/027935; U.S. Pat. No. 7,666,817; U.S. Patent Application Publication No. 20100173349, each of which is hereby incorporated by reference in its entirety), within linker sequences separating the epitope tags from the scaffold, within the N- and C-epitope terminal tags, and within other extracellular regions of the platform. Nucleic acid sequences encoding for OmpX-variant derived sequences were designed to eliminate potential protease cleavage sites by substituting flexible, turned linkers comprised predominantly of glycine and serine residues (i.e., "Gly-Ser linkers"). The nucleic acid sequences were made by PCR and standard molecule biology techniques and transformed into bacteria.

A CP polypeptide or protein molecule, as defined above, is a substrate-resistant circularly permuted variant of a bacterial outer membrane protein derived from bacteria, including, but not limited to *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis,* or *Klebsiella pneumoniae*. The molecule need not be physically derived from the particular isolate in question, but may be synthetically or recombinantly produced.

The amino acid sequences of a number of OmpX proteins are known. Representative sequences from bacteria are listed in the National Center for Biotechnology Information (NCBI) database. See, for example, NCBI entries: *Escherichia coli* OmpX, Accession No. P0A917; *Serratia marcescens* OmpX, Accession No. AAS78634; *Salmonella enterica* subsp. *enterica* serovar *Choleraesuis* str. SC-B67 ail and ompX homolog, Accession No. YP_219185; *Salmonella enterica* subsp. *enterica* serovar *Typhi* OmpX precursor, Accession No. CAD05280; *Enterobacter cloacae* OmpX, Accession No. P25253; *Yersinia pseudotuberculosis* IP 32953 OmpX, Accession No. YP_071052; *Yersinia pseudotuberculosis* IP 32953 OmpX, Accession No. YP_071052; *Shigella flexneri* OmpX precursor, Accession No. P0A920; *Escherichia coli* OmpX precursor, Accession No. P0A918; *Escherichia coli* OmpX precursor, Accession No. P0A919; *Salmonella enterica* subsp. *enterica* serovar *Typhi* Ty2 OmpX, Accession No. NP_805818; *Shigella flexneri* 2a str. 301 OmpX, Accession No. NP_706692; *Yersinia pestis* KIM OmpX, Accession No. NP_669000; *Salmonella enterica* subsp. *enterica* serovar *Typhi* str. CT18 OmpX, Accession No. NP_455368; *Salmonella typhimurium* LT2 OmpX, Accession No. NP_459810; *Escherichia coli* 0157:H7 str. *Sakai* OmpX, Accession No. NP_308919; *Escherichia coli* 0157:H7 EDL933 OmpX, Accession No. NP_286578; *Shigella flexneri* 2a str. 2457T OmpX, Accession No. NP_836469; *Salmonella enterica* subsp. *enterica* serovar *Choleraesuis* str. SC-B67 OmpX, Accession No. YP_215816; *Yersinia pestis* C092 OmpX, Accession No. NP_406040; *Yersinia pestis* biovar *Microtus* str. 91001 OmpX, Accession No. NP_993650; *Escherichia coli* CFT073 OmpX, Accession No. NP_752830; *Salmonella enterica* subsp. *enterica* serovar *Paratyphi* A str. ATCC 9150 OmpX, Accession No. YP_151143; *Erwinia carotovora* subsp. *atroseptica* SCRI1043 OmpX, Accession No. YP_050855; *Erwinia carotovora* subsp. *atroseptica* SCRI1043 OmpX, Accession No. YP_050855; *Escherichia coli* APEC 01 OmpX precursor, Accession No. ABJ00194; *Shigella boydii* Sb227 OmpX, Accession No. YP 407207; *Escherichia coli* UTI89 OmpX, Accession No. ABE06304; *Yersinia pestis* KIM OmpX, Accession No. NP_669349; *Yersinia pestis* KIM OmpX, Accession No. NP_668646; *Escherichia coli* 0157:H7 EDL933 OmpX, Accession No. AAG55186; *Shigella flexneri* 2a str. 2457T OmpX, Accession No. 15 AAP16275; *Escherichia coli* APEC 01 OmpX precursor, Accession No. YP_851908; *Escherichia coli* UTI89 OmpX, Accession No. YP_539835; and *Shigella sonnei* Ss046 OmpX, Accession No. YP_309776; all of which sequences (as entered by the date of filing of this application) are herein incorporated by reference.

The term "displayed" polypeptide, also referred to herein as a display moiety, a displayed moiety or DM, refers to a polypeptide or other molecule linked to the N- or C-terminus of a carrier polypeptide, e.g., CYTX-CP, or a variant thereof for display at the surface of a bacterial cell to produce a display platform (DP). In some embodiments, a DM is capable of interacting physically with arbitrary compositions of matter (biological or non-biological), and exhibits a biological activity (e.g., affinity, specificity, catalysis, assembly etc.) substantially similar to the corresponding free polypeptide in solution. In other words, the DM interacts with or binds a given target molecule in a manner that is substantially similar to that when the polypeptide is in its native environment and not attached to the CP, e.g., CYTX-CP, or a variant thereof.

Bacterial display can be used in combination with magnetic-activated cell sorting (MACS) and/or fluorescence-activated cell sorting (FACS) and/or other affinity-based selection techniques for quantitative library analysis and screening for CYTX-DPs that display polypeptides or peptides efficiently (see, e.g., Rice et al. (2006) Protein Sci.

15:825-836; U.S. Patent Application Publication No. 2005/0196406; Daugherty et al. (2000) J. Immuunol. Methods 243(1-2):211-2716; Georgiou (2000) Adv. Protein Chem. 55:293-315; Daugherty et al. (2000) Proc. Natl. Acad. Sci. U.S.A. 97(5):20293418; Olsen et al. (2003) Methods Mol. Biol. 230:329-342; and Boder et al. (2000) Proc. Natl. Acad. Sci. U.S.A. 97(20):10701-10705; herein incorporated by reference in their entireties). Analysis of the display efficiency of a CYTX-DP is facilitated by the use of a display system comprising a label (e.g., phycoerythrin, Alexa dye, fluorescein, YPet, CyPet) that allows detection of the displayed polypeptide at the bacterial cell surface.

A CYTX-DP can display a single DM on either the N-terminus or the C-terminus of the DP. Alternatively, a CYTX-DP can display two DMs simultaneously one on each of the N- and C-termini of the DP. In one embodiment, a CYTX-DP can display at least two DMs simultaneously, at least one on either or both of the N- and C-termini of the DP. In some embodiments, a DM is capable of interacting physically with arbitrary compositions of matter (biological or non-biological), and exhibits a biological activity (e.g., affinity, specificity, catalysis, assembly etc.) substantially similar to the corresponding free polypeptide in solution. In other words, the displayed DM interacts with or binds a given target molecule in a manner that is substantially similar to that when the polypeptide is in its native environment and not attached to the CYTX-CP or a variant thereof.

Biterminal display has numerous advantages, including the ability to quantify the amount of the CYTX-DP displayed on the cell surface and to screen libraries on both termini simultaneously. For this purpose, a CYTX-DP can include one or more DMs and one or more tags (T) in order to allow detection of surface display. The quantification of the display level during library screening by labeling of a DP allows for polypeptides with a high affinity but low display level to be differentiated from polypeptides with a high display level but moderate affinity. Moreover, biterminal display allows for the possibility of creating peptide libraries on each terminus where both peptides can bind to separate regions of the same protein target, causing increased binding affinity and specificity through avidity.

Additionally, linkers may be inserted between a DM of interest and either the N- or C-terminus of the CYTX-DP to which it is connected in order to avoid steric hindrance between simultaneously displayed DMs and/or their binding partners. For example, a long flexible linker comprising multiple repeats of the sequence GGGS (SEQ ID NO: 33) (e.g., $(GGGS)_4$ (SEQ ID NO: 34), $(GGGS)_5$ (SEQ ID NO: 35), or $(GGGS)_6$ (SEQ ID NO: 36)) can be used to increase the accessibility of proteins to ligands and to avoid steric hindrance when using biterminal display.

Polynucleotides encoding CYTX-DPs of the present invention can be produced in any number of ways, all of which are well known in the art.

In one embodiment, the polynucleotides are generated using recombinant techniques, well known in the art. One of skill in the art could readily determining nucleotide sequences that encode the desired CYTX-DPs using standard methodology and the teachings herein.

Oligonucleotide probes can be devised based on the known sequences of OmpX proteins and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired CYTX-DPs. See, e.g., Sambrook et al., supra, for a description of techniques used to obtain and isolate DNA.

The sequences encoding the CYTX-DPs can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) 1 *Biol. Chem.* 259:6311; Stemmer et al. (1995) *Gene* 1 164:49-53.

Recombinant techniques are readily used to clone sequences encoding CYTX-DPs useful in the claimed invention that can then be mutagenized in vitro by the replacement of the appropriate base pair(s) to result in the codon for the desired amino acid. Such a change can include as little as one base pair, effecting a change in single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression in bacteria or other cell types as disclosed herein. (See Examples). The invention also includes expression constructs for expressing a given DM as an N-terminal fusion protein, a C-terminal fusion protein, or biterminal fusion protein, i.e., linked or fused directly to the CYTX-CP present on the external surface of a bacterial cell. Display and expression of a DM as an N-terminal or C-terminal or biterminal fusion with a CYTX-DP is accomplished by topological permutation of an OmpX protein as described in U.S. patent application Ser. No. 10/920,244, now issued as U.S. Pat. No. 7,256,038, which is herein incorporated by reference. Sequence rearrangement of an OmpX protein can be accomplished using overlap extension PCR methods known in the art in order to create either an N-terminal or C-terminal fusion construct, or alternatively, a biterminal fusion construct. See Ho, et al. (1989) Gene 77(1):51-59, which is herein incorporated by reference. As will be apparent from the teachings herein, a wide variety of vectors encoding CYTX-DPs coupled to one or more DMs can be generated by creating expression constructs that operably link, in various combinations, polynucleotides encoding CYTX-DPs and DMs.

Numerous cloning vectors are known to those of skill in the art, and the selection of an appropriate cloning vector is a matter of choice. Examples of recombinant DNA vectors for cloning include pBAD33, pB30D, pBR322, pACYC177, pKT230, pGV1106, pLAFR1, pME290, pHV14, pBD9, pll61, and pUC6. See, generally, *DNA Cloning: Vols. I & II*, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired CYTX-DP and DM(s) is transcribed into RNA in the host cell transformed by a vector containing this expression construction. The coding sequence may contain a naturally occurring OmpX signal peptide sequence or a heterologous signal sequence (e.g., from another outer membrane protein such as OmpA, OmpT, OmpC, OmpF, OmpN, LamB, FepA, FecA, or the like) to promote expression of the CYTX-DP at the surface of a bacterial host cell.

Other regulatory sequences may also be desirable that allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound (e.g., a regulatable promoter for controlled transcription).

In some embodiments, a vector comprising the regulatable promoter araBAD is used to control transcription. Expression and display of the polypeptide is then accomplished by induction of protein expression by contacting with arabinose, in some embodiments, for about 10 to about 60 minutes, and in some embodiments, for about 10 to about 20 minutes at 25° C. Controlling expression and display minimizes potential avidity effects that can result from excessive surface concentration of the displayed peptide.

Expression vectors of the present invention may also utilize a low copy origin of replication (e.g., p15A) in order to minimize the metabolic burden on the bacterial host cell such that the clonal representation of the polypeptide library is not affected by growth competition during library propagation. Additionally, expression vectors of the present invention may include a selectable marker such as an antibacterial resistance gene to a bacteriocidal antibiotic (e.g., chloramphenicol acetyltransferase, beta lactamase, or the like).

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al. supra.

The expression vector is then used to transform an appropriate bacterial host cell. A number of bacterial hosts are known in the art, including but not limited to, *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis*, or *Klebsiella pneumoniae*, which will find use with the present expression constructs.

In some embodiments, a bacterial strain is chosen that is deficient in proteolytic machinery in order to prevent protein degradation See Meerman, H. J., Nature Biotechnol. 12(11): 1107-1110, which is herein incorporated by reference. In some embodiments, a bacterial strain that makes truncated or otherwise modified lipopolysaccharides on its surface may be used to minimize steric effects upon binding to large biomolecules including proteins, viruses, cells, and the like. In some embodiments, the bacterial host has a genotype that aids the expression vector in regulating more tightly the production of the polypeptide to be displayed. The bacterial host may be modified using methods known in the art, including random mutagenesis, DNA shuffling, genome shuffling, gene addition libraries, and the like. As exemplified herein, *Escherichia coli* strain, MC1061 is a suitable bacterial host for display of DMs using CYTX-DPs of the invention. The MC1061 strain exhibits (1) high transformation efficiency of greater than about $5\times10^9$ per microgram of DNA, (2) a short doubling time, i.e., 40 minutes or less, during exponential growth phase, (3) high level display of the given polypeptide, and (4) effective maintenance of the expression ON and OFF states. Additional bacterial hosts include, but are not limited to, *E. coli* strains DH-10β, *E. coli* C41(DE3), *E. coli* C43(DE3), and *E. coli* TG1 cells.

In some embodiments, the expression vectors and libraries of the present invention incorporate (1) the use of a regulatable expression vector that allows on-off control of the production of the CYTX-CP or variant thereof, (2) efficient restriction sites immediately adjacent to a randomized site for insertion of cloned DNA encoding a random DM fused to the N-terminus, C-terminus or both termini of the CYTX-DP to facilitate library construction, (3) time and temperature-controlled induction periods to obtain optimal display levels that result in higher quality results, (4) the use of a bacterial strain having a high plasmid transformation efficiency for transformation, (5) the use of optimized library construction protocols to construct large libraries, (6) the use of multiple-plasmid transformation to yield a larger number of unique DMs for a given number of host cells, (7) the use of cell concentration to enable complete processing of larger numbers of sequences (e.g., $10^{11}$, $10^{12}$, $10^{13}$, or a larger number depending on sorting capability), or (8) any combination thereof.

In some embodiments of the present invention, a DNA library is constructed containing greater than about $10^8$ sequences, and in some embodiments, more than about $10^{10}$ unique sequence members, using methods known in the art. This library size is used since library size has been shown to correlate with the quality (affinity and specificity) of the selected sequences. See Griffiths, A. D. and D. S. Tawfik (2000) Curr. Opin. Biotechnol. 11(4):338-53, which is herein incorporated by reference.

In some embodiments, a polypeptide library may be prepared by introduction and expression of nucleic acid sequences that encode polypeptides having about 1 to about 1000, in some embodiments, about 2 to about 30 amino acids in length. In some embodiments, the polypeptide is greater than 25 amino acids, greater than 50 amino acids, greater than 75 amino acids, greater than 100 amino acids, greater than 125 amino acids, greater than 150 amino acids, greater than 175 amino acids, greater than 200 amino acids, greater than 225 amino acids, greater than 250 amino acids, greater than 275 amino acids, greater than 300 amino acids long, greater than 350 amino acids long, greater than 400 amino acids long, or greater than 450 amino acids long. In some embodiments, the polypeptide is no more than 8 amino acids, of no more than 10 amino acids, of no more than 15 amino acids, of no more than 20 amino acids, of no more than 25 amino acids, of no more than 30 amino acids, of no more than 35 amino acids, or of no more than 40 amino acids. In certain embodiments, high DNA concentrations of more than about 0.1 ug per ul are used during transformation such that the transformed host cell contains one or more independent plasmid molecules. Transformation with multiple plasmids yields a larger number of unique peptides in the same volume of liquid, providing better overall results than when transformation is performed with only one molecule per cell. In some embodiments, a mixture of a plurality of different expression vectors and/or plasmids may be employed, for example, to allow cooperative binding of two different displayed peptides on the same surface, or to present a protein having multiple subunits, and the like.

A desired number of DMs, e.g., polypeptides, may be displayed for different purposes. As exemplified herein, the method of the present invention utilizes an induction period of about 10 minutes to about 16 hours to control total expression levels of the display polypeptide and the mode of the subsequent screen or selection such that the level of expression has no measurable effect upon the cell growth rate. In some embodiments, shorter time periods may be used to reduce avidity effects in order to allow selection of high affinity monovalent interactions. As provided herein, the ability to control display speeds the process and yields higher quality results, e.g., sequences that bind to a target with higher affinity.

In some embodiments, a cell concentration by a factor of about 10 may be used to enable complete processing of the entire pool of diversity in a volume of about 10 to about 100 ml. The library may be expanded by propagation by a factor of more than about 100-fold under conditions that prevent synthesis of the library elements, for example, with glucose to repress araBAD or lac promoters, and aliquots of the library may be prepared to represent a number of clones that is more than about three fold greater than the total number of library members.

For library selection, a subset of the total library, either randomly divided, or chosen for specific properties could be used as a starting point for screening. Either MACS and/or FACS and/or other suitable selection methods known in the art may be used. Alternatively, methods known in the art that enable physical retention of desired clones and dilution or removal of undesired clones may be used. For example, the library may be grown in a chemostat providing continuous growth, diluting out only those cells that do not bind to a capture agent retained in the vessel. Alternatively, hosts may be cultured with medium having ingredients that promote growth of desired clones.

Cell sorting instrumentation is applied as a quantitative library screening tool to isolate the highest affinity clones from a magnetically enriched population. Several different approaches can be applied for quantitative screening. In some embodiments, screening is based on the basis of either equilibrium binding affinity (Equilibrium Screen). In some embodiments, screening is based on dissociation rate constants (Kinetic Screen). In some embodiments, screening is based on competitive advantage (Competition Screening) to select for clones that exhibit superior ligand interaction at increasing concentrations. See Daugherty, P. S., et al. (2000) J. Immunol. Methods 243(1-2):211-227; and Boder, E. T. and K. D. Wittrup (1998) Biotechnology Progress 14(1):55-62, which are herein incorporated by reference in their entireties. For equilibrium screening, cell populations are labeled with limiting concentrations of the target proteins, and all cells exhibiting fluorescence intensities above background autofluorescence are collected.

Instead of using random synthetic peptides to provide genetic diversity, fragment genomic DNA of varying lengths, cDNA of varying lengths, shuffled DNAs, and consensus generated sequences may be employed in accordance with the present invention.

Non-natural amino acids having functionality not represented among natural amino acids, e.g., metal binding, photoactivity, chemical functionality, and the like, may be displayed on the surface using a suitable bacterial host. In this case, the library or an equivalent library may be transformed into strains engineered to produce non-natural amino acids. See Kiick, K. L. et al. (2001) FEBS Lett. 502(1-2): 25-30; Kiick, K. L., et al. (2002) PNAS USA 99(1):19-24; Kirshenbaum, K., et al. (2002) Chembiochem. 3(2-3):235-237; and Sharma, N., et al. (2000) FEBS Lett. 467(1):37-40, which are herein incorporated by reference. Peptides incorporating non-natural amino acids are isolated by selection or screening for functions that require inclusion of the non-natural monomers into the displayed polypeptide.

Displayed polypeptides may be made to include post-translation modifications, including glycosylation, phosphorylation, hydroxylation, amidation, and the like, by introduction of a gene or set of genes performing the desired modifications into the strain used for screening and selection, e.g., MC1061 or comparable host strain. Genes performing such post-translational modifications may be isolated from cDNA or genomic libraries by cotransformation with the library and screening for the desired function using FACS or another suitable method. For example, post-translational glycosylation activities (enzymes) can be found co-transforming.

The polypeptides displayed by CYTX-DP or a variant thereof possess a length that preserves the folding and export of the carrier protein while presenting significant sequence and structural diversity. In some embodiments, the CYTX-CP or variant thereof used as a carrier protein may be modified by rational redesign or directed evolution by the methods described herein to increase levels of display or enhance polypeptide presentation. For example, the linker between the native N- and C-termini of OmpX may be optimized by random point or cassette mutagenesis and screened for enhanced presentation. In addition, mutations may be incorporated into the CYTX-CP scaffold that increase the display efficiency of a DM (e.g., substitutions at positions 165 and 166).

Terminal fusion display allows for high mobility of the surface displayed molecule, increased accessibility to target molecules, and simple proteolytic cleavage of the displayed peptide for production of soluble peptides. Terminal fusion display also enables the identification of novel substrates and ligands, e.g., for proteases, peptidases, kinases, receptors, and antibodies. The expression vectors according to the present invention provide a direct way for enhancing the conformational diversity and surface mobility of surface anchored peptides and polypeptides. Through the increased mobility resulting from terminal fusion (as opposed to insertional fusions), the apparent affinity of a polypeptide binding to its corresponding target molecule or material more closely resembles that of the peptide in solution. The N-terminal or C-terminal or biterminal display vectors allow the retention of an energetically stable outer membrane protein structure, compatible with folding, transport, and assembly for efficient display of a given DM on the bacterial cell surface.

In some embodiments, a cDNA library may be cloned into the display position of the N-terminal or C-terminal or biterminal fusion expression vector, with a terminal affinity tag, such as a T7 tag epitope, or a label, or the like, appended to a terminus of the cDNA clone allowing for measurement of the total display level on the cell surface. As used herein, the term "affinity tag" refers to a biomolecule, such as a polypeptide segment, that can be attached to a second biomolecule to provide for purification or detection of the second biomolecule or provide sites for attachment of the second biomolecule to a substrate. Examples of affinity tags include a polyhistidine tract, protein A (Nilsson et al. (1985) EMBO J. 4:1075; Nilsson et al. (1991) Methods Enzymol. 198:3, glutathione S transferase (Smith and Johnson (1988) Gene 67:31), Glu-Glu affinity tag (Grussenmeyer et al., (1985) PNAS USA 82:7952), substance P, FLAG peptide (Hopp et al. (1988) Biotechnology 6:1204), streptavidin binding peptide, or other antigenic epitope or binding domain, and the like, (Ford et al. (1991) Protein Expression and Purification 2:950), all of which are herein incorporated by reference. As used herein, a "label" is a molecule or atom that can be conjugated to a biomolecule to render the biomolecule or form of the biomolecule, such as a conjugate, detectable or measurable. Examples of labels include chelators, photoactive agents, radioisotopes, fluorescent agents, paramagnetic ions, and the like.

The presence of surface localized proteins may be monitored using an antibody or reagent specific for the tag or label according to methods known in the art. Cells binding to a target protein may be then selected using MACS and/or FACS and/or other suitable selection technique(s).

The library pool may be incubated with a fluorescent label of a first wavelength (such as a label emitting green color) and then a second fluorescent label of a second wavelength (such as a label emitting red color) to identify the presence of a full length cDNA of interest. Clones that exhibit both wavelengths are then isolated from the library directly using cell sorting methods known in the art. In some embodiments, the polypeptides of an N-terminal, C-terminal, or biterminal fusion expression vector may be isolated or purified from the outer surface of the host. In other words, a polypeptide may be expressed using an N-terminal, C-terminal, or biterminal fusion expression vector and then produced in a soluble form (free in solution) by introducing a suppressible codon downstream of the given polypeptide. Alternatively, a protease susceptible linker may be used in place of the "suppressible" codon. The polypeptides are displayed on the surface at high density by induction, such as with arabinose for a period of about 2 hours. The cells are washed once or twice in a compatible buffer, such as PBS, to remove undesired proteins and other debris, the cells are concentrated, and a protease is added to the cell suspension. The proteolytically cleaved polypeptide is then harvested by removal of the bacteria by low-speed centrifugation, and transfer of the supernatant into a fresh tube.

The present invention provides compositions and methods for screening a library of cells presenting DM, e.g., candidate peptides, in peptide display scaffolds to identify a peptide that interacts with an enzyme, where the scaffolds are more resistant to protease degradation. The substrate-resistant cellular libraries of peptide sequences disclosed herein provide a qualitative and/or quantitative approach to identify a peptide ligand for an enzyme as well as determining the specificity of the peptide that interacts with an enzyme (e.g., a substrate for the enzyme or an inhibitor of the activity of the enzyme).

In contrast to phagemid or phage libraries displaying DM, e.g., candidate peptides, the peptide display scaffolds disclosed herein provide display of up to about $10^3$-$10^4$ copies of the candidate peptide on the surface of a single cell, thereby enabling identification of a peptide ligand for an enzyme as well as providing for quantitative and qualitative measurement of the interaction between the candidate peptide displayed in the peptide display scaffold and the enzyme.

The methods are based on the use of single-cell fluorescence as an indicator of substrate conversion enabling library screening. Likewise, whole-cell fluorescence measurements enable calculation of substrate cleavage kinetics for isolated clones, eliminating the need to prepare soluble substrates using synthetic or recombinant methods. Finally, the cell libraries disclosed herein can be manipulated with relative ease and amplified indefinitely by growth without introducing measurable library bias. As such, this approach enables generation of candidate peptide libraries of arbitrary amino acid compositions and lengths that are self-renewing. Given the simplicity of library manipulation and screening, CYTX-DPs provide a scalable solution to rapidly identify candidate peptides as well as characterize enzymes, such as proteases.

In general, the peptide display scaffolds include a transmembrane carrier protein having N-terminal and C-terminal DM-presenting domains that are accessible at a surface of the cell outer membrane, i.e. are displayed at the extracellular surface of the cell outer membrane. The peptide display scaffolds include at least one N-terminal and C-terminal domain and at least one N-terminal and C-terminal detectable domains. When expressed in a cell, the peptide display scaffolds display the candidate peptides as terminal fusion proteins thereby providing a more accurate measurement of the interaction capability between the candidate peptide and the tested enzyme. In other words, the measurement of the interaction between terminally displayed candidate peptides and enzymes provided by the present peptide display scaffolds more closely approximates values obtained from measurements of the same interaction in solution with soluble peptides. The peptide display scaffolds are described in greater detail below.

The peptide display scaffolds allow the display of DM, e.g., candidate peptides, at either the N-terminal domain or the C-terminal domain as well as simultaneous display of a different peptide at each of the N-terminal domain and the C-terminal domain.

In some embodiments, the peptide display scaffolds are generally described by Formula (I) as follows:

$$[\text{T-DM}]\text{-CYTX-CP} \quad \text{(I)}$$

wherein CYTX-CP is a transmembrane protein that includes at least the amino acid sequence of SEQ ID NO: 1, SEQ ID NO: 56 or SEQ ID NO: 57, DM is a candidate peptide or other displayed moiety; and T is a detectable moiety (e.g., affinity tag), wherein when the peptide display scaffold is expressed in a cell, T-DM is accessible at a surface of the cell outer membrane (e.g., T-DM is on the extracellular surface of the cell). It is to be understood that the T-DM may be at either the N-terminus or the C-terminus.

In certain embodiments, DM is [S-Ci] or [Ci-S] and the peptide display scaffold is generally described by Formula (II) or Formula (III) as follows:

$$[\text{T-S-C}_i]\text{-CYTX-CP} \quad \text{(II)}$$

$$[\text{T-C}_i\text{-S}]\text{-CYTX-CP} \quad \text{(III)}$$

wherein S is a known substrate for the enzyme, Ci is a candidate inhibitor for the enzyme, CYTX-CP is a transmembrane protein that includes at least the amino acid sequence of SEQ ID NO: 1, SEQ ID NO: 56 or SEQ ID NO:

57, and T is a detectable moiety (e.g., affinity tag), wherein when the peptide display scaffold is expressed in a cell, T-S-Ci and D-Ci-S is accessible at a surface of the cell outer membrane (e.g., T1-S-Ci are T1-Ci-S are on the extracellular surface of the cell). It is to be understood that the T-S-Ci (or T-Ci-S) may be at either the N-terminus or the C-terminus.

In other embodiments, DM is [A-Cs] or [Cs-A] and the peptide display scaffold is generally described by Formula (IV) or Formula (V) as follows:

[T-A-$C_s$]—CYTX-CP (IV)

[T-$C_s$-A]-CYTX-CP (V)

wherein A is an allosteric regulator for the enzyme, Cs is a candidate substrate for the enzyme, CYTX-CP is a transmembrane protein that includes at least the amino acid sequence of SEQ ID NO: 1, SEQ ID NO: 56 or SEQ ID NO: 57, and T is a detectable moiety (e.g., affinity tag), wherein when the peptide display scaffold is expressed in a cell, T1-A-Cs and T1-Cs-A are accessible at a surface of the cell outer membrane (e.g., T1-A-Cs and T1-$C_s$-A are on the extracellular surface of the cell). It is to be understood that the T1-A-Cs (or T1-Cs-A) may be at either the N-terminus or the C-terminus.

Figures 1A, 1B:
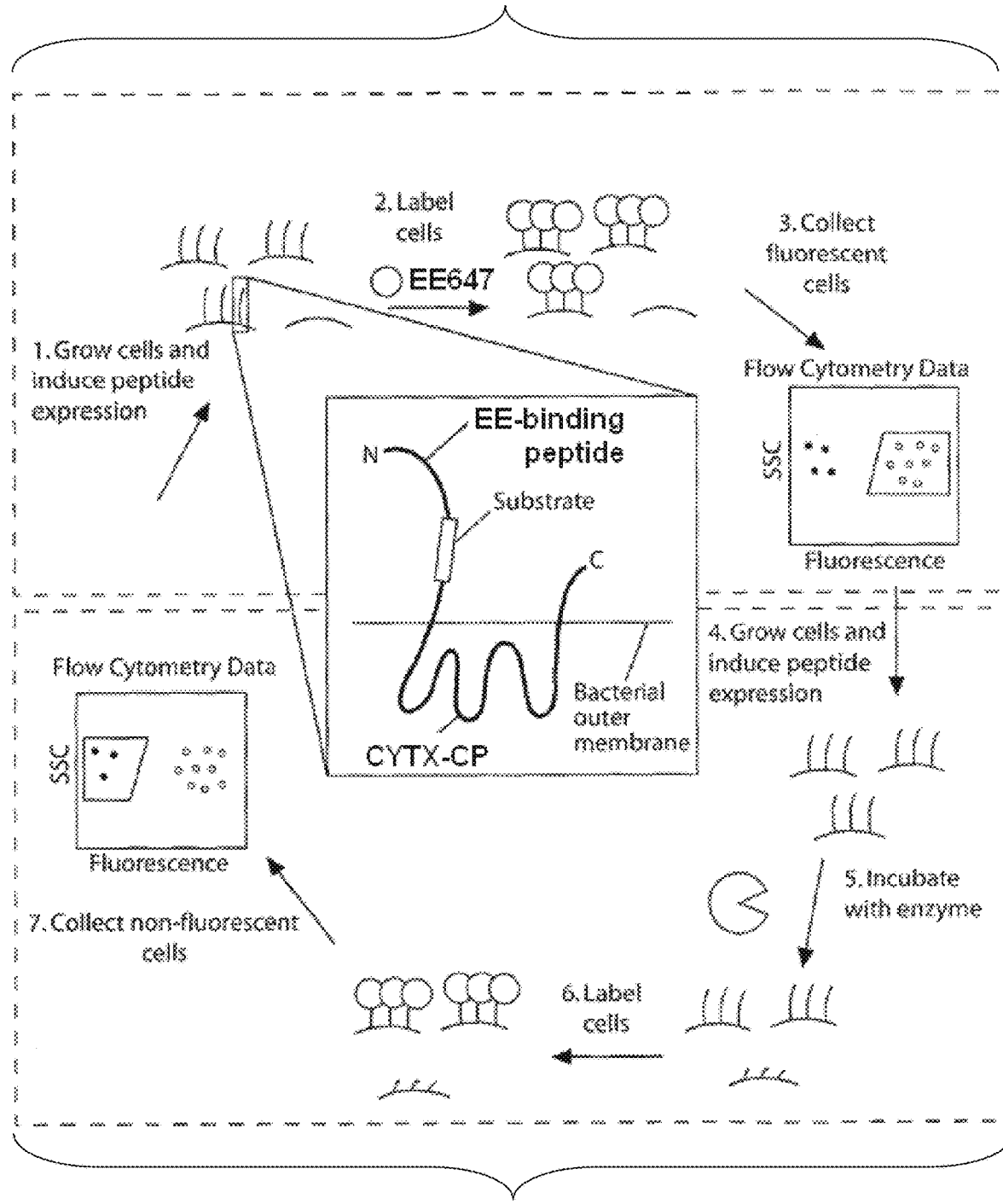
Figure 2:
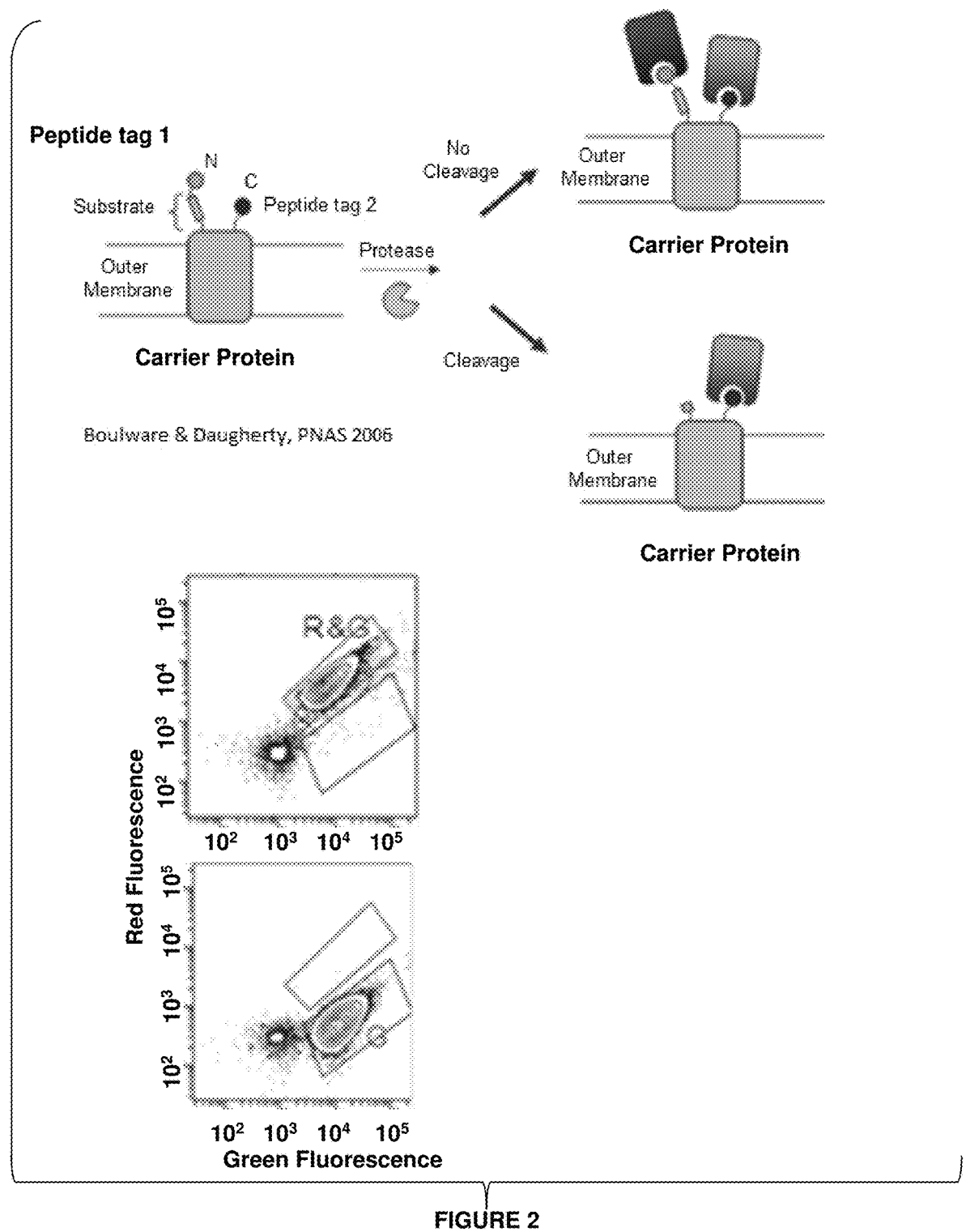
Figure 3E:
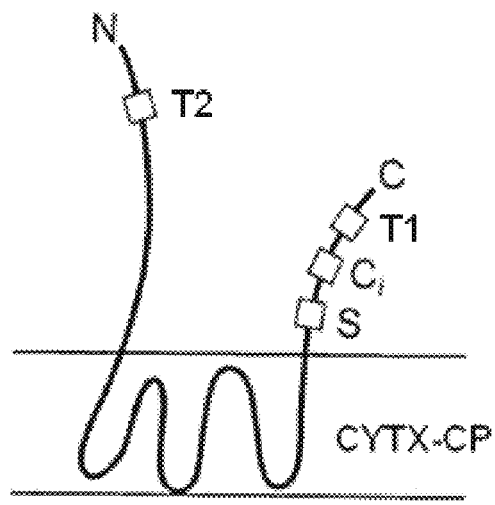
Figure 3F:
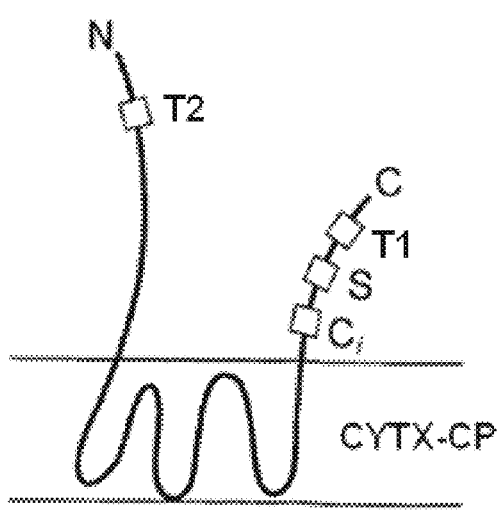
Figure 4A:
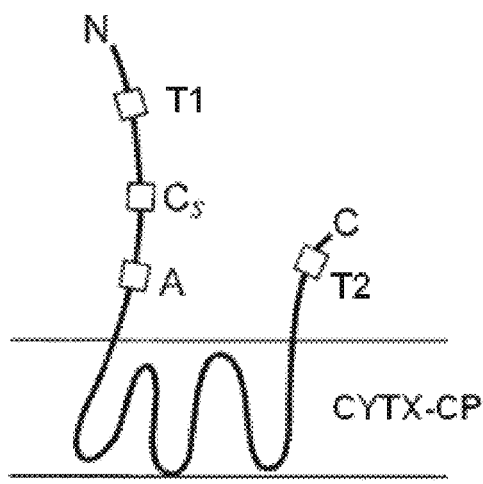
Figure 4B:
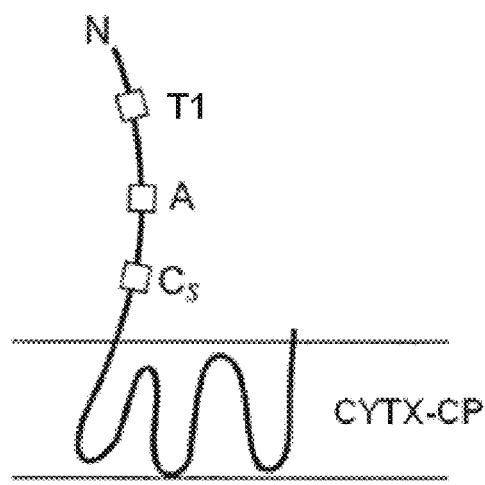
Figure 4C:
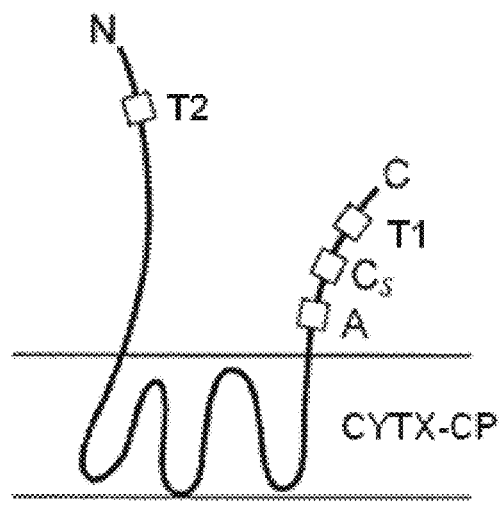
Figure 4D:
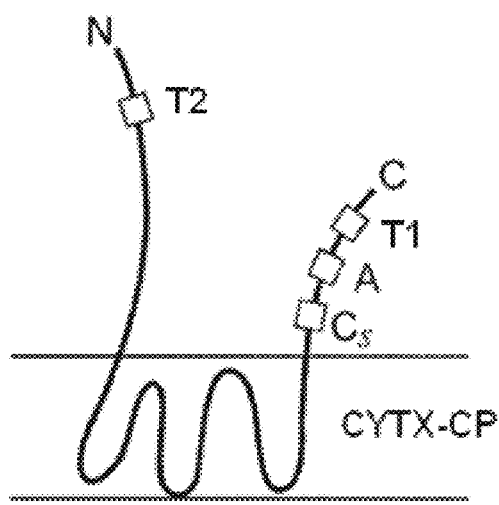
Figure 5A:
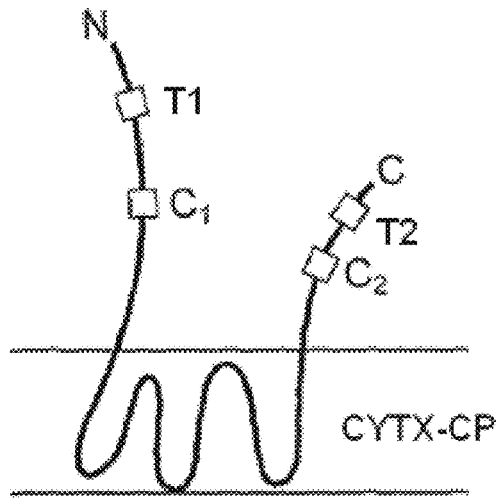
Figure 5B:
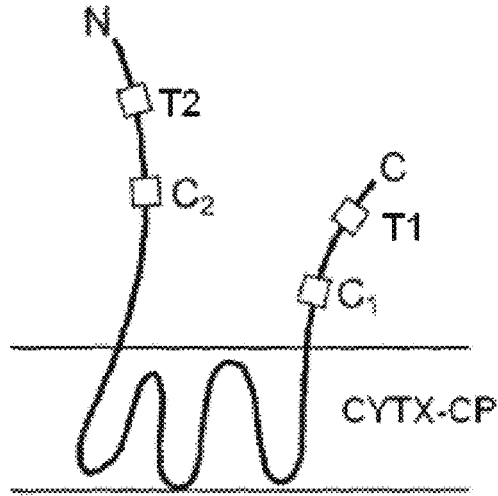
Figure 5C:
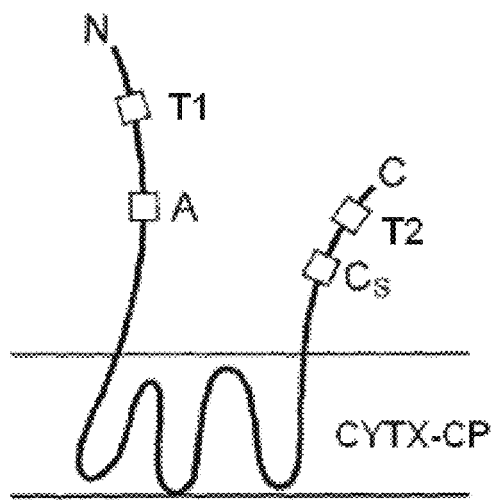
Figure 5D:
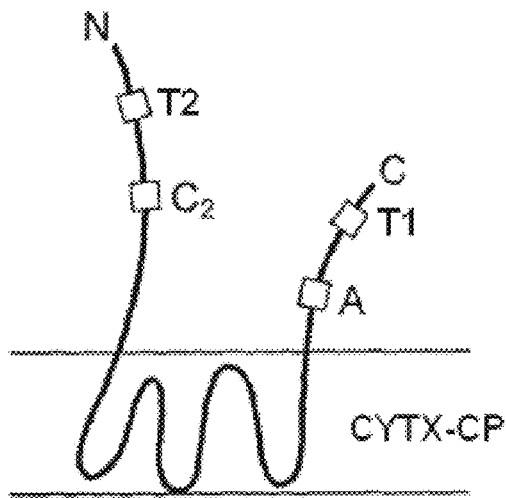
Figure 5E:
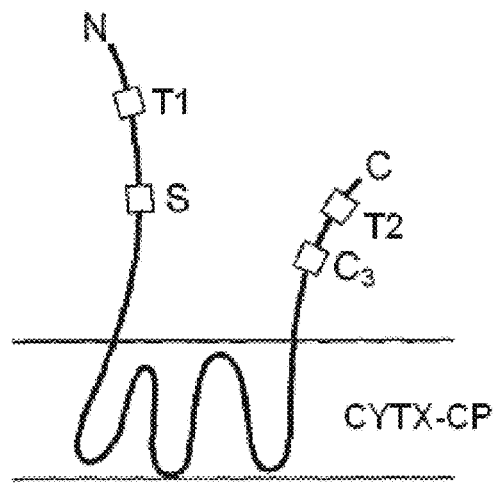
Figure 5F:
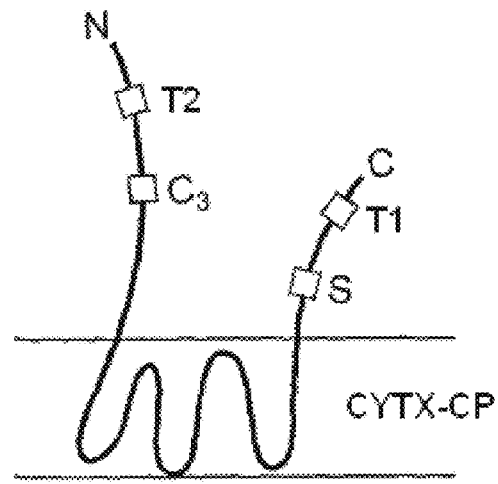

In some embodiments, the peptide display scaffolds are generally described by Formula (VI) as follows:

[$T_1$-DM]-CYTX-CP-[T2] (VI)

wherein CYTX-CP is a transmembrane protein that includes at least the amino acid sequence of SEQ ID NO: 1, SEQ ID NO: 56 or SEQ ID NO: 57, DM is a candidate peptide; and $T_1$ and T2 are first and second detectable moieties (e.g., affinity tags), wherein T1 and T2 are different and wherein when the peptide display scaffold is expressed in a cell, T1-DM and T2 are accessible at a surface of the cell outer membrane (e.g., T1-DM and T2 are on the extracellular surface of the cell) and wherein when T1 is present (e.g., provides a detectable signal by binding of an affinity ligand labeled fluorescent moiety) T2 does not provide a detectable signal; in some embodiments, both T1 and T2 provide detectable signals (FIG. 3, panels A and B). It is to be understood that the T1-DM may be at either the N-terminus or the C-terminus and T2 may be at either the N-terminus or the C-terminus. For example, when the T1-DM is at the N-terminus the T2 is at the C-terminus (FIG. 3, panel A) and when the T1-DM is at the C-terminus the T2 is at the N-terminus (FIG. 3, panel B).

In certain embodiments, DM is [S-$C_i$] or [Ci-S} and the peptide display scaffold is generally described by Formula (VII) or Formula (VIII) as follows:

[T1-S-$C_i$]-CYTX-CP-[T2] (VII)

[T1 $C_i$-S]-CYTX-CP-[T2] (VIII)

wherein S is a substrate for the enzyme, Ci is a candidate inhibitor for the enzyme, CYTX-CP is a transmembrane protein that includes at least the amino acid sequence of SEQ ID NO: 1, SEQ ID NO: 56 or SEQ ID NO: 57, and T1 and T2 are first and second detectable moieties (e.g., affinity tags), wherein T1 and T2 are different and wherein when the peptide display scaffold is expressed in a cell, T1-Ci-S, and T2 are accessible at a surface of the cell outer membrane (e.g., T1-S-Ci, T1-Ci-S, and T2 are on the extracellular surface of the cell) and wherein when T1 is present (e.g., provides a detectable signal by binding of an affinity ligand labeled fluorescent moiety) T2 does not provide a detectable signal; in some embodiments, both T1 and T2 provide detectable signals. (FIG. 3, panels C, D, E, and F). It is to be understood that the T1-S-Ci (or T1-Ci-S) may be at either the N-terminus or the C-terminus and T2 may be at either the N-terminus or the C-terminus. For example, when the T1-S-C1 (or T1-Ci-S) is at the N-terminus the T2 is at the C-terminus (FIG. 3, panels C and D) and when the T1-S-Ci (or T1-Ci-S) is at the C-terminus the T2 is at the N-terminus (FIG. 3, panels E and F).

In other embodiments, DM is [A-Cs] or [Cs-A] and the peptide display scaffold is generally described by Formula (IX) or Formula (X) as follows:

[T1-A-$C_s$]-CYTX-CP-[T2] (IX)

[T1-$C_s$-A]-CYTX-CP-[T2] (X)

wherein A is an allosteric regulator for the enzyme, $C_s$ is a candidate substrate for the enzyme, CYTX-CP is a transmembrane protein that includes at least the amino acid sequence of SEQ ID NO: 1, SEQ ID NO: 56 or SEQ ID NO: 57, and T1 and T2 are first and second detectable moieties (e.g., affinity tags), wherein T1 and T2 are different and wherein when the peptide display scaffold is expressed in a cell, T1-A-Cs, T1-Cs-A, and T2 are accessible at a surface of the cell outer membrane (e.g., T1-A-Cs, T1-Cs-A, and T2 are on the extracellular surface of the cell) and wherein when T1 is present T2 does not provide a detectable signal; in some embodiments, both T1 and T2 provide detectable signals (FIG. 4, panels A, B, C, and D). It is to be understood that the T1-A-Cs (or T1-Cs-A) may be at either the N-terminus or the C-terminus and T2 may be at either the N-terminus or the C-terminus. For example, when the T1-A-Cs (or T1-Cs-A) is at the N-terminus the T2 is at the C-terminus (FIG. 4, panels A and B) and when the T1-A-Cs (or T1-$C_s$-A) is at the C-terminus the T2 is at the N-terminus (FIG. 4, panels C and D).

In other embodiments, the peptide display scaffolds are generally described by Formula (XI) as follows:

[T1-$C_1$]-CYTX-CP-[$C_2$-T2] (XI)

wherein CYTX-CP is a transmembrane protein that includes at least the amino acid sequence of SEQ ID NO: 1, SEQ ID NO: 56 or SEQ ID NO: 57, CI and C2 are first and second candidate peptides, wherein C1 and C2 are not the same; T1 and T2 are first and second detectable moieties (e.g., affinity tags), wherein T1 and T2 are not the same; and wherein when the peptide display scaffold is expressed in a cell, T1-C1 and C2-T2 are accessible at a surface of the cell outer membrane (e.g., T1-C1 and C2-T2 are on the extracellular surface of the cell) (FIG. 5, panels A and B). It is to be understood that the T1-C1 may be at either the N-terminus or the C-terminus and C2-T2 may be at either the N-terminus or the C-terminus. For example, when the T1-C1 is at the N-terminus the C2-T2 is at the C-terminus (FIG. 5, panel A) and when the T1-C1 is at the C-terminus the C2-T2 is at the N-terminus (FIG. 5, panel B). In certain embodiments, C1 is an allosteric regulator and C2 is a candidate substrate (FIG. 5, panels C and D). In other embodiments, C1 is a known substrate and C2 is a candidate inhibitor (FIG. 5, panels E and F).

Exemplary transmembrane proteins (CYTX-CP) and methods for modifying the same for use with the peptide display scaffolds are described in greater detail in the Examples provided herein. It should be noted that any transmembrane protein localized on the outer surface of a biological entity, presenting one or more loop sequences accessible on the cell surface and the like may be modified in order to generate and present a C-terminus, an N-terminus, or both at the outer surface of a biological entity and fused with a DM is suitable for use with the peptide display scaffolds.

In certain embodiments, the peptide display scaffolds further include a flexible linker between the transmembrane protein (CYTX-CP) and one or both of the N-terminal and C-terminal domains, such as T1-DM, T1-Ci-S, T1-A-Cs, T1-Cs-A, T2, T1-C1 and C2-T2. For example, in some embodiments, the peptide display scaffold further includes a linker between DM and CYTX-CP or at least one linker between $C_1$ and CYTX-CP or C2 and CYTX-CP.

A linker suitable for use with the peptide display scaffold will be one that provides flexibility to the N-terminal or C-terminal domains when present and does not interfere with the presentation of the candidate peptide on the surface of the cell. The flexible linker will be variable length, such as from about 3 amino acids to about 25 amino acids, including about 4 amino acids to about 23 amino acids, about 5 amino acids to about 20 amino acids, about 6 amino acids to about 18 amino acids, about 7 amino acids to about 16 amino acids, about 8 amino acids to about 14 amino acids, and about 9 amino acids to about 12 amino acids.

Exemplary flexible linkers include glycine polymers (G), glycine-serine polymers (including, for example, $(GS)_n$, (GSGGS) (SEQ ID NO: 37) and (GGGS) (SEQ ID NO: 34), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are of interest since both of these amino acids are relatively unstructured, and therefore may be able to serve as a neutral tether between components. Glycine polymers are of particular interests glycine accesses significantly more phi-psi space than even alanine, and is much less restricted tan residues with longer side chains (see Scheraga, Rev. Computational Chem. 11173-142 (1992)). Exemplary flexible linkers include, but are not limited Gly-Gly-Ser-Gly-Gly (SEQ ID NO: 38), Gly-Ser-Gly-Ser-Gly (SEQ ID NO: 39), Gly-Ser-Gly-Gly-Gly (SEQ ID NO: 40), Gly-Gly-Gly-Ser-Gly (SEQ ID NO: 41), Gly-Ser-Ser-Ser-Gly (SEQ ID NO: 42), and the like.

As described above, the candidate peptides (C) are generally situated on a cell surface accessible region of a peptide display scaffold, such that the candidate peptides can interact with extracellular or cell surface-associated elements. The candidate peptides can be screened to identify a peptide ligand for the tested enzyme. As used herein, "ligand" or "peptide ligand" refer to a molecule(s) that binds (e.g., by covalent or non-covalent interaction) to a binding partner molecule(s), e.g., a substrate, inhibitor, or allosteric regulator binding to an enzyme. The binding of the ligand to the binding partner may be at the active site, e.g., binding of a substrate or inhibitor with an enzyme, or at another secondary site e.g., binding of an allosteric regulator or non-competitive inhibitor with an enzyme. As such, exemplary candidate peptides include candidate enzyme substrates, candidate enzyme inhibitors, and the like.

Candidate peptides can range from about 2 amino acids in length to about 500 amino acids, including polypeptides ranging from about 2 to about 450, from about 2 to about 400, from about 2 to about 350, from about 2 to about 300, such as from about 2 to about 250 amino acids in length, from about 2 to about 200 amino acids in length, from about 2 to about 150 amino acids in length, from about 2 to about 100 amino acids in length, from about 2 to about 50 amino acids in length, from about 2 to about 40 amino acids in length, from about 2 to about 30 amino acids in length, from about 2 to about 25 amino acids in length, from about 2 to about 20 amino acids in length, from about 2 to about 15 amino acids in length, from about 2 to about 10 amino acids in length, being suitable. For example, in some embodiments, the candidate polypeptide is a single chain Fv (scFv) or other antibody fragment. In some embodiments wherein the candidate polypeptide is an antibody fragment, the antibody fragment is at least 50, at least 100, at least 150, at least 200, at least 250, at least 300, at least 350, at least 400, at least 450, or at least 500 amino acids in length. In some embodiments the antibody fragment is a scFv. In some embodiments the antibody fragment is a scFab or split chain Fab at different fusion locations. In some embodiments, the candidate polypeptide is a substrate. In some embodiments wherein the candidate polypeptide is a substrate, the substrate is no more than 15, no more than 10, or no more than 8 amino acids in length. In some embodiments, the candidate polypeptide is a masking moiety. In some embodiments wherein the candidate polypeptide is a masking moiety, the masking moiety is no more than 40 amino acids in length, In general, the candidate peptide are randomized, either fully randomized or are biased in their randomization, e.g., in nucleotide/residue frequency generally or per position. By "randomized" is meant that each candidate peptide consists of essentially random amino acids. As is more fully described below, the candidate peptides, or candidate nucleic acids encoding the same, are chemically synthesized, and thus may incorporate any amino acid or nucleotide at any position. The synthetic process can be designed to generate randomized peptides, to allow the formation of all or most of the possible combinations over the length of the peptide, thus forming a library of randomized candidate peptides.

As such, in some embodiments, the library of candidate peptides is fully randomized, with no sequence preferences or constants at any position. In other embodiments, the library of candidate peptides is biased. That is, some positions within the sequence are either held constant, or are selected from a limited number of possibilities. For example, in one embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The first and second detectable moieties/tags (T1 and T2) can be any detectable label/tag that provides a detectable signal that can be assessed qualitatively (positive/negative) and quantitatively (comparative degree of fluorescence). As noted in greater detail above, the first and second detectable moieties (T1 and T2) of a peptide display scaffold are different. As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens) and the like. The term "fluorescer" refers to a substance or a portion thereof that is capable of exhibiting fluorescence in the detectable range. Exemplary detectable moieties suitable for use with the peptide display scaffolds include affinity tags and fluorescent proteins.

The term "affinity tag" is used herein to denote a peptide segment that can be attached to peptide display scaffolds at position T (e.g., T1 or T2) that can be detected using a molecule that binds the affinity tag and provides a detectable signal (e.g., a fluorescent compound or protein). In principal, any peptide or protein for which an antibody or other specific binding agent is available can be used as an affinity tag. Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Also described herein are nucleic acid compositions encoding the peptide display scaffolds described herein. For example, the nucleic acid molecules encode the peptide display scaffolds of Formulas VI-XI. Nucleic acid compositions of particular interest comprise a sequence of DNA having an open reading frame that encodes a peptide display scaffold and is capable, under appropriate conditions, of being expressed and provide display of the candidate peptide at the extracellular surface of the cell outer membrane.

In certain embodiments, the nucleic acid encoding the peptide display scaffolds of Formulas VI-X may further include at least one restriction endonuclease site (e.g., a single endonuclease site or a multiple cloning site (e.g., polylinker)) between T1 and DM (or Cl, S, Cs, A) and at least one restriction endonuclease site (e.g., a single endonuclease site or a multiple cloning site (e.g., polylinker)) between CYTX-CP and T2. In other embodiments, the nucleic acid encoding the peptide display scaffold of Formula XI may further include at least one restriction endonuclease site (e.g., a single endonuclease site or a multiple cloning site (e.g., polylinker)) between T1 and C1 and at least one restriction endonuclease site (e.g., a single endonuclease site or a multiple cloning site (e.g., polylinker)) between T2 and C2. Also encompassed in this term are nucleic acids that are homologous, substantially similar or identical to the nucleic acids disclosed herein.

In certain embodiments, the nucleic acids may be present in an appropriate vector for extrachromosomal maintenance or for integration into a host genome, as described in greater detail below.

In some embodiments, the vector includes a nucleic acid encoding a peptide display scaffold generally described by Formula (XII) as follows:

$$[T1\text{-}RE]\text{-}CYTX\text{-}CP\text{-}[T2] \quad (XII)$$

wherein CYTX-CP is a transmembrane protein that includes at least the amino acid sequence of SEQ ID NO: 1, SEQ ID NO: 56 or SEQ ID NO: 57, RE is a restriction endonuclease site for insertion of a nucleic acid sequence encoding a candidate peptide; and T1 and T2 are first and second detectable moieties (e.g., affinity tags), wherein T1 and T2 are different.

In certain embodiments, the vector includes a nucleic acid encoding a peptide display scaffold generally described by Formula (XIII) or Formula (XIV) as follows:

$$[T1\text{-}Y\text{-}RE]\text{-}CYTX\text{-}CP\text{-}[T2] \quad (XIII)$$

$$[T1\text{-}RE\text{-}Y]\text{-}CYTX\text{-}CP\text{-}[T2] \quad (XIV)$$

wherein Y is a substrate for the enzyme or an allosteric regulator for the enzyme that includes at least the amino acid sequence of SEQ ID NO: 1, SEQ ID NO: 56 or SEQ ID NO: 57, RE is a restriction endonuclease site for insertion of a nucleic acid sequence encoding a candidate inhibitor for the enzyme, CYTX-CP is a transmembrane protein, and T1 and T2 are first and second detectable moieties (e.g., affinity tags), wherein T1 and T2 are different.

In other embodiments, the peptide display scaffolds are generally described by Formula (XV) as follows:

$$[T1\text{-}RE_1]\text{-}CYTX\text{-}CP\text{-}[RE_2\text{-}T2] \quad (XV)$$

wherein CYTX-CP is a transmembrane protein that includes at least the amino acid sequence of SEQ ID NO: 1, SEQ ID NO: 56 or SEQ ID NO: 57, RE1 and $RE_2$ are first and second restriction endonuclease sites, and T1 and T2 are first and second detectable moieties (e.g., affinity tags), wherein T1 and T2 are different and RE1 and RE2 are different.

Any restriction endonuclease site can be used at RE, $RE_1$, and $RE_2$ that provides for efficient restriction and insertion of a nucleic acid encoding a candidate peptide is suitable for use. Exemplary restriction endonuclease sites suitable for use include, but are not limited to, EagI, Not1, BamH1, Hind3, EcoR1, Hpa1, Sal1, Sfi1, Cla1, Rsr2, and the like.

It will be appreciated that in some embodiments it will be desirable to use a single polylinker having at least two more different endonuclease sites at the RE, RE1, and RE2. In such embodiments, the expression vector includes a polylinker at RE, RE1, and RE2 having at least two or more different restriction endonuclease sites (e.g., multiple cloning site). For example, in such embodiments, the vectors encoding the peptide display scaffold includes a polylinker having two or more sites to provide for insertion of a nucleic acid sequence encoding a candidate peptide using a first restriction endonuclease site and allow for excision of the nucleic acid once a specific clone that has been identified as being of particular interest using two flanking restriction endonuclease sites.

The polynucleotides and constructs thereof can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, NY, and under current regulations described in United States Dept. of HHS, National Institute of Health (NIH) Guidelines for Recombinant DNA Research.

Also provided are constructs comprising the nucleic acids described herein inserted into a vector, where such constructs may be used for a number of different screening applications as described in greater detail below. In some embodiments, a single vector (e.g., a plasmid) will contain nucleic acid coding sequence for a single peptide display scaffold. In other embodiments, a single vector (e.g., a plasmid) will contain nucleic acid coding sequence for a two or more peptide display scaffolds.

Viral and non-viral vectors may be prepared and used, including plasmids, which provide for replication of biosensor-encoding DNA and/or expression in a host cell. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transformation and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the peptide display scaffolds. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a polynucleotide is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Eukaryotic promoters suitable for use include, but are not limited to, the following: the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-59SS, 1984), the CMV promoter, the EF-1 promoter, Ecdysone-responsive promoter(s), tetracycline-responsive promoter, and the like.

Promoters may be, furthermore, either constitutive or regulatable. Inducible elements are DNA sequence elements that act in conjunction with promoters and may bind either repressors (e.g., lacO/LAC Iq repressor system in *E. coli*) or inducers (e.g., gall/GAL4 inducer system in yeast). In such cases, transcription is virtually "shut off" until the promoter is derepressed or induced, at which point transcription is "turned-on."

Expression vectors generally have convenient restriction sites located near the promoter sequence to provide for the insertion of nucleic acid sequences encoding heterologous proteins. A selectable marker operative in the expression host may be present. Expression vectors may be used for, among other things, the screening methods described in greater detail below.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. In some embodiments, a unicellular organism, such as *E. coli, B. subtilis, S. cerevisiae*, insect cells in combination with baculovirus vectors, or cells of a higher organism such as vertebrates, e.g., COS 7 cells, HEK 293, CHO, *Xenopus* Oocytes, etc., may be used as the expression host cells. In other situations, it is desirable to use eukaryotic cells, where the expressed protein will benefit from native folding and post-translational modifications.

Specific expression systems of interest include bacterial, yeast, insect cell and mammalian cell derived expression systems. Expression systems in bacteria include those described in Chang et al., *Nature* (1978) 275:615; Goeddel et al., *Nature* (1979) 281:544; Goeddel et al., *Nucleic Acids Res*. (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Mammalian expression is accomplished as described in Dijkema et al., *EMBO J*. (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem*. (1980) 102:255, U.S. Pat. Nos. 4,767,704, 4,657,866, 4,927,762, 4,560,655, WO 90/103430, WO 87/00195, and U.S. RE 30,985.

As will be appreciated by those in the art, the type of host cells suitable for use can vary widely. In some embodiments, the cell is a bacterial cell, a yeast cell or a mammalian cell. In some embodiments, the biological entity is a bacterial cell. In some embodiments, the bacterial cell is *Escherichia coli, Shigella sonnei, Shigella dysenteriae, Shigella flexneri, Salmonella typhii, Salmonella typhimurium, Salmonella enterica, Enterobacter aerogenes, Serratia marcescens, Yersinia pestis, Bacillus cereus, Bacillus subtilis*, or *Klebsiella pneumoniae*.

The constructs can be introduced into the host cell by any one of the standard means practiced by one with skill in the art to produce a cell line of the invention. The nucleic acid constructs can be delivered, for example, with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", and the like.

Also disclosed herein are cellular libraries of candidate peptide sequences including a plurality of cells each expressing a peptide display scaffold and presenting at least one candidate peptide. By a "plurality of cells" or a "population of host cells" herein is meant roughly from about $10^3$ cells to $10^{11}$ or $10^{13}$ cells. In some embodiments, such a cellular library comprises from $10^3$ to $10^5$ cells. In some embodiments, such a cellular library comprises from $10^4$ to $10^6$ cells. In some embodiments, such a cellular library comprises from $10^5$ to $10^7$ cells. In some embodiments, such a cellular library comprises from $10^6$ to $10^8$ cells. In some embodiments, such a cellular library comprises from $10^7$ to $10^9$ cells. In some embodiments, such a cellular library comprises from $10^8$ to $10^{10}$ cells. In some embodiments, such a cellular library comprises from $10^9$ to $10^{11}$ cells. In some embodiments, such a cellular library comprises from $10^{10}$ to $10^{12}$ cells. In some embodiments, such a cellular library comprises from $10^{11}$ to $10^{13}$ cells. In some embodiments, such a cellular library is of any size depending on sorting capability.

This plurality of cells comprises a cellular library, wherein generally each cell within the library includes at least one peptide display scaffold at the outer membrane. In certain embodiments, the library is enriched for cells expressing peptide display scaffolds presenting candidate peptides. By "enriched" is meant that the cells of the library exhibit at least one detectable signal from the peptide display scaffolds. The enrichment of the cells cane done by, for example, fluorescence activated cell sorting.

In some embodiments, each cell of the cellular library expresses a single type of peptide display scaffold. For example, each cell expresses at least one peptide display scaffold on the extracellular surface of the cell outer membrane, wherein all the peptide display scaffolds of the cell present the same candidate peptide.

In other embodiments, the cellular library includes cells expressing two or more different types of peptide display scaffolds, including three or more and four or more, etc. By "different types of peptide display scaffolds" is meant that each type of peptide display scaffold displayed on the surface of the cell presents a candidate peptide that is different than the candidate peptide presented by the other type of peptide display scaffold displayed on the surface of the cell. For example, in embodiments in which a cellular library includes a cell expressing a first and second peptide display scaffold, the candidate peptide presented by the first peptide display scaffold is different from the candidate peptide presented by the second peptide display scaffold. It will be appreciated by one of skill in the art that in such embodiments, the T1 and T2 of the first peptide display scaffold will be different than the T1 and T2 of the second peptide display scaffold.

In one embodiment, the CYTX-DP is a library of fully randomized candidate peptides, with no sequence preferences or constants at any position. In another embodiment, the CYTX-DP is a library of biased candidate peptides. That is, some positions within the sequence are either held constant, or are selected from a limited number of possibilities. For example, in one embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In another embodiment, the bias is towards peptides that interact with known classes of enzymes, e.g., proteases. A number of molecules or protein domains are suitable as starting points for the generation of biased randomized candidate regulator polypeptides. A large number of small molecule domains are known that confer a common function, structure or affinity In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. In addition, agonists and antagonists of any number of molecules may be used as the basis of biased randomization of candidate regulator polypeptides as well.

Applications

The present invention may be broadly applied to methods to isolate, improve or otherwise alter, peptide and polypeptide sequences that perform useful or desired functions including binding, catalysis, assembly, transport, and the like. For example, the CYTX-DPs of the present invention may be used to isolate peptide molecular transformation catalysts, develop whole-cell reagents, discover peptides that promote self-assembly, discover in vivo targeting peptides for drug and gene delivery, discover and improve peptides binding to materials surfaces, e.g., semiconductors, mapping proteins such as protein contacts, and biomolecular networks, identifying enzyme substrates and/or inhibitors, identifying receptor agonists and/or antagonists, isolating inhibitors of bacterial or viral pathogenesis, discovering peptides that mediate endocytosis and cellular entry, mapping antibody and protein epitopes including multiplex mapping, identifying peptide mimics of non-peptide ligands, isolating metal binding peptides, e.g., for bioremediation, nano-wire synthesis, according to methods known in the art, and modifying antibodies or other proteins. See Georgiou, G., et al. (1997) Nat. Biotechnol. 15(1):29-34; Pasqualini, R. and E. Ruoslahti (1996) Nature 380(6572):364-366; Whaley, S. R., et al. (2000) Nature 405(6787):665-668; Fields, S. and R. Sternglanz (1994) Trends in Genetics 10(8):286-292; Kim, W. C., et al. (2000) J. Biomol. Screen. 5(6):435-440; Yang, W. P., et al. (1995) J. Mol. Biol. 254(3): 392-403; Poul, M. A., et al. (2000) J. Mol. Biol. 301(5):1149-1161; James, L. C., et al. (2003) Science 299(5611):1362-1367; Feldhaus, M. J., et al. (2003) Nat. Biotechnol. 21(2):163-170; Kjaergaard, K., et al. (2001) Appl. Environ. Microbiol. 67(12):5467-5473, and Shusta, E. V., et al. (1999) Curr. Opin. Biotechnol. 10(2):117-122, which are herein incorporated by reference.

As provided herein, the CYTX-DPs of the present invention may be used to elucidate consensus sequences while maintaining diversity in selected populations according to methods known in the art. See Smith, G. P. and A. M. Fernandez (2004) Biotechniques 36(4):610-614, 616, 618; and Lowman, H. B. (1997) Ann. Rev. Biophys. Biomol. Struct. 26:401-424, which are herein incorporated by reference.

In some embodiments, the DMs may increase the frequency at which high affinity binders occur relative to the prior art that enables longer consensus motifs and secondary structures to be determined. See Nakamura, G. R., et al. (2002) PNAS USA 99(3):1303-1308, which is herein incorporated by reference.

The CYTX-DPs of the present invention used in conjunction with FACS provides fine discrimination of clonal affinity, and quantitative separations that take advantage of this sensitivity. See Van Antwerp, J. J. and K. D. Wittrup (2000) Biotechnol. Prog. 16(1):31-37; and Daugherty, P. S., et al. (1998) Protein Eng. 11(9):825-832, which are herein incorporated by reference. Specifically, the fine affinity discrimination provided by FACS allowed isolation of the best sequences binding to streptavidin, CRP, and anti-T7•tag Mab. Further, the display systems herein routinely enabled identification of beneficial cysteine placements to form putative disulfide constrained loops conferring high binding affinity without explicit library design, which alleviates the need to construct and screen twenty or more different libraries, and removes critical assumptions that have limited the affinities of isolated ligands in earlier studies. See Giebel, L. B., et al. (1995) Biochemistry 34(47): 15430-15435; Deshayes, K., et al. (2002) Chem. Biol. 9(4):495-505; and Nakamura, G. R., et al. (2002) PNAS USA 99(3):1303-1308, which are herein incorporated by reference.

The present invention provides construction of a single library of sufficient size and quality enables routine isolation of high affinity cyclic peptides. For the construction of intrinsically fluorescent libraries, a ribosomal binding site (RBS) known in the art may be introduced downstream of the carrier protein, e.g., CYTX-CP, followed by a suitable fluorescent protein, e.g., alaj GFP. See Bessette, P. H. and P. S. Daugherty (2004) Biotechnology Progress 20 (1), which is herein incorporated by reference. The resulting bacteria, when expression is induced by the addition of 0.2% arabinose, are both intrinsically labeled and display DMs as N- or C-terminal fusion proteins. Alternatively, the order may be reversed such that the fluorescent protein is expressed first, followed by the RBS and the permuted OMP sequence.

Sequences with about 10 to about 100 fold higher affinity may be obtained by randomization of non-consensus residues and kinetic FACS selection (using biotin as a competitor). Streptavidin binding peptides may be used as genetically encoded biotin mimics to eliminate the need for chemical labeling of proteins with biotin. Thus, a streptavidin binding peptide selected and affinity matured using this process could be fused, using recombinant methods known in the art, to either the C or N-terminus of at least one given nucleic acid molecule. Expression of the nucleic acid molecule would produce a polypeptide having a C- or N-terminal peptide tag capable of binding to the commonly used affinity reagent, streptavidin, which may be eluted from the reagent by the simple addition of biotin.

The polypeptide display systems of the present invention allow the creation of renewable whole cell binding reagents in non-specialized laboratories since this method is technically accessible and libraries are reusable. This approach has already proven useful for selecting cell-specific binding peptides, and for performing diagnostic assays using flow cytometry and fluorescence microscopy (unpublished data). Furthermore, the surface displayed polypeptides can be used for parallel or multiplex ligand isolation, and clones can be processed with efficient single-cell deposition units present on many cell sorters. See Feldhaus, M. J., et al. (2003) Nat. Biotechnol. 21(2):163-170, which is herein incorporated by reference. Consequently, the CYTX-DPs of the present invention may be used in proteomic applications including proteome-wide ligand screens for protein-detecting array development. See Kodadek, T. (2001) Chem. Biol. 8(2):105-115, which is herein incorporated by reference.

In one embodiment, CYTX-DPs of the invention can be used in display libraries for screening polypeptides for biological activity. A polypeptide display library, as described herein, is provided comprising CYTX-DPs carrying a plurality of DMs displayed on bacterial cells. The polypeptides are contacted with a target molecule of interest and assayed for biological activity in the presence of the target molecule in order to identify displayed DMs that have biological activity. For this purpose, any CYTX-DP described herein can be used in the polypeptide display library for screening polypeptides. The polypeptide display library can include DMs fused to the N- or C- or both termini of the CYTX-DPs. The biological activity assayed can be enzymatic activity, substrate activity, ligand-binding activity, agonist activity, antagonist activity, transport activity, or any other biological activity. Any target molecule can be chosen, including but not limited to, a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, or an inorganic molecule.

As used herein, "interact" or "interaction" with respect to a candidate peptide and an enzyme is meant the recognition and involvement between the enzyme and peptide to produce an effect either on the peptide or the enzyme. For example, "interaction" includes cleavage of a candidate substrate by the enzyme, inhibition of an enzyme by a candidate inhibitor, modulation of enzyme specificity and/or activity by a candidate allosteric regulator, modulation of enzyme specificity and/or activity with respect to a candidate peptide (e.g., candidate substrate or candidate inhibitor) by a known allosteric regulator, and the like. As such, exemplary candidate peptides include candidate enzyme substrates, candidate enzyme inhibitors, candidate allosteric regulators of enzymes, and the like.

In certain embodiments, the invention includes a method of screening a library of polypeptides for the ability to bind to a target molecule, the method comprising: a) providing a polypeptide display library comprising CYTX-DPs carrying a plurality of DMs displayed on bacterial cells, b) contacting the plurality of DMs with the target molecule, and c) identifying at least one displayed DM that binds to the target molecule.

The target molecule may comprise a detectable label in order to facilitate detection of binding of the target molecule to the displayed polypeptides. Detectable labels suitable for use in the present invention include any composition detectable by spectroscopic, photochemical, biochemical, immunochemical, electrical, optical, or chemical means. Useful labels in the present invention include biotin or other streptavidin-binding proteins for staining with labeled streptavidin conjugate, magnetic beads (e.g., Dynabeads™), fluorescent dyes (e.g., phycoerythrin, YPet, fluorescein, Texas red, rhodamine, green fluorescent protein, and the like, see, e.g., Molecular Probes, Eugene, Oreg., USA), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

In some embodiments, the N-terminal, C-terminal, or biterminal fusion CYTX-DPs of the present invention can be used for the identification of substrates, such as protease or kinase substrates, from substrate libraries. Accordingly, a CYTX-DP can be modified to express a fluorescent protein using methods known in the art. For example, the use of a bicistronic expression vector comprising a CYTX-DP, (2) a ribosomal binding site downstream of the CYTX-DP sequence, and (3) a label such as a green fluorescent protein suitable for efficient detection using fluorescence activated cell sorting (e.g., alajGFP). Expression is then monitored through the intensity of green fluorescence. For example, a library of protease or peptide substrates is created using methods known in the art. The substrates are fused to the N-terminus or C-terminus or both termini of CYTX-DPs using an expression vector expressing a green fluorescent protein. The substrate library is constructed such that a label or an affinity tag suitable for fluorescence labeling is fused to the free terminus of a DM on the cell surface. Host cells expressing the substrate library labeled with a red fluorescent protein are grown, and cells that are green but not red are removed from the population to eliminate the isolation of false positive clones. The library is then incubated with an enzyme (e.g., a protease or peptidase), and cells that lose red fluorescence while retaining green fluorescence are isolated from the population using FACS.

In some embodiments, the N-terminal, C-terminal, or biterminal fusion CYTX-DPs of the present invention can be used to construct whole cells that can be used as reagents. For example, one or more peptides identified using the methods herein, binding to a protein, virus, or cellular receptor, or synthetic composition of matter, are displayed on the outer surface of a bacterial cell at a desired surface density. Cells can then be coupled directly to a material, e.g., glass/silicon, gold, polymer, by virtue of peptides selected to bind these materials, and used to capture in solution molecules binding to various other displayed peptides on the same cell. For optical detection, cells can co-express a fluorescent or luminescent reporter molecule such GFP, or luciferase. Flow cytometry, or fluorescence microscopy can be used to detect binding of molecular recognition element displaying cells to the target agent, e.g., virus, cell, particle, bead, and the like.

The polypeptide display systems of the present invention allow the creation of renewable whole cell binding reagents in non-specialized laboratories since this method is technically accessible and libraries are reusable. This approach has already proven useful for selecting cell-specific binding peptides, and for performing diagnostic assays using flow cytometry and fluorescence microscopy. Furthermore, the surface displayed polypeptides can be used for parallel or multiplex ligand isolation, and clones can be processed with efficient single-cell deposition units present on many cell sorters. See Feldhaus, M. J., et al. (2003) Nat. Biotechnol. 21(2):163-170, which is herein incorporated by reference. Consequently, the expression vectors of the present invention may be used in proteomic applications including proteome-wide ligand screens for protein-detecting array development. See Kodadek, T. (2001) Chem. Biol. 8(2):105-115, which is herein incorporated by reference.

In some embodiments, the display systems using CYTX-CP polypeptides of the present invention can be used for the identification of substrates, such as protease and peptidase substrates, from substrate libraries. Accordingly, an expression vector may be modified to express a fluorescent protein using methods known in the art. For example, the use of a bicistronic expression vector comprising (1) a CYTX-CP polypeptide, (2) a ribosomal binding site downstream of the CYTX-CP nucleic acid sequence, and (3) label such as a green fluorescent protein suitable for efficient detection using fluorescence activated cell sorting, such as alaj GFP. Expression is then monitored through the intensity of green fluorescence.

A library of the substrates is created using methods known in the art. The substrates are fused to the CYTX-CP expression system, respectively. The substrate library is constructed such that a label or an affinity tag suitable for fluorescence labeling is fused to the free terminus of the DM on the cell surface. The library is then grown, and cells that are green but not red are removed from the population to eliminate the isolation of false positive clones. The library is then incubated with the enzyme (e.g., a protease or peptidase), and cells that lose red fluorescence while retaining green fluorescence are isolated from the population using FACS.

In some embodiments, the CYTX-CP expression vectors of the present invention can be used to construct whole cells that can be used as reagents. For example, one or more peptides identified using the methods herein, binding to a protein, virus, or cellular receptor, or synthetic composition of matter, are displayed on the outer surface of E. coli at a desired surface density. Cells can then be coupled directly to a material, e.g., glass/silicon, gold, polymer, by virtue of peptides selected to bind these materials, and used to capture in solution molecules binding to various other displayed peptides on the same cell. For optical detection, cells can co-express a fluorescent or luminescent reporter molecule such GFP, or luciferase. Flow cytometry, or fluorescence microscopy can be used to detect binding of molecular recognition element displaying cells to the target agent, e.g., virus, cell, particle, bead, and the like.

Figure 6A:
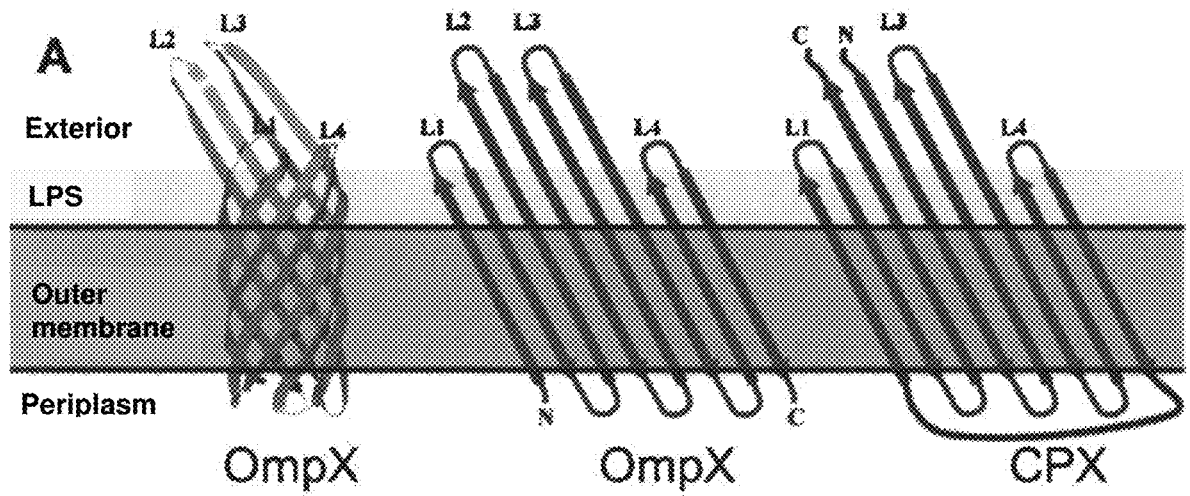

It should be noted that although the use of bacterial proteins are exemplified herein, a variety of surface localized proteins possessing surface exposed loops may be modified according to the present invention to provide expression vectors that allow the display of polypeptides on the outer surface of viruses, and prokaryotic and eukaryotic cells including phage, bacteria, yeast, and mammalian cells. A variety of surface localized proteins known in the art may be used. In *Escherichia coli* and substantially similar species, such proteins include OmpA, OmpX, OmpT, OmpC, OmpF, OmpG, OmpN, LamB, FepA, FecA, and other beta-barrel outer membrane proteins. Proteins that exhibit a topology substantially similar to that shown in FIGS. 6A-6C, i.e., present either a C- or N-terminus on the outer surface of bacteria, may also be used according to the present invention. One of ordinary skill in the art may readily identify and screen for the various surface localized proteins that may be used in accordance with the present invention.

The following examples are intended to illustrate but not to limit the invention.

Example 1: Materials & Methods

Structural Analysis and Design: The structures of all Outer Membrane Protein (Omp) family members that have been determined, including structures of OmpX, were analyzed using PyMol software (Schrodinger, Portland, OR (formerly DeLano Scientific). OmpX structural modifications were developed by visual inspection and by using PyMOL tools and scripts. Molecular biology and engineering of constructs were developed using Vector NTI Suite 11 (Life Technologies, Grand Island, NY).

Reagents and Strains: Oligonucleotides were ordered from Elim Biopharmaceutical (Hayward, CA). The vector was modified from pBAD33 including removing and introducing restriction sites (Boulware, K. T. & Daugherty, P. S., (2006) *PNAS*, 103(20), 7583-7588). Molecular biology reagents including PCR reagents, restriction endonucleases and ligation reagents were from Lucigen (Middleton, WI) and New England Biolabs (Ipswich, MA). Streptavidin-conjugated phycoerythrin (SA-PE) (Invitrogen) was used without modifications. YPet fused to the SH3 domain of Mona was produced and used as described in U.S. Pat. No. 7,666,817 B2, issued Feb. 23, 2010. The N-terminal epitope tag sequence of the CYTX-DP platform was a short version of the Glu-Glu epitope tag (binds EYMPME (SEQ ID NO: 8), or EFMPME (SEQ ID NO: 43) sequences). The antibody targeting this tag was the monoclonal mouse IgG1 anti-Glu-Glu (Covance, Princeton, NJ), also referred to herein as Anti-EE or EE. The C-terminal epitope tag sequence of the CYTX-DP platform was an eight poly-His epitope tag (HHHHHHHH) (SEQ ID NO: 13). The antibody targeting this tag was a monoclonal mouse IgG1 anti-6×His (R&D Systems, Minneapolis, MN). The secondary antibody targeting hCTLA-4Fc was a monoclonal mouse IgG1 and the human CTLA-4-Fc was CHO-cell expressed (R&D Systems, Minneapolis, MN). Fluorescence labeling kits were AlexaFluor 488 nm and 647 nm labeling kits from Life Technologies (formerly Invitrogen). For example, anti-EE antibody was labeled with Alexa 647 and designated EE647; anti-His monoclonal antibody was labeled with Alexa 647 and designated His647. The conjugated mouse IgG1s were at a stock concentration of about 1 mg/ml in PBS and stored at 4 degrees C. *E. coli* strains used were DH-10β from NEB, MC1061 ((Casadaban, M. J. & Cohen, S. N. (1980) *JMB*, 138, 179-207) and Lucigen), and C41(DE3) and CD43 (DE3) (Lucigen and OverExpress, France). Bacteria cultures were grown at 37° C. with vigorous shaking for construct development in Luria-Bertaini (LB) broth supplemented with 25-35 micrograms per ml (μg/ml) chloramphenicol (CM), unless another antibiotic was specified. Bacterial cultures were grown at 28° C. to 37° C. for protein expression in LB broth with CM (unless another antibiotic was specified) and also supplemented with 0.01% to 0.04% arabinose for induction. The enzymes human plasmin (Haematologic Technologies Inc., Essex Junction, VT) and recombinant human urokinase-type Plasminogen Activator (uPA) (Analytical Biological Services Inc., Wilmington, DE) were used without modifications. Human synovial fluid samples (Analytical Biological Services, Inc.) were used without modifications.

Substrate Cleavage and Platform Stability Analysis: Susceptibility of eCLiPS platforms (see e.g., FIGS. 20-22, and 26-28) and CYTX-DP platforms (see e.g., FIGS. 23-25, and 29-31) to cleavage by proteases, either specifically at a substrate site or throughout extracellular portions of the platform, was evaluated as follows. Bacteria transformed by plasmids encoding eCLiPS3.0 or CYTX-DP platforms were grown overnight, subcultured by dilution into fresh media (1:50 dilution), and grown for 1.5 to 2 hours. The subculture was then induced with 0.04% arabinose and incubated with shaking at 37° C. for 1 hour. To stop further growth, cells were incubated on ice for 15-30 minutes. Cell aliquots were harvested and washed with PBS (pH 7.4). To test for protease cleavage susceptibility, cells were pelleted by centrifugation, the supernatant removed, and the cells resuspended in reaction buffer containing the test enzyme. This reaction mixture was incubated at 37° C. static. To stop the reaction, cells were removed and diluted 10-fold in PBS, pelleted by centrifugation, and resuspended in PBS containing SA-PE (20 μg/mL) or YPet-MONA (50 nM) for eCLiPS3.0 platforms or in PBS containing EE647 (1 μg/ml) or His647 (2 ug/ml) for CYTX-DP platforms. After incubation on ice (30 min), cells were washed with PBS and analyzed using a FACSAria™ cell sorter in a manner similar to that described in U.S. Pat. No. 7,666,817 B2, ibid.

Assays to measure uPA hydrolysis of CYTX-DP platforms containing uPA substrates 1203 or 1204 (i.e., CYTX-DP-1203 or CYTX-DP-1204 platforms, respectively) were performed in TBST (50 mM Tris, 150 mM NaCl, 0.05% Tween20, pH 7.4) with 1 nM-1.25 micromolar (μM) uPA. Such hydrolysis was compared to that of uPA mixed with eCLiP3.0-1203 or eCLiPS3.0-1204. Background hydrolysis of the regions flanking the substrate site (using eCLiPs3.0-NSUB and CYTX-DP-NSUB), was measured under each reaction condition to ensure that hydrolysis occurred in the designated substrate region. NSUB refers to a non-cleavable substrate. Typically an NSUB comprises a Glycine-Serine linker of about 1 to about 8 amino acids. See for example, SEQ ID NO: 23.

Assays to measure susceptibility of eCLiPS3.0-NSUB or CYTX-DP-NSUB platforms to human plasmin cleavage were performed in 50 mM Tris-HCl, pH. 7.5, supplemented with 100 mM NaCl, 0.01% Tween20, and 1 mM EDTA with 100 nM-312.5 μM human plasmin.

Assays to measure susceptibility of eCLiPS3.0-NSUB or CYTX-DP-NSUB platforms to human synovial fluid were performed with synovial fluid samples in 10%-90% PBS, pH 7.4.

Amino- and Carboxy-terminus Labeling Conditions for eCLiPS3.0: Streptavidin conjugated phycoerythrin (SA-PE) was used for labeling streptavidin binding affinity ligand on the N-termini of eCLiPS3.0. Fluorescent protein YPet fused to the SH3 domain of Mona was used for labeling the MONA binding affinity ligand on the C-termini of eCLiPS3.0. For optimum labeling of cells without protease reaction, the cells were incubated for 30 min at 4° C. with SA-PE (20 μg/imL) or YPet-MONA (50 nM).

Amino- and Carboxy-terminus Labeling Conditions for CYTX-DP: Alexa-647 conjugated anti-EE antibody (EE647) was used for labeling EE binding affinity ligand on the N-termini of CYTX-DP. Alexa-647 conjugated anti-His antibody (His647) was used for labeling the 8-His binding affinity ligand on the C-termini of CYTX-DP. For optimum labeling of cells without protease reaction, the cells were incubated for 30 min at 4° C. with Alexa-647 (1 μg/mL) or His647 (2 μg/ml).

Kinetic Data Analysis: The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$\text{Conversion}_{CLiPS} = \frac{FL_- - FL_+}{FL_- - FL_0} \quad [1]$$

where $(FL_-)$ is the fluorescence after incubating without enzyme, $(FL_+)$ is fluorescence after incubation with enzyme, and $(FL_0)$ is fluorescence of unlabeled cells. Given that the expected substrate concentrations that were used are significantly below the expected $K_M$ of the substrate for the target protease, the Michaelis-Menton model simplifies to $$\frac{d[S]}{dt} = -\frac{k_{cat}}{k_M}[S][E] \quad [2]$$

allowing substrate conversion to be expressed as $$\text{Conversion}_{MM} = 1 - \exp\left(-\frac{k_{cat}}{k_M}[E] \cdot t\right) \quad [3]$$

where [S] is the substrate concentration, [E] is enzyme concentration and t is time. To determine the second order rate constant ($k_{cat}/K_M$), the time dependent conversion for each substrate was fit to equation [3].

Binding Screening: For expression screening and clone analysis, cultures were grown into log-phase or near saturation (>8 hours) and sub-cultured by dilution into fresh medium (range from 1/50 to 1/15 dilution) and grown over-night at 28 to 37 degrees C. These cultures were induced with 0.01 to 0.04% arabinose during this overnight subculture. The optical density at 600 nm (OD600) was measured to estimate cell concentration in order to normalize the cultures to the same cell density after the cultures were chilled on ice for 30-60 minutes. A calculation per labeling experiment volume required a maximum of OD600=0.5 for 50 uL cells for a 50 uL labeling reaction; when smaller labeling volumes were used, then fewer cells were used maintaining the equivalent of OD60=0.5 for 50 uL cells for a 50 uL labeling reaction. Cells were washed in 1 mL 1×PBS or 1 ml 1×PBS supplemented with 1% BSA and were pelleted by centrifugation at 3500×g for 5 minutes at 4 degrees C. Subsequently, washed cells were labeled in 1×PBS or 1×PBS supplemented with 1% BSA for 30-60 minutes on ice in the dark. Cells were pelleted by centrifugation at 3500×g for 5 minutes at 4 degrees C. Cells were re-suspended in 1×PBS 0.3-0.5 mL and analyzed using a FACSAria custom-ordered sorter (Becton Dickinson, Franklin Lakes, NJ).

Example 2: Strategy for Producing a More Protease Resistant Display Platform

This Example provides the strategy for producing a display platform for peptides that is less susceptible to protease cleavage.

Since CLiPS (see e.g., PCT Publication No. WO 2005/047461; PCT Publication No. WO 2009/014726; U.S. Pat. Nos. 7,256,038; 7,612,019; U.S. Patent Application Publication No. 2010/0113303; PCT Publication No. WO 2007/027935; U.S. Pat. No. 7,666,817; U.S. Patent Application Publication No. 20100173349, each of which is hereby incorporated by reference in its entirety) is used to isolate novel protease substrates, it was desirable to create a more robust display platform with improved properties of stability toward target proteases that were known to digest the platform and toward complex mixtures with high protease activity (e.g., synovial fluids). This improved platform, CYTX-DP, allows for more effective protease substrate libraries, mask libraries and, surprisingly, scFv engineering for antibody, protein, probody and pro-protein discovery due to overall stability and engineering of the extracellular domains.

Figure 6B:
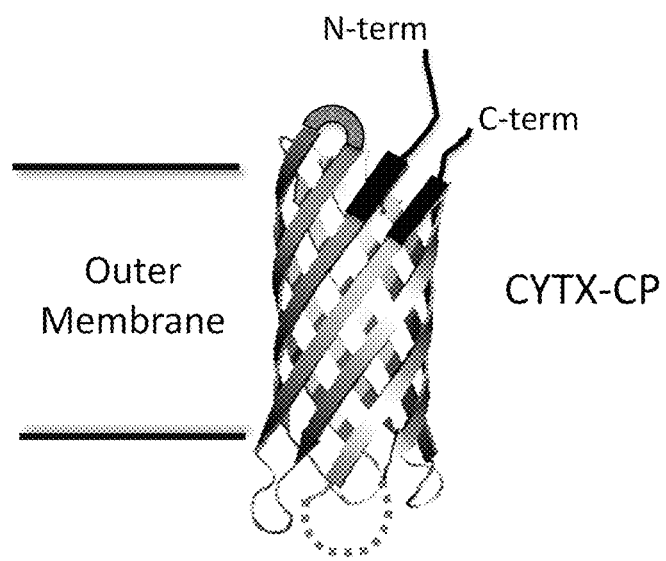
Figure 6C:
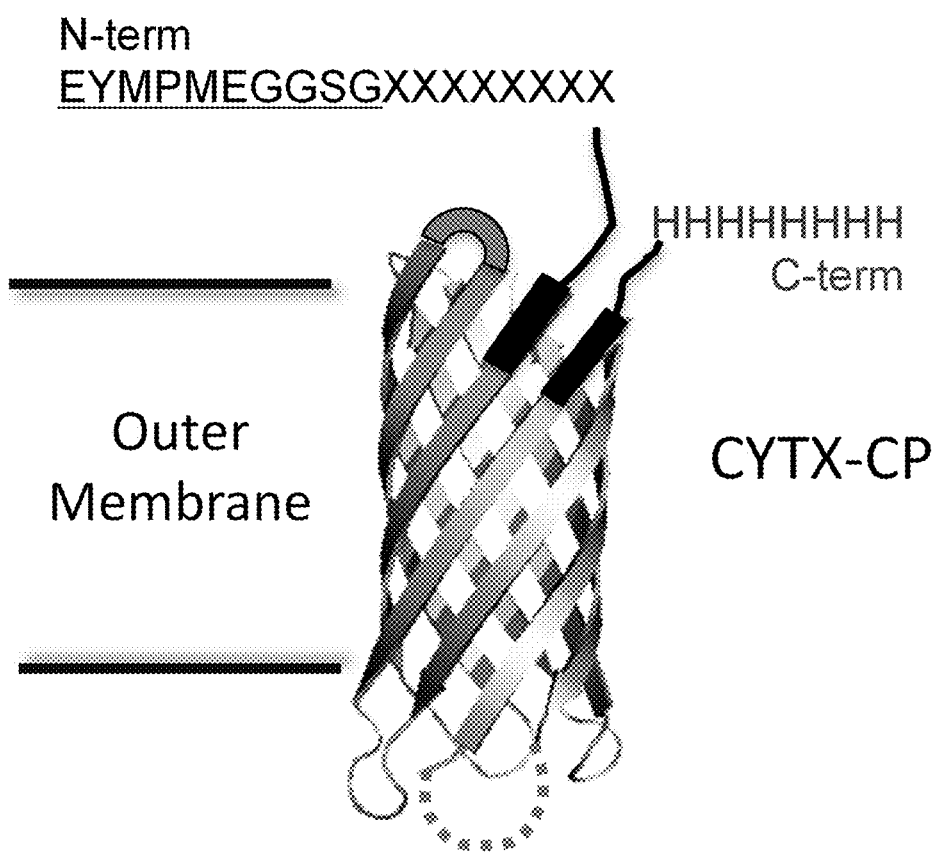
Figure 7:
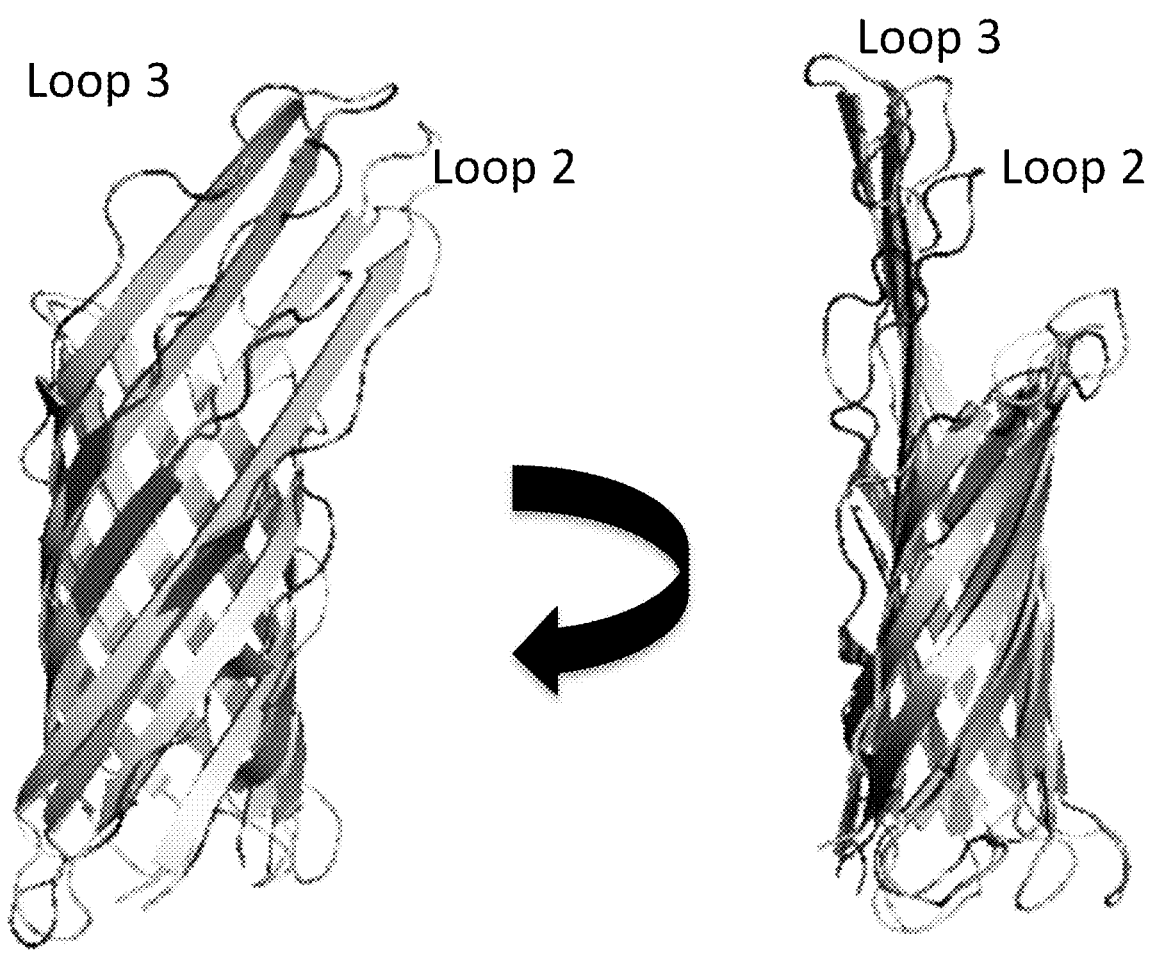
FIG. 7 depicts two views of a 3-dimensional X-ray crystallography structure (grey) of OmpX superimposed on a 3-dimensional NMR spectroscopy structure (black) of OmpX. Loops 2 and 3 are more flexible in the NMR structure than in the x-ray crystal structure; the NMR structure also reveals that the beta-strands are more dynamic and therefore represent potential sources of protease liability.

Since the CLiPS platform had been notably susceptible to protease degradation outside the substrate library site, the structure and amino acid sequences of OmpX and CLiPS was analyzed for sites to decrease the protease liability. Structural analysis highlighted Arg, Lys and Asp amino acid residues on the OmpX loops 2 and 3 that were likely above the lipopolysaccharides (LPS) of the outer membrane and therefore exposed to proteases with specificity to those residues (FIG. 6B, 6C). Inspection and overlay of the Omp structures in the protein database (RCSB Protein Data Bank, available online) provided additional anchor points above which the Omp/CLiPS transmembrane domain would be flexible and exposed to proteases (FIG. 7); this analysis also considered liabilities. Additionally, amino acid sequence analysis showed similar amino acid residues in the N-terminal and C-terminal tags.

Figure 8:
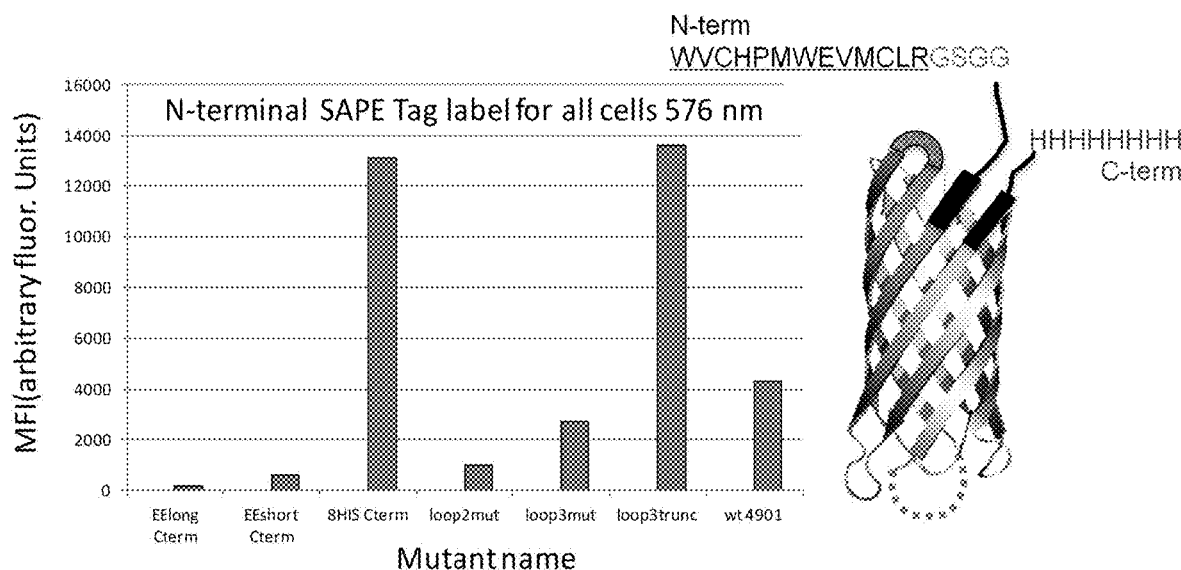
FIG. 8 is a graph and an illustration depicting the screening of various aspects of previous cellular libraries of peptide display systems. Truncating loop 3 of circularly permuted OmpX and replacing the C-terminal tag with an 8×HIS tag improved the display characteristics, while loop 2 mutations decreased overall polypeptide display.

These analyses were used to modify the CLiPS platform using standard molecular biology techniques. The fragments of OmpX loop 2, the CLiPS residues/structure leading from and to the C- and N-terminal tags and substrates, were analyzed by site-directed mutagenesis of the respective amino acids to alanine residues for decreased labeling on the bacterial surface (FIG. 8). The fragments of OmpX loop 2, the CLiPS residues/structure leading from and to the C- and N-terminal tags were converted to flexible GlyGlySer (GGS) repeat linkers (so-called "GS" flexible linkers, also referred to herein as GS linkers) compatible with the length of the replaced structures leading into the membrane buried beta-sheet structures. The GS linkers allowed the epitope tags to be labeled and also to be stable toward many proteases due to the nature of glycine-rich sequences being less protease sensitive. The OmpX loop 3 was also considered a protease liability. It was truncated, while retaining residues for the beta-sheet structure in the membrane; glycine residues and a proline residue were incorporated to stabilize the hairpin turn.

Example 3. Production of Improved Display Platforms

This Example describes the production of display platforms from which protease-labile amino acid sequences have been removed. Such display platforms are called CYTX-DP display platforms.

The plasmid comprising eCLiPS3.0-GSNS, the display platform from which CYTX-DP-GSNS, which includes an EagI restriction site at the C-terminus prior to the histidine tag and is referred to herein as "CYTX-DP-GSNS," was produced is designated pB33-GSNS1-GGS4-eCLiPS3.0 PHB4901; the amino acid sequence of eCLIPS3.0-GSNS is shown in FIG. 10 (designated N-termTag_stop_CLiPS_G-SNS). This is a CLiPS construct with the legumain "GSNS" substrate (SEQ ID NO: 10) and a SA-PE N-terminal tag and a YPET C-terminal tag; this YPET tag is designated BV99 and has amino acid sequence HISQWKPKVPNREDKYKK (SEQ ID NO: 18). After protease-labile regions of eCLiPS3.0-GSNS were identified for mutagenesis, standard molecular biology techniques were used to mutate and truncate that platform to make the CYTX-DP-GSNS display platform (i.e., a CYTX-DP platform comprising a legumain GSNS substrate). The schematic diagram in FIG. 9 shows the signal peptide of eCLiPS3.0 was kept the same along with the stop codon. The N- and C-terminal tags of CYTX-DP are smaller and different than those of eCLiPS3.0: CYTX-DP has an N-terminal Glu-Glu (EE) tag with the sequence, EYMPME (SEQ ID NO: 8) and a C-terminal 8-His tag with the sequence, HHHHHHHH (SEQ ID NO: 13).

The amino acid sequence of the CYTX-DP-GSNS platform, which includes a signal peptide (underlined) (SEQ ID NO: 6)—Linker 1 (L1) (SEQ ID NO: 7)—EE tag (SEQ ID NO: 8)—Linker 3 (L3) (SEQ ID NO: 59)—GSNS Substrate (SEQ ID NO: 10)—Linker 3 (L3) (SEQ ID NO: 11)—transmembrane region (i.e., mutated circularly permuted outer membrane protein) (SEQ ID NO: 1)—Linker 4 (L4) (SEQ ID NO: 83)—His tag (SEQ ID NO: 13)—stop codon (*), where brackets indicate the location of each of the elements, is:

(SEQ ID NO: 2)
[MKKIACLSALAAVLAFTAGTSVA][GQSGQ][EYMPME][GGSGQSGQG

S][GSNS][GSSGGQGGSGGSGGSGGSGGSA][YYGITAGPAYRINDWAS

IYGVVGVGYGSGPGGSYGFSYGAGLQFNPMENVALDFSYEQSRIRSVDVG

TWILSVGYRFGSKSRRATSTVTGGYAQSDAQGQMNKMGGFNLKYRYEEDN

SPLGVIGSFTYT][GGSGGSSGQTAAG][HHHHHHHH][*]

This CYTX-DP-GSNS platform is encoded by the following nucleic acid sequence:

(SEQ ID NO: 3)
atgaaaaaaattgcatgtctttcagcactggccgcagttctggctttcac cgcaggtacttccgtagctggtcaatctggacaggaatacatgccgatgg aaggagggtctggccagtctggccagggttctggcagcaattccggttct agcggtggccagggtggcagcggtggctctggtggttccggtggctctgg tggctctgcgtactacggcatcactgctggtccggcttaccgcattaacg actgggcaagcatctacggtgtagtgggtgtgggttatggttctggcccg ggtggttcttacggtttctcctacggtgcgggtctgcagttcaacccgat ggaaaacgttgctctggacttctcttacgagcagagccgtattcgtagcg ttgacgtaggcacctggattctgtccgttggttaccgcttcggctccaaa tcccgccgtgcgacttctactgtaactggcggttacgcacagagcgacgc tcagggccaaatgaacaaaatgggcggtttcaacctgaaataccgctatg aagaagacaacagcccgctgggtgtgatcggttctttcacttacaccggc ggctctggtggttctagcggtcaaacggccgctggtcaccatcaccacca tcatcaccactaa Another suitable CYTX-DP platform is a variant of the CYTX-DP-GSNS platform, where the EagI restriction site is replaced with a NotI restrictions site. This version, referred to herein as "CYTX-DP-GSNS (NotI)" includes a signal peptide (underlined) (SEQ ID NO: 6)—Linker 1 (L1) (SEQ ID NO: 7)—EE tag (SEQ ID NO: 8)—Linker 3 (L3) (SEQ ID NO: 59)—GSNS Substrate (SEQ ID NO: 10)—Linker 3 (L3) (SEQ ID NO: 11)—transmembrane region (i.e., mutated circularly permuted outer membrane protein) (SEQ ID NO: 1)—Linker 4 (L4) (SEQ ID NO: 12)—His tag (SEQ ID NO: 13)—stop codon (*), where brackets indicate the location of each of the elements, is:

(SEQ ID NO: 60)

[MKKIACLSALAAVLAFTAGTSVA][GQSGQ][EYMPME][GGSGQSGQG

S][GSNS][GSSGGQGGSGGSGGSGGSGGSA][YYGITAGPAYRINDWAS

IYGVVGVGYGSGPGGSYGFSYGAGLQFNPMENVALDFSYEQSRIRSVDVG

-continued

TWILSVGYRFGSKSRRATSTVTGGYAQSDAQGQMNKMGGFNLKYRYEEDN

SPLGVIGSFTYT][GGSGGSSGQAAAG][HHHHHHHH][*]

The mature CYTX-DP-GSNS platform (i.e., lacking the signal sequence) has the following amino acid sequence (Linker 1 (L1) (SEQ ID NO: 7)—EE tag (SEQ ID NO: 8)—Linker 3 (L3) (SEQ ID NO: 59)—GSNS Substrate (SEQ ID NO: 10)—Linker 3 (L3) (SEQ ID NO: 11)—transmembrane region (i.e., mutated circularly permuted outer membrane protein) (SEQ ID NO: 1)—Linker 4 (L4) (SEQ ID NO: 83)—His tag (SEQ ID NO: 13)—stop codon (*), where brackets indicate the location of each of the elements):

(SEQ ID NO: 4)

[GQSGQ][EYMPME][GGSGQSGQGS][GSNS][GSSGGQGGSGGSGGSG

GSGGSA][YYGITAGPAYRINDWASIYGVVGVGYGSGPGGSYGFSYGAGL

QFNPMENVALDFSYEQSRIRSVDVGTWILSVGYRFGSKSRRATSTVTGGY

AQSDAQGQMNKMGGFNLKYRYEEDNSPLGVIGSFTYT][GGSGGSSGQTA

AG][HHHHHHHH][*]

The mature CYTX-DP-GSNS platform is encoded by the following nucleic acid sequence:

(SEQ ID NO: 5)

ggtcaatctggacaggaatacatgccgatggaaggagggtctggccagtc tggccagggttctggcagcaattccggttctagcggtggccagggtggca gcggtggctctggtggttccggtggctctggtggctctgcgtactacggc atcactgctggtccggcttaccgcattaacgactgggcaagcatctacgg tgtagtgggtgtgggttatggttctggcccgggtggttcttacggtttct cctacggtgcgggtctgcagttcaacccgatggaaaacgttgctctggac ttctcttacgagcagagccgtattcgtagcgttgacgtaggcacctggat tctgtccgttggttaccgcttcggctccaaatcccgccgtgcgacttcta ctgtaactggcggttacgcacagagcgacgctcagggccaaatgaacaaa atgggcggtttcaacctgaaataccgctatgaagaagacaacagcccgct gggtgtgatcggttctttcacttacaccggcggctctggtggttctagcg gtcaaacggccgctggtcaccatcaccaccatcatcaccactaa Another suitable mature CYTX-DP platform is a variant of the mature CYTX-DP-GSNS platform, where the EagI restriction site is replaced with a NotI restrictions site. This version, referred to herein as "mature CYTX-DP-GSNS (NotI)" includes Linker 1 (L1) (SEQ ID NO: 7)—EE tag (SEQ ID NO: 8)—Linker 3 (L3) (SEQ ID NO: 59)—GSNS Substrate (SEQ ID NO: 10)—Linker 3 (L3) (SEQ ID NO: 11)—transmembrane region (i.e., mutated circularly permuted outer membrane protein) (SEQ ID NO: 1)—Linker 4 (L4) (SEQ ID NO: 12)—His tag (SEQ ID NO: 13)—stop codon (*), where brackets indicate the location of each of the elements, is:

(SEQ ID NO: 58)

[GQSGQ][EYMPME][GGSGQSGQGS][GSNS][GSSGGQGGSGGSGGSG

GSGGSA][YYGITAGPAYRINDWASIYGVVGVGYGSGPGGSYGFSYGAGL

QFNPMENVALDFSYEQSRIRSVDVGTWILSVGYRFGSKSRRATSTVTGGY

-continued

AQSDAQGQMNKMGGFNLKYRYEEDNSPLGVIGSFTYT][GGSGGSSGQAA
AG][HHHHHHHH][*]

FIG. 10 demonstrates alignment of nucleic acid sequences encoding the described CYTX-DP-GSNS display platform (upper rows) and eCLiPS3.0-GSNS display platform (lower rows). The two nucleic acid sequences are 74.7% identical. FIG. 11 demonstrates alignment of the amino acid sequences of the described CYTX-DP-GSNS display platform (upper rows) and eCLiPS3.0-GSNS display platform (lower rows). The two amino acid sequences are 71.2% identical.

FIGS. 23-25 and FIGS. 29-31 are schematic representations of the amino acid sequence and structural arrangement of various embodiments of display platforms according to the present invention.

In some embodiments, the nucleotide sequence encoding the C-terminus of CYTX-CP is modified at the EagI/NotI restriction site before the nucleotide sequence encoding the 8×His tag to substitute a nucleotide sequence encoding one of the following C-termini incorporating the His tag: EagI variant (TAAGHHHHHHHH*) (SEQ ID NO: 53), or NotI variant (AAAGHHHHHHHH*) (SEQ ID NO: 54). In one embodiment a nucleotide sequence encoding a TLA-TAIL is substituted into a nucleotide sequence encoding a scFv-containing DP at the NotI restriction site near the C-terminus to encode a TLA-TAIL His tag (AAAGE-IVLTQSPGTLVTVSSHHHHHHHH*) (SEQ ID NO: 55); such a tag can lead to enhanced labeling.

Example 4. Characterization of Substrate Cleavage Kinetics in CLiPS and CYTX-DP Scaffolds This Example compares the ability of a protease to cleave its substrate in CYTX-DP display platform versus in a CLiPS display platform.

Cultures of clones, each comprising a plasmid encoding CYTX-DP-1203 (i.e., a CYTX-DP platform comprising substrate 1203, depicted in FIG. 30), CYTX-DP-1204 (depicted in FIG. 31), eCLiPS3.0-1203 (depicted in FIG. 27), or eCLiPS3.0-1204 (depicted in FIG. 28), respectively, were grown and exposed to uPA protease under the conditions described in the Examples herein. Relative cleavage kinetics of the substrates in the various platforms was assessed using flow cytometry. The individual clones exhibited uniform substrate turnover, as determined by flow cytometry. In this way, the extent of conversion for each clone could be determined at several different protease concentrations and fit to a Michaelis-Menton model (see Kinetic Data Analysis section in Example 1). FIG. 13 demonstrates that the observed second order rate constant ($k_{cat}/K_M$) for each substrate was comparable across both the CLiPS and CYTX-DP platforms. Background hydrolysis of the regions flanking the substrate site (using eCLiPS3.0-NSUB (depicted in FIG. 26) and CYTX-DP-NSUB (depicted in FIG. 29)), was measured under each reaction condition to ensure that hydrolysis occurred in the designated substrate region.

Example 5. Protease Resistance of the CLiPS and CYTX-DP Display Platforms

This Example compares the stability of the CYTX-DP and CLiPS display platforms in the presence of the protease plasmin.

Cultures of clones, each comprising a plasmid encoding CYTX-DP-NSUB or eCLiPS3.0-NSUB, were grown and exposed to plasmin under the conditions described in the Examples herein. Loss of either the N-terminal or C-terminal affinity tag from either display platform resulted in a reduction of the mean fluorescence intensity, which was assessed by flow cytometry. Conversion of each platform to a platform lacking either the N-terminal or C-terminal affinity tag was then determined (see Kinetic Data Analysis section herein). Loss of either affinity tag due to protease cleavage in the non-substrate region would be detrimental to the ability to screen libraries in the presence of human plasmin. Both the N-terminal and C-terminal affinity tags of CYTX-DP showed increased resistance over CLiPS in the presence of human plasmin, as shown in FIGS. 14A, 14B. The significantly greater stabilities exhibited by CYTX-DP over CLiPS improves the ability to select substrates from CYTX-DP substrate libraries. In addition, the 52-fold greater stability of the N-terminus in CYTX-DP allows the characterization of substrate resistance against undesirable proteases (e.g., proteases in serum or at an off-target site) at substantially higher protease concentrations.

Example 6. Improved Resistance of the CYTX-DP Display Platform in the Presence of Synovial Fluid This Example shows the improved stability of CYTX-DP against a complex mixture expected to contain a spectrum of proteases.

Cultures of clones, each comprising a plasmid encoding CYTX-DP-NSUB or eCLiPS3.0-NSUB, were grown and exposed to human synovial fluid samples under the conditions described in the Examples herein. Synovial fluid was expected to have a wide range of protease species at varying concentrations. Loss of either the N-terminal or C-terminal affinity tag from either display platform resulted in a reduction of the mean fluorescence intensity, which was assessed by flow cytometry. Loss of either affinity tag due to protease cleavage in the non-substrate region would be detrimental to the ability to screen libraries in the presence of synovial fluid. FIG. 15 demonstrates that the N-terminal affinity tag of CYTX-DP shows increased resistance over that of CLiPS in the presence of synovial fluid during a 1 hr incubation at 37° C.

Example 7. Characterization of scFv Expressed at the C-Terminus of CYTX-DP

The use of a multi-copy display on whole cells enabled simple and direct quantitation of expression on the bacterial cell surface. Plasmids encoding scFv F5 or scFv OKT3 fused to CYTX-DP at the C-terminus before the C-terminal 8×His epitope tag (referred to as display platform CYTX-DP-scFvF5-Cterm, or CYTX-DP-scFvOKT3-Cterm, respectively) were expressed in *E. coli* DH-10β overnight with induction started from a 1/20-1/50 dilution of a nearly saturated culture. The sequences for the F5 scFv and OKT3 scFv are shown below:

F5 scFv amino acid sequence:
(SEQ ID NO: 44)
QVQLVESGGGLVQPGGSLRLSCAASGFTFRSYAMSWVRQAPGKGLEWVSA

ISGRGDNTYYADSVKGRFTISRDNSKNTLYLQMNSLRAEDTAVYYCAKMT

SNAFAFDYWGQGTLVTVSSGGGGSGGGGSGGGGSQSVLTQPPSVSGAPGQ

RVTISYTGSSSNIGAGYGVHWYQQLPGTAPKLLIYGNTNRPSQVPDRFSG

-continued
FKSGTSASLAITGLQAEDEADYYCQSYDSSLSQWVFGGGTKLTVLGAAAE

QKLISEEDLNGAA

OKT3 scFv amino acid sequence:
(SEQ ID NO: 45)
QVQLQQSGAELARPGASVKMSCKASGYTFTRYTMHWVKQRPGQGLEWIGY

INPSRGYTNYNQKFKDKATLTTDKSSTAYMQLSSLTSEDSAVYYCARYY

DDHYCLDYWGQGTTLTVSSGGGGSGGGGSGGGGSQIVLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTFGSGTKLEINRADTAPTVSI

KLISEEDLNGAA

The following CYTX-DP platforms were used in the methods described herein. In some embodiments, the CYTX-DP platform includes a signal peptide ("SS"). In some embodiments, the CYTX-DP platform is a mature version, which does not include a signal peptide. These embodiments are referred to herein as "mature CYTX-DP platforms."

In some embodiments, the scFv was expressed at the C-terminus of the CYTX-DP platform. These embodiments are referred to herein as "C-terminal CYTX-DP Platforms" and include the following structural arrangement from N-terminus to C-terminus: SS-T1-L1-CP-scFv-L2-T2.

In some embodiments, the scFv was expressed at the N-terminus of the CYTX-DP platform. These embodiments are referred to herein as "N-terminal CYTX-DP Platforms" and include the following structural arrangement from N-terminus to C-terminus: (SS-T1-L1-scFv-CP-L2-T2). In some embodiments, the scFv was expressed at the N-terminus of the CYTX-DP platform, and the C-terminus included a tail sequence ("TAIL"). These embodiments are referred to herein as "N-terminal scFv, C-terminal Tail CYTX-DP Platforms" and include the following structural arrangement from N-terminus to C-terminus: (SS-T1-L1-scFv-CP-L2-TAIL-T2).

C-terminal CYTX-DP Platforms with Signal
Sequence (SS-T1-L1-CP-scFv-L2-T2):
F5 C-terminal CYTX-DP platform (SS-T1-L1-
CP-F5scFv-L2-T2)
(SEQ ID NO: 62)
MKKIACLSALAAVLAFTAGTSVAGQSGQEYMPMEGGSGQSGQGSGSNSGS

SGGQGGSGGSGGSGGSGGSAYYGITAGPAYRINDWASIYGVVGVGYGSGP

GGSYGFSYGAGLQFNPMENVALDFSYEQSRIRSVDVGTWILSVGYRFGSK

SRRATSTVTGGYAQSDAQGQMNKMGGFNLKYRYEEDNSPLGVIGSFTYTG

GSGGSSGQAAAGQVQLVESGGGLVQPGGSLRLSCAASGFTFRSYAMSWVR

QAPGKGLEWVSAISGRGDNTYYADSVKGRFTISRDNSKNTLYLQMNSLRA

EDTAVYYCAKMTSNAFAFDYWGQGTLVTVSSGGGGSGGGGSGGGGSQSVL

TQPPSVSGAPGQRVTISYTGSSSNIGAGYGVHWYQQLPGTAPKLLIYGNT

NRPSQVPDRFSGFKSGTSASLAITGLQAEDEADYYCQSYDSSLSQWVFGG

GTKLTVLGAAAEQKLISEEDLNGAAHHHHHH*

OKT3 C-terminal CYTX-DP platform (SS-T1-L1-
CP-OKT3scFv-L2-T2)
(SEQ ID NO: 63)
MKKIACLSALAAVLAFTAGTSVAGQSGQEYMPMEGGSGQSGQGSGSNSGS -continued
SGGQGGSGGSGGSGGSGGSAYYGITAGPAYRINDWASIYGVVGVGYGSGP

GGSYGFSYGAGLQFNPMENVALDFSYEQSRIRSVDVGTWILSVGYRFGSK

SRRATSTVTGGYAQSDAQGQMNKMGGFNLKYRYEEDNSPLGVIGSFTYTG

GSGGSSGQAAAGQVQLQQSGAELARPGASVKMSCKASGYTFTRYTMHWVK

QRPGQGLEWIGYINPSRGYTNYNQKFKDKATLTTDKSSTAYMQLSSLTS

EDSAVYYCARYYDDHYCLDYWGQGTTLTVSSGGGGSGGGGSGGGGSQIVL

TQSPAIMSASPGEKVTMTCSASSSVSYMNWYQQKSGTSPKRWIYDTSKLA

SGVPAHFRGSGSGTSYSLTISGMEAEDAATYYCQQWSSNPFTFGSGTKLE

INRADTAPTVSIKLISEEDLNGAAHHHHHH*

N-terminal CYTX-DP Platforms with Signal
Sequence (SS-T1-L1-scFv-CP-L2-T2):
F5 N-terminal CYTX-DP platform (SS-T1-L1-
F5scFv-CP-L2-T2)
(SEQ ID NO: 64)
MKKIACLSALAAVLAFTAGTSVAGQSGQEYMPMEGGSGQSGGQVQLVESG

GGLVQPGGSLRLSCAASGFTFRSYAMSWVRQAPGKGLEWVSAISGRGDNT

YYADSVKGRFTISRDNSKNTLYLQMNSLRAEDTAVYYCAKMTSNAFAFDY

WGQGTLVTVSSGGGGSGGGGSGGGGSQSVLTQPPSVSGAPGQRVTISYTG

SSSNIGAGYGVHWYQQLPGTAPKLLIYGNTNRPSQVPDRFSGFKSGTSAS

LAITGLQAEDEADYYCQSYDSSLSQWVFGGGTKLTVLGAAAEQKLISEED

LNGSGGQGGSGGSGGSGGSGGSAYYGITAGPAYRINDWASIYGVVGVGYG

SGPGGSYGFSYGAGLQFNPMENVALDFSYEQSRIRSVDVGTWILSVGYRF

GSKSRRATSTVTGGYAQSDAQGQMNKMGGFNLKYRYEEDNSPLGVIGSFT

YTGGSGGSSGQTAAGHHHHHHHH*

OKT3 N-terminal CYTX-DP platform
(SS-T1-L1-OKT3scFv-CP-L2-T2)
(SEQ ID NO: 65)
MKKIACLSALAAVLAFTAGTSVAGQSGQEYMPMEGGSGQSGGQVQLQQSG

AELARPGASVKMSCKASGYTFTRYTMHWVKQRPGQGLEWIGYINPSRGYT

NYNQKFKDKATLTTDKSSTAYMQLSSLTSEDSAVYYCARYYDDHYCLDY

WGQGTTLTVSSGGGGSGGGGSGGGGSQIVLTQSPAIMSASPGEKVTMTCS

ASSSVSYMNWYQQKSGTSPKRWIYDTSKLASGVPAHFRGSGSGTSYSLTI

SGMEAEDAATYYCQQWSSNPFTFGSGTKLEINRADTAPTVSIKLISEEDL

NGSGGQGGSGGSGGSGGSGGSAYYGITAGPAYRINDWASIYGVVGVGYGS

GPGGSYGFSYGAGLQFNPMENVALDFSYEQSRIRSVDVGTWILSVGYRFG

SKSRRATSTVTGGYAQSDAQGQMNKMGGFNLKYRYEEDNSPLGVIGSFTY

TGGSGGSSGQTAAGHHHHHHHH*

N-terminal scFv, C-terminal Tail CYTX-DP
Platforms with Signal Sequence (SS-T1-L1-
scFv-CP-L2-TAIL-T2):
F5 N-terminal scFv, C-terminal Tail CYTX-DP
platform (SS-T1-L1-F5scFv-CP-L2-TAIL-T2)
(SEQ ID NO: 66)
MKKIACLSALAAVLAFTAGTSVAGQSGQEYMPMEGGSGQSGGQVQLVESG

GGLVQPGGSLRLSCAASGFTFRSYAMSWVRQAPGKGLEWVSAISGRGDNT

YYADSVKGRFTISRDNSKNTLYLQMNSLRAEDTAVYYCAKMTSNAFAFDY

WGQGTLVTVSSGGGGSGGGGSGGGGSQSVLTQPPSVSGAPGQRVTISYTG

SSSNIGAGYGVHWYQQLPGTAPKLLIYGNTNRPSQVPDRFSGFKSGTSAS

LAITGLQAEDEADYYCQSYDSSLSQWVFGGGTKLTVLGAAAEQKLISEED
LNGSGGQGGSGGSGGSGGSGGSAYYGITAGPAYRINDWASIYGVVGVGYG
SGPGGSYGFSYGAGLQFNPMENVALDFSYEQSRIRSVDVGTWILSVGYRF
GSKSRRATSTVTGGYAQSDAQGQMNKMGGFNLKYRYEEDNSPLGVIGSFT
YTGGSGGSSGQAAAGEIVLTQSPGTLVTVSSHHHHHHHH*

Mature C-terminal CYTX-DP Platforms
(T1-L1-CP-scFv-L2-T2):
Mature F5 C-terminal CYTX-DP platform
(T1-L1-CP-F5scFv-L2-T2)

(SEQ ID NO: 67)

GQSGQEYMPMEGGSGQSGQGSGSNSGSSGGQGGSGGSGGSGGSGGSAYYG

ITAGPAYRINDWASIYGVVGVGYGSGPGGSYGFSYGAGLQFNPMENVALD

FSYEQSRIRSVDVGTWILSVGYRFGSKSRRATSTVTGGYAQSDAQGQMNK

MGGFNLKYRYEEDNSPLGVIGSFTYTGGSGGSSGQAAAGQVQLVESGGGL

VQPGGSLRLSCAASGFTFRSYAMSWVRQAPGKGLEWVSAISGRGDNTYYA

DSVKGRFTISRDNSKNTLYLQMNSLRAEDTAVYYCAKMTSNAFAFDYWGQ

GTLVTVSSGGGGSGGGGSGGGGSQSVLTQPPSVSGAPGQRVTISYTGSSS

NIGAGYGVHWYQQLPGTAPKLLIYGNTNRPSQVPDRFSGFKSGTSASLAI

TGLQAEDEADYYCQSYDSSLSQWVFGGGTKLTVLGAAAEQKLISEEDLNG

AAHHHHHH*

Mature OKT3 C-terminal CYTX-DP platform
(T1-L1-CP-OKT3scFv-L2-T2)

(SEQ ID NO: 68)

GQSGQEYMPMEGGSGQSGQGSGSNSGSSGGQGGSGGSGGSGGSGGSAYYG

ITAGPAYRINDWASIYGVVGVGYGSGPGGSYGFSYGAGLQFNPMENVALD

FSYEQSRIRSVDVGTWILSVGYRFGSKSRRATSTVTGGYAQSDAQGQMNK

MGGFNLKYRYEEDNSPLGVIGSFTYTGGSGGSSGQAAAGQVQLQQSGAEL

ARPGASVKMSCKASGYTFTRYTMHWVKQRPGQGLEWIGYINPSRGYTNYN

QKFKDKATLTTDKSSSTAYMQLSSLTSEDSAVYYCARYYDDHYCLDYWGQ

GTTLTVSSGGGGSGGGGSGGGGSQIVLTQSPAIMSASPGEKVTMTCSASS

SVSYMNWYQQKSGTSPKRWIYDTSKLASGVPAHFRGSGSGTSYSLTISGM

EAEDAATYYCQQWSSNPFTFGSGTKLEINRADTAPTVSIKLISEEDLNGA

AHHHHHH*

Mature N-terminal CYTX-DP Platforms
(T1-L1-scFv-CP-L2-T2):
Mature F5 N-terminal CYTX-DP platform
(T1-L1-F5scFv-CP-L2-T2)

(SEQ ID NO: 69)

GQSGQEYMPMEGGSGQSGGQVQLVESGGGLVQPGGSLRLSCAASGFTFRS

YAMSWVRQAPGKGLEWVSAISGRGDNTYYADSVKGRFTISRDNSKNTLYL

QMNSLRAEDTAVYYCAKMTSNAFAFDYWGQGTLVTVSSGGGGSGGGGSGG

GGSQSVLTQPPSVSGAPGQRVTISYTGSSSNIGAGYGVHWYQQLPGTAPK

LLIYGNTNRPSQVPDRFSGFKSGTSASLAITGLQAEDEADYYCQSYDSSL

SQWVFGGGTKLTVLGAAAEQKLISEEDLNGSGGQGGSGGSGGSGGSGGSA

YYGITAGPAYRINDWASIYGVVGVGYGSGPGGSYGFSYGAGLQFNPMENV

-continued

ALDFSYEQSRIRSVDVGTWILSVGYRFGSKSRRATSTVTGGYAQSDAQGQ

MNKMGGFNLKYRYEEDNSPLGVIGSFTYTGGSGGSSGQTAAGHHHHHHH

H*

Mature OKT3 N-terminal CYTX-DP platform
(T1-L1-OKT3scFv-CP-L2-T2)

(SEQ ID NO: 70)

GQSGQEYMPMEGGSGQSGGQVQLQQSGAELARPGASVKMSCKASGYTFTR

YTMHWVKQRPGQGLEWIGYINPSRGYTNYNQKFKDKATLTTDKSSSTAYM

QLSSLTSEDSAVYYCARYYDDHYCLDYWGQGTTLTVSSGGGGSGGGGSGG

GGSQIVLTQSPAIMSASPGEKVTMTCSASSSVSYMNWYQQKSGTSPKRWI

YDTSKLASGVPAHFRGSGSGTSYSLTISGMEAEDAATYYCQQWSSNPFTF

GSGTKLEINRADTAPTVSIKLISEEDLNGSGGQGGSGGSGGSGGSGGSAY

YGITAGPAYRINDWASIYGVVGVGYGSGPGGSYGFSYGAGLQFNPMENVA

LDFSYEQSRIRSVDVGTWILSVGYRFGSKSRRATSTVTGGYAQSDAQGQM

NKMGGFNLKYRYEEDNSPLGVIGSFTYTGGSGGSSGQTAAGHHHHHHHH*

Mature N-terminal scFv, C-terminal Tail
CYTX-DP Platforms (T1-L1-scFv-CP-L2-TAIL-
T2):
Mature N-terminal scFv, C-terminal Tail
F5 CYTX-DP platform (T1-L1-F5scFv-CP-L2-
T2)

(SEQ ID NO: 71)

GQSGQEYMPMEGGSGQSGGQVQLVESGGGLVQPGGSLRLSCAASGFTFRS

YAMSWVRQAPGKGLEWVSAISGRGDNTYYADSVKGRFTISRDNSKNTLYL

QMNSLRAEDTAVYYCAKMTSNAFAFDYWGQGTLVTVSSGGGGSGGGGSGG

GGSQSVLTQPPSVSGAPGQRVTISYTGSSSNIGAGYGVHWYQQLPGTAPK

LLIYGNTNRPSQVPDRFSGFKSGTSASLAITGLQAEDEADYYCQSYDSSL

SQWVFGGGTKLTVLGAAAEQKLISEEDLNGSGGQGGSGGSGGSGGSGGSA

YYGITAGPAYRINDWASIYGVVGVGYGSGPGGSYGFSYGAGLQFNPMENV

ALDFSYEQSRIRSVDVGTWILSVGYRFGSKSRRATSTVTGGYAQSDAQGQ

MNKMGGFNLKYRYEEDNSPLGVIGSFTYTGGSGGSSGQAAAGEIVLTQSP

GTLVTVSSHHHHHHHH*

Expression was induced with 0.01% arabinose or suppressed with 0.2% glucose for >12 hours at 28° C. with vigorous shaking after which cells were put on ice for 1 hour. The OD600 for each culture was measured and samples were normalized for cells to OD600 of 0.5 for 50 uL of cells per labeling or binding experiment. Cells were washed with 1 ml PBS (phosphates buffered saline) at 4° C. and centrifuged at 3500×g for 5 min at 4° C. Labeling was done at 1/500 N-terminal epitope tag label (anti-EE 647 label) or 1/100 C-terminal epitope tag label (anti-poly-His 488 label) with 0.1% BSA for 1 hour on ice. Cells were centrifuged at 3500×g for 5 minutes and supernatant aspirated. Prior to flow cytometry (FACSAria) analysis, cells were re-suspended in 0.3 to 0.5 mL ice cold PBS. Based on unlabeled cells being in the lower left quadrant on a log-scale, cells were determined to be expressing scFv and labeling when shifted above the 'dark' population by 1-2 log shift in fluorescence intensity. The suppressed cell population had slightly different characteristics due to the changes in cell populations shape and size, where gating for both the suppressed and induced population improved selection of labeled populations. Overall, both CYTX-DP-scFvF5-

Cterm and CYTX-DP-scFvOKT3-Cterm expressed at levels from 2.8- to 9-fold over un-induced or suppressed cells, when labeled with the tags at either the N- or C-terminus, as shown in FIG. 16.

Example 8. Characterization of scFv Expressed on the N- or C-Terminus of CYTX-DP The use of a multi-copy display on whole cells enabled simple and direct quantitation of expression on the bacterial cell surface. Plasmids encoding scFv F5 or scFv OKT3 fused to CYTX-DP at either the C-terminus before the C-terminal 8×His epitope tag (CYTX-DP-scFvF5-Cterm, or CYTX-DP-scFvOKT3-Cterm, respectively) or at the N-terminus after the N-terminal EE epitope tag (CYTX-DP-scFvF5-Nterm or CYTX-DP-scFvOKT3-Nterm, respectively) were expressed in *E. coli* DH-10β overnight with induction started from a 1/20-1/50 dilution of a nearly saturated culture. Expression was induced with 0.01% arabinose or suppressed with 0.2% glucose for >12 hours at 28° C. with vigorous shaking after which cells were put on ice for 1 hour. The OD600 for each culture was measured and samples were normalized for cells to OD600 of 0.5 for 50 uL of cells per labeling or binding experiment. Cells were washed with 1 ml PBS (phosphates buffered saline) at 4° C. and centrifuged at 3500×g for 5 min at 4° C. Labeling was done at 1/500 N-terminal epitope tag label (anti-EE 647 label) with 0.1% BSA for 1 hour on ice. Cells were centrifuged at 3500×g for 5 minutes and supernatant aspirated. Prior to flow cytometry (FACSAria) analysis, cells were re-suspended in 0.3 to 0.5 mL ice cold PBS. Based on unlabeled cells being in the lower left quadrant on a bi-log-scale dot plot, cells were determined to be expressing scFv and labeling at the N-terminal EE epitope tag with anti-EE mIgG1-AlexaFluor647 when shifted above the 'dark' population by 1-2 log shift in fluorescence intensity (arbitrary units). The suppressed cell population had slightly different characteristics due to the changes in cell populations' shape and size, where gating for both the suppressed and induced population improved selection of labeled populations. FIG. 17 demonstrates that F5 scFv expressed and labeled 4-fold over un-induced cells as the N-terminal fusion with CYTX-DP (CYTX-DP-scFvF5-Nterm) and 14-fold over un-induced as the C-terminal fusion with CYTX-DP (CYTX-DP-scFvF5-Cterm); OKT3 scFv expressed 8-fold over un-induced cells for both the N-terminal and C-terminal fusions with CYTX-DP (CYTX-DP-scFvOKT3-Nterm and CYTX-DP-scFvOKT3-Cterm, respectively). In summary, scFvs expressed as fusions with CYTX-DP at either the N-terminus or the C-terminus and labeled at the N-terminal epitope tag.

Example 9. Characterization of scFv Expression and Antigen Binding when scFv is Fused at the N-Terminus of CYTX-DPs The use of a multi-copy display on whole cells enabled simple and direct quantitation of expression and antigen binding on the bacterial cell surface. Plasmids encoding scFv F5 or anti-CTLA-4 clone 2 fused to CYTX-DP at the N-terminus after the N-terminal EE epitope tag display platforms CYTX-DP-scFvF5-Nterm or CYTX-DP-anti-CTLA4-Nterm, respectively). were expressed in *E. coli* DH-10β or *E. coli* C41(DE3) overnight with induction started from a 1/20 dilution of a nearly saturated culture. The sequence for the F5 scFv is shown above in SEQ ID NO: 44. The sequence for the anti-CTLA-4 clone 2 scFv is shown below:

```
Anti-CTLA-4 clone 2 scFv amino acid sequence:
                                        (SEQ ID NO: 46)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPLTFG

GGTKVEIKRSGGSTITSYNVYYTKLSSSGTQVQLVQTGGGVVQPGRSLRL

SCAASGSTFSSYAMSWVRQAPGKGLEWVSAISGSGGSTYYADSVKGRFTI

SRDNSKNTLYLQMNSLRAEDTAVYYCATNSLYWYFDLWGRGTLVTVSSAS
```

An additional scFv sequence characterized using these methods includes the following anti-gp130 scFv sequence:

```
Anti-gp130 amino acid Sequence (Hv - L - Lv)
                                        (SEQ ID NO: 72)
EVQLLESGGGLVQPGGSLRLSCAASGFTFSSYAMSWVRQAPGKGLEWVSS

IGSRGQNTRYADSVKGRFTISRDNSKNTLYLQMNSLRAEDTAVYYCAKII

STFDYWGQGTLVTVSSGGGGSGGGGSGGGGSTDIQMTQSPSSLSASVGDR

VTITCRASQSISSYLNWYQQKPGKAPKLLIYDASRLQSGVPSRFSGSGSG

TDFTLTISSLQPEDFATYYCQQQETMPPTFGQGTKVEIKR
```

The following CYTX-DP platforms were used in the methods described herein. In some embodiments, the CYTX-DP platform includes a signal peptide ("SS"). In some embodiments, the CYTX-DP platform is a mature version, which does not include a signal peptide. These embodiments are referred to herein as "mature CYTX-DP platforms."

In some embodiments, the scFv was expressed at the N-terminus of the CYTX-DP platform. These embodiments are referred to herein as "N-terminal CYTX-DP Platforms" and include the following structural arrangement from N-terminus to C-terminus: (SS-T1-L1-scFv-CP-L2-T2). In some embodiments, the scFv was expressed at the N-terminus of the CYTX-DP platform, and the C-terminus included a tail sequence ("TAIL"). These embodiments are referred to herein as "N-terminal scFv, C-terminal Tail CYTX-DP Platforms" and include the following structural arrangement from N-terminus to C-terminus: (SS-T1-L1-scFv-CP-L2-TAIL-T2).

```
N-terminal CYTX-DP Platforms with Signal
Sequence (SS-T1-L1-scFv-CP-L2-T2):
anti-CTLA-4 N-terminal CYTX-DP platform
(SS-T1-L1-CTLA-4scFv-CP-L2-T2)
                                        (SEQ ID NO: 73)
MKKIACLSALAAVLAFTAGTSVAGQSGQEYMPMEGGSGQSGGEIVLTQSP

GTLSLSPGERATLSCRASQSVSSSYLAWYQQKPGQAPRLLIYGASSRATG

IPDRFSGSGSGTDFTLTISRLEPEDFAVYYCQQYGSSPLTFGGGTKVEIK

RSGGSTITSYNVYYTKLSSSGTQVQLVQTGGGVVQPGRSLRLSCAASGST

FSSYAMSWVRQAPGKGLEWVSAISGSGGSTYYADSVKGRFTISRDNSKNT

LYLQMNSLRAEDTAVYYCATNSLYWYFDLWGRATLVTVSSASGSGGQGGS

GGSGGSGGSGGSAYYGITAGPAYRINDWASIYGVVGVGYGSGPGGSYGFS

YGAGLQFNPMENVALDFSYEQSRIRSVDVGTWILSVGYRFGSKSRRATST
```

-continued
VTGGYAQSDAQGQMNKMGGFNLKYRYEEDNSPLGVIGSFTYTGGSGGSSG

QTAAGHHHHHHHH* anti-gp130 N-terminal CYTX-DP platform
(SS-T1-L1-gp130scFv-CP-L2-T2)
(SEQ ID NO: 74)
MKKIACLSALAAVLAFTAGTSVAGQSGQEYMPMEGGSGQSGGEVQLLESG

GGLVQPGGSLRLSCAASGFTFSSYAMSWVRQAPGKGLEWVSSIGSRGQNT

RYADSVKGRFTISRDNSKNTLYLQMNSLRAEDTAVYYCAKIISTFDYWGQ

GTLVTVSSGGGGSGGGGSGGGGSTDIQMTQSPSSLSASVGDRVTITCRAS

QSISSYLNWYQQKPGKAPKLLIYDASRLQSGVPSRFSGSGSGTDFTLTIS

SLQPEDFATYYCQQQETMPPTFGQGTKVEIKRSGGQGGSGGSGGSGGSG

GSAYYGITAGPAYRINDWASIYGVVGVGYGSGPGGSYGFSYAGLQFNPM

ENVALDFSYEQSRIRSVDVGTWILSVGYRFGSKSRRATSTVTGGYAQSDA

QGQMNKMGGFNLKYRYEEDNSPLGVIGSFTYTGGSGGSSGQTAAGHHHHH

HHH*

N-terminal scFv, C-terminal Tail CYTX-DP
Platforms with Signal Sequence (SS-T1-L1-
scFv-CP-L2-TAIL-T2):
anti-CTLA-4 CYTX-DP platform (SS-T1-L1-
CTLA-4scFv-CP-L2-TAIL-T2)
(SEQ ID NO: 75)
MKKIACLSALAAVLAFTAGTSVAGQSGQEYMPMEGGSGQSGGEIVLTQSP

GTLSLSPGERATLSCRASQSVSSSYLAWYQQKPGQAPRLLIYGASSRATG

IPDRFSGSGSGTDFTLTISRLEPEDFAVYYCQQYGSSPLTFGGGTKVEIK

RSGGSTITSYNVYYTKLSSSGTQVQLVQTGGGVVQPGRSLRLSCAASGST

FSSYAMSWVRQAPGKGLEWVSAISGSGGSTYYADSVKGRFTISRDNSKNT

LYLQMNSLRAEDTAVYYCATNSLYWYFDLWGRATLVTVSSASGSGGQGGS

GGSGGSGGSGGSAYYGITAGPAYRINDWASIYGVVGVGYGSGPGGSYGFS

YGAGLQFNPMENVALDFSYEQSRIRSVDVGTWILSVGYRFGSKSRRATST

VTGGYAQSDAQGQMNKMGGFNLKYRYEEDNSPLGVIGSFTYTGGSGGSSG

QAAAGEIVLTQSPGTLVTVSSHHHHHHHH* anti-gp130 CYTX-DP platform
(SS-T1-L1-gp130scFv-CP-L2-TAIL-T2)
(SEQ ID NO: 76)
MKKIACLSALAAVLAFTAGTSVAGQSGQEYMPMEGGSGQSGGEVQLLESG

GGLVQPGGSLRLSCAASGFTFSSYAMSWVRQAPGKGLEWVSSIGSRGQNT

RYADSVKGRFTISRDNSKNTLYLQMNSLRAEDTAVYYCAKIISTFDYWGQ

GTLVTVSSGGGGSGGGGSGGGGSTDIQMTQSPSSLSASVGDRVTITCRAS

QSISSYLNWYQQKPGKAPKLLIYDASRLQSGVPSRFSGSGSGTDFTLTIS

SLQPEDFATYYCQQQETMPPTFGQGTKVEIKRSGGQGGSGGSGGSGGSG

GSAYYGITAGPAYRINDWASIYGVVGVGYGSGPGGSYGFSYAGLQFNPM

ENVALDFSYEQSRIRSVDVGTWILSVGYRFGSKSRRATSTVTGGYAQSDA

QGQMNKMGGFNLKYRYEEDNSPLGVIGSFTYTGGSGGSSGQAAAGEIVLT

QSPGTLVTVSSHHHHHHHH*

Mature N-terminal CYTX-DP Platforms
(T1-L1-scFv-CP-L2-T2):
Mature anti-CTLA-4 N-terminal CYTX-DP
platform (T1-L1-CTLA-4scFv-CP-L2-T2)
(SEQ ID NO: 77)
GQSGQEYMPMEGGSGQSGGEIVLTQSPGTLSLSPGERATLSCRASQSVSS

SYLAWYQQKPGQAPRLLIYGASSRATGIPDRFSGSGSGTDFTLTISRLEP

EDFAVYYCQQYGSSPLTFGGGTKVEIKRSGGSTITSYNVYYTKLSSSGTQ

VQLVQTGGGVVQPGRSLRLSCAASGSTFSSYAMSWVRQAPGKGLEWVSAI

SGSGGSTYYADSVKGRFTISRDNSKNTLYLQMNSLRAEDTAVYYCATNSL

YWYFDLWGRATLVTVSSASGSGGQGGSGGSGGSGGSGGSAYYGITAGPAY

RINDWASIYGVVGVGYGSGPGGSYGFSYAGLQFNPMENVALDFSYEQSR

IRSVDVGTWILSVGYRFGSKSRRATSTVTGGYAQSDAQGQMNKMGGFNLK

YRYEEDNSPLGVIGSFTYTGGSGGSSGQTAAGHHHHHHHH*

Mature anti-gp130 N-terminal CYTX-DP
platform (T1-L1-gp130scFv-CP-L2-T2)
(SEQ ID NO: 78)
GQSGQEYMPMEGGSGQSGGEVQLLESGGGLVQPGGSLRLSCAASGFTFSS

YAMSWVRQAPGKGLEWVSSIGSRGQNTRYADSVKGRFTISRDNSKNTLYL

QMNSLRAEDTAVYYCAKIISTFDYWGQGTLVTVSSGGGGSGGGGSGGGGS

TDIQMTQSPSSLSASVGDRVTITCRASQSISSYLNWYQQKPGKAPKLLIY

DASRLQSGVPSRFSGSGSGTDFTLTISSLQPEDFATYYCQQQETMPPTFG

QGTKVEIKRSGGQGGSGGSGGSGGSGGSAYYGITAGPAYRINDWASIYG

VVGVGYGSGPGGSYGFSYAGLQFNPMENVALDFSYEQSRIRSVDVGTWI

LSVGYRFGSKSRRATSTVTGGYAQSDAQGQMNKMGGFNLKYRYEEDNSPL

GVIGSFTYTGGSGGSSGQTAAGHHHHHHHH*

Mature N-terminal scFv, C-terminal Tail
CYTX-DP Platforms (T1-L1-scFv-CP-L2-TAIL-
T2):
Mature anti-CTLA-4 CYTX-DP platform
(T1-L1-CTLA-4scFv-CP-L2-TAIL-T2)
(SEQ ID NO: 79)
GQSGQEYMPMEGGSGQSGGEIVLTQSPGTLSLSPGERATLSCRASQSVSS

SYLAWYQQKPGQAPRLLIYGASSRATGIPDRFSGSGSGTDFTLTISRLEP

EDFAVYYCQQYGSSPLTFGGGTKVEIKRSGGSTITSYNVYYTKLSSSGTQ

VQLVQTGGGVVQPGRSLRLSCAASGSTFSSYAMSWVRQAPGKGLEWVSAI

SGSGGSTYYADSVKGRFTISRDNSKNTLYLQMNSLRAEDTAVYYCATNSL

YWYFDLWGRATLVTVSSASGSGGQGGSGGSGGSGGSGGSAYYGITAGPAY

RINDWASIYGVVGVGYGSGPGGSYGFSYAGLQFNPMENVALDFSYEQSR

IRSVDVGTWILSVGYRFGSKSRRATSTVTGGYAQSDAQGQMNKMGGFNLK

YRYEEDNSPLGVIGSFTYTGGSGGSSGQAAAGEIVLTQSPGTLVTVSSHH

HHHHHH*

Mature anti-gp130 CYTX-DP platform
(SS-T1-L1-gp130scFv-CP-L2-TAIL-T2)
(SEQ ID NO: 80)
GQSGQEYMPMEGGSGQSGGEVQLLESGGGLVQPGGSLRLSCAASGFTFSS

YAMSWVRQAPGKGLEWVSSIGSRGQNTRYADSVKGRFTISRDNSKNTLYL

QMNSLRAEDTAVYYCAKIISTFDYWGQGTLVTVSSGGGGSGGGGSGGGGS

TDIQMTQSPSSLSASVGDRVTITCRASQSISSYLNWYQQKPGKAPKLLIY

DASRLQSGVPSRFSGSGSGTDFTLTISSLQPEDFATYYCQQQETMPPTFG

QGTKVEIKRSGGQGGSGGSGGSGGSGGSAYYGITAGPAYRINDWASIYG

-continued

```
VVGVGYGSGPGGSYGFSYGAGLQFNPMENVALDFSYEQSRIRSVDVGTWI
LSVGYRFGSKSRRATSTVTGGYAQSDAQGQMNKMGGFNLKYRYEEDNSPL
GVIGSFTYTGGSGGSSGQAAAGEIVLTQSPGTLVTVSSHHHHHHHH*
```

Expression was induced with supplementing the culture with 0.01% arabinose for >12 hours at 28° C. or 37° C. with vigorous shaking after which cells were put on ice for 1 hour. The OD600 for each culture was measured and samples were normalized for cells to OD600 of 0.5 for 50 uL of cells per labeling or binding experiment. Cells were washed with 1 ml PBS (phosphates buffered saline) supplemented with 1% BSA at 4° C. and centrifuged at 3500×g for 5 min at 4° C. To measure expression, cells were labeled for 1 hour on ice in PBS supplemented with 1% BSA with the N-terminal EE epitope mIgG1 conjugated with AlexaFluor647 at 1/100 dilution (the APC channel y-axis in panels A-D of FIG. 18). To measure ability of the display platforms to bind CTLA-4 antigen, cells were incubated for 1 hour on ice in PBS supplemented with 1% BSA with human CTLA-4Fc at 0.06 mg/ml along with 1/200 anti-human Fc IgG-AlexaFluor488. The antibodies in display platforms CYTX-DP-scFvF5-Nterm and CYTX-DP-antiCTLA4-Nterm expressed at the percentages shown in the APC channel y-axis, FIG. 18, Panels A-D, upper left quadrant, gate P3. The antibodies in CYTX-DP-scFvF5-Nterm and CYTX-DP-antiCTLA4-Nterm expressed at 16% (the FITC channel x-axis, FIG. 18, Panels A, B, gate P3) as a heterogeneous population in DH-10β at 28 degrees C. The antibodies in CYTX-DP-antiCTLA4-Nterm expressed at 6.4% with a separate population in the upper left quadrant (FIG. 18, Panel C, gate P3) in C41(DE3) at 28 degrees. The anti-CTLA4 in CYTX-DP-antiCTLA4-Nterm expressed at 11% with a separate population in the upper left quadrant (FIG. 18, Panel D, gate P3) in C41(DE3) at 37 degrees. For CTLA-4 antigen binding, the antibodies in CYTX-DP-scFvF5-Nterm and CYTX-DP-antiCTLA4-Nterm expressed on DH-10β at 28° C. bound human CTLA-4-Fc at less than 1% (FIG. 18, Panels E, F gate Antigen binding). For CTLA-4 antigen binding, the anti-CTLA-4 in CYTX-DP-antiCTLA4-Nterm expressed on C41(DE3) at 28 and 37° C. bound human CTLA-4-Fc at less than 1% and 2.5%, respectively (FIG. 18, Panel G, H, gate Antigen binding). Anti-CTLA-4 clone 2 antibody appears to display as a functional antibody on E. coli C41(DE3) cells in view of the antibody's ability to bind CTLA-4 antigen. Expression of the anti-gp130 antibody scFv in C43(DE3) E. coli. Panel I shows N-terminal labeling with anti-EE epitope tag antibody conjugated with Alex488. Six percent of the population is expressing the anti-EE epitope tag. Panel J shows that the anti-gp130 scFv expressing bacteria bind biotinylated soluble, human gp130 and are labeled with secondary streptavidin-PE (SAPE) at 1/50 dilution. 2.7% of the population binds soluble gp130.

Example 10. Comparison of scFv Expression in CLiPS and CYTX-DP Platforms in Different Cell Types The use of a multi-copy display on whole cells enabled simple and direct quantitation of expression and antigen binding on the bacterial cell surface. Plasmids encoding scFv F5 or anti-CTLA-4 clone 2 fused to either eCLiPS3.0 or CYTX-DP at the N-terminus after the N-terminal SAPE (in CLiPS) or EE epitope tag (in CYTX-DP) (i.e., eCLiPS3.0-scFvF5-Nterm, eCLiPS3.0-antiCTLA4-Nterm, CYTX-DP-scFvF5-Nterm or CYTX-DP-antiCTLA4-Nterm) were expressed in E. coli DH-10β, E. coli C41(DE3), or E. coli C43(DE3) (a C41(DE3) variant) overnight with induction started from a 1/20 dilution of a nearly saturated culture, as indicated in FIG. 19. Expression was induced by supplementing the culture with 0.01% arabinose for >12 hours at 28° C. with vigorous shaking after which cells were put on ice for 1 hour. The OD600 for each culture was measured and samples were normalized for cells to OD600 of 0.5 for 50 uL of cells per labeling experiment. Cells were washed with 1 ml PBS (phosphates buffered saline) supplemented with 1% BSA at 4° C. and centrifuged at 3500×g for 5 min at 4 degrees C. To measure expression, cells were labeled for 1 hour on ice in PBS supplemented with 1% BSA with the N-terminal epitope tag label SAPE at 1/150 dilution for CLiPS (the PE channel x-axis in FIG. 19, panels A and C) or mIgG1 conjugated with AlexaFluor647 at 1/100 dilution for CYTX-DP (the APC channel y-axis in FIG. 19, panels B and D). None of the cells transformed with plasmids encoding eCLiPS3.0-scFvF5-Nterm or eCLiPS3.0-expressed F5 scFv or anti-CTLA-4 antibody, respectively (FIG. 19, Panel A, C). In contrast, F5 scFv and anti-CLTA-4 antibody were expressed in all cell types transformed with plasmids encoding CYTX-DP-scFvF5-Nterm or CYTX-DP-antiCTLA4-Nterm, with a range from 8-30% (FIG. 19, Panel B, D).

Example 11. Construction of Libraries Comprising CYTX-DP Platforms with Substrate or Substrate Library DMs This Example describes a method to produce a library of the embodiments that encodes a CYTX-DP with a DM that is either a substrate or a library of substrates.

Vector pB33-GSNS1-GGS4-eCLiPS3.0 PHB4901 was mutated to remove the BglI site by a single point mutation C→G at nucleotide position 109 using the Quikchange Lightning mutagenesis kit (Agilent Technologies, Santa Clara, CA, formerly Stratagene). A nucleic acid molecule encoding CYTX-DP-GSNS was sub-cloned into the vector between the BamHI and HindIII sites. The nucleotides encoding the N-terminal substrate site (DM) boundaries of the CYTX-DP were designed to be non-compatible BglI sites in the nucleotide sequence encoding the linker between the N-terminal tag and the transmembrane domain (CYTX-CP) in order to use inexpensive, small oligonucleotide cassettes for small substrates, peptides and libraries and quality controlled cut vector. Into this substrate site between the BglI sites, a fragment of the *B. subtilis* structural SacB gene, a commonly used molecular biology stuffer sequence, was sub-cloned in order to achieve a better quality cut vector; this could also be done by cutting a second time with another enzyme. The vector was digested overnight at 37° C. with 50 U BglI (NEB) per 150 ug of vector. Antarctic phosphatase (NEB) was then used for 30 minutes at 37° C. to remove phosphate groups from the vector DNA followed by heat inactivation at 65° C. for 10 minutes before agarose gel purification. Substrate oligonucleotides or substrate library oligonucleotides having top and bottom strands with compatible BglI ends and chemical phosphorylation with standard desalting purification were ordered from standard DNA synthesis vendors (e.g., Elim Biopharm, Fremont CA or IDT, Coralville, Iowa). Top and bottom oligonucleotides were mixed in equimolar amounts, annealed with a −0.5° C. gradient from 99° C. to 4° C. using an annealing protocol. Digested vector and annealed substrate insert DNA were mixed in various ratios for ligation and piloted for the best molar ratio. Ligation was performed at room temperature overnight; ligase (NEB or Lucigen) was heat inactivated at 70° C. and dialyzed against water. Ligation scale-up was conducted in a 100 mg ligation reaction for library production and much less for single clones. The electroporation protocol for bacteria used 2 to 5 uL DNA per 25-50 uL bacterial cells thawed on wet ice and using protocols from the vendor (Lucigen, Middleton, WI). Cells were plated or grown in liquid culture over-night at 37° C. and subsequently pooled and frozen to −80° C. for long-term storage.

Example 12. Selection of a Known Positive from a Negative Background

To demonstrate the utility of the display platforms (DPs) of the disclosure for selection of substrates cleaved by proteases using FACS a clone expressing a known substrate (referred to herein as 1204) was spiked into a background of a known negative (ssNSUB). One round of selection was performed by cleavage of the mixed population using recombinant human uPA (rh uPA) at a final concentration of 100 nM. The populations were then analyzed by FACS and the cells that shifted into the P3 gate (FIGS. 32A-32D) were sorted into a fresh tube. Cells were then grown overnight, labeled and analyzed by flow cytometry to determine the level of enrichment.

Samples A-D (FIGS. 32A-32D) were analyzed for percentage of cells in the P3 gate and the data was plotted (FIG. 33): the data shows that after a single round of FACS the positive portion of the population is enriched from 1% to 15-20%.

Example 13. Selection of Novel Substrates for MT-SP1

To demonstrate the utility of the display platforms (DPs) of the disclosure for selection of substrates cleaved by proteases using FACS, a substrate library consisting of eight random amino acids was constructed using the CYTX-DP platforms of the disclosure. In some embodiments, the CYTX-DP platform includes an EagI site on the C-terminus prior to the histidine tag. In some embodiments, the CYTX-DP platform includes a NotI site on the C-terminus prior to the histidine tag. Examples of such DPs include, but are not limited, to DPs having amino acid sequence SEQ ID NO: 81 shown below or amino acid sequence SEQ ID NO: 82 shown below, where each member of the substrate library has a random 8-amino acid sequence in the position indicated XXXXXXXX (SEQ ID NO: 61).

CYTX-DP for Substrate Selection (S-CP CYTX-DP comprising T1-L1-S-L2-CP-L3-T2):
S-CYTX-DP with NotI site:
(SEQ ID NO: 81)
EYMPMEGGSGQSGQXXXXXXXXSGGQGGSGGSGGSGGSGGSAYYGITAGP

AYRINDWASIYGVVGVGYGSGPGGSYGFSYGAGLQFNPMENVALDFSYEQ

SRIRSVDVGTWILSVGYRFGSKSRRATSTVTGGYAQSDAQGQMNKMGGFN

LKYRYEEDNSPLGVIGSFTYTGGSGGSSGQAAAGHHHHHHHH

S-CYTX-DP with EagI site:
(SEQ ID NO: 82)
EYMPMEGGSGQSGQXXXXXXXXSGGQGGSGGSGGSGGSGGSAYYGITAGP

AYRINDWASIYGVVGVGYGSGPGGSYGFSYGAGLQFNPMENVALDFSYEQ

SRIRSVDVGTWILSVGYRFGSKSRRATSTVTGGYAQSDAQGQMNKMGGFN

LKYRYEEDNSPLGVIGSFTYTGGSGGSSGQTAAGHHHHHHHH

A library comprising a DP having amino acid sequence SEQ ID NO: 82 was then screened using three rounds of selection with MT-SP1.

The naïve library was initially prepared for selections by MACS to remove non-expressing members. Round 0 (post-MACS) then underwent three further rounds of FACS sorting to select a final pool of substrates (FIG. 34).

90 clones form the final pool of substrates were sequenced and the sequences were aligned using CLC Main Workbench (CLC bio). Using this alignment amino acid positions were designated for each substrate relative to the arginine residue at the expected site of cleavage (between residues P1 and P1').

As MT-SP1 substrates have been discovered and published previously using phage display by Takeuchi et al (J Biol Chem. 2000) we could directly compare the frequency of amino acids present at positions P1', P2, P3 and P4, the data is presented in FIG. 35.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for identifying a peptide substrate for an enzyme, comprising:
   a) contacting a cell or other replicable biological entity with an enzyme, the cell comprising a cell outer membrane and expressing a peptide display scaffold, the peptide display scaffold comprising a fusion protein comprising a formula selected from the group consisting of:
      i) T1-DM-carrier protein-T2; and
      ii) T1-carrier protein-DM-T2;
      wherein the carrier protein (CP) is a circularly permuted bacterial outer membrane protein comprising an amino acid sequence selected from the group consisting of SEQ ID NO: 1, SEQ ID NO: 56 and SEQ ID NO: 57;
      wherein DM comprises a member of a library of candidate peptide substrates for the enzyme;
      wherein T1 and T2 are first and second detectable moieties; and wherein T1-DM and T2 in formula i), or T1 and DM-T2 in formula ii) are accessible at the extracellular surface of the cell outer membrane and the N- or C-terminus of the fusion protein is accessible at the extracellular surface of the cell outer membrane; and
      wherein prior to contacting the cell with the enzyme, the cell exhibits a detectable T1 signal;
   b) detecting the presence of a detectable T2 signal in the absence of a detectable T1 signal, thereby identifying the member of the library of candidate peptide substrates as a peptide substrate for the enzyme.

2. The method of claim 1, wherein the enzyme is a protease.

3. The method of claim 1, wherein said detecting is by fluorescence activated cell sorting.

4. The method of claim 1, wherein prior to contacting the cell with the enzyme, the cell exhibits a detectable T1 signal and a detectable T2 signal.

5. The method of claim 1, wherein T1 and T2 are not the same.

6. The method of claim 1, wherein the fusion protein further comprises at least one linker, wherein the linker is between DM and CP, the linker is between T2 and CP, the linker is between T1 and DM, or a combination thereof.

7. The method of claim 1, wherein detectable moieties T1 and T2 are affinity tags.

8. The method of claim 1, wherein T1-DM is located at an N-terminal domain of said fusion protein and T2 is located at a C-terminal domain of said fusion protein.

9. The method of claim 1, wherein T1-DM is located at a C-terminal domain of said fusion protein and T2 is located at an N-terminal domain of said fusion protein.

* * * * *

SEQUENCE LISTING

```
<160> NUMBER OF SEQ ID NOS: 87

<210> SEQ ID NO 1
<211> LENGTH: 129
<212> TYPE: PRT
<213> ORGANISM: Artificial Sequence
<220> FEATURE:
<223> OTHER INFORMATION: chemically synthesized

<400> SEQUENCE: 1

Tyr Tyr Gly Ile Thr Ala Gly Pro Ala Tyr Arg Ile Asn Asp Trp Ala
1               5                   10                  15

Ser Ile Tyr Gly Val Val Gly Val Gly Tyr Gly Ser Gly Pro Gly Gly
            20                  25                  30

Ser Tyr Gly Phe Ser Tyr Gly Ala Gly Leu Gln Phe Asn Pro Met Glu
```

```
                35                  40                  45
Asn Val Ala Leu Asp Phe Ser Tyr Glu Gln Ser Arg Ile Arg Ser Val
        50                  55                  60
Asp Val Gly Thr Trp Ile Leu Ser Val Gly Tyr Arg Phe Gly Ser Lys
65                  70                  75                  80
Ser Arg Arg Ala Thr Ser Thr Val Thr Gly Tyr Ala Gln Ser Asp
                85                  90                  95
Ala Gln Gly Gln Met Asn Lys Met Gly Gly Phe Asn Leu Lys Tyr Arg
                100                 105                 110
Tyr Glu Glu Asp Asn Ser Pro Leu Gly Val Ile Gly Ser Phe Thr Tyr
                115                 120                 125
Thr

<210> SEQ ID NO 2
<211> LENGTH: 220
<212> TYPE: PRT
<213> ORGANISM: Artificial Sequence
<220> FEATURE:
<223> OTHER INFORMATION: chemically synthesized

<400> SEQUENCE: 2

Met Lys Lys Ile Ala Cys Leu Ser Ala Leu Ala Ala Val Leu Ala Phe
1               5                   10                  15
Thr Ala Gly Thr Ser Val Ala Gly Gln Ser Gln Glu Tyr Met Pro
                20                  25                  30
Met Glu Gly Gly Ser Gly Gln Ser Gln Gly Ser Gly Ser Asn Ser
                35                  40                  45
Gly Ser Ser Gly Gly Gln Gly Gly Ser Gly Gly Ser Gly Gly Ser Gly
        50                  55                  60
Gly Ser Gly Gly Ser Ala Tyr Tyr Gly Ile Thr Ala Gly Pro Ala Tyr
65                  70                  75                  80
Arg Ile Asn Asp Trp Ala Ser Ile Tyr Gly Val Val Gly Val Gly Tyr
                85                  90                  95
Gly Ser Gly Pro Gly Gly Ser Tyr Gly Phe Ser Tyr Gly Ala Gly Leu
                100                 105                 110
Gln Phe Asn Pro Met Glu Asn Val Ala Leu Asp Phe Ser Tyr Glu Gln
                115                 120                 125
Ser Arg Ile Arg Ser Val Asp Val Gly Thr Trp Ile Leu Ser Val Gly
                130                 135                 140
Tyr Arg Phe Gly Ser Lys Ser Arg Arg Ala Thr Ser Thr Val Thr Gly
145                 150                 155                 160
Gly Tyr Ala Gln Ser Asp Ala Gln Gly Gln Met Asn Lys Met Gly Gly
                165                 170                 175
Phe Asn Leu Lys Tyr Arg Tyr Glu Glu Asp Asn Ser Pro Leu Gly Val
                180                 185                 190
Ile Gly Ser Phe Thr Tyr Thr Gly Gly Ser Gly Gly Ser Ser Gly Gln
                195                 200                 205
Thr Ala Ala Gly His His His His His His
210                 215                 220

<210> SEQ ID NO 3
<211> LENGTH: 663
<212> TYPE: DNA
<213> ORGANISM: Artificial Sequence
<220> FEATURE:
<223> OTHER INFORMATION: chemically synthesized
```

<400> SEQUENCE: 3

```
atgaaaaaaa ttgcatgtct ttcagcactg ccgcagttc tggctttcac cgcaggtact      60
tccgtagctg gtcaatctgg acaggaatac atgccgatgg aaggagggtc tggccagtct    120
ggccagggtt ctggcagcaa ttccggttct agcggtggcc agggtggcag cggtggctct    180
ggtggttccg gtggctctgg tggctctgcg tactacggca tcactgctgg tccggcttac    240
cgcattaacg actgggcaag catctacggt gtagtgggtg tgggttatgg ttctggcccg    300
ggtggttctt acggtttctc ctacggtgcg ggtctgcagt tcaacccgat ggaaaacgtt    360
gctctggact tctcttacga gcagagccgt attcgtagcg ttgacgtagg cacctggatt    420
ctgtccgttg gttaccgctt cggctccaaa tcccgccgtg cgacttctac tgtaactggc    480
ggttacgcac agagcgacgc tcagggccaa atgaacaaaa tgggcggttt caacctgaaa    540
taccgctatg aagaagacaa cagcccgctg ggtgtgatcg gttctttcac ttacaccggc    600
ggctctggtg gttctagcgg tcaaacggcc gctggtcacc atcaccacca tcatcaccac    660
taa                                                                    663
```

<210> SEQ ID NO 4
<211> LENGTH: 197
<212> TYPE: PRT
<213> ORGANISM: Artificial Sequence
<220> FEATURE:
<223> OTHER INFORMATION: chemically synthesized

<400> SEQUENCE: 4

```
Gly Gln Ser Gly Gln Glu Tyr Met Pro Met Glu Gly Gly Ser Gly Gln
1               5                   10                  15

Ser Gly Gln Gly Ser Gly Ser Asn Ser Gly Ser Ser Gly Gly Gln Gly
            20                  25                  30

Gly Ser Gly Gly Ser Gly Gly Ser Gly Gly Ser Gly Gly Ser Ala Tyr
        35                  40                  45

Tyr Gly Ile Thr Ala Gly Pro Ala Tyr Arg Ile Asn Asp Trp Ala Ser
    50                  55                  60

Ile Tyr Gly Val Val Gly Val Gly Tyr Gly Ser Gly Pro Gly Gly Ser
65                  70                  75                  80

Tyr Gly Phe Ser Tyr Gly Ala Gly Leu Gln Phe Asn Pro Met Glu Asn
                85                  90                  95

Val Ala Leu Asp Phe Ser Tyr Glu Gln Ser Arg Ile Arg Ser Val Asp
            100                 105                 110

Val Gly Thr Trp Ile Leu Ser Val Gly Tyr Arg Phe Gly Ser Lys Ser
        115                 120                 125

Arg Arg Ala Thr Ser Thr Val Thr Gly Gly Tyr Ala Gln Ser Asp Ala
    130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Thr Ala Ala Gly His His His
            180                 185                 190

His His His His His
        195
```

<210> SEQ ID NO 5
<211> LENGTH: 594
<212> TYPE: DNA

<213> ORGANISM: Artificial Sequence
<220> FEATURE:
<223> OTHER INFORMATION: chemically synthesized

<400> SEQUENCE: 5

```
ggtcaatctg dacaggaata catgccgatg gaaggagggt ctggccagtc tggccagggt    60
tctggcagca attccggttc tagcggtggc cagggtggca gcggtggctc tggtggttcc   120
ggtggctctg gtggctctgc gtactacggc atcactgctg gtccggctta ccgcattaac   180
gactgggcaa gcatctacgg tgtagtgggt gtgggttatg gttctggccc gggtggttct   240
tacggtttct cctacggtgc gggtctgcag ttcaacccga tggaaaacgt tgctctggac   300
ttctcttacg agcagagccg tattcgtagc gttgacgtag caccctggat tctgtccgtt   360
ggttaccgct tcggctccaa atcccgccgt gcgacttcta ctgtaactgg cggttacgca   420
cagagcgacg ctcagggcca aatgaacaaa atgggcggtt tcaacctgaa ataccgctat   480
gaagaagaca acagcccgct gggtgtgatc ggttctttca cttacaccgg cggctctggt   540
ggttctagcg gtcaaacggc cgctggtcac atcaccacc atcatcacca ctaa           594
```

<210> SEQ ID NO 6
<211> LENGTH: 23
<212> TYPE: PRT
<213> ORGANISM: Artificial Sequence
<220> FEATURE:
<223> OTHER INFORMATION: chemically synthesized

<400> SEQUENCE: 6

```
Met Lys Lys Ile Ala Cys Leu Ser Ala Leu Ala Ala Val Leu Ala Phe
  1               5                  10                  15

Thr Ala Gly Thr Ser Val Ala
              20
```

<210> SEQ ID NO 7
<211> LENGTH: 5
<212> TYPE: PRT
<213> ORGANISM: Artificial Sequence
<220> FEATURE:
<223> OTHER INFORMATION: chemically synthesized

<400> SEQUENCE: 7

```
Gly Gln Ser Gly Gln
  1               5
```

<210> SEQ ID NO 8
<211> LENGTH: 6
<212> TYPE: PRT
<213> ORGANISM: Artificial Sequence
<220> FEATURE:
<223> OTHER INFORMATION: chemically synthesized

<400> SEQUENCE: 8

```
Glu Tyr Met Pro Met Glu
  1               5
```

<210> SEQ ID NO 9
<211> LENGTH: 10
<212> TYPE: PRT
<213> ORGANISM: Artificial Sequence
<220> FEATURE:
<223> OTHER INFORMATION: chemically synthesized

<400> SEQUENCE: 9

Gly Gly Ser Gly Gln Ser Gly Gln Gly Gly

```
<210> SEQ ID NO 10
<211> LENGTH: 4
<212> TYPE: PRT
<213> ORGANISM: Artificial Sequence
<220> FEATURE:
<223> OTHER INFORMATION: chemically synthesized

<400> SEQUENCE: 10

Gly Ser Asn Ser
1

<210> SEQ ID NO 11
<211> LENGTH: 22
<212> TYPE: PRT
<213> ORGANISM: Artificial Sequence
<220> FEATURE:
<223> OTHER INFORMATION: chemically synthesized

<400> SEQUENCE: 11

Gly Ser Ser Gly Gly Gln Gly Gly Ser Gly Gly Ser Gly Gly Ser Gly
1               5                   10                  15

Gly Ser Gly Gly Ser Ala
            20

<210> SEQ ID NO 12
<211> LENGTH: 13
<212> TYPE: PRT
<213> ORGANISM: Artificial Sequence
<220> FEATURE:
<223> OTHER INFORMATION: chemically synthesized

<400> SEQUENCE: 12

Gly Gly Ser Gly Gly Ser Ser Gly Gln Ala Ala Ala Gly
1               5                   10

<210> SEQ ID NO 13
<211> LENGTH: 8
<212> TYPE: PRT
<213> ORGANISM: Artificial Sequence
<220> FEATURE:
<223> OTHER INFORMATION: chemically synthesized

<400> SEQUENCE: 13

His His His His His His His His
1               5

<210> SEQ ID NO 14
<211> LENGTH: 13
<212> TYPE: PRT
<213> ORGANISM: Artificial Sequence
<220> FEATURE:
<223> OTHER INFORMATION: chemically synthesized

<400> SEQUENCE: 14

Trp Val Cys His Pro Met Trp Glu Val Met Cys Leu Arg
1               5                   10

<210> SEQ ID NO 15
<211> LENGTH: 4
<212> TYPE: PRT
<213> ORGANISM: Artificial Sequence
<220> FEATURE:
<223> OTHER INFORMATION: chemically synthesized

<400> SEQUENCE: 15
```

Gly Gly Ser Gly
1

<210> SEQ ID NO 16
<211> LENGTH: 152
<212> TYPE: PRT
<213> ORGANISM: Artificial Sequence
<220> FEATURE:
<223> OTHER INFORMATION: chemically synthesized

<400> SEQUENCE: 16

Asp Tyr Asn Lys Asn Gln Tyr Tyr Gly Ile Thr Ala Gly Pro Ala Tyr
1               5                   10                  15

Arg Ile Asn Asp Trp Ala Ser Ile Tyr Gly Val Val Gly Val Gly Tyr
            20                  25                  30

Gly Lys Phe Gln Thr Thr Glu Tyr Pro Thr Tyr Lys His Asp Thr Ser
        35                  40                  45

Asp Tyr Gly Phe Ser Tyr Gly Ala Gly Leu Gln Phe Asn Pro Met Glu
    50                  55                  60

Asn Val Ala Leu Asp Phe Ser Tyr Glu Gln Ser Arg Ile Arg Ser Val
65                  70                  75                  80

Asp Val Gly Thr Trp Ile Leu Ser Val Gly Tyr Arg Phe Gly Ser Lys
                85                  90                  95

Ser Arg Arg Ala Thr Ser Thr Val Thr Gly Gly Tyr Ala Gln Ser Asp
            100                 105                 110

Ala Gln Gly Gln Met Asn Lys Met Gly Gly Phe Asn Leu Lys Tyr Arg
        115                 120                 125

Tyr Glu Glu Asp Asn Ser Pro Leu Gly Val Ile Gly Ser Phe Thr Tyr
    130                 135                 140

Thr Glu Lys Ser Arg Thr Ala Ser
145                 150

<210> SEQ ID NO 17
<211> LENGTH: 3
<212> TYPE: PRT
<213> ORGANISM: Artificial Sequence
<220> FEATURE:
<223> OTHER INFORMATION: chemically synthesized

<400> SEQUENCE: 17

Gly Gly Ser
1

<210> SEQ ID NO 18
<211> LENGTH: 18
<212> TYPE: PRT
<213> ORGANISM: Artificial Sequence
<220> FEATURE:
<223> OTHER INFORMATION: chemically synthesized

<400> SEQUENCE: 18

His Ile Ser Gln Trp Lys Pro Lys Val Pro Asn Arg Glu Asp Lys Tyr
1               5                   10                  15

Lys Lys

<210> SEQ ID NO 19
<211> LENGTH: 8
<212> TYPE: PRT
<213> ORGANISM: Artificial Sequence
<220> FEATURE:
<223> OTHER INFORMATION: chemically synthesized

```
<400> SEQUENCE: 19

Thr Gly Arg Gly Pro Ser Trp Val
1               5

<210> SEQ ID NO 20
<211> LENGTH: 13
<212> TYPE: PRT
<213> ORGANISM: Artificial Sequence
<220> FEATURE:
<223> OTHER INFORMATION: chemically synthesized

<400> SEQUENCE: 20

Gly Gly Ser Gly Gly Ser Gly Gly Ser Gly Gly Ser Gly
1               5                  10

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Leu Ser Gly Arg Ser Asp Asn His
1               5

<210> SEQ ID NO 22
<211> LENGTH: 8
<212> TYPE: PRT
<213> ORGANISM: Artificial Sequence
<220> FEATURE:
<223> OTHER INFORMATION: chemically synthesized

<400> SEQUENCE: 22

Gly Gly Ser Gly Gln Ser Gly Gln
1               5

<210> SEQ ID NO 23
<211> LENGTH: 8
<212> TYPE: PRT
<213> ORGANISM: Artificial Sequence
<220> FEATURE:
<223> OTHER INFORMATION: chemically synthesized

<400> SEQUENCE: 23

Gly Gly Gly Ser Gly Gly Gly Ser
1               5

<210> SEQ ID NO 24
<211> LENGTH: 20
<212> TYPE: PRT
<213> ORGANISM: Artificial Sequence
<220> FEATURE:
<223> OTHER INFORMATION: chemically synthesized

<400> SEQUENCE: 24

Ser Gly Gly Gln Gly Gly Ser Gly Gly Ser Gly Gly Ser Gly Gly Ser
1               5                  10                  15

Gly Gly Ser Ala
            20

<210> SEQ ID NO 25
<211> LENGTH: 228
<212> TYPE: PRT
<213> ORGANISM: Artificial Sequence
```

<220> FEATURE:
<223> OTHER INFORMATION: chemically synthesized

<400> SEQUENCE: 25

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Trp Val Cys His
            20                  25                  30

Pro Met Trp Glu Val Met Cys Leu Arg Gly Ser Gly Gln Ser Gly
        35                  40                  45

Gln Gly Gly Gly Ser Gly Asp Tyr Asn Lys Asn Gln Tyr Tyr Gly
    50                  55                  60

Ile Thr Ala Gly Pro Ala Tyr Arg Ile Asn Asp Trp Ala Ser Ile Tyr
65                  70                  75                  80

Gly Val Val Gly Val Gly Tyr Gly Lys Phe Gln Thr Thr Glu Tyr Pro
                85                  90                  95

Thr Tyr Lys His Asp Thr Ser Asp Tyr Gly Phe Ser Tyr Gly Ala Gly
            100                 105                 110

Leu Gln Phe Asn Pro Met Glu Asn Val Ala Leu Asp Phe Ser Tyr Glu
        115                 120                 125

Gln Ser Arg Ile Arg Ser Val Asp Val Gly Thr Trp Ile Leu Ser Val
    130                 135                 140

Gly Tyr Arg Phe Gly Ser Lys Ser Arg Arg Ala Thr Ser Thr Val Thr
145                 150                 155                 160

Gly Gly Tyr Ala Gln Ser Asp Ala Gln Gly Gln Met Asn Lys Met Gly
                165                 170                 175

Gly Phe Asn Leu Lys Tyr Arg Tyr Glu Glu Asp Asn Ser Pro Leu Gly
            180                 185                 190

Val Ile Gly Ser Phe Thr Tyr Thr Glu Lys Ser Arg Thr Ala Ser Gly
        195                 200                 205

Gly Ser His Ile Ser Gln Trp Lys Pro Lys Val Pro Asn Arg Glu Asp
    210                 215                 220

Lys Tyr Lys Lys
225

<210> SEQ ID NO 26
<211> LENGTH: 245
<212> TYPE: PRT
<213> ORGANISM: Artificial Sequence
<220> FEATURE:
<223> OTHER INFORMATION: chemically synthesized

<400> SEQUENCE: 26

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Trp Val Cys His
            20                  25                  30

Pro Met Trp Glu Val Met Cys Leu Arg Gly Ser Gly Gln Ser Gly
        35                  40                  45

Gln Gly Gly Thr Gly Arg Gly Pro Ser Trp Val Gly Ser Gly Gly
    50                  55                  60

Ser Gly Gly Ser Gly Gly Ser Gly Asp Tyr Asn Lys Asn Gln Tyr Tyr
65                  70                  75                  80

Gly Ile Thr Ala Gly Pro Ala Tyr Arg Ile Asn Asp Trp Ala Ser Ile
                85                  90                  95

Tyr Gly Val Val Gly Val Gly Tyr Gly Lys Phe Gln Thr Thr Glu Tyr

```
                    100                 105                 110
Pro Thr Tyr Lys His Asp Thr Ser Asp Tyr Gly Phe Ser Tyr Gly Ala
            115                 120                 125

Gly Leu Gln Phe Asn Pro Met Glu Asn Val Ala Leu Asp Phe Ser Tyr
        130                 135                 140

Glu Gln Ser Arg Ile Arg Ser Val Asp Val Gly Thr Trp Ile Leu Ser
145                 150                 155                 160

Val Gly Tyr Arg Phe Gly Ser Lys Ser Arg Arg Ala Thr Ser Thr Val
                165                 170                 175

Thr Gly Gly Tyr Ala Gln Ser Asp Ala Gln Gly Gln Met Asn Lys Met
            180                 185                 190

Gly Gly Phe Asn Leu Lys Tyr Arg Tyr Glu Glu Asp Asn Ser Pro Leu
        195                 200                 205

Gly Val Ile Gly Ser Phe Thr Tyr Thr Glu Lys Ser Arg Thr Ala Ser
    210                 215                 220

Gly Gly Ser His Ile Ser Gln Trp Lys Pro Lys Val Pro Asn Arg Glu
225                 230                 235                 240

Asp Lys Tyr Lys Lys
            245

<210> SEQ ID NO 27
<211> LENGTH: 245
<212> TYPE: PRT
<213> ORGANISM: Artificial Sequence
<220> FEATURE:
<223> OTHER INFORMATION: chemically synthesized

<400> SEQUENCE: 27

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Trp Val Cys His
            20                  25                  30

Pro Met Trp Glu Val Met Cys Leu Arg Gly Gly Ser Gly Gln Ser Gly
        35                  40                  45

Gln Gly Gly Leu Ser Gly Arg Ser Asp Asn His Gly Gly Ser Gly Gly
    50                  55                  60

Ser Gly Gly Ser Gly Gly Ser Gly Asp Tyr Asn Lys Asn Gln Tyr Tyr
65                  70                  75                  80

Gly Ile Thr Ala Gly Pro Ala Tyr Arg Ile Asn Asp Trp Ala Ser Ile
                85                  90                  95

Tyr Gly Val Val Gly Val Gly Tyr Gly Lys Phe Gln Thr Thr Glu Tyr
            100                 105                 110

Pro Thr Tyr Lys His Asp Thr Ser Asp Tyr Gly Phe Ser Tyr Gly Ala
        115                 120                 125

Gly Leu Gln Phe Asn Pro Met Glu Asn Val Ala Leu Asp Phe Ser Tyr
    130                 135                 140

Glu Gln Ser Arg Ile Arg Ser Val Asp Val Gly Thr Trp Ile Leu Ser
145                 150                 155                 160

Val Gly Tyr Arg Phe Gly Ser Lys Ser Arg Arg Ala Thr Ser Thr Val
                165                 170                 175

Thr Gly Gly Tyr Ala Gln Ser Asp Ala Gln Gly Gln Met Asn Lys Met
            180                 185                 190

Gly Gly Phe Asn Leu Lys Tyr Arg Tyr Glu Glu Asp Asn Ser Pro Leu
        195                 200                 205

Gly Val Ile Gly Ser Phe Thr Tyr Thr Glu Lys Ser Arg Thr Ala Ser
```

```
                210                 215                 220
Gly Gly Ser His Ile Ser Gln Trp Lys Pro Lys Val Pro Asn Arg Glu
225                 230                 235                 240

Asp Lys Tyr Lys Lys
                245

<210> SEQ ID NO 28
<211> LENGTH: 220
<212> TYPE: PRT
<213> ORGANISM: Artificial Sequence
<220> FEATURE:
<223> OTHER INFORMATION: chemically synthesized

<400> SEQUENCE: 28

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
                20                  25                  30

Met Glu Gly Gly Ser Gly Gln Ser Gly Gln Gly Gly Ser Gly Gly
            35                  40                  45

Gly Ser Ser Gly Gly Gln Gly Gly Ser Gly Gly Ser Gly Gly Ser Gly
50                  55                  60

Gly Ser Gly Gly Ser Ala Tyr Tyr Gly Ile Thr Ala Gly Pro Ala Tyr
65                  70                  75                  80

Arg Ile Asn Asp Trp Ala Ser Ile Tyr Gly Val Val Gly Val Gly Tyr
                85                  90                  95

Gly Ser Gly Pro Gly Gly Ser Tyr Gly Phe Ser Tyr Gly Ala Gly Leu
            100                 105                 110

Gln Phe Asn Pro Met Glu Asn Val Ala Leu Asp Phe Ser Tyr Glu Gln
        115                 120                 125

Ser Arg Ile Arg Ser Val Asp Val Gly Thr Trp Ile Leu Ser Val Gly
130                 135                 140

Tyr Arg Phe Gly Ser Lys Ser Arg Ala Thr Ser Thr Val Thr Gly
145                 150                 155                 160

Gly Tyr Ala Gln Ser Asp Ala Gln Gly Gln Met Asn Lys Met Gly Gly
                165                 170                 175

Phe Asn Leu Lys Tyr Arg Tyr Glu Glu Asp Asn Ser Pro Leu Gly Val
            180                 185                 190

Ile Gly Ser Phe Thr Tyr Thr Gly Gly Ser Gly Gly Ser Ser Gly Gln
        195                 200                 205

Ala Ala Ala Gly His His His His His His
210                 215                 220

<210> SEQ ID NO 29
<211> LENGTH: 220
<212> TYPE: PRT
<213> ORGANISM: Artificial Sequence
<220> FEATURE:
<223> OTHER INFORMATION: chemically synthesized

<400> SEQUENCE: 29

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
                20                  25                  30

Met Glu Gly Gly Ser Gly Gln Ser Gly Gln Thr Gly Arg Gly Pro Ser
            35                  40                  45
```

Trp Val Ser Gly Gly Gln Gly Ser Gly Gly Ser Gly
 50              55              60

Gly Ser Gly Gly Ser Ala Tyr Tyr Gly Ile Thr Ala Gly Pro Ala Tyr
 65                  70                  75                  80

Arg Ile Asn Asp Trp Ala Ser Ile Tyr Gly Val Val Gly Val Gly Tyr
                 85                  90                  95

Gly Ser Gly Pro Gly Gly Ser Tyr Gly Phe Ser Tyr Gly Ala Gly Leu
             100                 105                 110

Gln Phe Asn Pro Met Glu Asn Val Ala Leu Asp Phe Ser Tyr Glu Gln
             115                 120                 125

Ser Arg Ile Arg Ser Val Asp Val Gly Thr Trp Ile Leu Ser Val Gly
 130                 135                 140

Tyr Arg Phe Gly Ser Lys Ser Arg Arg Ala Thr Ser Thr Val Thr Gly
145                 150                 155                 160

Gly Tyr Ala Gln Ser Asp Ala Gln Gly Gln Met Asn Lys Met Gly Gly
                 165                 170                 175

Phe Asn Leu Lys Tyr Arg Tyr Glu Glu Asp Asn Ser Pro Leu Gly Val
             180                 185                 190

Ile Gly Ser Phe Thr Tyr Thr Gly Gly Ser Gly Gly Ser Ser Gly Gln
             195                 200                 205

Ala Ala Ala Gly His His His His His His
 210                 215                 220

<210> SEQ ID NO 30
<211> LENGTH: 220
<212> TYPE: PRT
<213> ORGANISM: Artificial Sequence
<220> FEATURE:
<223> OTHER INFORMATION: chemically synthesized

<400> SEQUENCE: 30

Met Lys Lys Ile Ala Cys Leu Ser Ala Leu Ala Ala Val Leu Ala Phe
1                   5                  10                  15

Thr Ala Gly Thr Ser Val Ala Gly Gln Ser Gly Gln Glu Tyr Met Pro
                 20                  25                  30

Met Glu Gly Gly Ser Gly Gln Ser Gly Gln Leu Ser Gly Arg Ser Asp
             35                  40                  45

Asn His Ser Gly Gly Gly Gly Ser Gly Gly Ser Gly Gly Ser Gly
 50              55              60

Gly Ser Gly Gly Ser Ala Tyr Tyr Gly Ile Thr Ala Gly Pro Ala Tyr
 65                  70                  75                  80

Arg Ile Asn Asp Trp Ala Ser Ile Tyr Gly Val Val Gly Val Gly Tyr
                 85                  90                  95

Gly Ser Gly Pro Gly Gly Ser Tyr Gly Phe Ser Tyr Gly Ala Gly Leu
             100                 105                 110

Gln Phe Asn Pro Met Glu Asn Val Ala Leu Asp Phe Ser Tyr Glu Gln
             115                 120                 125

Ser Arg Ile Arg Ser Val Asp Val Gly Thr Trp Ile Leu Ser Val Gly
 130                 135                 140

Tyr Arg Phe Gly Ser Lys Ser Arg Arg Ala Thr Ser Thr Val Thr Gly
145                 150                 155                 160

Gly Tyr Ala Gln Ser Asp Ala Gln Gly Gln Met Asn Lys Met Gly Gly
                 165                 170                 175

Phe Asn Leu Lys Tyr Arg Tyr Glu Glu Asp Asn Ser Pro Leu Gly Val
             180                 185                 190

Ile Gly Ser Phe Thr Tyr Thr Gly Gly Ser Gly Ser Ser Gly Gln
        195                 200                 205

Ala Ala Ala Gly His His His His His His His
        210                 215                 220

<210> SEQ ID NO 31
<211> LENGTH: 10
<212> TYPE: PRT
<213> ORGANISM: Artificial Sequence
<220> FEATURE:
<223> OTHER INFORMATION: chemically synthesized

<400> SEQUENCE: 31

Glu Tyr Met Pro Met Glu Gly Gly Ser Gly
1               5                   10

<210> SEQ ID NO 32
<211> LENGTH: 6
<212> TYPE: PRT
<213> ORGANISM: Artificial Sequence
<220> FEATURE:
<223> OTHER INFORMATION: chemically synthesized

<400> SEQUENCE: 32

Gly Gly Gln Ser Gly Gln
1               5

<210> SEQ ID NO 33
<211> LENGTH: 4
<212> TYPE: PRT
<213> ORGANISM: Artificial Sequence
<220> FEATURE:
<223> OTHER INFORMATION: chemically synthesized

<400> SEQUENCE: 33

Gly Gly Gly Ser
1

<210> SEQ ID NO 34
<211> LENGTH: 4
<212> TYPE: PRT
<213> ORGANISM: Artificial Sequence
<220> FEATURE:
<223> OTHER INFORMATION: chemically synthesized

<400> SEQUENCE: 34

Gly Gly Gly Ser
1

<210> SEQ ID NO 35
<211> LENGTH: 4
<212> TYPE: PRT
<213> ORGANISM: Artificial Sequence
<220> FEATURE:
<223> OTHER INFORMATION: chemically synthesized

<400> SEQUENCE: 35

Gly Gly Gly Ser
1

<210> SEQ ID NO 36
<211> LENGTH: 4
<212> TYPE: PRT
<213> ORGANISM: Artificial Sequence
<220> FEATURE:
<223> OTHER INFORMATION: chemically synthesized

```
<400> SEQUENCE: 36

Gly Gly Gly Ser
1

<210> SEQ ID NO 37
<211> LENGTH: 5
<212> TYPE: PRT
<213> ORGANISM: Artificial Sequence
<220> FEATURE:
<223> OTHER INFORMATION: chemically synthesized

<400> SEQUENCE: 37

Gly Ser Gly Gly Ser
1               5

<210> SEQ ID NO 38
<211> LENGTH: 5
<212> TYPE: PRT
<213> ORGANISM: Artificial Sequence
<220> FEATURE:
<223> OTHER INFORMATION: chemically synthesized

<400> SEQUENCE: 38

Gly Gly Ser Gly Gly
1               5

<210> SEQ ID NO 39
<211> LENGTH: 5
<212> TYPE: PRT
<213> ORGANISM: Artificial Sequence
<220> FEATURE:
<223> OTHER INFORMATION: chemically synthesized

<400> SEQUENCE: 39

Gly Ser Gly Ser Gly
1               5

<210> SEQ ID NO 40
<211> LENGTH: 5
<212> TYPE: PRT
<213> ORGANISM: Artificial Sequence
<220> FEATURE:
<223> OTHER INFORMATION: chemically synthesized

<400> SEQUENCE: 40

Gly Ser Gly Gly Gly
1               5

<210> SEQ ID NO 41
<211> LENGTH: 5
<212> TYPE: PRT
<213> ORGANISM: Artificial Sequence
<220> FEATURE:
<223> OTHER INFORMATION: chemically synthesized

<400> SEQUENCE: 41

Gly Gly Gly Ser Gly
1               5

<210> SEQ ID NO 42
<211> LENGTH: 5
<212> TYPE: PRT
<213> ORGANISM: Artificial Sequence
<220> FEATURE:
<223> OTHER INFORMATION: chemically synthesized

<400> SEQUENCE: 42
```

```
Gly Ser Ser Ser Gly
1               5

<210> SEQ ID NO 43
<211> LENGTH: 6
<212> TYPE: PRT
<213> ORGANISM: Artificial Sequence
<220> FEATURE:
<223> OTHER INFORMATION: chemically synthesized

<400> SEQUENCE: 43

Glu Phe Met Pro Met Glu
1               5

<210> SEQ ID NO 44
<211> LENGTH: 263
<212> TYPE: PRT
<213> ORGANISM: Artificial Sequence
<220> FEATURE:
<223> OTHER INFORMATION: chemically synthesized

<400> SEQUENCE: 44

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Thr Ser Asn Ala Phe Ala Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Val Thr Ile Ser Tyr Thr Gly Ser Ser
145                 150                 155                 160

Ser Asn Ile Gly Ala Gly Tyr Gly Val His Trp Tyr Gln Gln Leu Pro
                165                 170                 175

Gly Thr Ala Pro Lys Leu Leu Ile Tyr Gly Asn Thr Asn Arg Pro Ser
            180                 185                 190

Gln Val Pro Asp Arg Phe Ser Gly Phe Lys Ser Gly Thr Ser Ala Ser
        195                 200                 205

Leu Ala Ile Thr Gly Leu Gln Ala Glu Asp Ala Asp Tyr Tyr Cys
    210                 215                 220

Gln Ser Tyr Asp Ser Ser Leu Ser Gln Trp Val Phe Gly Gly Gly Thr
225                 230                 235                 240

Lys Leu Thr Val Leu Gly Ala Ala Ala Glu Gln Lys Leu Ile Ser Glu
                245                 250                 255

Glu Asp Leu Asn Gly Ala Ala
            260
```

```
<210> SEQ ID NO 45
<211> LENGTH: 262
<212> TYPE: PRT
<213> ORGANISM: Artificial Sequence
<220> FEATURE:
<223> OTHER INFORMATION: chemically synthesized

<400> SEQUENCE: 45

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Ala Asp Thr Ala Pro Thr Val Ser Ile Lys Leu Ile Ser Glu Glu
                245                 250                 255

Asp Leu Asn Gly Ala Ala
            260

<210> SEQ ID NO 46
<211> LENGTH: 250
<212> TYPE: PRT
<213> ORGANISM: Artificial Sequence
<220> FEATURE:
<223> OTHER INFORMATION: chemically synthesized

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg Ser Gly Gly
            100                 105                 110

Ser Thr Ile Thr Ser Tyr Asn Val Tyr Tyr Thr Lys Leu Ser Ser Ser
            115                 120                 125

Gly Thr Gln Val Gln Leu Val Gln Thr Gly Gly Val Val Gln Pro
130                 135                 140

Gly Arg Ser Leu Arg Leu Ser Cys Ala Ala Ser Gly Ser Thr Phe Ser
145                 150                 155                 160

Ser Tyr Ala Met Ser Trp Val Arg Gln Ala Pro Gly Lys Gly Leu Glu
                165                 170                 175

Trp Val Ser Ala Ile Ser Gly Ser Gly Gly Ser Thr Tyr Tyr Ala Asp
            180                 185                 190

Ser Val Lys Gly Arg Phe Thr Ile Ser Arg Asp Asn Ser Lys Asn Thr
            195                 200                 205

Leu Tyr Leu Gln Met Asn Ser Leu Arg Ala Glu Asp Thr Ala Val Tyr
210                 215                 220

Tyr Cys Ala Thr Asn Ser Leu Tyr Trp Tyr Phe Asp Leu Trp Gly Arg
225                 230                 235                 240

Gly Thr Leu Val Thr Val Ser Ser Ala Ser
                245                 250

<210> SEQ ID NO 47
<211> LENGTH: 205
<212> TYPE: PRT
<213> ORGANISM: Artificial Sequence
<220> FEATURE:
<223> OTHER INFORMATION: chemically synthesized

<400> SEQUENCE: 47

Gly Gln Ser Gly Gln Trp Val Cys His Pro Met Trp Glu Val Met Cys
 1               5                   10                  15

Leu Arg Gly Gly Ser Gly Gln Ser Gly Gln Gly Gly Gly Gly Ser Gly
                 20                  25                  30

Asp Tyr Asn Lys Asn Gln Tyr Tyr Gly Ile Thr Ala Gly Pro Ala Tyr
             35                  40                  45

Arg Ile Asn Asp Trp Ala Ser Ile Tyr Gly Val Val Gly Val Gly Tyr
 50                  55                  60

Gly Lys Phe Gln Thr Thr Glu Tyr Pro Thr Tyr Lys His Asp Thr Ser
 65                  70                  75                  80

Asp Tyr Gly Phe Ser Tyr Gly Ala Gly Leu Gln Phe Asn Pro Met Glu
                 85                  90                  95

Asn Val Ala Leu Asp Phe Ser Tyr Glu Gln Ser Arg Ile Arg Ser Val
            100                 105                 110

Asp Val Gly Thr Trp Ile Leu Ser Val Gly Tyr Arg Phe Gly Ser Lys
            115                 120                 125

Ser Arg Arg Ala Thr Ser Thr Val Thr Gly Gly Tyr Ala Gln Ser Asp
130                 135                 140

Ala Gln Gly Gln Met Asn Lys Met Gly Gly Phe Asn Leu Lys Tyr Arg
145                 150                 155                 160
```

Tyr Glu Glu Asp Asn Ser Pro Leu Gly Val Ile Gly Ser Phe Thr Tyr
                165                 170                 175

Thr Glu Lys Ser Arg Thr Ala Ser Gly Gly Ser His Ile Ser Gln Trp
        180                 185                 190

Lys Pro Lys Val Pro Asn Arg Glu Asp Lys Tyr Lys Lys
    195                 200                 205

<210> SEQ ID NO 48
<211> LENGTH: 222
<212> TYPE: PRT
<213> ORGANISM: Artificial Sequence
<220> FEATURE:
<223> OTHER INFORMATION: chemically synthesized

<400> SEQUENCE: 48

Gly Gln Ser Gly Gln Trp Val Cys His Pro Met Trp Glu Val Met Cys
1               5                   10                  15

Leu Arg Gly Gly Ser Gly Gln Ser Gly Gln Gly Gly Thr Gly Arg Gly
            20                  25                  30

Pro Ser Trp Val Gly Gly Ser Gly Ser Gly Gly Ser Gly Gly Ser
        35                  40                  45

Gly Asp Tyr Asn Lys Asn Gln Tyr Tyr Gly Ile Thr Ala Gly Pro Ala
    50                  55                  60

Tyr Arg Ile Asn Asp Trp Ala Ser Ile Tyr Gly Val Val Gly Val Gly
65                  70                  75                  80

Tyr Gly Lys Phe Gln Thr Thr Glu Tyr Pro Thr Tyr Lys His Asp Thr
                85                  90                  95

Ser Asp Tyr Gly Phe Ser Tyr Gly Ala Gly Leu Gln Phe Asn Pro Met
            100                 105                 110

Glu Asn Val Ala Leu Asp Phe Ser Tyr Glu Gln Ser Arg Ile Arg Ser
        115                 120                 125

Val Asp Val Gly Thr Trp Ile Leu Ser Val Gly Tyr Arg Phe Gly Ser
    130                 135                 140

Lys Ser Arg Arg Ala Thr Ser Thr Val Thr Gly Gly Tyr Ala Gln Ser
145                 150                 155                 160

Asp Ala Gln Gly Gln Met Asn Lys Met Gly Gly Phe Asn Leu Lys Tyr
                165                 170                 175

Arg Tyr Glu Glu Asp Asn Ser Pro Leu Gly Val Ile Gly Ser Phe Thr
            180                 185                 190

Tyr Thr Glu Lys Ser Arg Thr Ala Ser Gly Gly Ser His Ile Ser Gln
        195                 200                 205

Trp Lys Pro Lys Val Pro Asn Arg Glu Asp Lys Tyr Lys Lys
    210                 215                 220

<210> SEQ ID NO 49
<211> LENGTH: 222
<212> TYPE: PRT
<213> ORGANISM: Artificial Sequence
<220> FEATURE:
<223> OTHER INFORMATION: chemically synthesized

<400> SEQUENCE: 49

Gly Gln Ser Gly Gln Trp Val Cys His Pro Met Trp Glu Val Met Cys
1               5                   10                  15

Leu Arg Gly Gly Ser Gly Gln Ser Gly Gln Gly Gly Leu Ser Gly Arg
            20                  25                  30

Ser Asp Asn His Gly Gly Ser Gly Gly Ser Gly Gly Ser Gly Gly Ser
        35                  40                  45

```
Gly Asp Tyr Asn Lys Asn Gln Tyr Tyr Gly Ile Thr Ala Gly Pro Ala
    50                  55                  60

Tyr Arg Ile Asn Asp Trp Ala Ser Ile Tyr Gly Val Val Gly Val Gly
65                  70                  75                  80

Tyr Gly Lys Phe Gln Thr Thr Glu Tyr Pro Thr Tyr Lys His Asp Thr
                85                  90                  95

Ser Asp Tyr Gly Phe Ser Tyr Ala Gly Leu Gln Phe Asn Pro Met
                100                 105                 110

Glu Asn Val Ala Leu Asp Phe Ser Tyr Glu Gln Ser Arg Ile Arg Ser
            115                 120                 125

Val Asp Val Gly Thr Trp Ile Leu Ser Val Gly Tyr Arg Phe Gly Ser
    130                 135                 140

Lys Ser Arg Arg Ala Thr Ser Thr Val Thr Gly Gly Tyr Ala Gln Ser
145                 150                 155                 160

Asp Ala Gln Gly Gln Met Asn Lys Met Gly Gly Phe Asn Leu Lys Tyr
                165                 170                 175

Arg Tyr Glu Glu Asp Asn Ser Pro Leu Gly Val Ile Gly Ser Phe Thr
            180                 185                 190

Tyr Thr Gly Lys Ser Arg Thr Ala Ser Gly Gly Ser His Ile Ser Gln
            195                 200                 205

Trp Lys Pro Lys Val Pro Asn Arg Glu Asp Lys Tyr Lys Lys
    210                 215                 220

<210> SEQ ID NO 50
<211> LENGTH: 197
<212> TYPE: PRT
<213> ORGANISM: Artificial Sequence
<220> FEATURE:
<223> OTHER INFORMATION: chemically synthesized

<400> SEQUENCE: 50

Gly Gln Ser Gly Gln Glu Tyr Met Pro Met Glu Gly Gly Ser Gly Gln
1               5                   10                  15

Ser Gly Gln Gly Gly Gly Ser Gly Gly Gly Ser Ser Gly Gly Gln Gly
            20                  25                  30

Gly Ser Gly Gly Ser Gly Gly Ser Gly Gly Gly Gly Ser Ala Tyr
        35                  40                  45

Tyr Gly Ile Thr Ala Gly Pro Ala Tyr Arg Ile Asn Asp Trp Ala Ser
    50                  55                  60

Ile Tyr Gly Val Val Gly Val Gly Tyr Gly Ser Gly Pro Gly Gly Ser
65                  70                  75                  80

Tyr Gly Phe Ser Tyr Gly Ala Gly Leu Gln Phe Asn Pro Met Glu Asn
                85                  90                  95

Val Ala Leu Asp Phe Ser Tyr Glu Gln Ser Arg Ile Arg Ser Val Asp
                100                 105                 110

Val Gly Thr Trp Ile Leu Ser Val Gly Tyr Arg Phe Gly Ser Lys Ser
            115                 120                 125

Arg Arg Ala Thr Ser Thr Val Thr Gly Gly Tyr Ala Gln Ser Asp Ala
    130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Ala Ala Ala Gly His His His
            180                 185                 190
```

His His His His His
        195

<210> SEQ ID NO 51
<211> LENGTH: 197
<212> TYPE: PRT
<213> ORGANISM: Artificial Sequence
<220> FEATURE:
<223> OTHER INFORMATION: chemically synthesized

<400> SEQUENCE: 51

Gly Gln Ser Gly Gln Glu Tyr Met Pro Met Glu Gly Ser Gly Gln
1               5                   10                  15

Ser Gly Gln Thr Gly Arg Gly Pro Ser Trp Val Ser Gly Gln Gly
                20                  25                  30

Gly Ser Gly Gly Ser Gly Gly Ser Gly Gly Ser Gly Gly Ser Ala Tyr
            35                  40                  45

Tyr Gly Ile Thr Ala Gly Pro Ala Tyr Arg Ile Asn Asp Trp Ala Ser
        50                  55                  60

Ile Tyr Gly Val Val Gly Val Gly Tyr Gly Ser Gly Pro Gly Gly Ser
65                  70                  75                  80

Tyr Gly Phe Ser Tyr Gly Ala Gly Leu Gln Phe Asn Pro Met Glu Asn
                85                  90                  95

Val Ala Leu Asp Phe Ser Tyr Glu Gln Ser Arg Ile Arg Ser Val Asp
                100                 105                 110

Val Gly Thr Trp Ile Leu Ser Val Gly Tyr Arg Phe Gly Ser Lys Ser
            115                 120                 125

Arg Arg Ala Thr Ser Thr Val Thr Gly Gly Tyr Ala Gln Ser Asp Ala
130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Ala Ala Ala Gly His His His
            180                 185                 190

His His His His His
        195

<210> SEQ ID NO 52
<211> LENGTH: 197
<212> TYPE: PRT
<213> ORGANISM: Artificial Sequence
<220> FEATURE:
<223> OTHER INFORMATION: chemically synthesized

<400> SEQUENCE: 52

Gly Gln Ser Gly Gln Glu Tyr Met Pro Met Glu Gly Ser Gly Gln
1               5                   10                  15

Ser Gly Gln Leu Ser Gly Arg Ser Asp Asn His Ser Gly Gln Gly
                20                  25                  30

Gly Ser Gly Gly Ser Gly Gly Ser Gly Gly Ser Gly Gly Ser Ala Tyr
            35                  40                  45

Tyr Gly Ile Thr Ala Gly Pro Ala Tyr Arg Ile Asn Asp Trp Ala Ser
        50                  55                  60

Ile Tyr Gly Val Val Gly Val Gly Tyr Gly Ser Gly Pro Gly Gly Ser
65                  70                  75                  80

Tyr Gly Phe Ser Tyr Gly Ala Gly Leu Gln Phe Asn Pro Met Glu Asn

```
                85                  90                  95

Val Ala Leu Asp Phe Ser Tyr Glu Gln Ser Arg Ile Arg Ser Val Asp
            100                 105                 110

Val Gly Thr Trp Ile Leu Ser Val Gly Tyr Arg Phe Gly Ser Lys Ser
        115                 120                 125

Arg Arg Ala Thr Ser Thr Val Thr Gly Gly Tyr Ala Gln Ser Asp Ala
    130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Ala Ala Ala Gly His His His
            180                 185                 190

His His His His His
        195

<210> SEQ ID NO 53
<211> LENGTH: 12
<212> TYPE: PRT
<213> ORGANISM: Artificial Sequence
<220> FEATURE:
<223> OTHER INFORMATION: chemically synthesized

<400> SEQUENCE: 53

Thr Ala Ala Gly His His His His His His His His
1               5                   10

<210> SEQ ID NO 54
<211> LENGTH: 12
<212> TYPE: PRT
<213> ORGANISM: Artificial Sequence
<220> FEATURE:
<223> OTHER INFORMATION: chemically synthesized

<400> SEQUENCE: 54

Ala Ala Ala Gly His His His His His His His His
1               5                   10

<210> SEQ ID NO 55
<211> LENGTH: 28
<212> TYPE: PRT
<213> ORGANISM: Artificial Sequence
<220> FEATURE:
<223> OTHER INFORMATION: chemically synthesized

<400> SEQUENCE: 55

Ala Ala Ala Gly Glu Ile Val Leu Thr Gln Ser Pro Gly Thr Leu Val
1               5                   10                  15

Thr Val Ser Ser His His His His His His His His
            20                  25

<210> SEQ ID NO 56
<211> LENGTH: 142
<212> TYPE: PRT
<213> ORGANISM: Artificial Sequence
<220> FEATURE:
<223> OTHER INFORMATION: chemically synthesized

<400> SEQUENCE: 56

Tyr Tyr Gly Ile Thr Ala Gly Pro Ala Tyr Arg Ile Asn Asp Trp Ala
1               5                   10                  15

Ser Ile Tyr Gly Val Val Gly Val Gly Tyr Gly Ser Gly Pro Gly Gly
```

```
                20                  25                  30

Ser Tyr Gly Phe Ser Tyr Gly Ala Gly Leu Gln Phe Asn Pro Met Glu
            35                  40                  45

Asn Val Ala Leu Asp Phe Ser Tyr Glu Gln Ser Arg Ile Arg Ser Val
        50                  55                  60

Asp Val Gly Thr Trp Ile Leu Ser Val Gly Tyr Arg Phe Gly Ser Lys
65                  70                  75                  80

Ser Arg Arg Ala Thr Ser Thr Val Thr Gly Gly Tyr Ala Gln Ser Asp
                85                  90                  95

Ala Gln Gly Gln Met Asn Lys Met Gly Gly Phe Asn Leu Lys Tyr Arg
            100                 105                 110

Tyr Glu Glu Asp Asn Ser Pro Leu Gly Val Ile Gly Ser Phe Thr Tyr
        115                 120                 125

Thr Gly Gly Ser Gly Gly Ser Ser Gly Gln Thr Ala Ala Gly
    130                 135                 140

<210> SEQ ID NO 57
<211> LENGTH: 142
<212> TYPE: PRT
<213> ORGANISM: Artificial Sequence
<220> FEATURE:
<223> OTHER INFORMATION: chemically synthesized

<400> SEQUENCE: 57

Tyr Tyr Gly Ile Thr Ala Gly Pro Ala Tyr Arg Ile Asn Asp Trp Ala
1               5                   10                  15

Ser Ile Tyr Gly Val Val Gly Val Gly Tyr Gly Ser Gly Pro Gly Gly
            20                  25                  30

Ser Tyr Gly Phe Ser Tyr Gly Ala Gly Leu Gln Phe Asn Pro Met Glu
        35                  40                  45

Asn Val Ala Leu Asp Phe Ser Tyr Glu Gln Ser Arg Ile Arg Ser Val
    50                  55                  60

Asp Val Gly Thr Trp Ile Leu Ser Val Gly Tyr Arg Phe Gly Ser Lys
65                  70                  75                  80

Ser Arg Arg Ala Thr Ser Thr Val Thr Gly Gly Tyr Ala Gln Ser Asp
                85                  90                  95

Ala Gln Gly Gln Met Asn Lys Met Gly Gly Phe Asn Leu Lys Tyr Arg
            100                 105                 110

Tyr Glu Glu Asp Asn Ser Pro Leu Gly Val Ile Gly Ser Phe Thr Tyr
        115                 120                 125

Thr Gly Gly Ser Gly Gly Ser Ser Gly Gln Ala Ala Ala Gly
    130                 135                 140

<210> SEQ ID NO 58
<211> LENGTH: 197
<212> TYPE: PRT
<213> ORGANISM: Artificial Sequence
<220> FEATURE:
<223> OTHER INFORMATION: chemically synthesized

<400> SEQUENCE: 58

Gly Gln Ser Gly Gln Glu Tyr Met Pro Met Glu Gly Gly Ser Gly Gln
1               5                   10                  15

Ser Gly Gln Gly Ser Gly Ser Asn Ser Gly Ser Ser Gly Gly Gln Gly
            20                  25                  30

Gly Ser Gly Gly Ser Gly Gly Ser Gly Gly Ser Gly Gly Ser Ala Tyr
        35                  40                  45
```

```
Tyr Gly Ile Thr Ala Gly Pro Ala Tyr Arg Ile Asn Asp Trp Ala Ser
 50                  55                  60

Ile Tyr Gly Val Val Gly Val Gly Tyr Gly Ser Gly Pro Gly Gly Ser
 65                  70                  75                  80

Tyr Gly Phe Ser Tyr Gly Ala Gly Leu Gln Phe Asn Pro Met Glu Asn
                 85                  90                  95

Val Ala Leu Asp Phe Ser Tyr Glu Gln Ser Arg Ile Arg Ser Val Asp
                100                 105                 110

Val Gly Thr Trp Ile Leu Ser Val Gly Tyr Arg Phe Gly Ser Lys Ser
                115                 120                 125

Arg Arg Ala Thr Ser Thr Val Thr Gly Gly Tyr Ala Gln Ser Asp Ala
130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Ala Ala Ala Gly His His His
                180                 185                 190

His His His His His
        195
```

<210> SEQ ID NO 59
<211> LENGTH: 10
<212> TYPE: PRT
<213> ORGANISM: Artificial Sequence
<220> FEATURE:
<223> OTHER INFORMATION: chemically synthesized

<400> SEQUENCE: 59

```
Gly Gly Ser Gly Gln Ser Gly Gln Gly Ser
1               5                   10
```

<210> SEQ ID NO 60
<211> LENGTH: 220
<212> TYPE: PRT
<213> ORGANISM: Artificial Sequence
<220> FEATURE:
<223> OTHER INFORMATION: chemically synthesized

<400> SEQUENCE: 60

```
Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
                20                  25                  30

Met Glu Gly Gly Ser Gly Gln Ser Gln Gly Ser Gly Ser Asn Ser
            35                  40                  45

Gly Ser Ser Gly Gly Gln Gly Ser Gly Gly Ser Gly Gly Ser Gly
    50                  55                  60

Gly Ser Gly Gly Ser Ala Tyr Tyr Gly Ile Thr Ala Gly Pro Ala Tyr
 65                  70                  75                  80

Arg Ile Asn Asp Trp Ala Ser Ile Tyr Gly Val Val Gly Val Gly Tyr
                85                  90                  95

Gly Ser Gly Pro Gly Gly Ser Tyr Gly Phe Ser Tyr Gly Ala Gly Leu
                100                 105                 110

Gln Phe Asn Pro Met Glu Asn Val Ala Leu Asp Phe Ser Tyr Glu Gln
                115                 120                 125

Ser Arg Ile Arg Ser Val Asp Val Gly Thr Trp Ile Leu Ser Val Gly
                130                 135                 140
```

```
Tyr Arg Phe Gly Ser Lys Ser Arg Ala Thr Ser Thr Val Thr Gly
145                 150                 155                 160

Gly Tyr Ala Gln Ser Asp Ala Gln Gly Gln Met Asn Lys Met Gly Gly
                165                 170                 175

Phe Asn Leu Lys Tyr Arg Tyr Glu Glu Asp Asn Ser Pro Leu Gly Val
            180                 185                 190

Ile Gly Ser Phe Thr Tyr Thr Gly Gly Ser Gly Gly Ser Ser Gly Gln
        195                 200                 205

Ala Ala Ala Gly His His His His His His
        210                 215                 220
```

<210> SEQ ID NO 61
<211> LENGTH: 8
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(8)
<223> OTHER INFORMATION: X is any amino acid

<400> SEQUENCE: 61

```
Xaa Xaa Xaa Xaa Xaa Xaa Xaa Xaa
1               5
```

<210> SEQ ID NO 62
<211> LENGTH: 481
<212> TYPE: PRT
<213> ORGANISM: Artificial Sequence
<220> FEATURE:
<223> OTHER INFORMATION: chemically synthesized

<400> SEQUENCE: 62

```
Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gln Gly Ser Gly Ser Asn Ser
        35                  40                  45

Gly Ser Ser Gly Gly Gln Gly Gly Ser Gly Ser Gly Gly Ser Gly
    50                  55                  60

Gly Ser Gly Gly Ser Ala Tyr Tyr Gly Ile Thr Ala Gly Pro Ala Tyr
65                  70                  75                  80

Arg Ile Asn Asp Trp Ala Ser Ile Tyr Gly Val Val Gly Val Gly Tyr
                85                  90                  95

Gly Ser Gly Pro Gly Gly Ser Tyr Gly Phe Ser Tyr Gly Ala Gly Leu
            100                 105                 110

Gln Phe Asn Pro Met Glu Asn Val Ala Leu Asp Phe Ser Tyr Glu Gln
        115                 120                 125

Ser Arg Ile Arg Ser Val Asp Val Gly Thr Trp Ile Leu Ser Val Gly
    130                 135                 140

Tyr Arg Phe Gly Ser Lys Ser Arg Ala Thr Ser Thr Val Thr Gly
145                 150                 155                 160

Gly Tyr Ala Gln Ser Asp Ala Gln Gly Gln Met Asn Lys Met Gly Gly
                165                 170                 175

Phe Asn Leu Lys Tyr Arg Tyr Glu Glu Asp Asn Ser Pro Leu Gly Val
            180                 185                 190
```

```
Ile Gly Ser Phe Thr Tyr Thr Gly Ser Gly Ser Gly Gln
        195                 200             205

Ala Ala Ala Gly Gln Val Gln Leu Val Glu Ser Gly Gly Leu Val
210                 215                 220

Gln Pro Gly Gly Ser Leu Arg Leu Ser Cys Ala Ala Ser Gly Phe Thr
225                 230                 235                 240

Phe Arg Ser Tyr Ala Met Ser Trp Val Arg Gln Ala Pro Gly Lys Gly
                245                 250                 255

Leu Glu Trp Val Ser Ala Ile Ser Gly Arg Gly Asp Asn Thr Tyr Tyr
            260                 265                 270

Ala Asp Ser Val Lys Gly Arg Phe Thr Ile Ser Arg Asp Asn Ser Lys
        275                 280                 285

Asn Thr Leu Tyr Leu Gln Met Asn Ser Leu Arg Ala Glu Asp Thr Ala
    290                 295                 300

Val Tyr Tyr Cys Ala Lys Met Thr Ser Asn Ala Phe Ala Phe Asp Tyr
305                 310                 315                 320

Trp Gly Gln Gly Thr Leu Val Thr Val Ser Ser Gly Gly Gly Gly Ser
                325                 330                 335

Gly Gly Gly Gly Ser Gly Gly Gly Ser Gln Ser Val Leu Thr Gln
        340                 345                 350

Pro Pro Ser Val Ser Gly Ala Pro Gly Gln Arg Val Thr Ile Ser Tyr
                355                 360                 365

Thr Gly Ser Ser Ser Asn Ile Gly Ala Gly Tyr Gly Val His Trp Tyr
    370                 375                 380

Gln Gln Leu Pro Gly Thr Ala Pro Lys Leu Leu Ile Tyr Gly Asn Thr
385                 390                 395                 400

Asn Arg Pro Ser Gln Val Pro Asp Arg Phe Ser Gly Phe Lys Ser Gly
                405                 410                 415

Thr Ser Ala Ser Leu Ala Ile Thr Gly Leu Gln Ala Glu Asp Glu Ala
                420                 425                 430

Asp Tyr Tyr Cys Gln Ser Tyr Asp Ser Ser Leu Ser Gln Trp Val Phe
                435                 440                 445

Gly Gly Gly Thr Lys Leu Thr Val Leu Gly Ala Ala Ala Glu Gln Lys
450                 455                 460

Leu Ile Ser Glu Glu Asp Leu Asn Gly Ala Ala His His His His
465                 470                 475                 480

His

<210> SEQ ID NO 63
<211> LENGTH: 480
<212> TYPE: PRT
<213> ORGANISM: Artificial Sequence
<220> FEATURE:
<223> OTHER INFORMATION: chemically synthesized

<400> SEQUENCE: 63

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
                20                  25                  30

Met Glu Gly Gly Ser Gly Gln Gly Gln Gly Ser Gly Ser Asn Ser
            35                  40                  45

Gly Ser Ser Gly Gly Gln Gly Gly Ser Gly Gly Ser Gly
        50                  55                  60

Gly Ser Gly Gly Ser Ala Tyr Tyr Gly Ile Thr Ala Gly Pro Ala Tyr
```

Arg Ile Asn Asp Trp Ala Ser Ile Tyr Gly Val Val Gly Val Gly Tyr
65                  70                  75                  80

Gly Ser Gly Pro Gly Gly Ser Tyr Gly Phe Ser Tyr Gly Ala Gly Leu
            85                  90                  95

Gln Phe Asn Pro Met Glu Asn Val Ala Leu Asp Phe Ser Tyr Glu Gln
                100                 105                 110

Ser Arg Ile Arg Ser Val Asp Val Gly Thr Trp Ile Leu Ser Val Gly
            115                 120                 125

Tyr Arg Phe Gly Ser Lys Ser Arg Ala Thr Ser Thr Val Thr Gly
130                 135                 140

Gly Tyr Ala Gln Ser Asp Ala Gln Gly Gln Met Asn Lys Met Gly Gly
145                 150                 155                 160

Phe Asn Leu Lys Tyr Arg Tyr Glu Glu Asp Asn Ser Pro Leu Gly Val
                165                 170                 175

Ile Gly Ser Phe Thr Tyr Thr Gly Gly Ser Gly Gly Ser Gly Gln
            180                 185                 190

Ala Ala Ala Gly Gln Val Gln Leu Gln Gln Ser Gly Ala Glu Leu Ala
195                 200                 205

Arg Pro Gly Ala Ser Val Lys Met Ser Cys Lys Ala Ser Gly Tyr Thr
210                 215                 220

Phe Thr Arg Tyr Thr Met His Trp Val Lys Gln Arg Pro Gly Gln Gly
225                 230                 235                 240

Leu Glu Trp Ile Gly Tyr Ile Asn Pro Ser Arg Gly Tyr Thr Asn Tyr
            245                 250                 255

Asn Gln Lys Phe Lys Asp Lys Ala Thr Leu Thr Thr Asp Lys Ser Ser
                260                 265                 270

Ser Thr Ala Tyr Met Gln Leu Ser Ser Leu Thr Ser Glu Asp Ser Ala
            275                 280                 285

Val Tyr Tyr Cys Ala Arg Tyr Tyr Asp Asp His Tyr Cys Leu Asp Tyr
290                 295                 300

Trp Gly Gln Gly Thr Thr Leu Thr Val Ser Ser Gly Gly Gly Gly Ser
305                 310                 315                 320

Gly Gly Gly Gly Ser Gly Gly Gly Gly Ser Gln Ile Val Leu Thr Gln
            325                 330                 335

Ser Pro Ala Ile Met Ser Ala Ser Pro Gly Glu Lys Val Thr Met Thr
                340                 345                 350

Cys Ser Ala Ser Ser Ser Val Ser Tyr Met Asn Trp Tyr Gln Gln Lys
            355                 360                 365

Ser Gly Thr Ser Pro Lys Arg Trp Ile Tyr Asp Thr Ser Lys Leu Ala
370                 375                 380

Ser Gly Val Pro Ala His Phe Arg Gly Ser Gly Ser Gly Thr Ser Tyr
385                 390                 395                 400

Ser Leu Thr Ile Ser Gly Met Glu Ala Glu Asp Ala Ala Thr Tyr Tyr
            405                 410                 415

Cys Gln Gln Trp Ser Ser Asn Pro Phe Thr Phe Gly Ser Gly Thr Lys
                420                 425                 430

Leu Glu Ile Asn Arg Ala Asp Thr Ala Pro Thr Val Ser Ile Lys Leu
            435                 440                 445

Ile Ser Glu Glu Asp Leu Asn Gly Ala Ala His His His His His His
450                 455                 460

<210> SEQ ID NO 64

```
<211> LENGTH: 473
<212> TYPE: PRT
<213> ORGANISM: Artificial Sequence
<220> FEATURE:
<223> OTHER INFORMATION: chemically synthesized

<400> SEQUENCE: 64

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Gln Val Gln Leu Val Glu
        35                  40                  45

Ser Gly Gly Gly Leu Val Gln Pro Gly Gly Ser Leu Arg Leu Ser Cys
    50                  55                  60

Ala Ala Ser Gly Phe Thr Phe Arg Ser Tyr Ala Met Ser Trp Val Arg
65                  70                  75                  80

Gln Ala Pro Gly Lys Gly Leu Glu Trp Val Ser Ala Ile Ser Gly Arg
                85                  90                  95

Gly Asp Asn Thr Tyr Tyr Ala Asp Ser Val Lys Gly Arg Phe Thr Ile
            100                 105                 110

Ser Arg Asp Asn Ser Lys Asn Thr Leu Tyr Leu Gln Met Asn Ser Leu
        115                 120                 125

Arg Ala Glu Asp Thr Ala Val Tyr Tyr Cys Ala Lys Met Thr Ser Asn
    130                 135                 140

Ala Phe Ala Phe Asp Tyr Trp Gly Gln Gly Thr Leu Val Thr Val Ser
145                 150                 155                 160

Ser Gly Gly Gly Gly Ser Gly Gly Gly Ser Gly Gly Gly Gly Gly Ser
                165                 170                 175

Gln Ser Val Leu Thr Gln Pro Pro Ser Val Ser Gly Ala Pro Gly Gln
            180                 185                 190

Arg Val Thr Ile Ser Tyr Thr Gly Ser Ser Ser Asn Ile Gly Ala Gly
        195                 200                 205

Tyr Gly Val His Trp Tyr Gln Gln Leu Pro Gly Thr Ala Pro Lys Leu
    210                 215                 220

Leu Ile Tyr Gly Asn Thr Asn Arg Pro Ser Gln Val Pro Asp Arg Phe
225                 230                 235                 240

Ser Gly Phe Lys Ser Gly Thr Ser Ala Ser Leu Ala Ile Thr Gly Leu
                245                 250                 255

Gln Ala Glu Asp Glu Ala Asp Tyr Tyr Cys Gln Ser Tyr Asp Ser Ser
            260                 265                 270

Leu Ser Gln Trp Val Phe Gly Gly Gly Thr Lys Leu Thr Val Leu Gly
        275                 280                 285

Ala Ala Ala Glu Gln Lys Leu Ile Ser Glu Glu Asp Leu Asn Gly Ser
    290                 295                 300

Gly Gly Gln Gly Gly Ser Gly Gly Ser Gly Gly Ser Gly Gly Ser Gly
305                 310                 315                 320

Gly Ser Ala Tyr Tyr Gly Ile Thr Ala Gly Pro Ala Tyr Arg Ile Asn
                325                 330                 335

Asp Trp Ala Ser Ile Tyr Gly Val Gly Val Gly Tyr Gly Ser Gly
            340                 345                 350

Pro Gly Gly Ser Tyr Gly Phe Ser Tyr Gly Ala Gly Leu Gln Phe Asn
        355                 360                 365

Pro Met Glu Asn Val Ala Leu Asp Phe Ser Tyr Glu Gln Ser Arg Ile
    370                 375                 380
```

```
Arg Ser Val Asp Val Gly Thr Trp Ile Leu Ser Val Gly Tyr Arg Phe
385                 390                 395                 400

Gly Ser Lys Ser Arg Ala Thr Ser Thr Val Thr Gly Gly Tyr Ala
            405                 410                 415

Gln Ser Asp Ala Gln Gly Gln Met Asn Lys Met Gly Gly Phe Asn Leu
            420                 425                 430

Lys Tyr Arg Tyr Glu Glu Asp Asn Ser Pro Leu Gly Val Ile Gly Ser
            435                 440                 445

Phe Thr Tyr Thr Gly Gly Ser Gly Gly Ser Gly Gln Thr Ala Ala
    450                 455                 460

Gly His His His His His His His
465                 470
```

<210> SEQ ID NO 65
<211> LENGTH: 472
<212> TYPE: PRT
<213> ORGANISM: Artificial Sequence
<220> FEATURE:
<223> OTHER INFORMATION: chemically synthesized

<400> SEQUENCE: 65

```
Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Gln Val Gln Leu Gln Gln
            35                  40                  45

Ser Gly Ala Glu Leu Ala Arg Pro Gly Ala Ser Val Lys Met Ser Cys
50                  55                  60

Lys Ala Ser Gly Tyr Thr Phe Thr Arg Tyr Thr Met His Trp Val Lys
65                  70                  75                  80

Gln Arg Pro Gly Gln Gly Leu Glu Trp Ile Gly Tyr Ile Asn Pro Ser
                85                  90                  95

Arg Gly Tyr Thr Asn Tyr Asn Gln Lys Phe Lys Asp Lys Ala Thr Leu
            100                 105                 110

Thr Thr Asp Lys Ser Ser Ser Thr Ala Tyr Met Gln Leu Ser Ser Leu
            115                 120                 125

Thr Ser Glu Asp Ser Ala Val Tyr Tyr Cys Ala Arg Tyr Tyr Asp Asp
130                 135                 140

His Tyr Cys Leu Asp Tyr Trp Gly Gln Gly Thr Thr Leu Thr Val Ser
145                 150                 155                 160

Ser Gly Gly Gly Gly Ser Gly Gly Gly Gly Ser Gly Gly Gly Gly Ser
                165                 170                 175

Gln Ile Val Leu Thr Gln Ser Pro Ala Ile Met Ser Ala Ser Pro Gly
            180                 185                 190

Glu Lys Val Thr Met Thr Cys Ser Ala Ser Ser Val Ser Tyr Met
            195                 200                 205

Asn Trp Tyr Gln Gln Lys Ser Gly Thr Ser Pro Lys Arg Trp Ile Tyr
    210                 215                 220

Asp Thr Ser Lys Leu Ala Ser Gly Val Pro Ala His Phe Arg Gly Ser
225                 230                 235                 240

Gly Ser Gly Thr Ser Tyr Ser Leu Thr Ile Ser Gly Met Glu Ala Glu
                245                 250                 255

Asp Ala Ala Thr Tyr Tyr Cys Gln Gln Trp Ser Ser Asn Pro Phe Thr
            260                 265                 270
```

```
Phe Gly Ser Gly Thr Lys Leu Glu Ile Asn Arg Ala Asp Thr Ala Pro
        275                 280                 285

Thr Val Ser Ile Lys Leu Ile Ser Glu Glu Asp Leu Asn Gly Ser Gly
        290                 295                 300

Gly Gln Gly Gly Ser Gly Gly Ser Gly Gly Ser Gly Gly Ser Gly Gly
305                 310                 315                 320

Ser Ala Tyr Tyr Gly Ile Thr Ala Gly Pro Ala Tyr Arg Ile Asn Asp
                325                 330                 335

Trp Ala Ser Ile Tyr Gly Val Val Gly Tyr Gly Ser Gly Pro
                340                 345                 350

Gly Gly Ser Tyr Gly Phe Ser Tyr Gly Ala Gly Leu Gln Phe Asn Pro
                355                 360                 365

Met Glu Asn Val Ala Leu Asp Phe Ser Tyr Glu Gln Ser Arg Ile Arg
        370                 375                 380

Ser Val Asp Val Gly Thr Trp Ile Leu Ser Val Gly Tyr Arg Phe Gly
385                 390                 395                 400

Ser Lys Ser Arg Arg Ala Thr Ser Thr Val Thr Gly Tyr Ala Gln
                405                 410                 415

Ser Asp Ala Gln Gly Gln Met Asn Lys Met Gly Phe Asn Leu Lys
                420                 425                 430

Tyr Arg Tyr Glu Glu Asp Asn Ser Pro Leu Gly Val Ile Gly Ser Phe
                435                 440                 445

Thr Tyr Thr Gly Gly Ser Gly Gly Ser Gly Gln Thr Ala Ala Gly
        450                 455                 460

His His His His His His His
465                 470

<210> SEQ ID NO 66
<211> LENGTH: 489
<212> TYPE: PRT
<213> ORGANISM: Artificial Sequence
<220> FEATURE:
<223> OTHER INFORMATION: chemically synthesized

<400> SEQUENCE: 66

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
                20                  25                  30

Met Glu Gly Gly Ser Gly Gln Ser Gly Gly Gln Val Gln Leu Val Glu
            35                  40                  45

Ser Gly Gly Gly Leu Val Gln Pro Gly Gly Ser Leu Arg Leu Ser Cys
50                  55                  60

Ala Ala Ser Gly Phe Thr Phe Arg Ser Tyr Ala Met Ser Trp Val Arg
65                  70                  75                  80

Gln Ala Pro Gly Lys Gly Leu Glu Trp Val Ser Ala Ile Ser Gly Arg
                85                  90                  95

Gly Asp Asn Thr Tyr Tyr Ala Asp Ser Val Lys Gly Arg Phe Thr Ile
                100                 105                 110

Ser Arg Asp Asn Ser Lys Asn Thr Leu Tyr Leu Gln Met Asn Ser Leu
            115                 120                 125

Arg Ala Glu Asp Thr Ala Val Tyr Tyr Cys Ala Lys Met Thr Ser Asn
        130                 135                 140

Ala Phe Ala Phe Asp Tyr Trp Gly Gln Gly Thr Leu Val Thr Val Ser
145                 150                 155                 160
```

Ser Gly Gly Gly Gly Ser Gly Gly Gly Ser Gly Gly Gly Ser
            165                 170                 175

Gln Ser Val Leu Thr Gln Pro Pro Ser Val Ser Gly Ala Pro Gly Gln
            180                 185                 190

Arg Val Thr Ile Ser Tyr Thr Gly Ser Ser Asn Ile Gly Ala Gly
            195                 200                 205

Tyr Gly Val His Trp Tyr Gln Gln Leu Pro Gly Thr Ala Pro Lys Leu
            210                 215                 220

Leu Ile Tyr Gly Asn Thr Asn Arg Pro Ser Gln Val Pro Asp Arg Phe
225                 230                 235                 240

Ser Gly Phe Lys Ser Gly Thr Ser Ala Ser Leu Ala Ile Thr Gly Leu
            245                 250                 255

Gln Ala Glu Asp Glu Ala Asp Tyr Tyr Cys Gln Ser Tyr Asp Ser Ser
            260                 265                 270

Leu Ser Gln Trp Val Phe Gly Gly Thr Lys Leu Thr Val Leu Gly
            275                 280                 285

Ala Ala Ala Glu Gln Lys Leu Ile Ser Glu Glu Asp Leu Asn Gly Ser
            290                 295                 300

Gly Gly Gln Gly Gly Ser Gly Ser Gly Ser Gly Gly Ser Gly
305                 310                 315                 320

Gly Ser Ala Tyr Tyr Gly Ile Thr Ala Gly Pro Ala Tyr Arg Ile Asn
            325                 330                 335

Asp Trp Ala Ser Ile Tyr Gly Val Val Gly Val Gly Tyr Gly Ser Gly
            340                 345                 350

Pro Gly Gly Ser Tyr Gly Phe Ser Tyr Gly Ala Gly Leu Gln Phe Asn
            355                 360                 365

Pro Met Glu Asn Val Ala Leu Asp Phe Ser Tyr Glu Gln Ser Arg Ile
            370                 375                 380

Arg Ser Val Asp Val Gly Thr Trp Ile Leu Ser Val Gly Tyr Arg Phe
385                 390                 395                 400

Gly Ser Lys Ser Arg Arg Ala Thr Ser Thr Val Thr Gly Gly Tyr Ala
            405                 410                 415

Gln Ser Asp Ala Gln Gly Gln Met Asn Lys Met Gly Gly Phe Asn Leu
            420                 425                 430

Lys Tyr Arg Tyr Glu Glu Asp Asn Ser Pro Leu Gly Val Ile Gly Ser
            435                 440                 445

Phe Thr Tyr Thr Gly Gly Ser Gly Gly Ser Gly Gln Ala Ala Ala
            450                 455                 460

Gly Glu Ile Val Leu Thr Gln Ser Pro Gly Thr Leu Val Thr Val Ser
465                 470                 475                 480

Ser His His His His His His His
            485

<210> SEQ ID NO 67
<211> LENGTH: 458
<212> TYPE: PRT
<213> ORGANISM: Artificial Sequence
<220> FEATURE:
<223> OTHER INFORMATION: chemically synthesized

<400> SEQUENCE: 67

Gly Gln Ser Gly Gln Glu Tyr Met Pro Met Glu Gly Gly Ser Gly Gln
1               5                   10                  15

Ser Gly Gln Gly Ser Gly Ser Asn Ser Gly Ser Ser Gly Gly Gln Gly
            20                  25                  30

```
Gly Ser Gly Gly Ser Gly Gly Ser Gly Gly Ser Ala Tyr
        35              40              45

Tyr Gly Ile Thr Ala Gly Pro Ala Tyr Arg Ile Asn Asp Trp Ala Ser
        50              55              60

Ile Tyr Gly Val Val Gly Val Gly Tyr Gly Ser Gly Pro Gly Gly Ser
65              70              75              80

Tyr Gly Phe Ser Tyr Gly Ala Gly Leu Gln Phe Asn Pro Met Glu Asn
                85              90              95

Val Ala Leu Asp Phe Ser Tyr Glu Gln Ser Arg Ile Arg Ser Val Asp
                100             105             110

Val Gly Thr Trp Ile Leu Ser Val Gly Tyr Arg Phe Gly Ser Lys Ser
            115             120             125

Arg Arg Ala Thr Ser Thr Val Thr Gly Gly Tyr Ala Gln Ser Asp Ala
        130             135             140

Gln Gly Gln Met Asn Lys Met Gly Gly Phe Asn Leu Lys Tyr Arg Tyr
145             150             155             160

Glu Glu Asp Asn Ser Pro Leu Gly Val Ile Gly Ser Phe Thr Tyr Thr
                165             170             175

Gly Gly Ser Gly Gly Ser Ser Gly Gln Ala Ala Ala Gly Gln Val Gln
            180             185             190

Leu Val Glu Ser Gly Gly Gly Leu Val Gln Pro Gly Gly Ser Leu Arg
        195             200             205

Leu Ser Cys Ala Ala Ser Gly Phe Thr Phe Arg Ser Tyr Ala Met Ser
        210             215             220

Trp Val Arg Gln Ala Pro Gly Lys Gly Leu Glu Trp Val Ser Ala Ile
225             230             235             240

Ser Gly Arg Gly Asp Asn Thr Tyr Tyr Ala Asp Ser Val Lys Gly Arg
                245             250             255

Phe Thr Ile Ser Arg Asp Asn Ser Lys Asn Thr Leu Tyr Leu Gln Met
                260             265             270

Asn Ser Leu Arg Ala Glu Asp Thr Ala Val Tyr Tyr Cys Ala Lys Met
        275             280             285

Thr Ser Asn Ala Phe Ala Phe Asp Tyr Trp Gly Gln Gly Thr Leu Val
        290             295             300

Thr Val Ser Ser Gly Gly Gly Gly Ser Gly Gly Gly Gly Ser Gly Gly
305             310             315             320

Gly Gly Ser Gln Ser Val Leu Thr Gln Pro Pro Ser Val Ser Gly Ala
            325             330             335

Pro Gly Gln Arg Val Thr Ile Ser Tyr Thr Gly Ser Ser Asn Ile
                340             345             350

Gly Ala Gly Tyr Gly Val His Trp Tyr Gln Gln Leu Pro Gly Thr Ala
        355             360             365

Pro Lys Leu Leu Ile Tyr Gly Asn Thr Asn Arg Pro Ser Gln Val Pro
    370             375             380

Asp Arg Phe Ser Gly Phe Lys Ser Gly Thr Ser Ala Ser Leu Ala Ile
385             390             395             400

Thr Gly Leu Gln Ala Glu Asp Glu Ala Asp Tyr Tyr Cys Gln Ser Tyr
            405             410             415

Asp Ser Ser Leu Ser Gln Trp Val Phe Gly Gly Gly Thr Lys Leu Thr
            420             425             430

Val Leu Gly Ala Ala Ala Glu Gln Lys Leu Ile Ser Glu Glu Asp Leu
        435             440             445
```

Asn Gly Ala Ala His His His His His His
    450                 455

<210> SEQ ID NO 68
<211> LENGTH: 457
<212> TYPE: PRT
<213> ORGANISM: Artificial Sequence
<220> FEATURE:
<223> OTHER INFORMATION: chemically synthesized

<400> SEQUENCE: 68

Gly Gln Ser Gly Gln Glu Tyr Met Pro Met Glu Gly Ser Gly Gln
1               5                   10                  15

Ser Gly Gln Gly Ser Gly Asn Ser Gly Ser Ser Gly Gly Gln Gly
            20                  25                  30

Gly Ser Gly Gly Ser Gly Gly Ser Gly Gly Ser Gly Gly Ser Ala Tyr
        35                  40                  45

Tyr Gly Ile Thr Ala Gly Pro Ala Tyr Arg Ile Asn Asp Trp Ala Ser
    50                  55                  60

Ile Tyr Gly Val Val Gly Val Tyr Gly Ser Gly Pro Gly Gly Ser
65                  70                  75                  80

Tyr Gly Phe Ser Tyr Gly Ala Gly Leu Gln Phe Asn Pro Met Glu Asn
                85                  90                  95

Val Ala Leu Asp Phe Ser Tyr Glu Gln Ser Arg Ile Arg Ser Val Asp
                100                 105                 110

Val Gly Thr Trp Ile Leu Ser Val Gly Tyr Arg Phe Gly Ser Lys Ser
            115                 120                 125

Arg Arg Ala Thr Ser Thr Val Thr Gly Gly Tyr Ala Gln Ser Asp Ala
            130                 135                 140

Gln Gly Gln Met Asn Lys Met Gly Gly Phe Asn Leu Lys Tyr Arg Tyr
145                 150                 155                 160

Glu Glu Asp Asn Ser Pro Leu Gly Val Ile Gly Ser Phe Thr Tyr Thr
                165                 170                 175

Gly Gly Ser Gly Gly Ser Ser Gly Gln Ala Ala Ala Gly Gln Val Gln
            180                 185                 190

Leu Gln Gln Ser Gly Ala Glu Leu Ala Arg Pro Gly Ala Ser Val Lys
        195                 200                 205

Met Ser Cys Lys Ala Ser Gly Tyr Thr Phe Thr Arg Tyr Thr Met His
210                 215                 220

Trp Val Lys Gln Arg Pro Gly Gln Gly Leu Glu Trp Ile Gly Tyr Ile
225                 230                 235                 240

Asn Pro Ser Arg Gly Tyr Thr Asn Tyr Asn Gln Lys Phe Lys Asp Lys
                245                 250                 255

Ala Thr Leu Thr Thr Asp Lys Ser Ser Ser Thr Ala Tyr Met Gln Leu
            260                 265                 270

Ser Ser Leu Thr Ser Glu Asp Ser Ala Val Tyr Tyr Cys Ala Arg Tyr
        275                 280                 285

Tyr Asp Asp His Tyr Cys Leu Asp Tyr Trp Gly Gln Gly Thr Thr Leu
    290                 295                 300

Thr Val Ser Ser Gly Gly Gly Ser Gly Gly Gly Ser Gly Gly
305                 310                 315                 320

Gly Gly Ser Gln Ile Val Leu Thr Gln Ser Pro Ala Ile Met Ser Ala
                325                 330                 335

Ser Pro Gly Glu Lys Val Thr Met Thr Cys Ser Ala Ser Ser Val
            340                 345                 350

```
Ser Tyr Met Asn Trp Tyr Gln Gln Lys Ser Gly Thr Ser Pro Lys Arg
            355                 360                 365

Trp Ile Tyr Asp Thr Ser Lys Leu Ala Ser Gly Val Pro Ala His Phe
370                 375                 380

Arg Gly Ser Gly Ser Gly Thr Ser Tyr Ser Leu Thr Ile Ser Gly Met
385                 390                 395                 400

Glu Ala Glu Asp Ala Ala Thr Tyr Tyr Cys Gln Gln Trp Ser Ser Asn
            405                 410                 415

Pro Phe Thr Phe Gly Ser Gly Thr Lys Leu Glu Ile Asn Arg Ala Asp
            420                 425                 430

Thr Ala Pro Thr Val Ser Ile Lys Leu Ile Ser Glu Glu Asp Leu Asn
            435                 440                 445

Gly Ala Ala His His His His His His
    450                 455

<210> SEQ ID NO 69
<211> LENGTH: 450
<212> TYPE: PRT
<213> ORGANISM: Artificial Sequence
<220> FEATURE:
<223> OTHER INFORMATION: chemically synthesized

<400> SEQUENCE: 69

Gly Gln Ser Gly Gln Glu Tyr Met Pro Met Glu Gly Gly Ser Gly Gln
1               5                   10                  15

Ser Gly Gly Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser Tyr Ala Met Ser Trp Val Arg Gln Ala Pro Gly Lys Gly Leu
50                  55                  60

Glu Trp Val Ser Ala Ile Ser Gly Arg Gly Asp Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Met Thr Ser Asn Ala Phe Ala Phe Asp Tyr Trp
        115                 120                 125

Gly Gln Gly Thr Leu Val Thr Val Ser Ser Gly Gly Gly Gly Ser Gly
130                 135                 140

Gly Gly Gly Ser Gly Gly Gly Gly Ser Gln Ser Val Leu Thr Gln Pro
145                 150                 155                 160

Pro Ser Val Ser Gly Ala Pro Gly Gln Arg Val Thr Ile Ser Tyr Thr
            165                 170                 175

Gly Ser Ser Ser Asn Ile Gly Ala Gly Tyr Gly Val His Trp Tyr Gln
        180                 185                 190

Gln Leu Pro Gly Thr Ala Pro Lys Leu Leu Ile Tyr Gly Asn Thr Asn
    195                 200                 205

Arg Pro Ser Gln Val Pro Asp Arg Phe Ser Gly Phe Lys Ser Gly Thr
210                 215                 220

Ser Ala Ser Leu Ala Ile Thr Gly Leu Gln Ala Glu Asp Glu Ala Asp
225                 230                 235                 240

Tyr Tyr Cys Gln Ser Tyr Asp Ser Ser Leu Ser Gln Trp Val Phe Gly
            245                 250                 255
```

```
Gly Gly Thr Lys Leu Thr Val Leu Gly Ala Ala Glu Gln Lys Leu
            260                 265                 270

Ile Ser Glu Glu Asp Leu Asn Gly Ser Gly Gln Gly Gly Ser Gly
            275                 280                 285

Gly Ser Gly Gly Ser Gly Gly Ser Gly Gly Ser Ala Tyr Tyr Gly Ile
            290                 295                 300

Thr Ala Gly Pro Ala Tyr Arg Ile Asn Asp Trp Ala Ser Ile Tyr Gly
305                 310                 315                 320

Val Val Gly Val Gly Tyr Gly Ser Pro Gly Gly Ser Tyr Gly Phe
                    325                 330                 335

Ser Tyr Gly Ala Gly Leu Gln Phe Asn Pro Met Glu Asn Val Ala Leu
                    340                 345                 350

Asp Phe Ser Tyr Glu Gln Ser Arg Ile Arg Ser Val Asp Val Gly Thr
                    355                 360                 365

Trp Ile Leu Ser Val Gly Tyr Arg Phe Gly Ser Lys Ser Arg Arg Ala
                    370                 375                 380

Thr Ser Thr Val Thr Gly Gly Tyr Ala Gln Ser Asp Ala Gln Gly Gln
385                 390                 395                 400

Met Asn Lys Met Gly Gly Phe Asn Leu Lys Tyr Arg Tyr Glu Glu Asp
                    405                 410                 415

Asn Ser Pro Leu Gly Val Ile Gly Ser Phe Thr Tyr Thr Gly Gly Ser
                    420                 425                 430

Gly Gly Ser Ser Gly Gln Thr Ala Ala Gly His His His His His
                    435                 440                 445

His His
    450

<210> SEQ ID NO 70
<211> LENGTH: 449
<212> TYPE: PRT
<213> ORGANISM: Artificial Sequence
<220> FEATURE:
<223> OTHER INFORMATION: chemically synthesized

<400> SEQUENCE: 70

Gly Gln Ser Gly Gln Glu Tyr Met Pro Met Glu Gly Gly Ser Gly Gln
1               5                   10                  15

Ser Gly Gly Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Gln Ile Val Leu Thr Gln Ser
145                 150                 155                 160
```

```
Pro Ala Ile Met Ser Ala Ser Pro Gly Glu Lys Val Thr Met Thr Cys
                165                 170                 175
Ser Ala Ser Ser Ser Val Ser Tyr Met Asn Trp Tyr Gln Gln Lys Ser
            180                 185                 190
Gly Thr Ser Pro Lys Arg Trp Ile Tyr Asp Thr Ser Lys Leu Ala Ser
        195                 200                 205
Gly Val Pro Ala His Phe Arg Gly Ser Gly Ser Gly Thr Ser Tyr Ser
    210                 215                 220
Leu Thr Ile Ser Gly Met Glu Ala Glu Asp Ala Ala Thr Tyr Tyr Cys
225                 230                 235                 240
Gln Gln Trp Ser Ser Asn Pro Phe Thr Phe Gly Ser Gly Thr Lys Leu
                245                 250                 255
Glu Ile Asn Arg Ala Asp Thr Ala Pro Thr Val Ser Ile Lys Leu Ile
            260                 265                 270
Ser Glu Glu Asp Leu Asn Gly Ser Gly Gln Gly Ser Gly Gly
        275                 280                 285
Ser Gly Ser Gly Gly Ser Gly Gly Ser Ala Tyr Tyr Gly Ile Thr
    290                 295                 300
Ala Gly Pro Ala Tyr Arg Ile Asn Asp Trp Ala Ser Ile Tyr Gly Val
305                 310                 315                 320
Val Gly Val Gly Tyr Gly Ser Gly Pro Gly Gly Ser Tyr Gly Phe Ser
                325                 330                 335
Tyr Gly Ala Gly Leu Gln Phe Asn Pro Met Glu Asn Val Ala Leu Asp
            340                 345                 350
Phe Ser Tyr Glu Gln Ser Arg Ile Arg Ser Val Asp Val Gly Thr Trp
        355                 360                 365
Ile Leu Ser Val Gly Tyr Arg Phe Gly Ser Lys Ser Arg Arg Ala Thr
    370                 375                 380
Ser Thr Val Thr Gly Gly Tyr Ala Gln Ser Asp Ala Gln Gly Gln Met
385                 390                 395                 400
Asn Lys Met Gly Gly Phe Asn Leu Lys Tyr Arg Tyr Glu Glu Asp Asn
                405                 410                 415
Ser Pro Leu Gly Val Ile Gly Ser Phe Thr Tyr Thr Gly Gly Ser Gly
            420                 425                 430
Gly Ser Ser Gly Gln Thr Ala Ala Gly His His His His His His
        435                 440                 445
His

<210> SEQ ID NO 71
<211> LENGTH: 466
<212> TYPE: PRT
<213> ORGANISM: Artificial Sequence
<220> FEATURE:
<223> OTHER INFORMATION: chemically synthesized

<400> SEQUENCE: 71

Gly Gln Ser Gly Gln Glu Tyr Met Pro Met Glu Gly Gly Ser Gly Gln
1               5                   10                  15
Ser Gly Gly Gln Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Arg Ser Tyr Ala Met Ser Trp Val Arg Gln Ala Pro Gly Lys Gly Leu
    50                  55                  60
Glu Trp Val Ser Ala Ile Ser Gly Arg Gly Asp Asn Thr Tyr Tyr Ala
```

```
              65                  70                  75                  80
Asp Ser Val Lys Gly Arg Phe Thr Ile Ser Arg Asp Asn Ser Lys Asn
                    85                  90                  95

Thr Leu Tyr Leu Gln Met Asn Ser Leu Arg Ala Glu Asp Thr Ala Val
                100                 105                 110

Tyr Tyr Cys Ala Lys Met Thr Ser Asn Ala Phe Ala Phe Asp Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Ser Gln Ser Val Leu Thr Gln Pro
145                 150                 155                 160

Pro Ser Val Ser Gly Ala Pro Gly Gln Arg Val Thr Ile Ser Tyr Thr
                165                 170                 175

Gly Ser Ser Ser Asn Ile Gly Ala Gly Tyr Gly Val His Trp Tyr Gln
                180                 185                 190

Gln Leu Pro Gly Thr Ala Pro Lys Leu Leu Ile Tyr Gly Asn Thr Asn
            195                 200                 205

Arg Pro Ser Gln Val Pro Asp Arg Phe Ser Gly Phe Lys Ser Gly Thr
        210                 215                 220

Ser Ala Ser Leu Ala Ile Thr Gly Leu Gln Ala Glu Asp Glu Ala Asp
225                 230                 235                 240

Tyr Tyr Cys Gln Ser Tyr Asp Ser Ser Leu Ser Gln Trp Val Phe Gly
                245                 250                 255

Gly Gly Thr Lys Leu Thr Val Leu Gly Ala Ala Ala Glu Gln Lys Leu
            260                 265                 270

Ile Ser Glu Glu Asp Leu Asn Gly Ser Gly Gly Gln Gly Gly Ser Gly
        275                 280                 285

Gly Ser Gly Gly Ser Gly Gly Ser Gly Gly Ser Ala Tyr Tyr Gly Ile
    290                 295                 300

Thr Ala Gly Pro Ala Tyr Arg Ile Asn Asp Trp Ala Ser Ile Tyr Gly
305                 310                 315                 320

Val Val Gly Val Gly Tyr Gly Ser Gly Pro Gly Ser Tyr Gly Phe
                325                 330                 335

Ser Tyr Gly Ala Gly Leu Gln Phe Asn Pro Met Glu Asn Val Ala Leu
            340                 345                 350

Asp Phe Ser Tyr Glu Gln Ser Arg Ile Arg Ser Val Asp Val Gly Thr
        355                 360                 365

Trp Ile Leu Ser Val Gly Tyr Arg Phe Gly Ser Lys Ser Arg Arg Ala
    370                 375                 380

Thr Ser Thr Val Thr Gly Gly Tyr Ala Gln Ser Asp Ala Gln Gly Gln
385                 390                 395                 400

Met Asn Lys Met Gly Gly Phe Asn Leu Lys Tyr Arg Tyr Glu Glu Asp
                405                 410                 415

Asn Ser Pro Leu Gly Val Ile Gly Ser Phe Thr Tyr Thr Gly Gly Ser
            420                 425                 430

Gly Gly Ser Ser Gly Gln Ala Ala Ala Gly Glu Ile Val Leu Thr Gln
        435                 440                 445

Ser Pro Gly Thr Leu Val Thr Val Ser Ser His His His His His
    450                 455                 460

His His
465

<210> SEQ ID NO 72
```

```
<211> LENGTH: 240
<212> TYPE: PRT
<213> ORGANISM: Artificial Sequence
<220> FEATURE:
<223> OTHER INFORMATION: chemically synthesized

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Ser Arg Gly Gln Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ile Ser Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asp Ala Ser Arg Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Gln Glu
    210                 215                 220

Thr Met Pro Pro Thr Phe Gly Gln Gly Thr Lys Val Glu Ile Lys Arg
225                 230                 235                 240

<210> SEQ ID NO 73
<211> LENGTH: 463
<212> TYPE: PRT
<213> ORGANISM: Artificial Sequence
<220> FEATURE:
<223> OTHER INFORMATION: chemically synthesized

<400> SEQUENCE: 73

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Ser Ser Ser Tyr Leu Ala Trp Tyr Gln
65                  70                  75                  80

Gln Lys Pro Gly Gln Ala Pro Arg Leu Leu Ile Tyr Gly Ala Ser Ser
```

```
                85                  90                  95
Arg Ala Thr Gly Ile Pro Asp Arg Phe Ser Gly Ser Gly Thr
            100                 105                 110
Asp Phe Thr Leu Thr Ile Ser Arg Leu Glu Pro Glu Asp Phe Ala Val
            115                 120                 125
Tyr Tyr Cys Gln Gln Tyr Ser Ser Pro Leu Thr Phe Gly Gly
            130                 135                 140
Thr Lys Val Glu Ile Lys Arg Ser Gly Ser Thr Ile Thr Ser Tyr
145                 150                 155                 160
Asn Val Tyr Tyr Thr Lys Leu Ser Ser Gly Thr Gln Val Gln Leu
                165                 170                 175
Val Gln Thr Gly Gly Val Val Gln Pro Gly Arg Ser Leu Arg Leu
                180                 185                 190
Ser Cys Ala Ala Ser Gly Ser Thr Phe Ser Ser Tyr Ala Met Ser Trp
            195                 200                 205
Val Arg Gln Ala Pro Gly Lys Gly Leu Glu Trp Val Ser Ala Ile Ser
            210                 215                 220
Gly Ser Gly Gly Ser Thr Tyr Tyr Ala Asp Ser Val Lys Gly Arg Phe
225                 230                 235                 240
Thr Ile Ser Arg Asp Asn Ser Lys Asn Thr Leu Tyr Leu Gln Met Asn
                245                 250                 255
Ser Leu Arg Ala Glu Asp Thr Ala Val Tyr Tyr Cys Ala Thr Asn Ser
            260                 265                 270
Leu Tyr Trp Tyr Phe Asp Leu Trp Gly Arg Ala Thr Leu Val Thr Val
            275                 280                 285
Ser Ser Ala Ser Gly Ser Gly Gly Gln Gly Gly Ser Gly Gly Ser Gly
290                 295                 300
Gly Ser Gly Gly Ser Gly Gly Ser Ala Tyr Tyr Gly Ile Thr Ala Gly
            305                 310                 315                 320
Pro Ala Tyr Arg Ile Asn Asp Trp Ala Ser Ile Tyr Gly Val Val Gly
                325                 330                 335
Val Gly Tyr Gly Ser Gly Pro Gly Gly Ser Tyr Gly Phe Ser Tyr Gly
                340                 345                 350
Ala Gly Leu Gln Phe Asn Pro Met Glu Asn Val Ala Leu Asp Phe Ser
                355                 360                 365
Tyr Glu Gln Ser Arg Ile Arg Ser Val Asp Val Gly Thr Trp Ile Leu
            370                 375                 380
Ser Val Gly Tyr Arg Phe Gly Ser Lys Ser Arg Arg Ala Thr Ser Thr
385                 390                 395                 400
Val Thr Gly Gly Tyr Ala Gln Ser Asp Ala Gln Gly Gln Met Asn Lys
                405                 410                 415
Met Gly Gly Phe Asn Leu Lys Tyr Arg Tyr Glu Glu Asp Asn Ser Pro
            420                 425                 430
Leu Gly Val Ile Gly Ser Phe Thr Tyr Thr Gly Gly Ser Gly Gly Ser
            435                 440                 445
Ser Gly Gln Thr Ala Ala Gly His His His His His His
450                 455                 460

<210> SEQ ID NO 74
<211> LENGTH: 453
<212> TYPE: PRT
<213> ORGANISM: Artificial Sequence
<220> FEATURE:
<223> OTHER INFORMATION: chemically synthesized
```

-continued

```
<400> SEQUENCE: 74

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Glu Val Gln Leu Leu Glu
        35                  40                  45

Ser Gly Gly Gly Leu Val Gln Pro Gly Gly Ser Leu Arg Leu Ser Cys
    50                  55                  60

Ala Ala Ser Gly Phe Thr Phe Ser Ser Tyr Ala Met Ser Trp Val Arg
65                  70                  75                  80

Gln Ala Pro Gly Lys Gly Leu Glu Trp Val Ser Ser Ile Gly Ser Arg
                85                  90                  95

Gly Gln Asn Thr Arg Tyr Ala Asp Ser Val Lys Gly Arg Phe Thr Ile
            100                 105                 110

Ser Arg Asp Asn Ser Lys Asn Thr Leu Tyr Leu Gln Met Asn Ser Leu
        115                 120                 125

Arg Ala Glu Asp Thr Ala Val Tyr Tyr Cys Ala Lys Ile Ile Ser Thr
    130                 135                 140

Phe Asp Tyr Trp Gly Gln Gly Thr Leu Val Thr Val Ser Ser Gly Gly
145                 150                 155                 160

Gly Gly Ser Gly Gly Gly Gly Ser Gly Gly Gly Gly Ser Thr Asp Ile
                165                 170                 175

Gln Met Thr Gln Ser Pro Ser Ser Leu Ser Ala Ser Val Gly Asp Arg
            180                 185                 190

Val Thr Ile Thr Cys Arg Ala Ser Gln Ser Ile Ser Ser Tyr Leu Asn
        195                 200                 205

Trp Tyr Gln Gln Lys Pro Gly Lys Ala Pro Lys Leu Leu Ile Tyr Asp
    210                 215                 220

Ala Ser Arg Leu Gln Ser Gly Val Pro Ser Arg Phe Ser Gly Ser Gly
225                 230                 235                 240

Ser Gly Thr Asp Phe Thr Leu Thr Ile Ser Ser Leu Gln Pro Glu Asp
                245                 250                 255

Phe Ala Thr Tyr Tyr Cys Gln Gln Gln Glu Thr Met Pro Pro Thr Phe
            260                 265                 270

Gly Gln Gly Thr Lys Val Glu Ile Lys Arg Gly Ser Gly Gly Gln Gly
        275                 280                 285

Gly Ser Gly Gly Ser Gly Gly Ser Gly Gly Ser Ala Tyr
    290                 295                 300

Tyr Gly Ile Thr Ala Gly Pro Ala Tyr Arg Ile Asn Asp Trp Ala Ser
305                 310                 315                 320

Ile Tyr Gly Val Val Gly Val Gly Tyr Gly Ser Pro Gly Gly Ser
                325                 330                 335

Tyr Gly Phe Ser Tyr Gly Ala Gly Leu Gln Phe Asn Pro Met Glu Asn
            340                 345                 350

Val Ala Leu Asp Phe Ser Tyr Glu Gln Ser Arg Ile Arg Ser Val Asp
        355                 360                 365

Val Gly Thr Trp Ile Leu Ser Val Gly Tyr Arg Phe Gly Ser Lys Ser
    370                 375                 380

Arg Arg Ala Thr Ser Thr Val Thr Gly Tyr Ala Gln Ser Asp Ala
385                 390                 395                 400

Gln Gly Gln Met Asn Lys Met Gly Gly Phe Asn Leu Lys Tyr Arg Tyr
                405                 410                 415
```

```
Glu Glu Asp Asn Ser Pro Leu Gly Val Ile Gly Ser Phe Thr Tyr Thr
                420                 425                 430

Gly Gly Ser Gly Gly Ser Ser Gly Gln Thr Ala Ala Gly His His His
            435                 440                 445

His His His His His
        450

<210> SEQ ID NO 75
<211> LENGTH: 479
<212> TYPE: PRT
<213> ORGANISM: Artificial Sequence
<220> FEATURE:
<223> OTHER INFORMATION: chemically synthesized

<400> SEQUENCE: 75

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Glu Ile Val Leu Thr Gln
        35                  40                  45

Ser Pro Gly Thr Leu Ser Leu Ser Pro Gly Glu Arg Ala Thr Leu Ser
    50                  55                  60

Cys Arg Ala Ser Gln Ser Val Ser Ser Ser Tyr Leu Ala Trp Tyr Gln
65                  70                  75                  80

Gln Lys Pro Gly Gln Ala Pro Arg Leu Leu Ile Tyr Gly Ala Ser Ser
                85                  90                  95

Arg Ala Thr Gly Ile Pro Asp Arg Phe Ser Gly Ser Gly Ser Gly Thr
            100                 105                 110

Asp Phe Thr Leu Thr Ile Ser Arg Leu Glu Pro Glu Asp Phe Ala Val
        115                 120                 125

Tyr Tyr Cys Gln Gln Tyr Gly Ser Ser Pro Leu Thr Phe Gly Gly Gly
    130                 135                 140

Thr Lys Val Glu Ile Lys Arg Ser Gly Gly Ser Thr Ile Thr Ser Tyr
145                 150                 155                 160

Asn Val Tyr Tyr Thr Lys Leu Ser Ser Ser Gly Thr Gln Val Gln Leu
                165                 170                 175

Val Gln Thr Gly Gly Gly Val Val Gln Pro Gly Arg Ser Leu Arg Leu
            180                 185                 190

Ser Cys Ala Ala Ser Gly Ser Thr Phe Ser Ser Tyr Ala Met Ser Trp
        195                 200                 205

Val Arg Gln Ala Pro Gly Lys Gly Leu Glu Trp Val Ser Ala Ile Ser
    210                 215                 220

Gly Ser Gly Gly Ser Thr Tyr Tyr Ala Asp Ser Val Lys Gly Arg Phe
225                 230                 235                 240

Thr Ile Ser Arg Asp Asn Ser Lys Asn Thr Leu Tyr Leu Gln Met Asn
                245                 250                 255

Ser Leu Arg Ala Glu Asp Thr Ala Val Tyr Tyr Cys Ala Thr Asn Ser
            260                 265                 270

Leu Tyr Trp Tyr Phe Asp Leu Trp Gly Arg Ala Thr Leu Val Thr Val
        275                 280                 285

Ser Ser Ala Ser Gly Ser Gly Gly Gln Gly Gly Ser Gly Gly Ser Gly
    290                 295                 300

Gly Ser Gly Gly Ser Gly Gly Ser Ala Tyr Tyr Gly Ile Thr Ala Gly
305                 310                 315                 320
```

```
Pro Ala Tyr Arg Ile Asn Asp Trp Ala Ser Ile Tyr Gly Val Val Gly
                325                 330                 335

Val Gly Tyr Gly Ser Gly Pro Gly Gly Ser Tyr Gly Phe Ser Tyr Gly
            340                 345                 350

Ala Gly Leu Gln Phe Asn Pro Met Glu Asn Val Ala Leu Asp Phe Ser
        355                 360                 365

Tyr Glu Gln Ser Arg Ile Arg Ser Val Asp Val Gly Thr Trp Ile Leu
    370                 375                 380

Ser Val Gly Tyr Arg Phe Gly Ser Lys Ser Arg Arg Ala Thr Ser Thr
385                 390                 395                 400

Val Thr Gly Gly Tyr Ala Gln Ser Asp Ala Gln Gly Gln Met Asn Lys
                405                 410                 415

Met Gly Gly Phe Asn Leu Lys Tyr Arg Tyr Glu Glu Asp Asn Ser Pro
            420                 425                 430

Leu Gly Val Ile Gly Ser Phe Thr Tyr Thr Gly Gly Ser Gly Gly Ser
        435                 440                 445

Ser Gly Gln Ala Ala Ala Gly Glu Ile Val Leu Thr Gln Ser Pro Gly
    450                 455                 460

Thr Leu Val Thr Val Ser Ser His His His His His His His
465                 470                 475

<210> SEQ ID NO 76
<211> LENGTH: 469
<212> TYPE: PRT
<213> ORGANISM: Artificial Sequence
<220> FEATURE:
<223> OTHER INFORMATION: chemically synthesized

<400> SEQUENCE: 76

Met Lys Lys Ile Ala Cys Leu Ser Ala Leu Ala Ala Val Leu Ala Phe
1               5                   10                  15

Thr Ala Gly Thr Ser Val Ala Gly Gln Ser Gly Gln Glu Tyr Met Pro
            20                  25                  30

Met Glu Gly Gly Ser Gly Gln Ser Gly Gly Glu Val Gln Leu Leu Glu
        35                  40                  45

Ser Gly Gly Gly Leu Val Gln Pro Gly Gly Ser Leu Arg Leu Ser Cys
    50                  55                  60

Ala Ala Ser Gly Phe Thr Phe Ser Ser Tyr Ala Met Ser Trp Val Arg
65                  70                  75                  80

Gln Ala Pro Gly Lys Gly Leu Glu Trp Val Ser Ser Ile Gly Ser Arg
                85                  90                  95

Gly Gln Asn Thr Arg Tyr Ala Asp Ser Val Lys Gly Arg Phe Thr Ile
            100                 105                 110

Ser Arg Asp Asn Ser Lys Asn Thr Leu Tyr Leu Gln Met Asn Ser Leu
        115                 120                 125

Arg Ala Glu Asp Thr Ala Val Tyr Tyr Cys Ala Lys Ile Ile Ser Thr
    130                 135                 140

Phe Asp Tyr Trp Gly Gln Gly Thr Leu Val Thr Val Ser Ser Gly Gly
145                 150                 155                 160

Gly Gly Ser Gly Gly Gly Gly Ser Gly Gly Gly Gly Ser Thr Asp Ile
                165                 170                 175

Gln Met Thr Gln Ser Pro Ser Ser Leu Ser Ala Ser Val Gly Asp Arg
            180                 185                 190

Val Thr Ile Thr Cys Arg Ala Ser Gln Ser Ile Ser Ser Tyr Leu Asn
        195                 200                 205
```

Trp Tyr Gln Gln Lys Pro Gly Lys Ala Pro Lys Leu Leu Ile Tyr Asp
210                 215                 220

Ala Ser Arg Leu Gln Ser Gly Val Pro Ser Arg Phe Ser Gly Ser Gly
225                 230                 235                 240

Ser Gly Thr Asp Phe Thr Leu Thr Ile Ser Ser Leu Gln Pro Glu Asp
                245                 250                 255

Phe Ala Thr Tyr Tyr Cys Gln Gln Glu Thr Met Pro Pro Thr Phe
                260                 265                 270

Gly Gln Gly Thr Lys Val Glu Ile Lys Arg Gly Ser Gly Gly Gln Gly
                275                 280                 285

Gly Ser Gly Gly Ser Gly Gly Ser Gly Gly Ser Gly Ser Ala Tyr
290                 295                 300

Tyr Gly Ile Thr Ala Gly Pro Ala Tyr Arg Ile Asn Asp Trp Ala Ser
305                 310                 315                 320

Ile Tyr Gly Val Val Gly Val Gly Tyr Gly Ser Gly Pro Gly Gly Ser
                325                 330                 335

Tyr Gly Phe Ser Tyr Gly Ala Gly Leu Gln Phe Asn Pro Met Glu Asn
                340                 345                 350

Val Ala Leu Asp Phe Ser Tyr Glu Gln Ser Arg Ile Arg Ser Val Asp
                355                 360                 365

Val Gly Thr Trp Ile Leu Ser Val Gly Tyr Arg Phe Gly Ser Lys Ser
                370                 375                 380

Arg Arg Ala Thr Ser Thr Val Thr Gly Gly Tyr Ala Gln Ser Asp Ala
385                 390                 395                 400

Gln Gly Gln Met Asn Lys Met Gly Phe Asn Leu Lys Tyr Arg Tyr
                405                 410                 415

Glu Glu Asp Asn Ser Pro Leu Gly Val Ile Gly Ser Phe Thr Tyr Thr
                420                 425                 430

Gly Gly Ser Gly Gly Ser Gly Gln Ala Ala Ala Gly Glu Ile Val
                435                 440                 445

Leu Thr Gln Ser Pro Gly Thr Leu Val Thr Val Ser Ser His His His
450                 455                 460

His His His His His
465

<210> SEQ ID NO 77
<211> LENGTH: 440
<212> TYPE: PRT
<213> ORGANISM: Artificial Sequence
<220> FEATURE:
<223> OTHER INFORMATION: chemically synthesized

<400> SEQUENCE: 77

Gly Gln Ser Gly Gln Glu Tyr Met Pro Met Glu Gly Gly Ser Gly Gln
1               5                   10                  15

Ser Gly Gly Glu Ile Val Leu Thr Gln Ser Pro Gly Thr Leu Ser Leu
                20                  25                  30

Ser Pro Gly Glu Arg Ala Thr Leu Ser Cys Arg Ala Ser Gln Ser Val
                35                  40                  45

Ser Ser Ser Tyr Leu Ala Trp Tyr Gln Gln Lys Pro Gly Gln Ala Pro
                50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

```
Arg Leu Glu Pro Glu Asp Phe Ala Val Tyr Tyr Cys Gln Gln Tyr Gly
            100                 105                 110

Ser Ser Pro Leu Thr Phe Gly Gly Gly Thr Lys Val Glu Ile Lys Arg
            115                 120                 125

Ser Gly Gly Ser Thr Ile Thr Ser Tyr Asn Val Tyr Tyr Thr Lys Leu
        130                 135                 140

Ser Ser Ser Gly Thr Gln Val Gln Leu Val Gln Thr Gly Gly Gly Val
145                 150                 155                 160

Val Gln Pro Gly Arg Ser Leu Arg Leu Ser Cys Ala Ala Ser Gly Ser
                165                 170                 175

Thr Phe Ser Ser Tyr Ala Met Ser Trp Val Arg Gln Ala Pro Gly Lys
            180                 185                 190

Gly Leu Glu Trp Val Ser Ala Ile Ser Gly Ser Gly Gly Ser Thr Tyr
        195                 200                 205

Tyr Ala Asp Ser Val Lys Gly Arg Phe Thr Ile Ser Arg Asp Asn Ser
        210                 215                 220

Lys Asn Thr Leu Tyr Leu Gln Met Asn Ser Leu Arg Ala Glu Asp Thr
225                 230                 235                 240

Ala Val Tyr Tyr Cys Ala Thr Asn Ser Leu Tyr Trp Tyr Phe Asp Leu
                245                 250                 255

Trp Gly Arg Ala Thr Leu Val Thr Val Ser Ala Ser Gly Ser Gly
            260                 265                 270

Gly Gln Gly Gly Ser Gly Gly Ser Gly Gly Ser Gly Gly
            275                 280                 285

Ser Ala Tyr Tyr Gly Ile Thr Ala Gly Pro Ala Tyr Arg Ile Asn Asp
        290                 295                 300

Trp Ala Ser Ile Tyr Gly Val Val Gly Val Gly Tyr Gly Ser Gly Pro
305                 310                 315                 320

Gly Gly Ser Tyr Gly Phe Ser Tyr Gly Ala Gly Leu Gln Phe Asn Pro
                325                 330                 335

Met Glu Asn Val Ala Leu Asp Phe Ser Tyr Glu Gln Ser Arg Ile Arg
            340                 345                 350

Ser Val Asp Val Gly Thr Trp Ile Leu Ser Val Gly Tyr Arg Phe Gly
        355                 360                 365

Ser Lys Ser Arg Arg Ala Thr Ser Thr Val Thr Gly Gly Tyr Ala Gln
        370                 375                 380

Ser Asp Ala Gln Gly Gln Met Asn Lys Met Gly Gly Phe Asn Leu Lys
385                 390                 395                 400

Tyr Arg Tyr Glu Glu Asp Asn Ser Pro Leu Gly Val Ile Gly Ser Phe
                405                 410                 415

Thr Tyr Thr Gly Gly Ser Gly Gly Ser Ser Gly Gln Thr Ala Ala Gly
            420                 425                 430

His His His His His His His His
        435                 440

<210> SEQ ID NO 78
<211> LENGTH: 430
<212> TYPE: PRT
<213> ORGANISM: Artificial Sequence
<220> FEATURE:
<223> OTHER INFORMATION: chemically synthesized

<400> SEQUENCE: 78

Gly Gln Ser Gly Gln Glu Tyr Met Pro Met Glu Gly Gly Ser Gly Gln
1               5                   10                  15
```

```
Ser Gly Gly Glu Val Gln Leu Leu Glu Ser Gly Gly Leu Val Gln
            20                  25                  30

Pro Gly Gly Ser Leu Arg Leu Ser Cys Ala Ala Ser Gly Phe Thr Phe
                35                  40                  45

Ser Ser Tyr Ala Met Ser Trp Val Arg Gln Ala Pro Gly Lys Gly Leu
 50                  55                  60

Glu Trp Val Ser Ser Ile Gly Ser Arg Gly Gln Asn Thr Arg Tyr Ala
65                   70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ile Ile Ser Thr Phe Asp Tyr Trp Gly Gln Gly
            115                 120                 125

Thr Leu Val Thr Val Ser Ser Gly Gly Gly Gly Ser Gly Gly Gly Gly
            130                 135                 140

Ser Gly Gly Gly Gly Ser Thr Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Ser Ile Ser Ser Tyr Leu Asn Trp Tyr Gln Gln Lys Pro Gly
                180                 185                 190

Lys Ala Pro Lys Leu Leu Ile Tyr Asp Ala Ser Arg Leu Gln Ser Gly
            195                 200                 205

Val Pro Ser Arg Phe Ser Gly Ser Gly Ser Gly Thr Asp Phe Thr Leu
            210                 215                 220

Thr Ile Ser Ser Leu Gln Pro Glu Asp Phe Ala Thr Tyr Tyr Cys Gln
225                 230                 235                 240

Gln Gln Glu Thr Met Pro Pro Thr Phe Gly Gln Gly Thr Lys Val Glu
                245                 250                 255

Ile Lys Arg Gly Ser Gly Gly Gln Gly Gly Ser Gly Gly Ser Gly Gly
            260                 265                 270

Ser Gly Gly Ser Gly Gly Ser Ala Tyr Tyr Gly Ile Thr Ala Gly Pro
            275                 280                 285

Ala Tyr Arg Ile Asn Asp Trp Ala Ser Ile Tyr Gly Val Val Gly Val
            290                 295                 300

Gly Tyr Gly Ser Gly Pro Gly Gly Ser Tyr Gly Phe Ser Tyr Gly Ala
305                 310                 315                 320

Gly Leu Gln Phe Asn Pro Met Glu Asn Val Ala Leu Asp Phe Ser Tyr
                325                 330                 335

Glu Gln Ser Arg Ile Arg Ser Val Asp Val Gly Thr Trp Ile Leu Ser
            340                 345                 350

Val Gly Tyr Arg Phe Gly Ser Lys Ser Arg Arg Ala Thr Ser Thr Val
            355                 360                 365

Thr Gly Gly Tyr Ala Gln Ser Asp Ala Gln Gly Gln Met Asn Lys Met
            370                 375                 380

Gly Gly Phe Asn Leu Lys Tyr Arg Tyr Glu Glu Asp Asn Ser Pro Leu
385                 390                 395                 400

Gly Val Ile Gly Ser Phe Thr Tyr Thr Gly Gly Ser Gly Gly Ser Ser
                405                 410                 415

Gly Gln Thr Ala Ala Gly His His His His His His
            420                 425                 430
```

<210> SEQ ID NO 79
<211> LENGTH: 456
<212> TYPE: PRT
<213> ORGANISM: Artificial Sequence
<220> FEATURE:
<223> OTHER INFORMATION: chemically synthesized

<400> SEQUENCE: 79

```
Gly Gln Ser Gly Gln Glu Tyr Met Pro Met Glu Gly Ser Gly Gln
1               5                   10                  15

Ser Gly Gly Glu Ile Val Leu Thr Gln Ser Pro Gly Thr Leu Ser Leu
                20                  25                  30

Ser Pro Gly Glu Arg Ala Thr Leu Ser Cys Arg Ala Ser Gln Ser Val
            35                  40                  45

Ser Ser Ser Tyr Leu Ala Trp Tyr Gln Gln Lys Pro Gly Gln Ala Pro
        50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Leu Thr Phe Gly Gly Gly Thr Lys Val Glu Ile Lys Arg
        115                 120                 125

Ser Gly Gly Ser Thr Ile Thr Ser Tyr Asn Val Tyr Tyr Thr Lys Leu
130                 135                 140

Ser Ser Ser Gly Thr Gln Val Gln Leu Val Gln Thr Gly Gly Gly Val
145                 150                 155                 160

Val Gln Pro Gly Arg Ser Leu Arg Leu Ser Cys Ala Ala Ser Gly Ser
                165                 170                 175

Thr Phe Ser Ser Tyr Ala Met Ser Trp Val Arg Gln Ala Pro Gly Lys
            180                 185                 190

Gly Leu Glu Trp Val Ser Ala Ile Ser Gly Ser Gly Gly Ser Thr Tyr
        195                 200                 205

Tyr Ala Asp Ser Val Lys Gly Arg Phe Thr Ile Ser Arg Asp Asn Ser
210                 215                 220

Lys Asn Thr Leu Tyr Leu Gln Met Asn Ser Leu Arg Ala Glu Asp Thr
225                 230                 235                 240

Ala Val Tyr Tyr Cys Ala Thr Asn Ser Leu Tyr Trp Tyr Phe Asp Leu
                245                 250                 255

Trp Gly Arg Ala Thr Leu Val Thr Val Ser Ser Ala Ser Gly Ser Gly
            260                 265                 270

Gly Gln Gly Gly Ser Gly Gly Ser Gly Gly Ser Gly Gly Ser Gly Gly
        275                 280                 285

Ser Ala Tyr Tyr Gly Ile Thr Ala Gly Pro Ala Tyr Arg Ile Asn Asp
290                 295                 300

Trp Ala Ser Ile Tyr Gly Val Val Gly Val Gly Tyr Gly Ser Gly Pro
305                 310                 315                 320

Gly Gly Ser Tyr Gly Phe Ser Tyr Gly Ala Gly Leu Gln Phe Asn Pro
                325                 330                 335

Met Glu Asn Val Ala Leu Asp Phe Ser Tyr Glu Gln Ser Arg Ile Arg
            340                 345                 350

Ser Val Asp Val Gly Thr Trp Ile Leu Ser Val Gly Tyr Arg Phe Gly
        355                 360                 365
```

```
Ser Lys Ser Arg Arg Ala Thr Ser Thr Val Thr Gly Gly Tyr Ala Gln
    370                 375                 380
Ser Asp Ala Gln Gly Gln Met Asn Lys Met Gly Gly Phe Asn Leu Lys
385                 390                 395                 400
Tyr Arg Tyr Glu Glu Asp Asn Ser Pro Leu Gly Val Ile Gly Ser Phe
                405                 410                 415
Thr Tyr Thr Gly Gly Ser Gly Gly Ser Ser Gly Gln Ala Ala Ala Gly
            420                 425                 430
Glu Ile Val Leu Thr Gln Ser Pro Gly Thr Leu Val Thr Val Ser Ser
        435                 440                 445
His His His His His His His
    450                 455

<210> SEQ ID NO 80
<211> LENGTH: 446
<212> TYPE: PRT
<213> ORGANISM: Artificial Sequence
<220> FEATURE:
<223> OTHER INFORMATION: chemically synthesized

<400> SEQUENCE: 80

Gly Gln Ser Gly Gln Glu Tyr Met Pro Met Glu Gly Gly Ser Gly Gln
1               5                   10                  15
Ser Gly Gly Glu Val Gln Leu Leu Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Ser Tyr Ala Met Ser Trp Val Arg Gln Ala Pro Gly Lys Gly Leu
    50                  55                  60
Glu Trp Val Ser Ser Ile Gly Ser Arg Gly Gln Asn Thr Arg Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Lys Ile Ile Ser Thr Phe Asp Tyr Trp Gly Gln Gly
        115                 120                 125
Thr Leu Val Thr Val Ser Ser Gly Gly Gly Gly Ser Gly Gly Gly Gly
    130                 135                 140
Ser Gly Gly Gly Gly Ser Thr Asp Ile Gln Met Thr Gln Ser Pro Ser
145                 150                 155                 160
Ser Leu Ser Ala Ser Val Gly Asp Arg Val Thr Ile Thr Cys Arg Ala
                165                 170                 175
Ser Gln Ser Ile Ser Ser Tyr Leu Asn Trp Tyr Gln Gln Lys Pro Gly
            180                 185                 190
Lys Ala Pro Lys Leu Leu Ile Tyr Asp Ala Ser Arg Leu Gln Ser Gly
        195                 200                 205
Val Pro Ser Arg Phe Ser Gly Ser Gly Ser Gly Thr Asp Phe Thr Leu
    210                 215                 220
Thr Ile Ser Ser Leu Gln Pro Glu Asp Phe Ala Thr Tyr Tyr Cys Gln
225                 230                 235                 240
Gln Gln Glu Thr Met Pro Pro Thr Phe Gly Gln Gly Thr Lys Val Glu
                245                 250                 255
Ile Lys Arg Gly Ser Gly Gly Gly Gly Ser Gly Gly Ser Gly Gly
            260                 265                 270
```

Ser Gly Gly Ser Gly Gly Ser Ala Tyr Tyr Gly Ile Thr Ala Gly Pro
            275                 280                 285

Ala Tyr Arg Ile Asn Asp Trp Ala Ser Ile Tyr Gly Val Val Gly Val
        290                 295                 300

Gly Tyr Gly Ser Gly Pro Gly Gly Ser Tyr Gly Phe Ser Tyr Gly Ala
305                 310                 315                 320

Gly Leu Gln Phe Asn Pro Met Glu Asn Val Ala Leu Asp Phe Ser Tyr
            325                 330                 335

Glu Gln Ser Arg Ile Arg Ser Val Asp Val Gly Thr Trp Ile Leu Ser
            340                 345                 350

Val Gly Tyr Arg Phe Gly Ser Lys Ser Arg Arg Ala Thr Ser Thr Val
        355                 360                 365

Thr Gly Gly Tyr Ala Gln Ser Asp Ala Gln Gly Gln Met Asn Lys Met
370                 375                 380

Gly Gly Phe Asn Leu Lys Tyr Arg Tyr Glu Glu Asp Asn Ser Pro Leu
385                 390                 395                 400

Gly Val Ile Gly Ser Phe Thr Tyr Thr Gly Ser Gly Gly Ser Ser
            405                 410                 415

Gly Gln Ala Ala Ala Gly Glu Ile Val Leu Thr Gln Ser Pro Gly Thr
        420                 425                 430

Leu Val Thr Val Ser Ser His His His His His His His
        435                 440                 445

<210> SEQ ID NO 81
<211> LENGTH: 192
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (15)..(22)
<223> OTHER INFORMATION: X is any amino acid

<400> SEQUENCE: 81

Glu Tyr Met Pro Met Glu Gly Gly Ser Gly Gln Ser Gly Gln Xaa Xaa
1               5                   10                  15

Xaa Xaa Xaa Xaa Xaa Xaa Ser Gly Gly Gln Gly Gly Ser Gly Gly Ser
                20                  25                  30

Gly Gly Ser Gly Gly Ser Gly Gly Ser Ala Tyr Tyr Gly Ile Thr Ala
            35                  40                  45

Gly Pro Ala Tyr Arg Ile Asn Asp Trp Ala Ser Ile Tyr Gly Val Val
        50                  55                  60

Gly Val Gly Tyr Gly Ser Gly Pro Gly Gly Ser Tyr Gly Phe Ser Tyr
65                  70                  75                  80

Gly Ala Gly Leu Gln Phe Asn Pro Met Glu Asn Val Ala Leu Asp Phe
                85                  90                  95

Ser Tyr Glu Gln Ser Arg Ile Arg Ser Val Asp Val Gly Thr Trp Ile
            100                 105                 110

Leu Ser Val Gly Tyr Arg Phe Gly Ser Lys Ser Arg Arg Ala Thr Ser
        115                 120                 125

Thr Val Thr Gly Gly Tyr Ala Gln Ser Asp Ala Gln Gly Gln Met Asn
    130                 135                 140

Lys Met Gly Gly Phe Asn Leu Lys Tyr Arg Tyr Glu Glu Asp Asn Ser
145                 150                 155                 160

Pro Leu Gly Val Ile Gly Ser Phe Thr Tyr Thr Gly Ser Gly Gly
                165                 170                 175

```
Ser Ser Gly Gln Ala Ala Gly His His His His His His His
        180                 185                 190
```

<210> SEQ ID NO 82
<211> LENGTH: 192
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (15)..(22)
<223> OTHER INFORMATION: X is any amino acid

<400> SEQUENCE: 82

```
Glu Tyr Met Pro Met Glu Gly Gly Ser Gly Gln Ser Gly Gln Xaa Xaa
1               5                   10                  15

Xaa Xaa Xaa Xaa Xaa Xaa Ser Gly Gly Gln Gly Gly Ser Gly Gly Ser
            20                  25                  30

Gly Gly Ser Gly Gly Ser Gly Ser Ala Tyr Tyr Gly Ile Thr Ala
            35                  40                  45

Gly Pro Ala Tyr Arg Ile Asn Asp Trp Ala Ser Ile Tyr Gly Val Val
50                  55                  60

Gly Val Gly Tyr Gly Ser Gly Pro Gly Gly Ser Tyr Gly Phe Ser Tyr
65                  70                  75                  80

Gly Ala Gly Leu Gln Phe Asn Pro Met Glu Asn Val Ala Leu Asp Phe
                85                  90                  95

Ser Tyr Glu Gln Ser Arg Ile Arg Ser Val Asp Val Gly Thr Trp Ile
            100                 105                 110

Leu Ser Val Gly Tyr Arg Phe Gly Ser Lys Ser Arg Arg Ala Thr Ser
        115                 120                 125

Thr Val Thr Gly Gly Tyr Ala Gln Ser Asp Ala Gln Gly Gln Met Asn
130                 135                 140

Lys Met Gly Gly Phe Asn Leu Lys Tyr Arg Tyr Glu Glu Asp Asn Ser
145                 150                 155                 160

Pro Leu Gly Val Ile Gly Ser Phe Thr Tyr Thr Gly Gly Ser Gly Gly
                165                 170                 175

Ser Ser Gly Gln Thr Ala Ala Gly His His His His His His His
        180                 185                 190
```

<210> SEQ ID NO 83
<211> LENGTH: 13
<212> TYPE: PRT
<213> ORGANISM: Artificial Sequence
<220> FEATURE:
<223> OTHER INFORMATION: chemically synthesized

<400> SEQUENCE: 83

```
Gly Gly Ser Gly Gly Ser Ser Gly Gln Thr Ala Ala Gly
1               5                   10
```

<210> SEQ ID NO 84
<211> LENGTH: 579
<212> TYPE: DNA
<213> ORGANISM: Artificial Sequence
<220> FEATURE:
<223> OTHER INFORMATION: chemically synthesized

<400> SEQUENCE: 84

```
gaatacatgc cgatggaagg agggtctggc cagtctggcc agggttctgg cagcaattcc    60
```

```
ggttctagcg gtggccaggg tggcagcggt ggctctggtg gttccggtgg ctctggtggc    120
tctgcgtact acggcatcac tgctggtccg gcttaccgca ttaacgactg ggcaagcatc    180
tacggtgtag tgggtgtggg ttatggttct ggcccgggtg gttcttacgg tttctcctac    240
ggtgcgggtc tgcagttcaa cccgatggaa aacgttgctc tggacttctc ttacgagcag    300
agccgtattc gtagcgttga cgtaggcacc tggattctgt ccgttggtta ccgcttcggc    360
tccaaatccc gccgtgcgac ttctactgta actggcggtt acgcacagag cgacgctcag    420
ggccaaatga acaaaatggg cggtttcaac ctgaaatacc gctatgaaga agacaacagc    480
ccgctgggtg tgatcggttc tttcacttac accggcggct ctggtggttc tagcggtcaa    540
acggccgctg gtcaccatca ccaccatcat caccactaa                            579
```

<210> SEQ ID NO 85
<211> LENGTH: 657
<212> TYPE: DNA
<213> ORGANISM: Artificial Sequence
<220> FEATURE:
<223> OTHER INFORMATION: chemically synthesized

<400> SEQUENCE: 85

```
tgggtgtgcc acccgatgtg ggaggtgatg tgcctgaggg gagggtctgg ccagtctggc     60
cagggtggag gcagcaattc cggtggcagc ggcggttctg gtggcagcgg tggctctggt    120
ggttccggtg actacaacaa aaaccagtac tacggcatca ctgctggtcc ggcttaccgc    180
attaacgact gggcaagcat ctacggtgta gtgggtgtgg gttatggtaa attccagacc    240
actgaatacc cgacctacaa acacgacacc agcgactacg ttctctccta cggtgcgggt    300
ctgcagttca acccgatgga aaacgttgct ctggacttct cttacgagca gagccgtatt    360
cgtagcgttg acgtaggcac ctggattctg tccgttggtt accgcttcgg ctccaaatcc    420
cgccgtgcga cttctactgt aactggcggt tacgcacaga gcgacgctca gggccaaatg    480
aacaaaatgg gcggtttcaa cctgaaatac cgctatgaag aagacaacag cccgctgggt    540
gtgatcggtt ctttcactta caccgagaaa agccgtactg caagcggcca aggtggccaa    600
cacatcagcc agtggaagcc gaaggtcccg aaccgcgagg acaaatacaa gaagtaa        657
```

<210> SEQ ID NO 86
<211> LENGTH: 192
<212> TYPE: PRT
<213> ORGANISM: Artificial Sequence
<220> FEATURE:
<223> OTHER INFORMATION: chemically synthesized

<400> SEQUENCE: 86

Glu Tyr Met Pro Met Glu Gly Gly Ser Gly Gln Ser Gly Gln Gly Ser
1               5                   10                  15

Gly Ser Asn Ser Gly Ser Ser Gly Gly Gln Gly Gly Ser Gly Gly Ser
            20                  25                  30

Gly Gly Ser Gly Gly Ser Gly Gly Ser Ala Tyr Tyr Gly Ile Thr Ala
        35                  40                  45

Gly Pro Ala Tyr Arg Ile Asn Asp Trp Ala Ser Ile Tyr Gly Val Val
    50                  55                  60

Gly Val Gly Tyr Gly Ser Gly Pro Gly Gly Tyr Gly Phe Ser Tyr
65                  70                  75                  80

Gly Ala Gly Leu Gln Phe Asn Pro Met Glu Asn Val Ala Leu Asp Phe
                85                  90                  95

Ser Tyr Glu Gln Ser Arg Ile Arg Ser Val Asp Val Gly Thr Trp Ile

```
            100                 105                 110
Leu Ser Val Gly Tyr Arg Phe Gly Ser Lys Ser Arg Ala Thr Ser
            115                 120                 125

Thr Val Thr Gly Gly Tyr Ala Gln Ser Asp Ala Gln Gly Gln Met Asn
    130                 135                 140

Lys Met Gly Gly Phe Asn Leu Lys Tyr Arg Tyr Glu Glu Asp Asn Ser
145                 150                 155                 160

Pro Leu Gly Val Ile Gly Ser Phe Thr Tyr Thr Gly Ser Gly Gly
                165                 170                 175

Ser Ser Gly Gln Thr Ala Ala Gly His His His His His His His
            180                 185                 190

<210> SEQ ID NO 87
<211> LENGTH: 217
<212> TYPE: PRT
<213> ORGANISM: Artificial Sequence
<220> FEATURE:
<223> OTHER INFORMATION: chemically synthesized

<400> SEQUENCE: 87

Trp Val Cys His Pro Met Trp Glu Val Met Cys Leu Arg Gly Gly Ser
1               5                   10                  15

Gly Gln Ser Gly Gln Gly Gly Ser Asn Ser Gly Gly Ser Gly Gly
                20                  25                  30

Ser Gly Gly Ser Gly Gly Ser Gly Gly Ser Gly Asp Tyr Asn Lys Asn
            35                  40                  45

Gln Tyr Tyr Gly Ile Thr Ala Gly Pro Ala Tyr Arg Ile Asn Asp Trp
    50                  55                  60

Ala Ser Ile Tyr Gly Val Val Gly Val Gly Tyr Gly Lys Phe Gln Thr
65                  70                  75                  80

Thr Glu Tyr Pro Thr Tyr Lys His Asp Thr Ser Asp Tyr Gly Phe Ser
                85                  90                  95

Tyr Gly Ala Gly Leu Gln Phe Asn Pro Met Glu Asn Val Ala Leu Asp
                100                 105                 110

Phe Ser Tyr Glu Gln Ser Arg Ile Arg Ser Val Asp Val Gly Thr Trp
            115                 120                 125

Ile Leu Ser Val Gly Tyr Arg Phe Gly Ser Lys Ser Arg Ala Thr
    130                 135                 140

Ser Thr Val Thr Gly Gly Tyr Ala Gln Ser Asp Ala Gln Gly Gln Met
145                 150                 155                 160

Asn Lys Met Gly Gly Phe Asn Leu Lys Tyr Arg Tyr Glu Glu Asp Asn
                165                 170                 175

Ser Pro Leu Gly Val Ile Gly Ser Phe Thr Tyr Thr Glu Lys Ser Arg
            180                 185                 190

Thr Ala Ser Gly Gln Gly Gly His Ile Ser Gln Trp Lys Pro Lys Val
        195                 200                 205

Pro Asn Arg Glu Asp Lys Tyr Lys Lys
    210                 215
```